US006225460B1

(12) United States Patent
Bischofberger et al.

(10) Patent No.: US 6,225,460 B1
(45) Date of Patent: *May 1, 2001

(54) NUCLEOTIDE ANALOGS

(75) Inventors: Norbert W. Bischofberger, San Carlos; Robert J. Jones, Millbrae; Murty N. Arimilli; Kuei-Ying Lin, both of Fremont; Michael S. Louie, San Mateo; Lawrence R. McGee, Pacifica; Ernest J. Prisbe; William A. Lee, both of Los Altos; Kenneth C. Cundy, Belmont, all of CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/247,497

(22) Filed: Feb. 10, 1999

Related U.S. Application Data

(60) Continuation of application No. 09/071,420, filed on May 1, 1998, now abandoned, which is a division of application No. 08/617,849, filed on May 6, 1996, now Pat. No. 5,798,340, which is a continuation of application No. PCT/US94/10539, filed on Sep. 16, 1994, which is a continuation-in-part of application No. 08/193,341, filed on Feb. 8, 1994, now abandoned, which is a continuation-in-part of application No. 08/123,483, filed on Sep. 17, 1993, now Pat. No. 5,656,745.

(51) Int. Cl.$^7$ .................................................. C07H 19/04
(52) U.S. Cl. .................. 536/26.1; 536/22.1; 536/25.34; 536/27.14; 536/27.21; 536/26.1; 562/553
(58) Field of Search ............................. 536/25.34, 27.14, 536/27.21, 26.1; 562/553

(56) References Cited

U.S. PATENT DOCUMENTS

| | | | |
|---|---|---|---|
| 3,524,846 | 8/1970 | Moffatt et al. | 260/211.5 |
| 4,369,181 | 1/1983 | Miller et al. | 424/180 |
| 4,590,269 | 5/1986 | Prisbe et al. | 544/244 |
| 4,670,424 | 6/1987 | MacCoss et al. | 514/81 |
| 4,724,233 | 2/1988 | De Clercq et al. | 514/81 |
| 4,801,710 | 1/1989 | MacCoss et al. | |
| 4,808,716 | 2/1989 | Holy et al. | 544/244 |
| 4,968,788 | 11/1990 | Farquhar | 536/27 |
| 5,043,339 | 8/1991 | Beauchamp | 514/278 |
| 5,047,533 | 9/1991 | Reist et al. | 544/244 |
| 5,142,051 | 8/1992 | Holy et al. | 544/244 |
| 5,208,221 | 5/1993 | Kim et al. | 514/81 |
| 5,247,085 | 9/1993 | Harnden et al. | 544/244 |
| 5,302,585 | 4/1994 | Yu et al. | 514/81 |
| 5,352,786 | 10/1994 | Jindrich et al. | 544/243 |
| 5,386,030 | 1/1995 | Kim et al. | 544/243 |
| 5,391,723 | 2/1995 | Priest | 536/22.1 |
| 5,495,006 | 2/1996 | Climie et al. | 536/24 |
| 5,527,803 | 6/1996 | Halazy et al. | 514/263 |
| 5,591,851 | 1/1997 | Alexander | 544/243 |
| 5,618,793 | 4/1997 | Cooper et al. | 514/19 |
| 5,618,803 | 4/1997 | Bodor | 518/81 |
| 5,618,964 | 4/1997 | Cheng et al. | 558/180 |
| 5,656,745 | 8/1997 | Bischofberger et al. | 536/25.34 |

FOREIGN PATENT DOCUMENTS

| | | |
|---|---|---|
| 2009 834 | 9/1970 | (DE) . |
| 41 38 584 | 5/1993 | (DE) . |
| 0 173 624 A2 | 3/1986 | (EP) . |
| 0206459 | 12/1986 | (EP) . |
| 0253412 | 1/1988 | (EP) . |
| 0 269 947 A1 | 6/1988 | (EP) . |
| 0 319 228 A3 | 11/1988 | (EP) . |
| 0 335 770 A2 | 10/1989 | (EP) . |
| 0 343 133 A1 | 11/1989 | (EP) . |
| 0 353 955 A2 | 2/1990 | (EP) . |
| 0 369 409 A1 | 5/1990 | (EP) . |
| 0 398 231 A2 | 11/1990 | (EP) . |
| 0 404 296 A1 | 12/1990 | (EP) . |
| 0 405 748 A1 | 1/1991 | (EP) . |
| 0479640 A2 | 9/1991 | (EP) . |
| 0 465 297 A1 | 1/1992 | (EP) . |
| 0 468 119 A1 | 1/1992 | (EP) . |
| 0 468 866 A1 | 1/1992 | (EP) . |
| 0 481 214 A1 | 4/1992 | (EP) . |
| 0 494 370 A1 | 7/1992 | (EP) . |
| 0 531 597 A1 | 3/1993 | (EP) . |
| 0 632 048 A1 | 6/1994 | (EP) . |
| 0 630 381 B1 | 12/1994 | (EP) . |
| 0 369 409 B1 | 1/1995 | (EP) . |
| 1243214 | 8/1971 | (GB) . |
| WO 88/05438 | 7/1988 | (WO) . |
| WO 91/19721 | 12/1991 | (WO) . |
| WO 92/01698 | 2/1992 | (WO) . |
| WO 92/09611 | 6/1992 | (WO) . |
| WO 92/13869 | 8/1992 | (WO) . |
| WO 94/03466 | 2/1994 | (WO) . |
| WO 94/03467 | 2/1994 | (WO) . |
| WO 95/07919 | 3/1995 | (WO) . |
| WO 95/07920 | 3/1995 | (WO) . |

OTHER PUBLICATIONS

Alexander et al., 59:1853, Collect Czech Chem Commun, 1994.

(List continued on next page.)

Primary Examiner—Christopher S. F. Low
Assistant Examiner—David Lukton
(74) Attorney, Agent, or Firm—Max D. Hensley

(57) ABSTRACT

Nucleotide analogs characterized by the presence of an amidate linked amino acid or an ester linked group which is bonded to the phosphorus atom of phosphonate nucleotide analogs are disclosed. The analogs comprise a phosphoamidate or ester bond that is hydrolyzed in vivo to yield a corresponding phosphonate nucleotide analog. Methods and intermediates for their synthesis and use are described.

2 Claims, 7 Drawing Sheets

OTHER PUBLICATIONS

Amari et al., "Isolation of experimental anti–AIDS glycerophospholipids by micro–preparative reversed–phase high–performance liquid chromatography", 590:153–161, J. Chromatog, 1992.

Andrei et al., "Comparative Activity of Selected Antiviral Compounds Against Clinical Isolates of Varicella Zoster Virus", 14:318–328, Eur J Clin Microbiol Infect Dis, 1995.

Bai et al, "Structural Specificity of Mucosal–Cell Transport and Metabolism of Peptide Drugs: Implication of Oral Peptide Drug Delivery", 9:969–979, Pharm Res, 1992.

Bischofberger et al., "1–[((S)–2–Hydroxy–2–Oxo–1,4, 2–Dioxaphosphorinan–5–yl)Methyl] Cytosine, an Intracellular Prodrug for (S)–1–(3–Hydroxy–2–Phosphonylmethoxypropyl)Cytosine with Improved Therapeutic Index In Vivo", 38:2387–2391, Antimicro AG & Chemo, 1994.

Bronson et al, "Synthesis and Biological Activity of Carbocyclic Derivatives of the Potent Antiviral Agent 9–[2–(Phosphonomethoxy)Ethyl]Guanine (PMEG)", 2:685–690, Bioorg Med Chem Lett, 1992.

Bruice et al., "Hydrolysis of a Phosphate Diester by Simultaneous Carboxylate and Carboxyl Group Participation in a Rigid System with Kinetically Unfavorable Rotamers Frozen Out", 117:3639–3640, J Am Chem Soc, 1995.

Charvet et al., "Inhibition of Human Immunodeficiency Virus Type 1 Replication by Phosphonoformate– and Phosphonoacetate–2',3'–Dideoxy–3'–thiacytidine Conjugates", 37:2216–2223, J Med Chem, 1994.

Coates et al., "(−)–2'–Deoxy–3'–Thiacytidine Is a Potent, Highly Selective Inhibitor of Human Immunodeficiency Virus Type 1 and Type 2 Replication In Vitro", 36(4):733–739, Antimicro AG & Chemo, 1992.

Colla et al, "Synthesis and Antiviral Activity of Water–Soluble Esters of Acyclovir [9–[(2–Hydroxyethoxy)methyl]guanine]", 26:602–604, J Med Chem, 1983.

Curley et al, "Synthesis and anti–HIV evaluation of some phosphoramidate derivatives of AZT: studies on the effect of chain elongation on biological activity", 14:345–356, Antiviral Res, 1990.

Dudley et al., "Pharmacokinetics of Stavudine in Patients with AIDS or AIDS–Related Complex", 166(3):480–485, The Journal of Infectious Diseases, 1992.

Farquhar et al, "Biologically Reversible Phosphate–Protective Groups", 72:324–325, J Pharm Sci, 1983.

Farrow et al, "Synthesis and Biological Properties of Novel Phosphotriesters: A New Approach to the Introduction of Biologically Active Nucleotides into Cells", 33:1400–1406, J Med Chem, 1990.

Freed et al, "Evidence for Acyloxymethyl Esters of Pyrimidine 5'–Deoxyribonucleotides as Extracellular Sources of Active 5'–Deoxyribonucleotides in Cultured Cells", 38:3193–3198, Biochem Pharm, 1989.

Freeman et al, "3'–Azido–3', 5'–dideoxythymidine–5'–methylphosphonic Acid Diphosphate: Synthesis and HIV–1 Reverse Transcriptase Inhibition", 35:3192–3196, J Med Chem, 1992.

Gabrielsen et al, "Synthesis and In Vivo Anti–RNA–Viral Evaluation of a Phosphoramidate Derivative of 6–Azauridine; Orotidylic Acid Decarboxylase Inhibitors, Pyrazofurin and 6–Azauridine; and 2–Thio–6–azauridine and its Triacetate", 17(I):149, Antiviral Res, 1992.

Glazier et al., "Potent Topical Anti–Herpes Activity of a Lipophilic Phosphorus Prodrug for the Antiviral Agent PMEA", p. A306—Poster, 8th International Conference on Antiviral Research, Santa Fe, NM, Apr. 23–28, 1995.

Gumport et al, "Structure of the DNA Ligase–Adenylate Intermediate: Lysine (epsilon–amino)–Linked Adenosine Monophosphoramidate", 68(10):2559–2563, Proc Natl Acad Sci, 1971.

Hasegawa et al., "Prodrugs of 2',3'–Didehydro–3'–deoxythymidine", 82(12):1232–1236, J Pharm Sci, Dec. 1993.

Hitchcock et al., "The Cyclic Congener of Cidofovir has Reduced Nephrotoxicity in Three Species", 26:A358 (poster), 8th ISAR Conference, Santa Fe, New Mexico, Apr. 23–25, 1995.

Hostetler et al., "Synthesis and Antiretroviral Activity of Phospholipid Analogs of Azidothymidine and Other Antiviral Nucleosides", 265(11):6112–6117, J Biol Chem, 1990.

Jacobson et al., "Phase I Trial of Valaciclovir, the L–Valyl Ester of Acyclovir, in Patients with Advanced Human Immunodeficiency Virus Disease", 38(7):1534–1540, Antimicro AG & Chemo, Jul. 1994.

Jones et al., "Minireview: nucleotide prodrugs", 27:1–17, Antiviral Res, 1995.

Juodka et al, "Synthesis of Diribonucleoside phospho–(P–>N)–Amino Acid Derivatives", 39:963–968, Collect Czech Chem Commun, 1974.

Kern et al., "Comparison of Efficacy and Toxicity of HPMPC and Cyclic HPMPC in Animal Models for Severe Herpesvirus Infections", 26:A329 (poster), 8th ISAR Conference, Santa Fe, New Mexico, Apr. 23–25, 1995.

Kim et al, "A Novel Synthesis of 1–OXA–HPMPA: A Potent Antiviral Agent Against Herpes Viruses", 33 (1):pp. 25–28, Tet Lett, 1992.

Kim et al, "Acyclic Purine Phosphonate Analogues as Antivral Agents. Synthesis and Structure–Activity Relationships", 33:1207–1213, J Med Chem, 1990.

Kim et al., "Synthesis and HIV Activity of Phosphonate Isosteres of D4T Monophosphate", 5(2):367–370, Bioorg Med Chem Lett, 1992.

Kjaersgaard et al., "Synthesis of 5–Homologous AZT and D4T Derivatives", 46:1016–1020, Acta Chemica Scandinavica, 1992.

Kumar et al., "Synthesis and Biological Evaluation of Some Cyclic Phosphoramidate Nucleoside Derivatives", 33:2368–2375, J Med Chem, 1990.

Lee et al., "Tissue Distribution and Bioavailability of Cyclic HPMPC, an Intracellular Prodrug of HPMPC", 26:A340 (Poster), 8th ISAR Conference, Santa Fe, New Mexico, 1995.

McGuigan et al, "Synthesis and anti–HIV activity of some haloalkyl phosphoramidate derivatives of 3'–azido–3'deoxythymidine (AZT): potent activity of the trichloroethyl methoxyalaninyl compound", 15:255–263, Antiviral Res, 1991.

McGuigan et al, "Phosphoramidate derivatives of AZT as inhibitors of HIV: studies on the carboxyl terminus", 4(2):97–101, Antiviral Chem & Chemo, 1993.

Mukaiyama et al, "Synthesis of Oligothymidylates and Nucleoside Cyclic Phosphates by Oxidation–Reduction Condensation", 94(24):8528–8532, J Am Chem Soc, 1972.

Mullah et al., "Potential Prodrug Derivatives of 2',3'–Didehydro–2',3'–dideoxynucleosides. Preparations and Antiviral Activities", 35:2728–2735, J Med Chem, 1992.

Nielsen et al, "Evaluation of Glycolamide Esters and Various Other Esters of Aspirin as True Aspirin Prodrugs", 32:727–734, J Med Chem, 1989.

Orchin, "The Vocabulary of Organic Chemistry", p. 283,, 1980.

Palu et al, "Cellular uptake of phosphonylmethoxyalkylpurine derivatives", 16:115–119, Antiviral Res, 1991.

Reymen et al., "Antiviral Activity of Selected Nucleoside Analogues Against Human Herpes Virus Type 6", 14:567–570, Nucls & Nuclt, 1995.

Rosenberg et al, "Synthesis of Potential Prodrugs and Metabolites of 9–(S)–(3–Hydroxy–2–Phosphonylmethoxypropyl)Adenines", 52:2792–2800, Collect Czech Chem Commun, 1987.

Rosenberg et al, "Phosphonylmethoxyalkyl and Phosphonylalkyl Derivatives of Adenine", 53:2753–2777, Collect Czech Chem Commun, 1988.

Sastry et al, "Membrane–Permeable Dideoxyuridine 5'–Monophosphate Analogue Inhibits Human Immunodeficiency Virus Infection", 41:441–445, Mol Pharm, 1992.

Serafinowska et al., "Synthesis and in Vivo Evaluation of Prodrugs of 9–[2–(Phosphonomethoxy)ethoxy]adenine", 38:1372–1379, J Med Chem, 1995.

Sergheraert et al., "Synthesis and Anti–HIV Evaluation of D4T and D4T 5'–Monophosphate Prodrugs", 36:826–830, J Med Chem, 1993.

Shaw et al., "Salicylate Ester Prodrugs of Cyclic HPMPC. I. Pharmacokinetics in Dogs.", 0.696527778, 7th North American ISSX Meeting, San Diego, CA, Oct. 20–24, 1996.

Smee et al., "Potent Anti–Murine Cytomegalovirus Activity and Reduced Nephrotoxicity of Ganciclovir Cyclic Phosphonate", 40(8):1964–1966, Antimicro AG & Chemo, Aug. 1996.

Srivastva et al, "Bioreversible Phosphate Protective Groups: Synthesis and Stability of Model Acyloxymethyl Phosphates", 12:118–129, Bioorg Chem, 1984.

Starrett et al, "Synthesis and in vitro evaluation of a phosphonate prodrug: bis(pivaloyloxymethyl)9–(2–phosphonylmethoxyethyl)adenine", 19:267–273, Antiviral Res, 1992.

Sueoka et al., "Salicylate Ester Prodrugs of Cyclic HPMPC. II. Species Differences in Metabolism In Vitro", 0.632638889, 7th North American ISSX Meeting, San Diego, CA, Oct. 20–24, 1996.

Wolff–Kugel et al, "Synthesis of New Carbocyclic Phosphonate Analogs of Dideoxypurine Nucleotides", 32(44):6341–6344, Tet Lett, 1991.

Wolff–Kugel et al., "Studies Towards the Synthesis of the Saturated and Unsaturated Carbocyclic Methylene Phosphonate Analogs of Dideoxyadenosine", 12(3&4):279–294, Nucls & Nuclt, 1993.

Xiong et al., "Kinetic Analysis of the Interaction of Cidofovir Diphosphate with Human Cytomegalovirus DNA Polymerase", 51:1563–1567, Biochem Pharm, 1996.

Yu et al, "Synthesis and Antiviral Activity of Methyl Derivatives of 9–[2–(Phosphonomethoxy)ethyl]guanine", 35:2958–2969, J Med Chem, Aug. 7, 1992.

Yuan et al., "Cyclic HPMPC: A Chemically Stable Intracellular Prodrug of HPMPC", 41:30 (Poster), AAPS Western Regional Meeting, San Jose, CA, Mar. 27–28, 1995.

van Wijk et al., "Synthesis, characterization and some properties of dideoxynucleoside analogs of citidine diphosphate diacylglycerol", 1165:45–52, Biochem Biophys Acta, 1992.

Andrei et al, "Comparative Activity of Selected Antiviral Compounds against Clinical Isolates of Human Cytomegalovirus", 10(12):1026–1033, Eur J Clin Microbiol Infect Dis, 1991.

Barnard et al, "Selective inhibition of cytomegaloviruses by 9–(3'–ethylphosphono–1'–hydroxymethyl–1'–propyloxymethyl)guanine", 22:77–89, Antiviral Res, 1993.

Beres, "Synthesis and Antitumor and Antiviral Properties of 5–Halo– and 5–(Trifluoromethyl)–2'–deoxyuridine 3',5'–Cyclic Monophosphates and Neutral Triesters", 29:1243–1249, J Med Chem, 1986.

Davies et al, "2'–Nor'2'–deoxyguanosine is an effective therapeutic agent for treatment of experimental herpes keratitis", 7:119–125, Antiviral Res, 1987.

Duke et al., "In vitro and in vivo activities of phosphate derivatives of 9–(1, 3–dihydroxy–2–propoxymethyl)–guanine against cytomegaloviruses", 6:299–308, Antiviral Res, 1986.

Engel, R., "Phosphonates as Analogues of Natural Phosphates", 77(3):349–367, Chem Rev, 1977.

Feng et al, "Combined treatment with 2'–nor–cGMP and ganciclovir against cytomegalovirus infection in a guinea pig model", 19:193–206, Antiviral Res, 1992.

Field et al, "Efficacy of 2'–nor–cyclicGMP in treatment of experimental herpes virus infections", 6:329–341, Antiviral Res, 1986.

Harnden et al, "Synthesis and Antiviral Activity of 9–Alkoxypurines. 1. 9–(3–Hydroxypropoxy)– and 9–[3–Hydroxy–2–(hydroxymethyl)propoxy]purines", 33:187–196, J Med Chem, 1990.

Ho et al, "Intracellular Metabolism of the Antiherpes Agent (S)–1–[3–Hydroxy–2–(phosphonylmethoxy)propyl]cytosine", 41:197–202, Mol Pharm, 1992.

Holy et al, "Acyclic nucleotide analogues: synthesis, antiviral activity and inhibitory effects on some cellular and virus–encoded enzymes in vitro", 13:295–312, Antiviral Res, 1990.

Holy et al, "Synthesis of (3–Hydroxy–2–Phosphonylmethoxypropyl) Derivatives of Heterocyclic Bases", 54:2470–2501, Collect Czech Chem Commun, 1989.

Jahne et al., "Preparation of Carbocyclic Phosphonate Nucleosides", 33(37):5335–5338, Tet Lett, 1992, Karkas et al, "Stereochemical considerations in the enzymatic phosphorylation and antiviral activity of acyclonucleosides. I. Phosphorylation of 2'–nor–2'–deoxyguanosine", 911:127–135, Biochem Biophys Acta, 1987.

Keim et al, "Amphotericin B Methyl Ester Hydrochloride and Amphotericin B: Comparative Acute Toxicity", 179(4073):584–585, Science, 1973.

Kraus, "New Phosphonate Analogues of 3'–thia–2', 3'–dideoxycytidine (BCH–189). Synthesis and Anti–HIV Evaluation.", 12(2):157–162, Nucls & Nuclt, 1993.

Li et al, "Activity of (S)–1–(3–hydroxy–2–phosphonylmethoxypropyl)cytosine (HPMPC) against guinea pig cytomegalovirus infection in cultured cells and in guinea pigs", 13:237–252, Antiviral Res, 1990.

Midoux, "Drug Targeting: Anti–HSV–1 Activity of Mannosylated Polymer–Bound 9–(2–Phosphonylmethoxyethyl Adenine", 167(3):1044–1049, Biochem Biophys Res Comm, 1990.

Nelson et al., 109:4058, J Am Chem Soc, 1987.

Reist et al, "Synthesis of Acyclonucleoside Phosphonates as Antivral Agents Against Cytomegalovirus", 13(1–3):539–550, Nucls & Nuclt, 1994.

Snoeck et al, "Antiviral activity of anti–cytomegalovirus agents (HPMPC, HPMPA) assessed by a flow cytometric method and DNA hybridization technique", 16:1–9, Antiviral Res, 1991.

Snoeck et al, "New acyclic nucleoside phosphonate derivatives as inhibitors of human cytomegalovirus", p. 327, Abstract No. 1334, 29th Interscience Conference on Antimicrobial Agents and Chemotherapy, Sep. 17–20, 1989.

Snoeck et al., pp. 337, Progress in Cytomegalovirus Research, 1991.

Starrett et al., "Synthesis, Oral Bioavailability Determination, and in Vitro Evaluation of Prodrugs of the Antiviral Agent 9–[2–(Phosphonomethoxy)ethyl]adenine (PMEA)", 37:1857–1864, J Med Chem, 1994.

Sundaralingam et al., "Stereochemistry of Nucleic Acids and Their Constituents. XXVII. The Crystal Structure of 5'–Methyleneadenosine 3',5'–Cyclic Monophosphate Monohydrate, a Biologically Active Analog of the Secondary Hormonal Messenger Cyclic Adenosine 3',5'–Monophospat . . . ", 94(14):5070–5076, J Am Chem Soc, 1972.

Tolman et al, "2'–nor–cGMP: A seco–Cyclic Nucleotide with Powerful Anti–DNA–Viral Activity\", 128(3):1329–1335, Biochem Biophys Res Comm, 1985.

Trost et al., 2:777–778, Comprehensive Organic Synthesis, 1991.

NUCLEOTIDE ANALOGS

This application is a continuation of U.S. Ser. No. 09/071,420, filed May 1, 1998, now abandoned, which is a divisional application of Ser. No. 08/617,849 filed May 6, 1996, now U.S. Pat. No. 5,798,340, which is a continuation application of PCT/US94/10539, filed Sep. 16, 1994, which is a continuation-in-part application of Ser. No. 08/193,341, filed Feb. 8, 1994, now abandoned, which is a continuation-in-part application of Ser. No. 08/123,483, filed Sep. 17, 1993, now U.S. Pat. No. 5,656,745.

BACKGROUND OF THE INVENTION

The present invention relates to novel nucleotide analog amidates and esters, their pharmaceutically acceptable acid addition salts, a process for their production, and to their use. The nucleotides of the present invention exhibit antitumor/antineoplastic activity, a broad spectrum of antimicrobial activity and certain other desirable activities.

Compounds related to the nucleotide analogs of the present invention may be found in: U.S. Pat. Nos. 5,043,339, 5,108,994 and 5,166,198; EP 206 459; EP 253 412; EP 269 947; EP 270 885; EP 319 228; EP 343 133; EP 398 231; EP 404 296; EP 465 297; EP 468 119; EP 468 866; EP 479 640; EP 481 214; EP 494 370; EP 531 597; PCT/GB91/01171; PCT/US92/01020; PCT/US92/05208; WO 91/19721; Bronson et al, *Bioorg Medicinal Chem Lett* (1992) 2:685–690; Bronson et al, *j Med Chem*, (1989) 32:1457–1463; Bronson et al, *Nucleotide Analogs as Antiviral Agents*, ACS Symposium Series 401, J. C. Martin, Ed., p. 72–87, American Chemical Society, Washington, D.C. (1989); Colla, et al, *J Med Chem* (1983) 26:602–604; Curley, et al, *Antiviral Res* (1990) 14:345–356; De Clercq, et al, *Nature*, (1986) 323:464–467; Farrow, et al, *J Med Chem* (1990) 33:1400–1406; Farquhar, et al, *J. Pharm Sci* (1983) 72:324–325; Freed, et al, *Biochem Pharmacol* (1989) 19:3193–3198; Freeman, et al, *J Med Chem* (1992) 35:3192–3196; Gabrielsen, B., et al, *Antiviral Res Suppl I* (1992) 17:149; Gumport, et al, *Proc Natl Acad Sci* (1971) 2559–2563; Juodka, et al, *Coll Czech Chem Commun* (1974) 39:963–968; Kim, et al, *Bioorg Medicinal Chem Lett* (1992) 2:367–370; Kim, et al, *Tet Lett* (1992) 33:25–28; Kim, et al, *J Med Chem* (1990) 33:1207–1213; Kumar, et al, *J Med Chem* (1990) 33:2368–2375; McGuigan, et al, *Antiviral Chem Chemother* (1993) 4:97–101; McGuigan, et al, *Antiviral Res* (1991) 15:255–263; Rosenberg, et al, *Coll Czech Chem Commun* (1988) 53:2753–2777; Rosenberg, et al, *Coll Czech Chem Commun* (1988) 52:2792–2800; Rosenberg, et al, *Coll Czech Chem Commun* (1988) 52:2801–2808; Starrett, et al, *Antiviral Res* (1992) 19:267–273; Yu, et al, *J Med Chem* (1992) 35:2958–2969; Wolff-Kugel, et al, *Tet Lett* (1991) 32:6341–6344.

A characteristic of nucleotide analogs or nucleotides having a phosphonate or a phosphate group is the presence of one or two negative charges associated with the phosphorus group at physiologic pH. The charge associated with moieties such as phosphate or phosphonate groups is believed to generally limit bioavailability by limiting cell membrane permeation via passive diffusion (Liebman, et al, *J. Biol. Chem.*, (1955) 216:823–830; Roll, et al, *J Biol Chem*, (1956) 220:439–444; Srivastava, et al, *Bioorg Chem* (1984) 12:118–129; Palu, et al, *Antiviral Res* (1991) 16:115–119; Sastry, et al, *Mol Pharmacol* (1992) 41:441–445). These compounds are often, therefore, given parenterally in order to enhance bioavailability by increasing serum or intracellular levels.

Other characteristics of nucleotide analogs that can limit their efficacy include unfavorable pharmacokinetic or pharmacodynamic properties, insufficient potency and/or unfavorable toxicity characteristics.

Studies were conducted to ameliorate one or more of the above-mentioned problems associated with nucleotide analog drugs. The present invention includes novel nucleotide analogs that are hydrolyzable in vivo. The nucleotide analogs can have improved bioavailability, improved pharmacokinetic or pharmacodynamic properties, enhanced potency and/or improved toxicity characteristics compared to the corresponding unmodified nucleotide analog. Methods to synthesize and use the compounds and methods to obtain and use antibodies that recognize the compounds are also disclosed.

SUMMARY OF THE INVENTION

In a principal embodiment, the objects of this invention are accomplished by a nucleotide analog amidate comprising a phosphonate radical wherein the improvement comprises an amino acid residue or polypeptide radical in which an amino group of the amino acid or polypeptide is bonded to the phosphorus atom of the nucleotide analog by an amidate bond, a carboxyl group of the amino acid residue or polypeptide radical is positioned such that it is capable as the free acid of hydrolyzing the phosphoroamidate bond, and the carboxyl group is blocked (such as by moieties including esters or amides). The nucleotide analog amidates of this invention are hydrolyzed in vivo to the corresponding nucleotide analog and are thus precursors of the corresponding nucleotide analog.

In accordance with this invention the nucleotide analog amidates or a physiologically acceptable salt thereof, have the structure of formula I

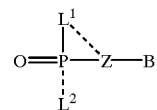

I wherein $L^1$ and $L^2$ are independently an amino acid or polypeptide residue bonded to the phosphorus atom of the nucleotide analog by an amidate bond, or $L^1$ or $L^2$ are an oxyester, thioester, a substituted or unsubstituted amine, or hydroxy, provided that one or both of $L^1$ and $L^2$ is an amino acid or polypeptide residue and any carboxyl group that is linked by less than about 5 atoms to the amidate N is esterified or amidated, the dotted lines represent facultative bonds and wherein, (i) P and Z are linked to form a compound of the formula Ib

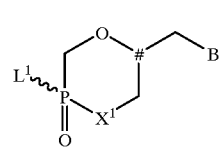

Ib or (ii) $L^1$ and Z are linked to form a compound of the formula Ic

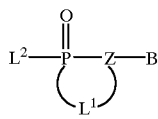

wherein
  substituents linked to carbon atoms designated # are in the R, S or RS configuration;
  $X^1$ is O or S;
  Z is —$CHR^7$—$R^{11}$—$(CH_2)_{m1}$—$C^{\#}(R^8)$ $((CH_2)_{m2}(R^9))$—$(CH_2)_{m3}$—$R^{10}$—$(CH_2)_{m4}$—, —Q—$C_6H_4$—$CH_2$—, —$CHR^7$—O—$CHR^7$—O—$CHR^7$—, —$CHR^7$—$(CHR^{13})_{m1}$—$CHR^{14}$—$R^{10}$—,

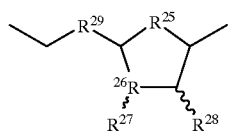

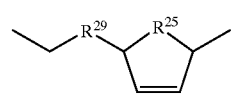

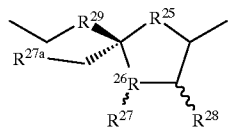

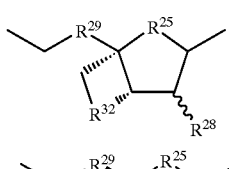

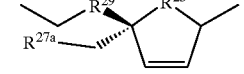

or VIII
wherein
  $R^7$ is H or $C_1$–$C_4$ alkyl;
  $R^8$ is H or $C_1$–$C_4$ alkyl, $C_2$–$C_4$ alkenyl, azidomethyl or azidoethyl;
  $R^9$ is halogen (F, Cl, Br or I), H or OH;
  $R^{10}$ is O, $CH_2$ or a chemical bond;
  $R^{11}$ is O, S, $CH_2$, CHF or $CF_2$;
  Q is —$C(R^{12})_2$—$CH_2$—, —$C(R^{12})_2$—O—, —$CR^{12}$=$CR^{12}$—, or —C≡C—, wherein each $R^{12}$ is independently H, or halogen;
  $R^{13}$ is H, halogen, OH, $CH_3$, $CH_2OH$, or $C_3$–$C_6$ acyloxymethyl;
  $R^{14}$ is H, halogen, OH, $CH_3$, $CH_2OH$, $C_3$–$C_6$ acyloxymethyl, or $C_2$–$C_6$ acyloxy;
  $R^{25}$ is $CH_2$, CHF or O;
  $R^{26}$ is CH or S, provided that when $R^{25}$ is CH, $R^{26}$ is not S;
  $R^{27}$ is H, OH, halogen, $N_3$, $C_1$–$C_4$ alkyl, $C_1$–$C_4$ alkoxy or, when $R^{26}$ is S, $R^{27}$ is absent;
  $R^{27a}$ is H, OH, halogen, $N_3$, $C_1$–$C_4$ alkyl, $C_1$–$C_4$ alkoxy;
  $R^{28}$ is H, OH, halogen, $N_3$, $C_1$–$C_4$ alkyl or $C_1$–$C_4$ alkoxy;
  $R^{29}$ is O, S, $CH_2$, CHF, $CF_2$;
  $R^{32}$ is O;
  m1 is an integer having a value from 0 to 4;
  m2 is an integer having a value from 0 to 4;
  m3 is an integer having a value from 0 to 4;
  m4 is an integer having a value from 0 to 4;
  B is a heterocyclic base; and
  substituents linked to the carbon atom designated $C^{\#}$ are in the R, S or RS configuration.

In a further embodiment the objects are accomplished by compounds of the formula II, IIa, IIb and IIc

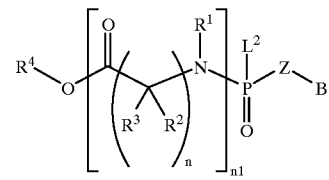

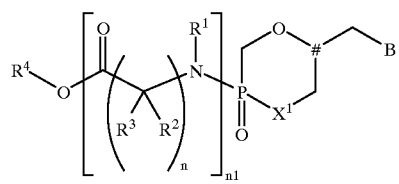

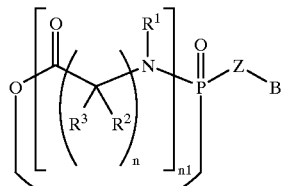

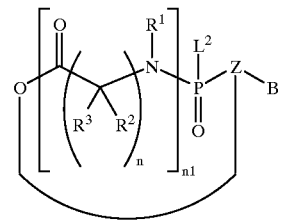

wherein $L^2$ is OR, SR or

III $$\left[ R^4{-}O{-}\overset{O}{\underset{}{C}}{-}\underset{\underset{R^3\ R^2}{|\ \ |}}{(C)_n}{-}\overset{R^1}{\underset{}{N}}{-} \right]_{n1}$$

n is an integer having a value from 1 to 5 and if n>1, each —$C(R^3)(R^2)$— may be the same or different;
n1 is an integer;
substituents linked to the carbon atom designated # are in the R, S or RS configuration;
R is H, $C_1$–$C_{20}$ alkyl which is unsubstituted or substituted by substituents independently selected from the group consisting of OH, O, N and halogen (F, Cl, Br, I), $C_3$–$C_{20}$ aryl which is unsubstituted or substituted by substituents independently selected from the group consisting of $C_1$–$C_6$ alkyl, $C_1$–$C_6$ alkoxy, $C_1$–$C_6$ haloalkyl (1 to 3 halogen atoms), cyano, nitro, OH, O, N and halogen or R is $C_4$–$C_{20}$ aryl-alkyl which is unsubstituted or substituted in the aryl moiety by substituents independently selected from the group consisting of $C_1$–$C_6$ alkyl, $C_1$–$C_6$ alkoxy, $C_1$–$C_6$ haloalkyl (1 to 3 halogen atoms), cyano, nitro, OH, O, N and halogen, or R is $C_3$–$C_{24}$ 1-acyloxy-1-alkyl ($C_1$–$C_8$ alkyl), or R is $C_6$–$C_{24}$ 1-acyloxy-1-aryl-1-alkyl ($C_1$–$C_6$ aryl, $C_1$–$C_4$ alkyl), or R is $C_3$–$C_{24}$ 1-acyloxy-2-alkoxy-1-alkyl ($C_1$–$C_8$ alkyl), or R is $C_3$–$C_{24}$ 1-acyloxy-2-haloalkyl ($C_1$–$C_8$ haloalkyl, 1 to 3 halogen atoms);

$R^1$ is H or $C_1$–$C_9$ alkyl which is unsubstituted or substituted by substituents independently selected from the group consisting of OH, O, N, $COOR^4$ and halogen, $C_3$–$C_6$ aryl which is unsubstituted or substituted by substituents independently selected from the group consisting of OH, O, N, $COOR^4$ and halogen or $C_3$–$C_9$ aryl-alkyl which is unsubstituted or substituted by substituents independently selected from the group consisting of OH, O, N, $COOR^4$ and halogen;

$R^2$ is H or $C_1$–$C_9$ alkyl which is unsubstituted or substituted by substituents independently selected from the group consisting of OH, O, N, $COOR^4$ and halogen, $C_3$–$C_6$ aryl which is unsubstituted or substituted by substituents independently selected from the group consisting of OH, O, N, $COOR^4$ and halogen or $C_3$–$C_9$ aryl-alkyl which is unsubstituted or substituted by substituents independently selected from the group consisting of OH, O, N, $COOR^4$ and halogen;

$R^3$ is C(O)—$OR^4$, amino, amide, guanidinyl, imidazolyl, indolyl, sulfoxide, phosphoryl, $C_1$–$C_3$ alkylamino, $C_1$–$C_3$ alkyldiamino, $C_1$–$C_6$ alkenylamino, hydroxy, thiol, $C_1$–$C_3$ alkoxy, $C_1$–$C_3$ alkthiol, $(CH_2)_n COOR^4$, $C_1$–$C_6$ alkyl which is unsubstituted or substituted with OH, halogen, SH, $NH_2$, phenyl, hydroxyphenyl or $C_7$–$C_{10}$ alkoxyphenyl; $C_2$–$C_6$ alkenyl which is unsubstituted or substituted with OH, halogen, SH, $NH_2$, phenyl, hydroxyphenyl or $C_7$–$C_{10}$ alkoxyphenyl; $C_6$–$C_{12}$ aryl which is unsubstituted or substituted with OH, halogen, SH, $NH_2$, phenyl, hydroxyphenyl or $C_7$–$C_{10}$ alkoxyphenyl; and $R^4$ is H provided that n1 greater than 1, or is $C_3$–$C_9$ alkyl which is substituted by substituents independently selected from the group consisting of OH, O, N and halogen, $C_3$–$C_6$ aryl which is substituted by substituents independently selected from the group consisting of OH, O, N and halogen or $C_3$–$C_9$ aryl-alkyl which is substituted by substituents independently selected from the group consisting of OH, O, N and halogen.

The structural formula I is meant to define compounds where the phosphorus (P) atom is tetravalent (PV oxidation state) and optionally linked via the facultative bonds shown as dotted lines to either $L^1$ or Z to form a heterocyclic ring containing at least the P atom itself and a nitrogen atom of $L^1$ or an atom present, usually oxygen (O), in Z. For such compounds, L2 and the facultative bond between P and Z is absent. Such heterocyclic rings will preferably be 5-, 6- or 7-membered, but are also 4-, 8-, 9-, 10-, 11- or 12-membered. Alternatively the P atom is covalently linked to $L^2$ with $L^1$ and Z optionally linked to each other to form a heterocyclic ring. The structure is not intended to include compounds where $L^1$, $L^2$ and a heterocyclic ring containing P and Z are present in the same molecule which would exceed the valency of P. Thus, an exemplary class of compounds is represented by the structure of formula I includes $(L^1)(L^2)P(O)$-Z-B (formula Id) where no heterocyclic rings are formed between any $L^1$, $L^2$, P, Z or B moiety.

$R^2$ includes methyl, ethyl, propyl, isopropyl and benzyl.

In another embodiment, the objects of this invention are accomplished by a nucleotide analog ester comprising a phosphonate radical and an ester moiety bonded to the phosphorus atom of the nucleotide analog. The nucleotide analog esters of this invention are hydrolyzed in vivo to the corresponding nucleotide analog and are thus precursors of the corresponding nucleotide analog, or can be used as intermediates in the synthesis of the nucleotide analog amidates.

The substructure Z can have a range of atoms between the base, B, and the phosphorus atom. For example, four atoms separate the heterocyclic base and phosphorus moieties when Z is of the formula —$CH_2$—O—$CH_2CH_2$—. In general, there will be from 2 to 16 atoms, preferably from 3 to 9 atoms, more preferably from 4 to 6 atoms that separate the heterocyclic base and the phosphorus atom. Thus, Z substructures of the formula —$CHR^7$—$R^{11}$—$(CH_2)_{m1}$—$C(R^8)((CH_2)_{m2}(R^9))$—$(CH_2)_{m3}$—$R^{10}$—$(CH_2)_{m4}$— may be characterized where the sum of m1, m3 and m4 is in a range between 0 and 12 or preferably in a range between 1 and 6, more preferably in a range between 1 and 4.

The nucleotide analog amidate and ester compounds of the instant invention include the corresponding salts, which may be base salts of the phosphonic acid moiety or an acid addition salt of the base in addition to the zwitterionic forms and/or solvates of compounds of formula I.

Some of the compounds of the present invention can exist as optical isomers and both racemic or scalemic and diastereomeric mixtures of these isomers which may exist for certain compounds as well as the individual optical isomers which are all within the scope of the present invention. Compounds of formula IIa in the R, S or RS configuration at the chiral carbon, designated # herein, are examples of compounds having optical isomers. While the scalemic mixtures can be separated into their individual isomers through well-known techniques such as, for example, the separation of diastereomeric salts formed with optically active adjuncts, e.g. acids or bases followed by conversion back to the optically active substrates; in most instances, for compounds of the present invention, the preferred optical isomer can be synthesized by means of stereospecific reactions, beginning with the appropriate stereoisomer of the desired starting material.

As indicated, the present invention also pertains to the salts, including pharmaceutically acceptable non-toxic salts of these compounds. Such salts may include those derived by combination of appropriate cations such as alkali and alkaline earth metal ions or ammonium and quaternary amino ions with the acid anion moiety of the phosphonic acid group. In addition salts may be formed from acid addition of certain organic and inorganic acids with basic centers of the purine, specifically guanine, or pyrimidine base. Finally it is to be understood that compounds of the present invention in their un-ionized as well as zwitterionic form and/or in the form of solvates are also considered part of the present invention.

In other embodiments, the foregoing nucleotide analog amidates and esters or their dihydroxy phosphonate hydrolysis products are labeled with a detectable tag such as a radioisotope (including $^{32}P$, $^{35}S$, $^{14}C$, $^3H$, $^{125}I$) a fluorescent moiety, an enzyme (including peroxidase, phosphatase) or the like.

In other embodiments, the foregoing nucleotide analog amidates comprise amino acid, dipeptide or tripeptide compounds (monosubstituted or disubstituted with identical or different amino acid, dipeptide or tripeptide substituents) that are capable of entry into eukaryotic cells via amino acid or peptide transporters present in eukaryotic cells in vivo or in vitro.

Also included are immunogens for raising antibodies which are capable of binding to the nucleotide analog amidates and esters of this invention and/or their dihydroxy phosphonate hydrolysis products, as well as antibodies capable of binding to the amidate and ester compounds of this invention or to their dihydroxy phosphonate hydrolysis products.

Chemical Structures

Structural formulas and substructures are represented as roman numerals (I, II, III, IV, V, etc) or as letters (B, Z, $L^1$, $L^2$, $R^1$, $R^2$, etc). The substructures Z and $Z^1$ represent linking groups between the heterocyclic base (B) and the phosphorus atom (P) of the phosphonate group in the nucleotide analogs described herein. Linking groups Z, such as —$CHR^7$—$R^{11}$—$(CH_2)_{m1}$—$C(R^8)((CH_2)_{m2}(R^9))$—$(CH_2)_{m3}$—$R^{10}$—$(CH_2)_{m4}$—, in the structure $(L^1)(L^2)P(O)$-Z-B have the structure $(L^1)(L^2)P(O)CHR^7$—$R^{11}$—$(CH_2)_{m1}$—$C(R^8)((CH_2)_{m2}(R^9))$—$(CH_2)_{m3}$—$R^{10}$—$(CH_2)_{m4}$—B (i.e. the heterocyclic base (B) is covalently linked to the unfilled valence on the right side of the structure and the phosphorus atom is linked to the unfilled valence on the left side).

DETAILED DESCRIPTION OF THE INVENTION

Figure 1:
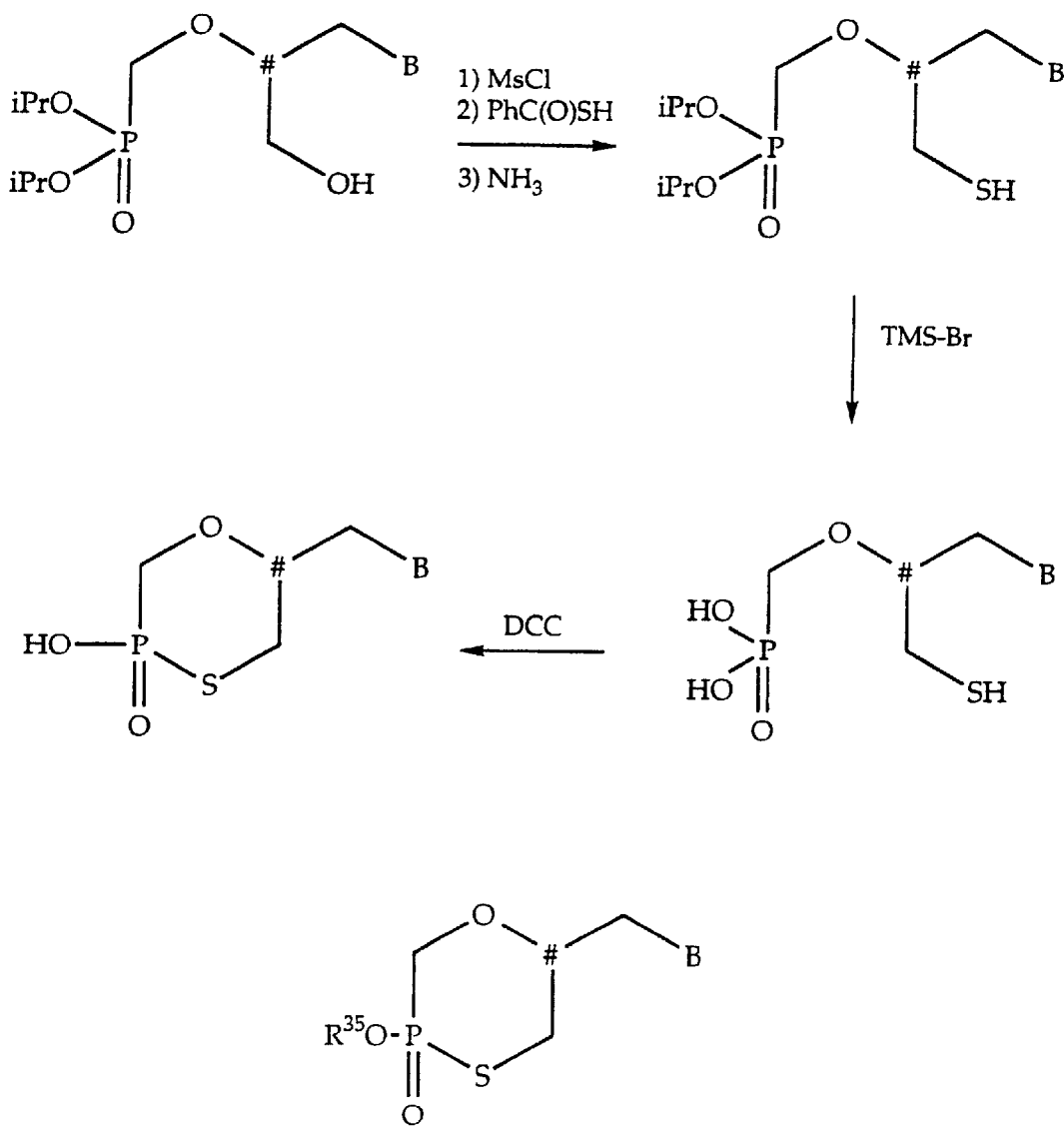
FIG. 1. Synthesis of formula Ib compounds where $X^1$ is S.
Figure 2:
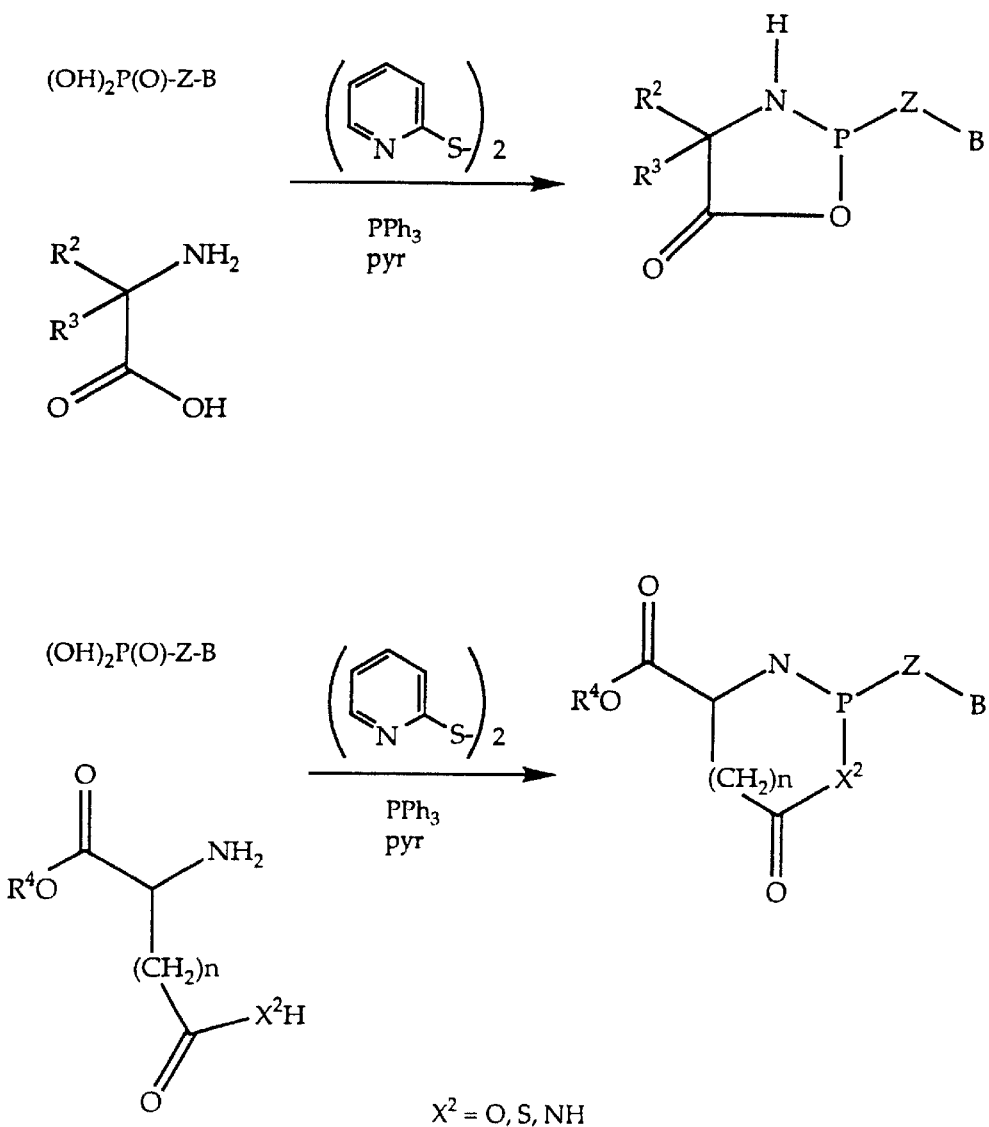
FIG. 2. Synthesis of formula Ia compounds.

Amino Acid Residues.

When groups $L^1$ or $L^2$ comprise an amino acid residue they comprise any naturally-occurring or synthetic amino acid residue, i.e., any moiety comprising at least one carboxyl and at least one amino residue directly linked by at least one carbon atom, typically a single (a) carbon atom. The nature and identity of the intervening structure located between the carboxyl and amino (amidate) groups can have a variety of structures including those described herein. All that is necessary is that the group have sufficient conformation and length to be capable of acid catalysis of the phosphoroamidate bond and release of the phosphonate when the free carboxyl is generated in vivo, e.g. by deesterification, deamidation or peptidolytic cleavage of the precursor. In general, the amino acids corresponding to the residues employed in the compounds of this invention are naturally occurring and have no pharmacological activity per se. However, optimal pharmacokinetic activity (substantially complete autocatalytic hydrolysis upon hydrolysis of the distal amide or ester bond) may be achieved by using non-naturally occurring amino acid residues. The intervening structure may be as simple as methylene (when the residue is glycyl) or substituted methylene (other α amino acids). The structure ordinarily contains up to about 5 carbon or hetero atoms in the direct linkage between the carboxyl carbon and the amidate nitrogen, as for example in the case of intervening ethylene, propylene, butylene, or pentylene groups or their substituted analogs, such as for example oxyesters in which O replaces carbon and, as appropriate, hydrogen. An example of such an intervening structure would be —CH—O—$CH(R^3)(R^2)$—. In general, fewer intervening atoms are employed when more rapid hydrolysis is desired, although it will be understood that larger structures are suitable if they possess sufficient flexibility or have conformations in which the carboxyl group is positioned in proximity to the amidate bond.

In general, the amino acid residue has the structure shown in formula III. Ordinarily, n is 1 or 2, $R^2$ is H and $R^3$ is a moiety containing one or more of the following groups: amino, carboxyl, amide, carboxyl ester, hydroxyl, $C_6$–$C_7$ aryl, ether, n-, s- or t-alkyl ($C_1$–$C_6$), guanidinyl, imidazolyl, indolyl, sulfhydryl, sulfoxide, and phosphoryl. The $R^2$ and $R^3$ substituents can have a wide variety of structures including those disclosed herein.

Ordinarily $R^2$ is H and $R^3$ is a side chain or group of a naturally occurring amino acid. With respect to the carboxyl-containing side chains it will be understood that if the C atom of the subject carboxyl is linked by 5 or less atoms to the phosphoamide N then the carboxyl optionally will be blocked, e.g. by esterification or amidation wherein the ester or amide bonds are hydrolyzable in vivo. $R^3$ also is taken together with $R^1$ to form a proline residue ($R^3$=—$CH_2$—$)_3$). Thus, $R^3$ is generally a side group such as H, —$CH_3$, —$CH(CH_3)_2$, —$CH_2$—$CH(CH_3)_2$, —$CHCH_3$—$CH_2$—$CH_3$, —$CH_2$—$C_6H_5$, —$CH_2$—$CH_2$—S—$CH_3$, —$CH_2OH$, —$CH(OH)$—$CH_3$, —$CH_2$—SH, —$CH_2$—$C_6H_4OH$, —$CH_2$—CO—$NH_2$, —$CH_2$—$CH_2$—CO—$NH_2$, —$CH_2$—COOH, —$CH_2$—$CH_2$—COOH, —$(CH_2)_4$—$NH_2$ and —$(CH_2)_3$—NH—$C(NH_2)$—$NH_2$. $R^3$ also includes 1-guanidinoprop-3-yl, benzyl, 4-hydroxybenzyl, imidazol-4-yl, indol-3-yl, methoxyphenyl and ethoxyphenyl. The optimal $R^3$ group is readily selected using routine assays.

When the amino acid residues contain one or more chiral centers, any of the D, L, meso, threo or erythro (as appropriate) racemates, scalemates or mixtures thereof, fall within the scope of this invention. In general, if it is desired to rely on non-enzymatic means of hydrolysis, D isomers should be used. On the other hand, L isomers may be more versatile since they can be susceptible to both non-enzymatic as well as potential targeted enzymatic hydrolysis, and are more efficiently transported by amino acid or dipeptidyl transport systems in the gastrointestinal tract.

Examples of suitable amino acid residues include the following:

Glycyl;

Aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid residues;

Amino acid amides such as glutaminyl and asparaginyl;

Polyamino- or polybasic-monocarboxylic acids such as arginine, lysine, β-aminoalanine, γ-aminobutyrine, ornithine, citruline, homoarginine, homocitrulline, 5-hydroxy-2,6-diaminohexanoic acid (commonly, hydroxylysine, including allohydroxylysine) and diarminobutyric acid residues;

Other basic amino acid residues such as histidinyl;

Diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid residues;

Imino acids such as proline, 4- or 3-hydroxy-2-pyrrolidinecarboxylic acid (commonly, hydroxyproline, including allohydroxyproline), γ-methylproline, pipecolic acid, 5-hydroxypipecolic acid, $—N([CH_2]_nCOOR^4)_2$, wherein n and $R^4$ are as defined above, and azetidine-2-carboxylic acid residues;

A mono- or di-alkyl (typically $C_1$–$C_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid; isoleucine, alloisoleucine, tert-leucine, β-methyltryptophan and α-amino-β-ethyl-β-phenylpropionic acid residues; β-phenylserinyl;

Aliphatic α-amino-β-hydroxy acids such as serine, β-hydroxyleucine, β-hydroxynorleucine, β-hydroxynorvaline, and α-amino-β-hydroxystearic acid residues;

α-Amino, α-, γ-, δ- or ε-hydroxy acids such as homoserine, γ-hydroxynorvaline, δ-hydroxynorvaline and epsilon-hydroxynorleucine residues; canavinyl and canalinyl; γ-hydroxyornithinyl;

2-hexosaminic acids such as D-glucosaminic acid or D-galactosaminic acid residues;

α-Amino-β-thiols such as penicillamine, β-thiolnorvaline or β-thiolbutyrine residues;

Other sulfur containing amino acid residues including cysteine; homocystine; β-phenylmethionine; methionine; S-allyl-L-cysteine sulfoxide; 2-thiolhistidine; cystathionine; and thiol ethers of cysteine or homocysteine;

Phenylalanine, tryptophan and ring-substituted α amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dicloro, o-, m- or p-methyl-, 2,4,6-trimethyl-, 2-ethoxy-5-nitro, 2-hydroxy-5-nitro and p-nitro-phenylalanine); furyl-, thienyl-, pyridyl-, pyrimidinyl-, purine or naphthylalanines; and tryptophan analogues and derivatives including kynurenine, 3-hydroxykynurenine, 2-hydroxytryptophan and 4-carboxytryptophan residues;

α-Amino substituted amino acid residues including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acid residues including serine, threonine, allothreonine, phosphoserine and phosphothreonine residues.

Any one of the foregoing or other known amino acids are suitably employed in this invention provided that they are capable of autocatalytically hydrolyzing the amidate bond. Thus, they must contain, or must, upon being converted (hydrolyzed) in vivo, contain a free carboxyl group. In general, the amino acids corresponding to the residues employed in the compounds of this invention are naturally occurring and have no pharmacological activity. However, optimal pharmacokinetic activity may be achieved by the use of non-naturally occurring amino acid residues.

Of particular interest are hydrophobic residues such as mono- or di-alkyl or aryl amino acids, cycloalkylamino acids and the like. These residues, together with $R^4$, contribute to cell permeability by increasing the partition coefficient of the nucleotide analog amidate. Typically, the residue does not contain a sulfhydryl or guanidino substituent.

Polypeptide Radicals.

If n1 is greater than 1, then the group shown in formula II, IIa, IIb or III is greater than 1, then the moiety comprises a polypeptide radical. This comprises dipeptides, short polypeptides of 3, 5 or 10 residues, or proteins having up to 100 or more residues. For the most part, dipeptides not containing aspartic or glutamic acid in the residue adjacent to the P atom, will not autocatalytically hydrolyze the amidate bond and therefore the carboxyl groups (generally 1 or 2) in the distal residue do not need to be esterified or amidated, i.e., $R^4$ can be H in these circumstances. However, if such compounds are intended to be used as precursors for the free phosphonate nucleotide analog in vivo, rather than as immunogens for example, the polypeptides ordinarily will contain a peptidolytic enzyme cleavage site at the peptide bond linking the first residue and the next residue distal to the phosphorus atom. Such cleavage sites are flanked by enzymatic recognition structures, e.g. particular residues recognized by a hydrolytic enzyme.

Peptidolytic enzymes are well known, and in particular include carboxypeptidases. Carboxypeptidases digest polypeptides by removing C-terminal residues, and are specific in many instances for particular C-terminal sequences. Such enzymes and their substrate requirements in general are well known. For example, a dipeptide having a given pair of residues and a free carboxyl terminus is covalently bonded through its α-amino group to the phosphorus atom of the invention nucleotide analogs. It is expected that this peptide will be cleaved by the appropriate dipeptidase or protease, leaving the carboxyl of the proximal amino acid residue to autocatalytically cleave the amidate bond.

Examples of suitable dipeptidyl groups (designated by their single letter code) include AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FL, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV.

Exemplary dipeptidyl compounds have the structure of formula IX wherein $R^2$ is H, $R^3$ is the side chain of a naturally occurring amino acid, $L^1$, $R^4$, B and Z are as defined above.

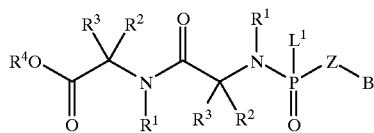

IX

Tripeptides are also useful. The sequence -X4-pro-X5- (where X4 is any amino acid residue and X5 is an amino acid residue, a carboxyl ester of proline or hydrogen) will be cleaved by luminal carboxypeptidase to yield X4 with a free carboxyl, which inb turn autocatalytically cleaves the phosphono amidate bond. X5 usually will be a benzyl ester of the carboxy group of X5. Thus, n1 is usually 1, 2 or 3, but may range up to 5, 10, 100 or more residues.

If the amino acid residue has 2 or more amine groups, e.g., a lysinyl or arginyl, or ornithinyl residue, then $R^3$ represents the group $-[C(R^6)_2]_{n2}N(R^2)-$ where n2 is 0 to 6, $R^6$ is H, $C_1-C_{20}$ alkyl, $C_6-C_{20}$ aryl, $C_7-C_{20}$ alkylaryl, $C_7-C_{20}$ arylalkyl, $C_1-C_{20}$ alkoxy, $C_6-C_{20}$ aryloxy or hydroxyl, and $R^2$ is defined above. Such compounds will contain a plurality of phosphonate moieties. For example when both the epsilon (ε)/delta (δ) and alpha (α) amino groups of lysine or ornithine are substituted with nucleotide phosphonate moieties the amidate is believed to be capable of releasing two molecules of active drug, each expected to emerge under different pharmacokinetics and therefore further sustaining the drug release.

The number of amino acid residues, n1, in the nucleotide analog amidates of this invention can vary extensively. Where n1=1, a single amino acid is found at the designated site, and where n1>1 then a polypeptide radical is present. Typically, n1 is 1 or 2, but may range up to 3, 5, 10 or 100 or more residues.

If the residue is immediately adjacent to the phosphonate atom and its side chain contains a carboxyl group, e.g. in the case of glutamic acid or aspartic acid, then this carboxylate is substituted with $R^4$.

The amidate group optionally is taken together with Z to form a cyclic amidate precursor. Such compounds have structure XIV.

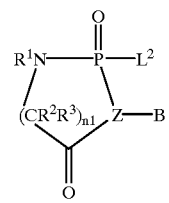

XIV wherein $L^2$, $R^1$, $R^2$, $R^3$, Z, n1 and B are as defined above. Typically, in this embodiment $R^3$ is not carboxyl, $R^2$ is H, and n1 is 1.

Hydrolysis of the cyclic amidates of formulas IIa–c and IV leaves a hydroxyl-substituted substructure Z and the free carboxyl, which in turn will autolyze the amidate. Substructures Z in which the methylene backbone is substituted with hydroxymethyl are advantageous in this embodiment, particularly linkers in compounds of the formula $-CH_2OCH(CH_2O-)CH_2-B$.

Heterocyclic Bases.

The compounds of this invention comprise any naturally-occurring heterocycle found in nucleic acids, nucleotides or nucleosides, or analogs thereof. The radicals of such heterocyclic bases, designated herein as B, are generally the purine, pyrimidine or related heterocycles shown in formulas X–XIII.

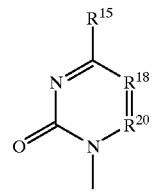

X

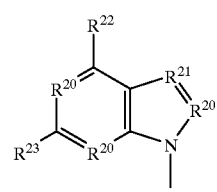

XI

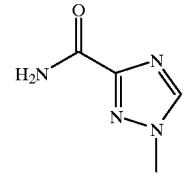

XII

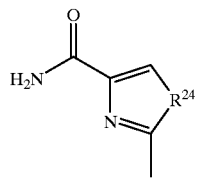

XIII wherein $R^{15}$ is H, OH, F, Cl, Br, I, $OR^{16}$, SH, $SR^{16}$, $NH_2$, or $NHR^{17}$;

$R^{16}$ is $C_1-C_6$ alkyl including $CH_3$, $CH_2CH_3$, $CH_2CCH$ (2-propynyl), $CH_2CHCH_2$ (2-allyl), $C_3H_7$;

$R^{17}$ is $C_1$–$C_6$ alkyl including $CH_3$, $CH_2CH_3$, $CH_2CCH$, $CH_2CHCH_2$, $C_3H_7$;

$R^{18}$ is N, CF, CCl, CBr, CI, $CR^{19}$ or $CSR^{19}$, $COR^{19}$;

$R^{19}$ is H, $C_1$–$C_9$ alkyl, $C_2$–$C_9$ alkenyl, $C_2$–$C_9$ alkynyl or $C_7$–$C_9$ aryl-alkyl unsubstituted or substituted by OH, O, N, F, Cl, Br or I including $CH_3$, $CH_2CH_3$, $CHCH_2$, $CHCHBr$, $CH_2CH_2Cl$, $CH_2CH_2F$, $CH_2CCH$, $CH_2CHCH_2$, $C_3H_7$, $CH_2OH$, $CH_2OCH_3$, $CH_2OC_2H_5$, $CH_2OCCH$, $CH_2OCH_2CHCH_2$, $CH_2C_3H_7$, $CH_2CH_2OH$, $CH_2CH_2OCH_3$, $CH_2CH_2OC_2H_5$, $CH_2CH_2OCCH$, $CH_2CH_2OCH_2CHCH_2$, $CH_2CH_2OC_3H_7$;

$R^{20}$ is N or CH;

$R^{21}$ is N, CH, CCN, $CCF_3$, CC≡CH or $CC(O)NH_2$;

$R^{22}$ is H, OH, $NH_2$, SH, $SCH_3$, $SCH_2CH_3$, $SCH_2CCH$, $SCH_2CHCH_2$, $SC_3H_7$, $NH(CH_3)$, $N(CH_3)_2$, $NH(CH_2CCH)$, $N(CH_2CH_3)_2$, $NH(CH_2CCH)$, $NH(CH_2CHCH_2)$, $NH(C_3H_7)$ or halogen (F, Cl, Br or I);

$R^{23}$ is H, OH, F, Cl, Br, I, $SCH_3$, $SCH_2CH_3$, $SCH_2CCH$, $SCH_2CHCH_2$, $SC_3H_7$, $OR^{16}$, $NH_2$, or $NHR^{17}$; and $R^{24}$ is O, S or Se.

B includes both protected and unprotected forms of the heterocyclic bases. Protecting groups for exocyclic amines and other groups are known (Greene and include N-benzoyl, isobutyryl, 4,4'-dimethoxytrityl (DMT) and the like. The selection of a protecting group will be apparent to the ordinary artisan and will depend on the nature of the labile group and the chemistry which the protecting group is expected to encounter, e.g., acidic, basic, oxidative, reductive or other conditions.

As used herein, $B^1$ is a protected heterocyclic base having the formula Xa, XIa, XIb, XIIa or XIIIa

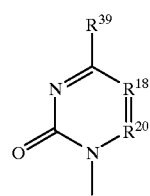

Xa

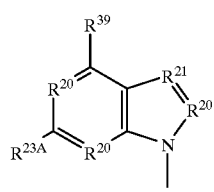

XIa

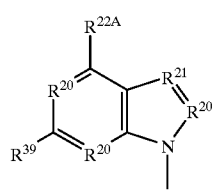

XIb

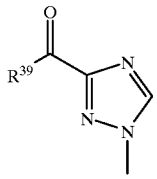

XIIa

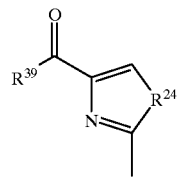

XIIIa wherein $R^{18}$, $R^{20}$, $R^{21}$, $R^{24}$ have the meanings previously defined; $R^{22A}$ is $R^{39}$ or $R^{22}$ provided that $R^{22}$ is not $NH_2$; $R^{23A}$ is $R^{39}$ or $R^{23}$ provided that $R^{23}$ is not $NH_2$; $R^{39}$ is $NHR^{40}$, $NHC(O)R^{36}$ or $NCR^{41}N(R^{38})_2$ wherein $R^{36}$ is $C_1$–$C_{19}$ alkyl, $C_1$–$C_{19}$ alkenyl, $C_3$–$C_{10}$ aryl, adamantoyl, alkylanyl, or $C_3$–$C_{10}$ aryl unsubstituted or substituted with 1 or 2 atoms or groups selected from halogen, methyl, ethyl, methoxy, ethoxy, hydroxy and cyano; $R^{38}$ is $C_1$–$C_{10}$ alkyl, or both $R^{38}$ together are 1-morpholino, 1-piperidine or 1-pyrrolidine; and $R^{41}$ is hydrogen or $CH_3$. For heterocyclic bases of structures XIa and XIb, if $R^{39}$ is present at $R^{22A}$ or $R^{23A}$, both $R^{39}$ groups on the same heterocyclic base will generally be the same. Exemplary $R^{40}$ include methyl, ethyl, propyl, isopropyl, butyl, isobutyl, t-butyl, pentyl, hexyl, octyl, decanyl, lauryl and hexadecyl).

Specific heterocyclic bases include hypoxanthine, inosine, thymine, uracil, xanthine, 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 1-deaza derivatives of 2-aminopurine, 2,6-diaminopurine, 2-amino-6-chloropurine, hypoxanthine, inosine and xanthine; 7-deaza derivatives of 2-aminopurine, 2,6-diaminopurine, 2-amino-6-chloropurine, hypoxanthine, inosine and xanthine; 3-deaza derivatives of 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil and the like.

Preferably, B is a 9-purinyl residue selected from guanyl, 3-deazaguanyl, 1-deazaguanyl, 8-azaguanyl, 7-deazaguanyl, adenyl, 3-deazaadenyl, 1-dezazadenyl, 8-azaadenyl, 7-deazaadenyl, 2,6-diaminopurinyl, 2-aminopurinyl, 6-chloro-2-aminopurinyl and 6-thio-2-aminopurinyl, or a B is a 1-pyrimidinyl residue selected from cytosinyl, 5-halocytosinyl, and 5-($C_1$–$C_3$-alkyl)cytosinyl.

The invention compounds, such as those of the formulas $(L^1)(RO)P(O)$-Z-B, are optionally esterified at the phosphorus atom by the group R defined above. Exemplary R groups include phenyl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 2-, 3- and 4-pyridinyl, 2-, 4- and 5-pyrimidinyl, 2-, 3- and 4-alkoxyphenyl ($C_1$–$C_{12}$ alkyl including 2-, 3- and 4-methoxyphenyl and 2-, 3- and 4-ethoxyphenyl), 2-, 3- and 4-halophenyl (including 2-, 3- and 4-fluorophenyl), 2,3-, 2,4-, 2,5-, 2,6-, 3,4- and 3,5-dihalophenyl (including 2,4-difluorophenyl and 2,4-dichlorophenyl), 2-, 3- and 4-haloalkylphenyl (1 to 5 halogen atoms, $C_1$–$C_{12}$ alkyl including 2-, 3- and 4-trifluoromethylphenyl and 2-, 3- and 4-trichloromethylphenyl), 2-, 3- and 4-cyanophenyl, carboalkoxyphenyl ($C_1$–$C_4$ alkyl including 2-, 3- and 4-carboethoxyphenyl (—$C_6H_4$—C(O)—$C_2H_5$) and 2,3-, 2,4-, 2,5-, 2,6-, 3,4- and 3,5-dicarboethoxyphenyl), 1-, 2-, 3-, and 4-pyridinyl (—$C_5H_4N$), 2-, 3- and 4-nitrophenyl, 2-, 3- and 4-haloalkylbenzyl (1 to 5 halogen atoms, $C_1$–$C_{12}$ alkyl including 4-trifluoromethylbenzyl), alkylsalicylphenyl ($C_1$–$C_4$ alkyl including 2-, 3- and 4-ethylsalicylphenyl), 2-,3- and 4-acetylphenyl, 1,8-dihydroxynaphthyl (—O—$C_{10}H_6$—OH or —O—$C_{10}H_6$—O—), 2,2'-dihydroxybiphenyl (—O—$C_6H_4$—$C_6H_4$—O—; both oxygen atoms are linked to the phosphorus atom), alkoxy ethyl [$C_1$–$C_6$ alkyl including —$CH_2$—$CH_2$—O—$CH_3$ (methoxy ethyl) and phenoxymethyl], aryloxy ethyl [$C_6$–$C_9$ aryl (including phenoxy ethyl) or $C_6$–$C_9$ aryl substituted by OH, $NH_2$, halo, $C_1$–$C_4$ alkyl or $C_1$–$C_4$ alkyl substituted by OH or by 1 to 3 halo atoms], —$C_6H_4$—$CH_2$—$N(CH_3)_2$, N-ethylmorpholino

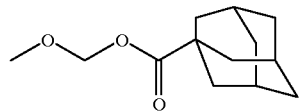

—$(CH_2)_2$—$N[(CH_2)_2(CH_2)_2]O)$, adamantoyl oxymethyl, pivaloyloxy(methoxyethyl)methyl (—CH($CH_2CH_2OCH_3$)—O—C(O)—C($CH_3)_3$),

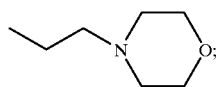

—O—$CH_2$—O—C(O)—$C_{10}H_{15}$), pivaloyloxymethyl (—$CH_2$—O—C(O)—C($CH_3)_3$), pivaloyloxy (methoxymethyl)-methyl (—CH($CH_2OCH_3$)—O—C(O)—C($CH_3)_3$), pivaloyloxyisobutyl (—CH(CH($CH_3)_2$)—O—C(O)—C($CH_3)_3$) isobutyryloxymethyl (—$CH_2$O—C(O)—$CH_2$—CH($CH_3)_2$), cyclohexanoyl oxymethyl (—$CH_2$O—C(O)—$C_6H_{11}$), phenyl (—$C_6H_5$), benzyl (—$CH_2$—$C_6H_5$), isopropyl (—CH($CH_3)_2$), t-butyl (—C($CH_3)_3$), —$CH_2$—$CH_3$, —$(CH_2)_2$—$CH_3$, —$(CH_2)_3$—$CH_3$, —$(CH_2)_4$—$CH_3$, —$(CH_2)_5$—$CH_3$, —$CH_2$—$CH_2F$, —$CH_2$—$CH_2Cl$, —$CH_2$—$CF_3$, —$CH_2$—$CCl_3$, $R^5$, $NHR^{6A}$ or $N(R^{6A})_2$ wherein $R^5$ is $CH_2C(O)N(R^{6A})_2$, $CH_2C(O)OR^{6A}$, $CH_2OC(O)R^{6A}$, $CH(R^{6A})OC(O)R^{6A}$, $CH_2C(R^{6A})_2CH_2OH$, $CH_2OR^{6A}$, NH—$CH_2$—C(O)O—$CH_2CH_3$, $N(CH_3)$—$CH_2$—C(O)O—$CH_2CH_3$, $NHR^{40}$, $CH_2$—O—C(O)—$C_6H_5$, $CH_2$—O—C(O)—$C_{10}H_{15}$, —$CH_2$—O—C(O)—$CH_2CH_3$, $CH_2$—O—C(O)—CH($CH_3)_2$, $CH_2$—O—C(O)—C($CH_3)_3$, $CH_2$—O—C(O)—$CH_2$—$C_6H_5$, wherein $R^{6A}$ is $C_1$–$C_{20}$ alkyl which is unsubstituted or substituted by substituents independently selected from the group consisting of OH, O, N and halogen (1 to 5 halogen atoms), $C_6$–$C_{20}$ aryl which is unsubstituted or substituted by substituents independently selected from the group consisting of OH, O, N and halogen (1 to 5 halogen atoms) or $C_7$–$C_{20}$ aryl-alkyl which is unsubstituted or substituted by substituents independently selected from the group consisting of OH, O, N and halogen (1 to 5 halogen atoms), provided that for compounds of formulas $N(R^{6A})_2$, $CH_2C(O)N(R^{6A})_2$, $CH_2C(O)OR^{6A}$, $CH_2OC(O)R^{6A}$, $CH(R^{6A})OC(O)R^{6A}$ and $CH_2C(R^{6A})_2$ $CH_2OH$, the total number of carbon atoms present is less than 25 (preferably the number of carbon atoms present is about 4 to about 14) and $R^{40}$ is $C_1$–$C_{20}$ alkyl.

The invention compounds are optionally alkylated at the α-nitrogen atom of the amino acid by the $R^1$ group defined above. Exemplary $R^1$ groups include H, $CH_3$, $CH_2CH_3$, benzyl, 4-O—N-methylpiperidinyl

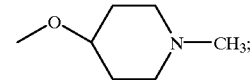

—O—CH[($CH_2)_2(CH_2)_2$]N($CH_3$)), 3-O—N-methylpiperidinyl and the like.

The invention compounds are optionally esterified at the amino acid carboxyl moiety by the $R^4$ group defined above. Exemplary $R^4$ groups include H, methyl, ethyl, propyl, isopropyl, butyl, t-butyl (C($CH_3)_3$), phenyl (—$C_6H_5$), benzyl (—$CH_2$—$C_6H_5$), 1-pyridyl, 3-pyridyl, 1-pyrimidinyl, N-ethylmorpholino (—$CH_2$—$CH_2$—N[($CH_2)_2(CH_2)_2$]O), N-2-propylmorpholino (—CH($CH_3$)—$CH_2$—N[($CH_2)_2(CH_2)_2$]O), methoxyethyl (—$CH_2$—$CH_2$—O—$CH_3$), 4-N-methylpiperidyl (—CH[($CH_2)_2(CH_2)_2$]N($CH_3$)), 3-N-methylpiperidyl, phenol which is 2-, 3-, or 4-substituted by $N(R^{30})_2$ where $R^{30}$ is independently H or $C_1$–$C_6$ alkyl unsubstituted or substituted by substituents independently selected from the group consisting of OH, O, N, $COOR^4$ and halogen or $C_6$–$C_{12}$ aryl unsubstituted or substituted by substituents independently selected from the group consisting of OH, O, N, $COOR^4$, $N(R^7)_2$ and halogen (including 2-, 3-, and 4-N,N-dimethylaminophenol and 2-, 3-, and 4-N,N-diethylaminophenol), 1-ethylpiperazinyl

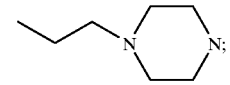

[—$CH_2$—$CH_2$—$NC_4H_8NH$], and $N^4$-substituted 1-ethylpiperazinyl (—$(CH_2)_2$—N[($CH_2)_2(CH_2)_2$]$NR^2$, where $R^2$ is as defined above).

Additional compounds that are included in the invention are nucleotide analog dimers that are linked via an amino or carboxyl group. As used herein, dimers (or trimers) refer to the presence of two (or three) nucleoside residues that comprise a compound. Thus, a -$L^1$-P(O)($L^1$)-Z-B or -P(O)($L^1$)-Z-B radical covalently linked to a -$L^1$-P(O)($L^1$)-Z-B or -P(O)($L^1$)-Z-B radical gives B-Z-P(O)($L^1$)-P(O)($L^1$)-Z-B, B-Z-P(O)($L^1$)-$L^1$-P(O)($L^1$)-Z-B or B-Z-P(O)($L^1$)-$L^1$-$L^1$-P(O)($L^1$)-Z-B.

Dimer nucleotide analogs are conveniently linked via amino acids, diamino acids, dicarboxylic amino acids, diamines or dicarboxylic acids such as β-aminoalanine, diaminobutyric acid, citrulline, homoarginine, homocitrulline, ornithine, γ-aminobutyric acid, arginine, histidine, asparagine, glutamine, β-hydroxyaspartic acid, β-hydroxyglutamic acid, β-methylaspartic acid, β-methylglutamic acid, 3-aminoadipic acid, 2-aminopimelic acid, 2-aminosuberic acid, β-amino acid analogs of lysine ($NH_2$—$(CH_2)_3$—CH($NH_2$)—$CH_2$—CH—C(O)OH), arginine, histidine, asparagine, glutamine and the like. Exemplary compounds include dimers linked via lysine or β-lysine having the formulas B-Z-P(O)(L)—NH—$(CH_2)_4$—CH(C(O)$OR^4$)—$NR^1$-P(O)(L)-Z-B and B-Z-P(O)(L)—

NH—$(CH_2)_3$—CH($CH_2$C(O)$OR^4$)—$NR^1$-P(O)(L)-Z-B and dimers linked via aspartic or glutamic acid having the formula B-Z-P(O)(L)-O—C(O)—$(CH_2)_{1-2}$—CH(C(O)$OR^4$)—$NR^1$-P(O)(L)-Z-B. L, Z and B are independently selected.

Nucleotide analogs comprising dipeptidyl or tripeptidyl L groups are also included in the compounds of the invention. Nucleotide radicals are linked through side chain groups (usually amino or carboxyl) or through amino and carboxyl groups of the amino acids. Exemplary dipeptidyl and tripeptidyl dimers and trimers include compounds of the formulas B-Z-P(O)($L^1$)-O—C(O)—$(CR^2R^3)_n$—$NR^1$—C(O)—$(CR^2R^3)_n$—$NR^1$-P(O)($L^1$)-Z-B, B-Z-P(O)($L^1$)-O—C(O)—$(CR^2R^3)_n$—$NR^1$C(O)—$(CR^2R^3)_n$—$NR^1$—O—C(O)—$(CR^2R^3)_n$—$NR^1$-P(O)($L^1$)-Z-B, B-Z-P(O)($L^1$)-O—C(O)—$CR^2(R^3$-P(O)($L^1$)-Z-B)-$NR^1$—(O)—$(CR^2R^3)_n$—$NR^1$-P(O)($L^1$)-Z-B and B-Z-P(O)($L^1$)-O—C(O)—$(CR^2R^3)_n$—$NR^1$—(O)—$CR^2(R^3$-P(O) ($L^1$)-Z-B)—$NR^1$-P(O)($L^1$)-Z-B. In order to provide a compound with a desired molar ratio of one Z-B compared to a second Z-B, tetramer, pentamer and higher polymer forms can also be prepared where Z and/or B are independently chosen.

As used herein, and unless modified by the immediate context: 1) the term alkyl, alkenyl and alkynyl refer to straight chain, branched and cyclic residues. Thus, $C_1$–$C_4$ alkyl includes methyl, ethyl, propyl, cyclopropyl, isopropyl, n-, sec-, iso- and tert-butyl, cyclobutyl and the like while alkenyl includes ethenyl, propenyl, isopropenyl, 1-, 2- and 3-butenyl, 1- and 2-isobutenyl and the like. The term alkyl also includes cyclic N-, S- or O-heterocarbonyl (such as piperidyl and morpholino). 2) The term aryl includes N-, S- or O-heteroaryl, including phenyl, 2- and 3-pyrrolyl, 2- and 3-thienyl, 2- and and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 2-, 3- and 4-pyridinyl, 2-, 4- and 5-pyrimidinyl. When "O" or "N" are substituted into aryl or alkyl this means that a ring or chain methyne or methylene is replaced by O, N or NH as the case may be. The term acyl means $R^x$—C(O)—, acyloxy means $R^x$—C(O)—O—, acyloxymethyl means $R^x$—C(O)—O—$CH_2$— and thus, for example, $C_{3-6}$ acyloxymethyl means $R^x$—C(O)—O—$CH_2$— wherein $R^x$ is a 1 to 4 carbon alkyl or aryl group (substituted or unsubstituted).

Nucleoside Phosphonates.

Table 1 lists a group of exemplary nucleotide analogs of formula I having the structure ($L^1$)($L^2$)P(O)-Z-B. These compounds generally have $L^1$ and $L^2$ groups that, when amino acids, are identical, although one of the amino acid groups can be different or replaced by another hydrolyzable group such as —O—$CH_2$—O—C(O)—C$(CH_3)_3$ or —O—$C_6H_5$ as listed below.

TABLE 1

| $L^1$, $L^2$* | —Z—B** |
|---|---|
| 1 —NH—$CH_2$—C(O)—$OR^4$ | 1 —$CH_2$—O—$CH_2$—$CH_2$—B |
| 2 —NH—CH($CH_3$)—C(O)—$OR^4$ | 2 —$CH_2$—O—$C^\#$H($CH_2$—$OR^4$)—$CH_2$—B |
| 3 —NH—CH($CH_3$)$_2$—C(O)—$OR^4$ | 3 —$CH_2$—O—$C^\#$H($CH_3$)—$CH_2$—B |
| 4 —NH—CH(CH($CH_3$)$_2$)—C(O)—$OR^4$ | 4 —$CH_2$—O—$C^\#$H($CH_2$F)—$CH_2$—B |
| 5 —NH—CH($CH_3$)($CH_3$)$_2$—C(O)—$OR^4$ | 5 —$CH_2$O—$C^\#$H(CH=$CH_2$)—$CH_2$—B |
| 6 —NH—$CH_2$—$CH_2$—$CH_2$—CH—C(O)$OR^4$ | 6 —$CH_2$—$C^\#$H($CH_2N_3$)—$CH_2$—B |
| 7 —NH—CH($CH_2$—$C_6H_5$)—C(O)—$OR^4$ | 7 *** |
| 8 —NH—CH($CH_2C_8NH_6$)—C(O)—$OR^4$ | 8 **** |
| 9 —NHCH($CH_2$—$CH_2$—S—$CH_3$)—C(O)—$OR^4$ | |
| 10 —NH—CH($CH_2$OH)—C(O)—$OR^4$ | |
| 11 —NH—CH(CH(OH)($CH_3$))—C(O)—$OR^4$ | |
| 12 —NH—CH(—$CH_2$SH)—C(O)—$OR^4$ | |
| 13 —NH—CH($CH_2$—$C_6H_5$OH)—C(O)—$OR^4$ | |
| 14 —NH—CH($CH_2$—C(O)—$NH_2$)—C(O)—$OR^4$ | |
| 15 —NH—CH($CH_2$—$CH_2$—C(O)—$NH_2$)—C(O)—$OR^4$ | |
| 16 —NH—CH($CH_2$C(O)—$OR^4$)—C(O)—$OR^4$ | |
| 17 —NH—CH($CH_2$$CH_2$C(O)—$OR^4$)—C(O)—$OR^4$ | |
| 18 —NH—CH($CH_2$$CH_2$$CH_2$$CH_2NH_2$)—C(O)—$OR^4$ | |
| 19 —NH—CH($CH_2$$CH_2$$CH_2$NHC(NH)($NH_2$))—C(O)—$OR^4$ | |
| 20 —NH—CH($CH_2$$C_3N_2H_3$)—C(O)—$OR^4$ | |
| 21 —NH—CH($CH_3$)$_2$—$CH_2$—C(O)—$OR^4$ | |
| 22 —NH—$CH_2$—$CH_2$—C(O)—$OR^4$ | |
| 23 —NH—CH($CH_2$—$C_6H_5$)—$CH_2$—C(O)—$OR^4$ | |
| 24 —NH—CH($CH_2$$CH_2$$CH_2$$NH_2$)—$CH_2$—C(O)—$OR^4$ | |
| 25 —NH—CH($CH_2$$CH_2$$CH_2$$CH_2NH_2$)—$CH_2$—C(O)—$OR^4$ | |
| 26 —NH—CH($CH_2$$CH_2$NHC(NH)($NH_2$))—$CH_2$—C(O)—$OR^4$ | |
| 27 —NH—CH(C(O)$OR^4$)—$CH_2$—C(O)—$OR^4$ | |
| 28 —NH—CH($CH_2$C(O)$OR^4$)—$CH_2$—C(O)—$OR^4$ | |
| 29 —NH—CH($CH_2$$CH_2$C(O)$OR^4$)—$CH_2$—C(O)—$OR^4$ | |
| 30 —N($CH_3$)—$CH_2$—C(O)—$OR^4$ | |
| 31 —$NHR^6$ | |
| 32 —O—$CH_2$—$CH_2$—N[$CH_2$)$_2$($CH_2$)$_2$]O | |
| 33 —O—$CH_2$—O—C(O)—$(CH_3)_3$ | |
| 34 —O—$CH_2$—O—C(O)—CH($CH_3$)$_2$ | |
| 35 —O—$CH_2$—O—C(O)—$CH_2C_6H_4$—O—$CH_2CH_3$ | |
| 36 —O—$CH_2$—O—C(O)—$C_{10}H_{15}$ | |
| 37 —O—$CH_2$—$C_6H_5$ | |
| 38 —O—$C_6H_5$ | |
| 39 —O—$CH_2$—$C_6H_4$N($CH_3$)$_2$ | |
| 40 —OH | |

B 1 adenin-9-yl

TABLE 1-continued 2 guanin-9-yl
3 cytosin-1-yl
4 2,6-diaminopurin-9-yl
5 2-aminopurin-9-yl
6 6-azacytosin-1-yl
7 1-deazaadenin-9-yl
8 3-deazaadenin-9-yl
9 8-azaadenin-9-yl
10 7-deaza-8-azaadenin-9-yl

*- $R^4$ includes H, propyl, isopropyl, t-butyl, phenyl, benzyl, 1-pyridinyl, 1-pyrimidinyl, N-ethylmorpholino, methoxyethyl, 4-hydroxy-N-methylpiperidinyl, 3-hydroxy-N-methylpiperidinyl, 1-ethylpiperazinyl; atoms with unfilled valences are linked to each other.
**- The carbon atom on the left of each structure is attached to the phosphorus atom; #- carbon atom having linked substituents in the R, S or RS configuration.
***- Z-B substructure 7 is of formula V where $R^{25}$ and $R^{29}$ are O and B is thymin-1-yl (base 11) or one of the heterocyclic bases listed (1–10).
****- Z-B substructure 8 is of formula IV where $R^{25}$ and $R^{29}$ are O, $R^{26}$ is S, $R^{27}$ is absent, $R^{28}$ is H and B is thymin-1-yl (base 11) or one of the heterocyclic bases listed (1–10) and includes the (+) and (−) enantiomers.

Compounds listed in Table 1 are designated herein by numbers assigned to $L^1$, $L^2$, Z and B according to the following convention, $L^1.L^2.Z.B$. Thus, compound 1.2.1.1, where $R^4$ is benzyl, represents $L^1$ structure 1 (—NH—$CH_2$—C(O)—O—$CH_2$—$C_6H_5$), $L^2$ structure 2 (—NH—CH($CH_3$)—C(O)—O—$CH_2$—$C_6H_5$), Z structure 1 (—$CH_2$—O—$CH_2$—$CH_2$—) and B structure 1 (adenin-9-yl). This compound would have the structure

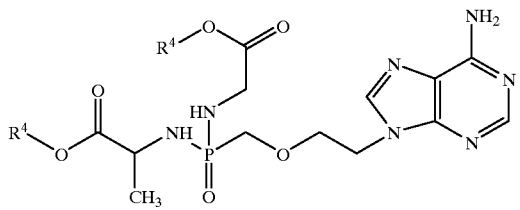

which corresponds to the compound designated herein bis (alanyl benzyl ester)PMEA. Similarly, for the compound 7.7.1.1, $L^1$ structure 7 (NH—CH($CH_2$—$C_6H_5$)—C(O)—$OR^4$), $L^2$ structure 7 (NH—CH($CH_2$—$C_6H_5$)—C(O)—$OR^4$), Z structure 2 (—$CH_2$—O—$CH_2$—$CH_2$—) and B structure 1 (adenin-9-yl) would have, when $R^4$ is methyl, the structure

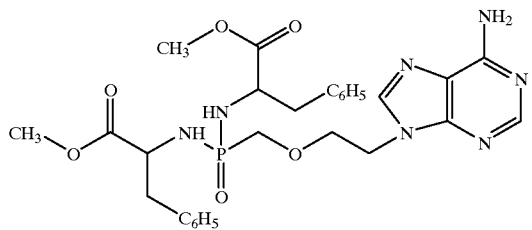

and would represent the compound designated herein bis (phenylalanyl methyl ester)PMEA. Exemplary compounds include 1.1.1.1, 2.1.1.1, 3.1.1.1, 4.1.1.1, 5.1.1.1, 6.1.1.1, 7.1.1.1, 8.1.1.1, 9.1.1.1, 10.1.1.1, 11.1.1.1, 12.1.1.1, 13.1.1.1, 14.1.1.1, 15.1.1.1, 16.1.1.1, 17.1.1.1, 18.1.1.1, 19.1.1.1, 20.1.1.1, 21.1.1.1, 22.1.1.1, 23.1.1.1, 24.1.1.1, 25.1.1.1, 26.1.1.1, 27.1.1.1, 28.1.1.1, 29.1.1.1, 30.1.1.1, 31.1.1.1, 32.1.1.1, 33.1.1.1, 34.1.1.1, 35.1.1.1, 36.1.1.1, 37.1.1.1, 38.1.1.1, 39.1.1.1, 40.1.1.1, 1.2.1.1, 2.2.1.1, 3.2.1.1, 4.2.1.1, 5.2.1.1, 6.2.1.1, 7.2.1.1, 8.2.1.1, 9.2.1.1, 10.2.1.1, 11.2.1.1, 12.2.1.1, 13.2.1.1, 14.2.1.1, 15.2.1.1, 16.2.1.1, 17.2.1.1, 18.2.1.1, 19.2.1.1, 20.2.1.1, 21.2.1.1, 22.2.1.1, 23.2.1.1, 24.2.1.1, 25.2.1.1, 26.2.1.1, 27.2.1.1, 28.2.1.1, 29.2.1.1, 30.2.1.1, 31.2.1.1, 32.2.1.1, 33.2.1.1, 34.2.1.1, 35.2.1.1, 36.2.1.1, 37.2.1.1, 38.2.1.1, 39.2.1.1, 40.2.1.1, 1.3.1.1, 2.3.1.1, 3.3.1.1, 4.3.1.1, 5.3.1.1, 6.3.1.1, 7.3.1.1, 8.3.1.1, 9.3.1.1, 10.3.1.1, 11.3.1.1, 12.3.1.1, 13.3.1.1, 14.3.1.1, 15.3.1.1, 16.3.1.1, 17.3.1.1, 18.3.1.1, 19.3.1.1, 20.3.1.1, 21.3.1.1, 22.3.1.1, 23.3.1.1, 24.3.1.1, 25.3.1.1, 26.3.1.1, 27.3.1.1, 28.3.1.1, 29.3.1.1, 30.3.1.1, 31.3.1.1, 32.3.1.1, 33.3.1.1, 34.3.1.1, 35.3.1.1, 36.3.1.1, 37.3.1.1, 38.3.1.1, 39.3.1.1, 40.3.1.1, 1.4.1.1, 2.4.1.1, 3.4.1.1, 4.4.1.1, 5.4.1.1, 6.4.1.1, 7.4.1.1, 8.4.1.1, 9.4.1.1, 10.4.1.1, 11.4.1.1, 12.4.1.1, 13.4.1.1, 14.4.1.1, 15.4.1.1, 16.4.1.1, 17.4.1.1, 18.4.1.1, 19.4.1.1, 20.4.1.1, 21.4.1.1, 22.4.1.1, 23.4.1.1, 24.4.1.1, 25.4.1.1, 26.4.1.1, 27.4.1.1, 28.4.1.1, 29.4.1.1, 30.4.1.1, 31.4.1.1, 32.4.1.1, 33.4.1.1, 34.4.1.1, 35.4.1.1, 36.4.1.1, 37.4.1.1, 38.4.1.1, 39.4.1.1, 40.4.1.1, 1.5.1.1, 2.5.1.1, 3.5.1.1, 4.5.1.1, 5.5.1.1, 6.5.1.1, 7.5.1.1, 8.5.1.1, 9.5.1.1, 10.5.1.1, 11.5.1.1, 12.5.1.1, 13.5.1.1, 14.5.1.1, 15.5.1.1, 16.5.1.1, 17.5.1.1, 18.5.1.1, 19.5.1.1, 20.5.1.1, 21.5.1.1, 22.5.1.1, 23.5.1.1, 24.5.1.1, 25.5.1.1, 26.5.1.1, 27.5.1.1, 28.5.1.1, 29.5.1.1, 30.5.1.1, 31.5.1.1, 32.5.1.1, 33.5.1.1, 34.5.1.1, 35.5.1.1, 36.5.1.1, 37.5.1.1, 38.5.1.1, 39.5.1.1, 40.5.1.1, 1.6.1.1, 2.6.1.1, 3.6.1.1, 4.6.1.1, 5.6.1.1, 6.6.1.1, 7.6.1.1, 8.6.1.1, 9.6.1.1, 10.6.1.1, 11.6.1.1, 12.6.1.1, 13.6.1.1, 14.6.1.1, 15.6.1.1, 16.6.1.1, 17.6.1.1, 18.6.1.1, 19.6.1.1, 20.6.1.1, 21.6.1.1, 22.6.1.1, 23.6.1.1, 24.6.1.1, 25.6.1.1, 26.6.1.1, 27.6.1.1, 28.6.1.1, 29.6.1.1, 30.6.1.1, 31.6.1.1, 32.6.1.1, 33.6.1.1, 34.6.1.1, 35.6.1.1, 36.6.1.1, 37.6.1.1, 38.6.1.1, 39.6.1.1, 40.6.1.1, 1.7.1.1, 2.7.1.1, 3.7.1.1, 4.7.1.1, 5.7.1.1, 6.7.1.1, 7.7.1.1, 8.7.1.1, 9.7.1.1, 10.7.1.1, 11.7.1.1, 12.7.1.1, 13.7.1.1, 14.7.1.1, 15.7.1.1, 16.7.1.1, 17.7.1.1, 18.7.1.1, 19.7.1.1, 20.7.1.1, 21.7.1.1, 22.7.1.1, 23.7.1.1, 24.7.1.1, 25.7.1.1, 26.7.1.1, 27.7.1.1, 28.7.1.1, 29.7.1.1, 30.7.1.1, 31.7.1.1, 32.7.1.1, 33.7.1.1, 34.7.1.1, 35.7.1.1, 36.7.1.1, 37.7.1.1, 38.7.1.1, 39.7.1.1, 40.7.1.1, 1.8.1.1, 2.8.1.1, 3.8.1.1, 4.8.1.1, 5.8.1.1, 6.8.1.1, 7.8.1.1, 8.8.1.1, 9.8.1.1, 10.8.1.1, 11.8.1.1, 12.8.1.1, 13.8.1.1, 14.8.1.1, 15.8.1.1, 16.8.1.1, 17.8.1.1, 18.8.1.1, 19.8.1.1, 20.8.1.1, 21.8.1.1, 22.8.1.1, 23.8.1.1, 24.8.1.1, 25.8.1.1, 26.8.1.1, 27.8.1.1, 28.8.1.1, 29.8.1.1, 30.8.1.1, 31.8.1.1, 32.8.1.1, 33.8.1.1, 34.8.1.1, 35.8.1.1, 36.8.1.1, 37.8.1.1, 38.8.1.1, 39.8.1.1, 40.8.1.1, 1.9.1.1, 2.9.1.1, 3.9.1.1, 4.9.1.1, 5.9.1.1, 6.9.1.1, 7.9.1.1, 8.9.1.1, 9.9.1.1, 10.9.1.1 11.9.1.1, 12.9.1.1, 13.9.1.1, 14.9.1.1, 15.9.1.1, 16.9.1.1, 17.9.1.1, 18.9.1.1, 19.9.1.1, 20.9.1.1, 21.9.1.1, 22.9.1.1, 23.9.1.1, 24.9.1.1, 25.9.1.1, 26.9.1.1, 27.9.1.1, 28.9.1.1, 29.9.1.1, 30.9.1.1, 31.9.1.1, 32.9.1.1, 33.9.1.1, 34.9.1.1, 35.9.1.1, 36.9.1.1, 37.9.1.1, 38.9.1.1, 39.9.1.1, 40.9.1.1, 1.10.1.1, 2.10.1.1, 3.10.1.1, 4.10.1.1, 5.10.1.1, 6.10.1.1, 7.10.1.1, 8.10.1.1, 9.10.1.1, 10.10.1.1, 11.10.1.1, 12.10.1.1, 13.10.1.1, 14.10.1.1, 15.10.1.1, 16.10.1.1, 17.10.1.1, 18.10.1.1, 19.10.1.1, 20.10.1.1, 21.10.1.1, 22.10.1.1, 23.10.1.1, 24.10.1.1, 25.10.1.1, 26.10.1.1, 27.10.1.1, 28.10.1.1, 29.10.1.1, 30.10.1.1, 31.10.1.1, 32.10.1.1, 33.10.1.1, 34.10.1.1, 35.10.1.1, 36.10.1.1, 37.10.1.1, 38.10.1.1, 39.10.1.1, 40.10.1.1, 1.11.1.1, 2.11.1.1, 3.11.1.1, 4.11.1.1, 5.11.1.1, 6.11.1.1, 7.11.1.1, 8.11.1.1, 9.11.1.1, 10.11.1.1, 11.11.1.1, 12.11.1.1, 13.11.1.1, 14.11.1.1, 15.11.1.1, 16.11.1.1, 17.11.1.1, 18.11.1.1, 19.11.1.1, 20.11.1.1, 21.11.1.1, 22.11.1.1, 23.11.1.1, 24.11.1.1, 25.11.1.1, 26.11.1.1, 27.11.1.1, 28.11.1.1, 29.11.1.1, 30.11.1.1, 31.11.1.1, 32.11.1.1, 33.11.1.1, 34.11.1.1, 35.11.1.1, 36.11.1.1, 37.11.1.1, 38.11.1.1, 39.11.1.1, 40.11.1.1, 1.12.1.1, 2.12.1.1, 3.12.1.1, 4.12.1.1, 5.12.1.1, 6.12.1.1, 7.12.1.1, 8.12.1.1, 9.12.1.1, 10.12.1.1, 11.12.1.1, 12.12.1.1, 13.12.1.1, 14.12.1.1, 15.12.1.1, 16.12.1.1, 17.12.1.1, 18.12.1.1, 19.12.1.1, 20.12.1.1, 21.12.1.1, 22.12.1.1, 23.12.1.1, 24.12.1.1, 25.12.1.1, 26.12.1.1, 27.12.1.1, 28.12.1.1, 29.12.1.1, 30.12.1.1, 31.12.1.1, 32.12.1.1, 33.12.1.1, 34.12.1.1, 35.12.1.1, 36.12.1.1, 37.12.1.1, 38.12.1.1, 39.12.1.1, 40.12.1.1, 1.13.1.1, 2.13.1.1, 3.13.1.1, 4.13.1.1, 5.13.1.1, 6.13.1.1, 7.13.1.1, 8.13.1.1, 9.13.1.1, 10.13.1.1, 11.13.1.1, 12.13.1.1, 13.13.1.1, 14.13.1.1, 15.13.1.1, 16.13.1.1, 17.13.1.1, 18.13.1.1, 19.13.1.1, 20.13.1.1, 21.13.1.1, 22.13.1.1, 23.13.1.1, 24.13.1.1, 25.13.1.1, 26.13.1.1, 27.13.1.1, 28.13.1.1, 29.13.1.1, 30.13.1.1, 31.13.1.1, 32.13.1.1, 33.13.1.1, 34.13.1.1, 35.13.1.1, 36.13.1.1, 37.13.1.1, 38.13.1.1, 39.13.1.1, 40.13.1.1, 1.14.1.1, 2.14.1.1, 3.14.1.1, 4.14.1.1, 5.14.1.1, 6.14.1.1, 7.14.1.1, 8.14.1.1, 9.14.1.1, 10.14.1.1, 11.14.1.1, 12.14.1.1, 13.14.1.1, 14.14.1.1, 15.14.1.1, 16.14.1.1, 17.14.1.1, 18.14.1.1, 19.14.1.1, 20.14.1.1, 21.14.1.1, 22.14.1.1, 23.14.1.1, 24.14.1.1, 25.14.1.1, 26.14.1.1, 27.14.1.1, 28.14.1.1, 29.14.1.1, 30.14.1.1, 31.14.1.1, 32.14.1.1, 33.14.1.1, 34.14.1.1, 35.14.1.1, 36.14.1.1, 37.14.1.1, 38.14.1.1, 39.14.1.1, 40.14.1.1, 1.15.1.1, 2.15.1.1, 3.15.1.1, 4.15.1.1, 5.15.1.1, 6.15.1.1, 7.15.1.1, 8.15.1.1, 9.15.1.1, 10.15.1.1, 11.15.1.1, 12.15.1.1, 13.15.1.1, 14.15.1.1, 15.15.1.1, 16.15.1.1, 17.15.1.1, 18.15.1.1, 19.15.1.1, 20.15.1.1, 21.15.1.1, 22.15.1.1, 23.15.1.1, 24.15.1.1, 25.15.1.1, 26.15.1.1, 27.15.1.1, 28.15.1.1, 29.15.1.1, 30.15.1.1, 31.15.1.1, 32.15.1.1, 33.15.1.1, 34.15.1.1, 35.15.1.1, 36.15.1.1, 37.15.1.1, 38.15.1.1, 39.15.1.1, 40.15.1.1, 1.16.1.1, 2.16.1.1, 3.16.1.1, 4.16.1.1, 5.16.1.1, 6.16.1.1, 7.16.1.1, 8.16.1.1, 9.16.1.1, 10.16.1.1, 11.16.1.1, 12.16.1.1, 13.16.1.1, 14.16.1.1, 15.17.1.1, 16.16.1.1, 17.17.1.1, 18.17.1.1, 19.17.1.1, 20.17.1.1, 21.17.1.1, 22.16.1.1, 23.16.1.1, 24.17.1.1, 25.17.1.1, 26.17.1.1, 27.17.1.1, 28.17.1.1, 29.17.1.1, 30.17.1.1, 31.16.1.1, 32.16.1.1, 33.16.1.1, 34.16.1.1, 35.16.1.1, 36.16.1.1, 37.16.1.1, 38.16.1.1, 39.16.1.1, 40.16.1.1, 1.17.1.1, 2.17.1.1, 3.17.1.1, 4.17.1.1, 5.17.1.1, 6.17.1.1, 7.18.1.1, 8.17.1.1, 9.17.1.1, 10.17.1.1, 11.17.1.1, 12.17.1.1, 13.17.1.1, 14.17.1.1, 15.17.1.1, 16.17.1.1, 17.17.1.1, 18.17.1.1, 19.17.1.1, 20.17.1.1, 21.17.1.1, 22.17.1.1, 23.17.1.1, 24.17.1.1, 25.17.1.1, 26.17.1.1, 27.17.1.1, 28.17.1.1, 29.17.1.1, 30.17.1.1, 31.17.1.1, 32.17.1.1, 33.17.1.1, 34.17.1.1, 35.17.1.1, 36.17.1.1, 37.17.1.1, 38.17.1.1, 39.17.1.1, 40.17.1.1, 1.18.1.1, 2.18.1.1, 3.18.1.1, 4.18.1.1, 5.18.1.1, 6.18.1.1, 7.18.1.1, 8.18.1.1, 9.18.1.1, 10.18.1.1, 11.18.1.1, 12.18.1.1, 13.18.1.1, 14.18.1.1, 15.18.1.1, 16.18.1.1, 17.18.1.1, 18.18.1.1, 19.18.1.1, 20.18.1.1, 21.18.1.1, 22.18.1.1, 23.18.1.1, 24.18.1.1, 25.18.1.1, 26.18.1.1, 27.18.1.1, 28.18.1.1, 29.18.1.1, 30.18.1.1, 31.18.11.1, 32.18.1.1, 33.18.1.1, 34.18.1.1, 35.18.1.1, 36.18.1.1, 37.18.1.1, 38.18.1.1, 39.18.1.1, 40.18.1.1, 1.19.1.1, 2.19 1.1, 3.19.1.1, 4.19.1.1, 5.19.1.1, 6.19.1.1, 7.19.1.1, 8.19.1.1, 9.19.1.1, 10.19.1.1, 11.19.1.1, 12.19.1.1, 13.19.1.1, 14.19.1.1, 15.19.1.1, 16.19.1.1, 17.19.1.1, 18.19.1.1, 19.19.1.1, 20.19.1.1, 21.19.1.1, 22.19.1.1, 23.19.1.1, 24.19.1.1, 25.19.1.1, 26.19.1.1, 27.19.1.1, 28.19.1.1, 29.19.1.1, 30.19.1.1, 31.19.1.1, 32.19.1.1, 33.19.1.1, 34.19.1.1, 35.19.1.1, 36.19.1.1, 37.19.1.1, 38.19.1.1, 39.19.1.1, 40.19.1.1, 1.20.1.1, 2.20.1.1, 3.20.1.1, 4.20.1.1, 5.20.1.1, 6.20.1.1, 7.20.1.1, 8.20.1.1, 9.20.1.1, 10.20.1.1, 11.20.1.1, 12.20.1.1, 13.20.1.1, 14.20.1.1, 15.20.1.1, 16.20.1.1, 17.20.1.1, 18.20.1.1, 19.20.1.1, 20.20.1.1, 21.20.1.1, 22.20.1.1, 23.20.1.1, 24.20.1.1, 25.20.1.1, 26.20.1.1, 27.20.1.1, 28.20.1.1, 29.20.1.1, 30.20.1.1, 31.20.1.1, 32.20.1.1, 33.20.1.1, 34.20.1.1, 35.20.1.1, 36.20.1.1, 37.20.1.1, 38.20.1.1, 39.20.1.1, 40.20.1.1, 1.21.1.1, 2.21.1.1, 3.21.1.1, 4.21.1.1, 5.21.1.1, 6.21.1.1, 7.21.1.1, 8.21.1.1, 9.21.1.1, 10.21.1.1, 11.21.1.1, 12.21.1.1, 13.21.1.1, 14.21.1.1, 15.21.1.1, 16.21.1.1, 17.21.1.1, 18.21.1.1, 19.21.1.1, 20.21.1.1, 21.21.1.1, 22.21.1.1, 23.21.1.1, 24.21.1.1, 25.21.1.1, 26.21.1.1, 27.21.1.1, 28.21.1.1, 29.21.1.1, 30.21.1.1, 31.21.1.1, 32.21.1.1, 33.21.1.1, 34.21.1.1, 35.21.1.1, 36.21.1.1, 37.21.1.1, 38.21.1.1, 39.21.1.1, 40.21.1.1, 1.22.1.1, 2.22.1.1, 3.22.1.1, 4.22.1.1, 5.22.1.1, 6.22.1.1, 7.22.1.1, 8.22.1.1, 9.22.1.1, 10.22.1.1, 11.22.1.1, 12.22.1.1, 13.22.1.1, 14.22.1.1, 15.22.1.1, 16.22.1.1, 17.22.1.1, 18.22.1.1, 19.22.1.1, 20.22.1.1, 21.22.1.1, 22.22.1.1, 23.22.1.1, 24.22.1.1, 25.22.1.1, 26.22.1.1, 27.22.1.1, 28.22.1.1, 29.22.1.1, 30.22.1.1, 31.22.1.1, 32.22.1.1, 33.22.1.1, 34.22.1.1, 35.22.1.1, 36.22.1.1, 37.22.1.1, 38.22.1.1, 39.22.1.1, 40.22.1.1, 1.23.1.1, 2.23.1.1, 3.23.1.1, 4.23.1.1, 5.23.1.1, 6.23.1.1, 7.23.1.1, 8.23.1.1, 9.23.1.1, 10.23.1.1, 11.23.1.1, 12.23.1.1, 13.23.1.1, 14.23.1.1, 15.23.1.1, 16.23.1.1, 17.23.1.1, 18.23.1.1, 19.23.1.1, 20.23.1.1, 21.23.1.1, 22.23.1.1, 23.23.1.1, 24.23.1.1, 25.23.1.1, 26.23.1.1, 27.23.1.1, 28.23.1.1, 29.23.1.1, 30.23.1.1, 31.23.1.1, 32.23.1.1, 33.23.1.1, 34.23.1.1, 35.23.1.1, 36.23.1.1, 37.23.1.1, 38.23.1.1, 39.23.1.1, 40.23.1.1, 1.24.1.1, 2.24.1.1, 3.24.1.1, 4.24.1.1, 5.24.1.1, 6.24.1.1, 7.24.1.1, 8.24.1.1, 9.24.1.1, 10.24.1.1, 11.24.1.1, 12.24.1.1, 13.24.1.1, 14.24.1.1, 15.24.1.1, 16.24.1.1, 17.24.1.1, 18.24.1.1, 19.24.1.1, 20.24.1.1, 21.24.1.1, 22.24.1.1, 23.24.1.1, 24.24.1.1, 25.24.1.1, 26.24.1.1, 27.24.1.1, 28.24.1.1, 29.24.1.1, 30.24.1.1, 31.24.1.1, 32.24.1.1, 33.24.1.1, 34.24.1.1, 35.24.1.1, 36.24.1.1, 37.24.1.1, 38.24.1.1, 39.24.1.1, 40.24.1.1, 1.25.1.1, 2.25.1.1, 3.25.1.1, 4.25.1.1, 5.25.1.1, 6.25.1.1, 7.25.1.1, 8.25.1.1, 9.25.1.1, 10.25.1.1, 11.25.1.1, 12.25.1.1, 13.25.1.1, 14.25.1.1, 15.25.1.1, 16.25.1.1, 17.25.1.1, 18.25.1.1, 19.25.1.1, 20.25.1.1, 21.25.1.1, 22.25.1.1, 23.25.1.1, 24.25.1.1, 25.25.1.1, 26.25.1.1, 27.25.1.1, 28.25.1.1, 29.25.1.1, 30.25.1.1, 31.25.1.1, 32.25.1.1, 33.25.1.1, 34.25.1.1, 35.25.1.1, 36.25.1.1, 37.25.1.1, 38.25.1.1, 39.25.1.1, 40.25.1.1, 1.26.1.1, 2.26.1.1, 3.26.1.1, 4.26.1.1, 5.26.1.1, 6.26.1.1, 7.26.1.1, 8.26.1.1, 9.26.1.1, 10.26.1.1, 11.26.1.1, 12.26.1.1, 13.26.1.1, 14.26.1.1, 15.26.1.1, 16.26.1.1, 17.26.1.1, 18.26.1.1, 19.26.1.1, 20.26.1.1, 21.26.1.1, 22.26.1.1, 23.26.1.1, 24.26.1.1, 25.26.1.1, 26.26.1.1, 27.26.1.1, 28.26.1.1, 29.26.1.1, 30.26.1.1, 31.26.1.1, 32.26.1.1, 33.26.1.1, 34.26.1.1, 35.26.1.1, 36.26.1.1, 37.26.1.1, 38.26.1.1, 39.26.1.1, 40.26.1.1, 1.27.1.1, 2.27.1.1, 3.27.1.1, 4.27.1.1, 5.27.1.1, 6.27.1.1, 7.27.1.1, 8.27.1.1, 9.27.1.1, 10.27.1.1, 11.27.1.1, 12.27.1.1, 13.27.1.1, 14.27.1.1, 15.27.1.1, 16.27.1.1, 17.27.1.1, 18.27.1.1, 19.27.1.1, 20.27.1.1, 21.27.1.1, 22.27.1.1, 23.27.1.1, 24.27.1.1, 25.27.1.1, 26.27.1.1, 27.27.1.1, 28.27.1.1, 29.27.1.1, 30.27.1.1, 31.27.1.1, 32.27.1.1, 33.27.1.1, 34.27.1.1, 35.27.1.1, 36.27.1.1, 37.27.1.1, 38.27.1.1, 39.27.1.1, 40.27.1.1, 1.28.1.1, 2.28.1.1, 3.28.1.1, 4.28.1.1, 5.28.1.1, 6.28.1.1, 7.28.1.1, 8.28.1.1, 9.28.1.1, 10.28.1.1, 11.28.1.1, 12.28.1.1, 13.28.1.1, 14.28.1.1, 15.28.1.1, 16.28.1.1, 17.28.1.1, 18.28.1.1, 19.28.1.1, 20.28.1.1, 21.28.1.1, 22.28.1.1, 23.28.1.1, 24.28.1.1, 25.28.1.1, 26.28.1.1, 27.28.1.1, 28.28.1.1, 29.28.1.1, 30.28.1.1, 31.28.1.1, 32.28.1.1, 33.28.1.1, 34.28.1.1, 35.28.1.1, 36.28.1.1, 37.28.1.1, 38.28.1.1, 39.28.1.1, 40.28.1.1, 1.29.1.1, 2.29.1.1, 3.29.1.1, 4.29.1.1, 5.29.1.1, 6.29.1.1, 7.29.1.1, 8.29.1.1, 9.29.1.1, 10.29.1.1, 11.29.1.1, 12.29.1.1, 13.29.1.1, 14.29.1.1, 15.29.1.1, 16.29.1.1, 17.29.1.1, 18.29.1.1, 19.29.1.1, 20.29.1.1, 21.29.1.1, 22.29.1.1, 23.29.1.1, 24.29.1.1, 25.29.1.1, 26.29.1.1, 27.29.1.1, 28.29.1.1, 29.29.1.1, 30.29.1.1, 31.29.1.1, 32.29.1.1, 33.29.1.1, 34.29.1.1, 35.29.1.1, 36.29.1.1, 37.29.1.1, 38.29.1.1, 39.29.1.1, 40.29.1.1, 1.1.1.2, 2.1.1.2, 3.1.1.2, 4.1.1.2, 5.1.1.2, 6.1.1.2, 7.1.1.2, 8.1.1.2, 9.1.1.2, 10.1.1.2, 11.1.1.2, 12.1.1.2, 13.1.1.2, 14.1.1.2, 15.1.1.2, 16.1.1.2, 17.1.1.2, 18.1.1.2, 19.1.1.2, 20.1.1.2, 21.1.1.2, 22.1.1.2, 23.1.1.2, 24.1.1.2, 25.1.1.2, 26.1.1.2, 27.1.1.2, 28.1.1.2, 29.1.1.2, 30.1.1.2, 31.1.1.2, 32.1.1.2, 33.1.1.2, 34.1.1.2, 35.1.1.2, 36.1.1.2, 37.1.1.2, 38.1.1.2, 39.1.1.2, 40.1.1.2, 1.2.1.2, 2.2.1.2, 3.2.1.2, 4.2.1.2, 5.2.1.2, 6.2.1.2, 7.2.1.2, 8.2.1.2, 9.2.1.2, 10.2.1.2, 11.2.1.2, 12.2.1.2, 13.2.1.2, 14.2.1.2, 15.2.1.2, 16.2.1.2, 17.2.1.2, 18.2.1.2, 19.2.1.2, 20.2.1.2, 21.2.1.2, 22.2.1.2, 23.2.1.2, 24.2.1.2, 25.2.1.2, 26.2.1.2, 27.2.1.2, 28.2.1.2, 29.2.1.2, 30.2.1.2, 31.2.1.2, 32.2.1.2, 33.2.1.2, 34.2.1.2, 35.2.1.2, 36.2.1.2, 37.2.1.2, 38.2.1.2, 39.2.1.2, 40.2.1.2, 1.3.1.2, 2.3.1.2, 3.3.1.2, 4.3.1.2, 5.3.1.2, 6.3.1.2, 7.3.1.2, 8.3.1.2, 9.3.1.2, 10.3.1.2, 11.3.1.2, 12.3.1.2, 13.3.1.2, 14.3.1.2, 15.3.1.2, 16.3.1.2, 17.3.1.2, 18.3.1.2, 19.3.1.2, 20.3.1.2, 21.3.1.2, 22.3.1.2, 23.3.1.2, 24.3.1.2, 25.3.1.2, 26.3.1.2, 27.3.1.2, 28.3.1.2, 29.3.1.2, 30.3.1.2, 31.3.1.2, 32.3.1.2, 33.3.1.2, 34.3.1.2, 35.3.1.2, 36.3.1.2, 37.3.1.2, 38.3.1.2, 39.3.1.2, 40.3.1.2, 1.4.1.2, 2.4.1.2, 3.4.1.2, 4.4.1.2, 5.4.1.2, 6.4.1.2, 7.4.1.2, 8.4.1.2, 9.4.1.2, 10.4.1.2, 11.4.1.2, 12.4.1.2, 13.4.1.2, 14.4.1.2, 15.4.1.2, 16.4.1.2, 17.4.1.2, 18.4.1.2, 19.4.1.2, 20.4.1.2, 21.4.1.2, 22.4.1.2, 23.4.1.2, 24.4.1.2, 25.4.1.2, 26.4.1.2, 27.4.1.2, 28.4.1.2, 29.4.1.2, 30.4.1.2, 31.4.1.2, 32.4.1.2, 33.4.1.2, 34.4.1.2, 35.4.1.2, 36.4.1.2, 37.4.1.2, 38.4.1.2, 39.4.1.2, 40.4.1.2, 1.5.1.2, 2.5.1.2, 3.5.1.2, 4.5.1.2, 5.5.1.2, 6.5.1.2, 7.5.1.2, 8.5.1.2, 9.5.1.2, 10.5.1.2, 11.5.1.2, 12.5.1.2, 13.5.1.2, 14.5.1.2, 15.5.1.2, 16.5.1.2, 17.5.1.2, 18.5.1.2, 19.5.1.2, 20.5.1.2, 21.5.1.2, 22.5.1.2, 23.5.1.2, 24.5.1.2, 25.5.1.2, 26.5.1.2, 27.5.1.2, 28.5.1.2, 29.5.1.2, 30.5.1.2, 31.5.1.2, 32.5.1.2, 33.5.1.2, 34.5.1.2, 35.5.1.2, 36.5.1.2, 37.5.1.2, 38.5.1.2, 39.5.1.2, 40.5.1.2, 1.6.1.2, 2.6.1.2, 3.6.1.2, 4.6.1.2, 5.6.1.2, 6.6.1.2, 7.6.1.2, 8.6.1.2, 9.6.1.2, 10.6.1.2, 11.6.1.2, 12.6.1.2, 13.6.1.2, 14.6.1.2, 15.6.1.2, 16.6.1.2, 17.6.1.2, 18.6.1.2, 19.6.1.2, 20.6.1.2, 21.6.1.2, 22.6.1.2, 23.6.1.2, 24.6.1.2, 25.6.1.2, 26.6.1.2, 27.6.1.2, 28.6.1.2, 29.6.1.2, 30.6.1.2, 31.6.1.2, 32.6.1.2, 33.6.1.2, 34.6.1.2, 35.6.1.2, 36.6.1.2, 37.6.1.2, 38.6.1.2, 39.6.1.2, 40.6.1.2, 1.7.1.2, 2.7.1.2, 3.7.1.2, 4.7.1.2, 5.7.1.2, 6.7.1.2, 7.7.1.2, 8.7.1.2, 9.7.1.2, 10.7.1.2, 11.7.1.2, 12.7.1.2, 13.7.1.2, 14.7.1.2, 15.7.1.2, 16.7.1.2, 17.7.1.2, 18.7.1.2, 19.7.1.2, 20.7.1.2, 21.7.1.2, 22.7.1.2, 23.7.1.2, 24.7.1.2, 25.7.1.2, 26.7.1.2, 27.7.1.2, 28.7.1.2, 29.7.1.2, 30.7.1.2, 31.7.1.2, 32.7.1.2, 33.7.1.2, 34.7.1.2, 35.7.1.2, 36.7.1.2, 37.7.1.2, 38.7.1.2, 39.7.1.2, 40.7.1.2, 1.8.1.2, 2.8.1.2, 3.8.1.2, 4.8.1.2, 5.8.1.2, 6.8.1.2, 7.8.1.2, 8.8.1.2, 9.8.1.2, 10.8.1.2, 11.8.1.2, 12.8.1.2, 13.8.1.2, 14.8.1.2, 15.8.1.2, 16.8.1.2, 17.8.1.2, 18.8.1.2, 19.8.1.2, 20.8.1.2, 21.8.1.2, 22.8.1.2, 23.8.1.2, 24.8.1.2, 25.8.1.2, 26.8.1.2, 27.8.1.2, 28.8.1.2, 29.8.1.2, 30.8.1.2, 31.8.1.2, 32.8.1.2, 33.8.1.2, 34.8.1.2, 35.8.1.2, 36.8.1.2, 37.8.1.2, 38.8.1.2, 39.8.1.2, 40.8.1.2, 1.9.1.2, 2.9.1.2, 3.9.1.2, 4.9.1.2, 5.9.1.2, 6.9.1.2, 7.9.1.2, 8.9.1.2, 9.9.1.2, 10.9.1.2, 11.9.1.2, 12.9.1.2, 13.9.1.2, 14.9.1.2, 15.9.1.2, 16.9.1.2, 17.9.1.2, 18.9.1.2, 19.9.1.2, 20.9.1.2, 21.9.1.2, 22.9.1.2, 23.9.1.2, 24.9.1.2, 25.9.1.2, 26.9.1.2, 27.9.1.2, 28.9.1.2, 29.9.1.2, 30.9.1.2, 31.9.1.2, 32.9.1.2, 33.9.1.2, 34.9.1.2, 35.9.1.2, 36.9.1.2, 37.9.1.2, 38.9.1.2, 39.9.1.2, 40.9.1.2, 1.10.1.2, 2.10.1.2, 3.10.1.2, 4.10.1.2, 5.10.1.2, 6.10.1.2, 7.10.1.2, 8.10.1.2, 9.10.1.2, 10.10.1.2, 11.10.1.2, 12.10.1.2, 13.10.1.2, 14.10.1.2, 15.10.1.2, 16.10.1.2, 17.10.1.2, 18.10.1.2, 19.10.1.2, 20.10.1.2, 21.10.1.2, 22.10.1.2, 23.10.1.2, 24.10.1.2, 25.10.1.2, 26.10.1.2, 27.10.1.2, 28.10.1.2, 29.10.1.2, 30.10.1.2, 31.10.1.2, 32.10.1.2, 33.10.1.2, 34.10.1.2, 35.10.1.2, 36.10.1.2, 37.10.1.2, 38.10.1.2, 39.10.1.2, 40.10.1.2, 1.11.1.2, 2.11.1.2, 3.11.1.2, 4.11.1.2, 5.11.1.2, 6.11.1.2, 7.11.1.2, 8.11.1.2, 9.11.1.2, 10.11.1.2, 11.11.1.2, 12.11.1.2, 13.11.1.2, 14.11.1.2, 15.11.1.2, 16.11.1.2, 17.11.1.2, 18.11.1.2, 19.11.1.2, 20.11.1.2, 21.11.1.2, 22.11.1.2, 23.11.1.2, 24.11.1.2, 25.11.1.2, 26.11.1.2, 27.11.1.2, 28.11.1.2, 29.11.1.2, 30.11.1.2, 31.11.1.2, 32.11.1.2, 33.11.1.2, 34.11.1.2, 35.11.1.2, 36.11.1.2, 37.11.1.2, 38.11.1.2, 39.11.1.2, 40.11.1.2, 1.12.1.2, 2.12.1.2, 3.12.1.2, 4.12.1.2, 5.12.1.2, 6.12.1.2, 7.12.1.2, 8.12.1.2, 9.12.1.2, 10.12.1.2, 11.12.1.2, 12.12.1.2, 13.12.1.2, 14.12.1.2, 15.12.1.2, 16.12.1.2, 17.12.1.2, 18.12.1.2, 19.12.1.2, 20.12.1.2, 21.12.1.2, 22.12.1.2, 23.12.1.2, 24.12.1.2, 25.12.1.2, 26.12.1.2, 27.12.1.2, 28.12.1.2, 29.12.1.2, 30.12.1.2, 31.12.1.2, 32.12.1.2, 33.12.1.2, 34.12.1.2, 35.12.1.2, 36.12.1.2, 37.12.1.2, 38.12.1.2, 39.12.1.2, 40.12.1.2, 1.13.1.2, 2.13.1.2, 3.13.1.2, 4.13.1.2, 5.13.1.2, 6.13.1.2, 7.13.1.2, 8.13.1.2, 9.13.1.2, 10.13.1.2, 11.13.1.2, 12.13.1.2, 13.13.1.2, 14.13.1.2, 15.13.1.2, 16.13.1.2, 17.13.1.2, 18.13.1.2, 19.13.1.2, 20.13.1.2, 21.13.1.2, 22.13.1.2, 23.13.1.2, 24.13.1.2, 25.13.1.2, 26.13.1.2, 27.13.1.2, 28.13.1.2, 29.13.1.2, 30.13.1.2, 31.13.1.2, 32.13.1.2, 33.13.1.2, 34.13.1.2, 35.13.1.2, 36.13.1.2, 37.13.1.2, 38.13.1.2, 39.13.1.2, 40.13.1.2, 1.14.1.2, 2.14.1.2, 3.14.1.2, 4.14.1.2, 5.14.1.2, 6.14.1.2, 7.14.1.2, 8.14.1.2, 9.14.1.2, 10.14.1.2, 11.14.1.2, 12.14.1.2, 13.14.1.2, 14.14.1.2, 15.14.1.2, 16.14.1.2, 17.14.1.2, 18.14.1.2, 19.14.1.2, 20.14.1.2, 21.14.1.2, 22.14.1.2, 23.14.1.2, 24.14.1.2, 25.14.1.2, 26.14.1.2, 27.14.1.2, 28.14.1.2, 29.14.1.2, 30.14.1.2, 31.14.1.2, 32.14.1.2, 33.14.1.2, 34.14.1.2, 35.14.1.2, 36.14.1.2, 37.14.1.2, 38.14.1.2, 39.14.1.2, 40.14.1.2, 1.15.1.2, 2.15.1.2, 3.15.1.2, 4.15.1.2, 5.15.1.2, 6.15.1.2, 7.15.1.2, 8.15.1.2, 9.15.1.2, 10.15.1.2, 11.15.1.2, 12.15.1.2, 13.15.1.2, 14.15.1.2, 15.15.1.2, 16.15.1.2, 17.15.1.2, 18.15.1.2, 19.15.1.2, 20.15.1.2, 21.15.1.2, 22.15.1.2, 23.15.1.2, 24.15.1.2, 25.15.1.2, 26.15.1.2, 27.15.1.2, 28.15.1.2, 29.15.1.2, 30.15.1.2, 31.15.1.2, 32.15.1.2, 33.15.1.2, 34.15.1.2, 35.15.1.2, 36.15.1.2, 37.15.1.2, 38.15.1.2, 39.15.1.2, 40.15.1.2, 1.16.1.2, 2.16.1.2, 3.16.1.2, 4.16.1.2, 5.16.1.2, 6.16.1.2, 7.16.1.2, 8.16.1.2, 9.16.1.2, 10.16.1.2, 11.16.1.2, 12.16.1.2, 13.16.1.2, 14.16.1.2, 15.16.1.2, 16.16.1.2, 17.16.1.2, 18.16.1.2, 19.16.1.2, 20.16.1.2, 21.16.1.2, 22.16.1.2, 23.16.1.2, 24.16.1.2, 25.16.1.2, 26.16.1.2, 27.16.1.2, 28.16.1.2, 29.16.1.2, 30.16.1.2, 31.16.1.2, 32.16.1.2, 33.16.1.2, 34.16.1.2, 35.16.1.2, 36.16.1.2, 37.16.1.2, 38.16.1.2, 39.16.1.2, 40.16.1.2, 1.17.1.2, 2.17.1.2, 3.17.1.2, 4.17.1.2, 5.17.1.2, 6.17.1.2, 7.17.1.2, 8.17.1.2, 9.17.1.2, 10.17.1.2, 11.17.1.2, 12.17.1.2, 13.17.1.2, 14.17.1.2, 15.17.1.2, 16.17.1.2, 17.17.1.2, 18.17.1.2, 19.17.1.2, 20.17.1.2, 21.17.1.2, 22.17.1.2, 23.17.1.2, 24.17.1.2, 25.17.1.2, 26.17.1.2, 27.17.1.2, 28.17.1.2, 29.17.1.2, 30.17.1.2, 31.17.1.2, 32.17.1.2, 33.17.1.2, 34.17.1.2, 35.17.1.2, 36.17.1.2, 37.17.1.2, 38.17.1.2, 39.17.1.2, 40.17.1.2, 1.18.1.2, 2.18.1.2, 3.18.1.2, 4.18.1.2, 5.18.1.2, 6.18.1.2, 7.18.1.2, 8.18.1.2, 9.18.1.2, 10.18.1.2, 11.18.1.2, 12.18.1.2, 13.18.1.2, 14.18.1.2, 15.18.1.2, 16.18.1.2, 17.18.1.2, 18.18.1.2, 19.18.1.2, 20.18.1.2, 21.18.1.2, 22.18.1.2, 23.18.1.2, 24.18.1.2, 25.18.1.2, 26.18.1.2, 27.18.1.2, 28.18.1.2, 29.18.1.2, 30.18.1.2, 31.18.1.2, 32.18.1.2, 33.18.1.2, 34.18.1.2, 35.18.1.2, 36.18.1.2, 37.18.1.2, 38.18.1.2, 39.18.1.2, 40.18.1.2, 1.19.1.2, 2.19.1.2, 3.19.1.2, 4.19.1.2, 5.19.1.2, 6.19.1.2, 7.19.1.2, 8.19.1.2, 9.19.1.2, 10.19.1.2, 11.19.1.2, 12.19.1.2, 13.19.1.2, 14.19.1.2, 15.19.1.2, 16.19.1.2, 17.19.1.2, 18.19.1.2, 19.19.1.2, 20.19.1.2, 21.19.1.2, 22.19.1.2, 23.19.1.2, 24.19.1.2, 25.19.1.2, 26.19.1.2, 27.19.1.2, 28.19.1.2, 29.19.1.2, 30.19.1.2, 31.19.1.2, 32.19.1.2, 33.19.1.2, 34.19.1.2, 35.19.1.2, 36.19.1.2, 37.19.1.2, 38.19.1.2, 39.19.1.2, 40.19.1.2, 1.20.1.2, 2.20.1.2, 3.20.1.2, 4.20.1.2, 5.20.1.2, 6.20.1.2, 7.20.1.2, 8.20.1.2, 9.20.1.2, 10.20.1.2, 11.20.1.2, 12.20.1.2, 13.20.1.2, 14.20.1.2, 15.20.1.2, 16.20.1.2, 17.20.1.2, 18.20.1.2, 19.20.1.2, 20.20.1.2, 21.20.1.2, 22.20.1.2, 23.20.1.2, 24.20.1.2, 25.20.1.2, 26.20.1.2, 27.20.1.2, 28.20.1.2, 29.20.1.2, 30.20.1.2, 31.20.1.2, 32.20.1.2, 33.20.1.2, 34.20.1.2, 35.20.1.2, 36.20.1.2, 37.20.1.2, 38.20.1.2, 39.20.1.2, 40.20.1.2, 1.21.1.2, 2.21.1.2, 3.21.1.2, 4.21.1.2, 5.21.1.2, 6.21.1.2, 7.21.1.2, 8.21.1.2, 9.21.1.2, 10.21.1.2, 11.21.1.2, 12.21.1.2, 13.21.1.2, 14.21.1.2, 15.21.1.2, 16.21.1.2, 17.21.1.2, 18.21.1.2, 19.21.1.2, 20.21.1.2, 21.21.1.2, 22.21.1.2, 23.21.1.2, 24.21.1.2, 25.21.1.2, 26.21.1.2, 27.21.1.2, 28.21.1.2, 29.21.1.2, 30.21.1.2, 31.21.1.2, 32.21.1.2, 33.21.1.2, 34.21.1.2, 35.21.1.2, 36.21.1.2, 37.21.1.2, 38.21.1.2, 39.21.1.2, 40.21.1.2, 1.22.1.2, 2.22.1.2, 3.22.1.2, 4.22.1.2, 5.22.1.2, 6.22.1.2, 7.22.1.2, 8.22.1.2, 9.22.1.2, 10.22.1.2, 11.22.1.2, 12.22.1.2, 13.22.1.2, 14.22.1.2, 15.22.1.2, 16.22.1.2, 17.22.1.2, 18.22.1.2, 19.22.1.2, 20.22.1.2, 21.22.1.2, 22.22.1.2, 23.22.1.2, 24.22.1.2, 25.22.1.2, 26.22.1.2, 27.22.1.2, 28.22.1.2, 29.22.1.2, 30.22.1.2, 31.22.1.2, 32.22.1.2, 33.22.1.2, 34.22.1.2, 35.22.1.2, 36.22.1.2, 37.22.1.2, 38.22.1.2, 39.22.1.2, 40.22.1.2, 1.23.1.2, 2.23.1.2, 3.23.1.2, 4.23.1.2, 5.23.1.2, 6.23.1.2, 7.23.1.2, 8.23.1.2, 9.23.1.2, 10.23.1.2, 11.23.1.2, 12.23.1.2, 13.23.1.2, 14.23.1.2, 15.23.1.2, 16.23.1.2, 17.23.1.2, 18.23.1.2, 19.23.1.2, 20.23.1.2, 21.23.1.2, 22.23.1.2, 23.23.1.2, 24.23.1.2, 25.23.1.2, 26.23.1.2, 27.23.1.2, 28.23.1.2, 29.23.1.2, 30.23.1.2, 31.23.1.2, 32.23.1.2, 33.23.1.2, 34.23.1.2, 35.23.1.2, 36.23.1.2, 37.23.1.2, 38.23.1.2, 39.23.1.2, 40.23.1.2, 1.24.1.2, 2.24.1.2, 3.24.1.2, 4.24.1.2, 5.24.1.2, 6.24.1.2, 7.24.1.2, 8.24.1.2, 9.24.1.2, 10.24.1.2, 11.24.1.2, 12.24.1.2, 13.24.1.2, 14.24.1.2, 15.24.1.2, 16.24.1.2, 17.24.1.2, 18.24.1.2, 19.24.1.2, 20.24.1.2, 21.24.1.2, 22.24.1.2, 23.24.1.2, 24.24.1.2, 25.24.1.2, 26.24.1.2, 27.24.1.2, 28.24.1.2, 29.24.1.2, 30.24.1.2, 31.24.1.2, 32.24.1.2, 33.24.1.2, 34.24.1.2, 35.24.1.2, 36.24.1.2, 37.24.1.2, 38.24.1.2, 39.24.1.2, 40.24.1.2, 1.25.1.2, 2.25.1.2, 3.25.1.2, 4.25.1.2, 5.25.1.2, 6.25.1.2, 7.25.1.2, 8.25.1.2, 9.25.1.2, 10.25.1.2, 11.25.1.2, 12.25.1.2, 13.25.1.2, 14.25.1.2, 15.25.1.2, 16.25.1.2, 17.25.1.2, 18.25.1.2, 19.25.1.2, 20.25.1.2, 21.25.1.2, 22.25.1.2, 23.25.1.2, 24.25.1.2, 25.25.1.2, 26.25.1.2, 27.25.1.2, 28.25.1.2, 29.25.1.2, 30.25.1.2, 31.25.1.2, 32.25.1.2, 33.25.1.2, 34.25.1.2, 35.25.1.2, 36.25.1.2, 37.25.1.2, 38.25.1.2, 39.25.1.2, 40.25.1.2, 1.26.1.2, 2.26.1.2, 3.26.1.2, 4.26.1.2, 5.26.1.2, 6.26.1.2, 7.26.1.2, 8.26.1.2, 9.26.1.2, 10.26.1.2, 11.26.1.2, 12.26.1.2, 13.26.1.2, 14.26.1.2, 15.26.1.2, 16.26.1.2, 17.26.1.2, 18.26.1.2, 19.26.1.2, 20.26.1.2, 21.26.1.2, 22.26.1.2, 23.26.1.2, 24.26.1.2, 25.26.1.2, 26.26.1.2, 27.26.1.2, 28.26.1.2, 29.26.1.2, 30.26.1.2, 31.26.1.2, 32.26.1.2, 33.26.1.2, 34.26.1.2, 35.26.1.2, 36.26.1.2, 37.26.1.2, 38.26.1.2, 39.26.1.2, 40.26.1.2, 1.27.1.2, 2.27.1.2, 3.27.1.2, 4.27.1.2, 5.27.1.2, 6.27.1.2, 7.27.1.2, 8.27.1.2, 9.27.1.2, 10.27.1.2, 11.27.1.2, 12.27.1.2, 13.27.1.2, 14.27.1.2, 15.27.1.2, 16.27.1.2, 17.27.1.2, 18.27.1.2, 19.27.1.2, 20.27.1.2, 21.27.1.2, 22.27.1.2, 23.27.1.2, 24.27.1.2, 25.27.1.2, 26.27.1.2, 27.27.1.2, 28.27.1.2, 29.27.1.2, 30.27.1.2, 31.27.1.2, 32.27.1.2, 33.27.1.2, 34.27.1.2, 35.27.1.2, 36.27.1.2, 37.27.1.2, 38.27.1.2, 39.27.1.2, 40.27.1.2, 1.28.1.2, 2.28.1.2, 3.28.1.2, 4.28.1.2, 5.28.1.2, 6.28.1.2, 7.28.1.2, 8.28.1.2, 9.28.1.2, 10.28.1.2, 11.28.1.2, 12.28.1.2, 13.28.1.2, 14.28.1.2, 15.28.1.2, 16.28.1.2, 17.28.1.2, 18.28.1.2, 19.28.1.2, 20.28.1.2, 21.28.1.2, 22.28.1.2, 23.28.1.2, 24.28.1.2, 25.28.1.2, 26.28.1.2, 27.28.1.2, 28.28.1.2, 29.28.1.2, 30.28.1.2, 31.28.1.2, 32.28.1.2, 33.28.1.2, 34.28.1.2, 35.28.1.2, 36.28.1.2, 37.28.1.2, 38.28.1.2, 39.28.1.2, 40.28.1.2, 1.29.1.2, 2.29.1.2, 3.29.1.2, 4.29.1.2, 5.29.1.2, 6.29.1.2, 7.29.1.2, 8.29.1.2, 9.29.1.2, 10.29.1.2, 11.29.1.2, 12.29.1.2, 13.29.1.2, 14.29.1.2, 15.29.1.2, 16.29.1.2, 17.29.1.2, 18.29.1.2, 19.29.1.2, 20.29.1.2, 21.29.1.2, 22.29.1.2, 23.29.1.2, 24.29.1.2, 25.29.1.2, 26.29.1.2, 27.29.1.2, 28.29.1.2, 29.29.1.2, 30.29.1.2, 31.29.1.2, 32.29.1.2, 33.29.1.2, 34.29.1.2, 35.29.1.2, 36.29.1.2, 37.29.1.2, 38.29.1.2, 39.29.1.2, 40.29.1.2, 1.1.3.1, 2.1.3.1, 3.1.3.1, 4.1.3.1, 5.1.3.1, 6.1.3.1, 7.1.3.1, 8.1.3.1, 9.1.3.1, 10.1.3.1, 11.1.3.1, 12.1.3.1, 13.1.3.1, 14.1.3.1, 15.1.3.1, 16.1.3.1, 17.1.3.1, 18.1.3.1, 19.1.3.1, 20.1.3.1, 21.1.3.1, 22.1.3.1, 23.1.3.1, 24.1.3.1, 25.1.3.1, 26.1.3.1, 27.1.3.1, 28.1.3.1, 29.1.3.1, 30.1.3.1, 31.1.3.1, 32.1.3.1, 33.1.3.1, 34.1.3.1, 35.1.3.1, 36.1.3.1, 37.1.3.1, 38.1.3.1, 39.1.3.1, 40.1.3.1, 1.2.3.1, 2.2.3.1, 3.2.3.1, 4.2.3.1, 5.2.3.1, 6.2.3.1, 7.2.3.1, 8.2.3.1, 9.2.3.1, 10.2.3.1, 11.2.3.1, 12.2.3.1, 13.2.3.1, 14.2.3.1, 15.2.3.1, 16.2.3.1, 17.2.3.1, 18.2.3.1, 19.2.3.1, 20.2.3.1, 21.2.3.1, 22.2.3.1, 23.2.3.1, 24.2.3.1, 25.2.3.1, 26.2.3.1, 27.2.3.1, 28.2.3.1, 29.2.3.1, 30.2.3.1, 31.2.3.1, 32.2.3.1, 33.2.3.1, 34.2.3.1, 35.2.3.1, 36.2.3.1, 37.2.3.1, 38.2.3.1, 39.2.3.1, 40.2.3.1, 1.3.3.1, 2.3.3.1, 3.3.3.1, 4.3.3.1, 5.3.3.1, 6.3.3.1, 7.3.3.1, 8.3.3.1, 9.3.3.1, 10.3.3.1, 11.3.3.1, 12.3.3.1, 13.3.3.1, 14.3.3.1, 15.3.3.1, 16.3.3.1, 17.3.3.1, 18.3.3.1, 19.3.3.1, 20.3.3.1, 21.3.3.1, 22.3.3.1, 23.3.3.1, 24.3.3.1, 25.3.3.1, 26.3.3.1, 27.3.3.1, 28.3.3.1, 29.3.3.1, 30.3.3.1, 31.3.3.1, 32.3.3.1, 33.33.1, 34.3.3.1, 35.3.3.1, 36.3.3.1, 37.3.3.1, 38.3.3.1, 39.3.3.1, 40.3.3.1, 1.4.3.1, 2.4.3.1, 3.4.3.1, 4.4.3.1, 5.4.3.1, 6.4.3.1, 7.4.3.1, 8.4.3.1, 9.4.3.1, 10.4.3.1, 11.4.3.1, 12.4.3.1, 13.4.3.1, 14.4.3.1, 15.4.3.1, 16.4.3.1, 17.4.3.1, 18.4.3.1, 19.4.3.1, 20.4.3.1, 21.4.3.1, 22.4.3.1, 23.4.3.1, 24.4.3.1, 25.4.3.1, 26.4.3.1, 27.4.3.1, 28.4.3.1, 29.4.3.1, 30.4.3.1, 31.4.3.1, 32.4.3.1, 33.4.3.1, 34.4.3.1, 35.4.3.1, 36.4.3.1, 37.4.3.1, 38.4.3.1, 39.4.3.1, 40.4.3.1, 1.5.3.1, 2.5.3.1, 3.5.3.1, 4.5.3.1, 5.5.3.1, 6.5.3.1, 7.5.3.1, 8.5.3.1, 9.5.3.1, 10.5.3.1, 11.5.3.1, 12.5.3.1, 13.5.3.1, 14.5.3.1, 15.5.3.1, 16.5.3.1, 17.5.3.1, 18.5.3.1, 19.5.3.1, 20.5.3.1, 21.5.3.1, 22.5.3.1, 23.5.3.1, 24.5.3.1, 25.5.3.1, 26.5.3.1, 27.5.3.1, 28.5.3.1, 29.5.3.1, 30.5.3.1, 31.5.3.1, 32.5.3.1, 33.5.3.1, 34.5.3.1, 35.5.3.1, 36.5.3.1, 37.5.3.1, 38.5.3.1, 39.5.3.1, 40.5.3.1, 1.6.3.1, 2.6.3.1, 3.6.3.1, 4.6.3.1, 5.6.3.1, 6.6.3.1, 7.6.3.1, 8.6.3.1, 9.6.3.1, 10.6.3.1, 11.6.3.1, 12.6.3.1, 13.6.3.1, 14.6.3.1, 15.6.3.1, 16.6.3.1, 17.6.3.1, 18.6.3.1, 19.6.3.1, 20.6.3.1, 21.6.3.1, 22.6.3.1, 23.6.3.1, 24.6.3.1, 25.6.3.1, 26.6.3.1, 27.6.3.1, 28.6.3.1, 29.6.3.1, 30.6.3.1, 31.6.3.1, 32.6.3.1, 33.6.3.1, 34.6.3.1, 35.6.3.1, 36.6.3.1, 37.6.3.1, 38.6.3.1, 39.6.3.1, 40.6.3.1, 1.7.3.1, 2.7.3.1, 3.7.3.1, 4.7.3.1, 5.7.3.1, 6.7.3.1, 7.7.3.1, 8.7.3.1, 9.7.3.1, 10.7.3.1, 11.7.3.1, 12.7.3.1, 13.7.3.1, 14.7.3.1, 15.7.3.1, 16.7.3.1, 17.7.3.1, 18.7.3.1, 19.7.3.1, 20.7.3.1, 21.7.3.1, 22.7.3.1, 23.7.3.1, 24.7.3.1, 25.7.3.1, 26.7.3.1, 27.7.3.1, 28.7.3.1, 29.7.3.1, 30.7.3.1, 31.7.3.1, 32.7.3.1, 33.7.3.1, 34.7.3.1, 35.7.3.1, 36.7.3.1, 37.7.3.1, 38.7.3.1, 39.7.3.1, 40.7.3.1, 1.8.3.1, 2.8.3.1, 3.8.3.1, 4.8.3.1, 5.8.3.1, 6.8.3.1, 7.8.3.1, 8.8.3.1, 9.8.3.1, 10.8.3.1, 11.8.3.1, 12.8.3.1, 13.8.3.1, 14.8.3.1, 15.8.3.1, 16.8.3.1, 17.8.3.1, 18.8.3.1, 19.8.3.1, 20.8.3.1, 21.8.3.1, 22.8.3.1, 23.8.3.1, 24.8.3.1, 25.8.3.1, 26.8.3.1, 27.8.3.1, 28.8.3.1, 29.8.3.1, 30.8.3.1, 31.8.3.1, 32.8.3.1, 33.8.3.1, 34.8.3.1, 35.8.3.1, 36.8.3.1, 37.8.3.1, 38.8.3.1, 39.8.3.1, 40.8.3.1, 1.9.3.1, 2.9.3.1, 3.9.3.1, 4.9.3.1, 5.9.3.1, 6.9.3.1, 7.9.3.1, 8.9.3.1, 9.9.3.1, 10.9.3.1, 11.9.3.1, 12.9.3.1, 13.9.3.1, 14.9.3.1, 15.9.3.1, 16.9.3.1, 17.9.3.1, 18.9.3.1, 19.9.3.1, 20.9.3.1, 21.9.3.1, 22.9.3.1, 23.9.3.1, 24.9.3.1, 25.9.3.1, 26.9.3.1, 27.9.3.1, 28.9.3.1, 29.9.3.1, 30.9.3.1, 31.9.3.1, 32.9.3.1, 33.9.3.1, 34.9.3.1, 35.9.3.1, 36.9.3.1, 37.9.3.1, 38.9.3.1, 39.9.3.1, 40.9.3.1, 1.10.3.1, 2.10.3.1, 3.10.3.1, 4.10.3.1, 5.10.3.1, 6.10.3.1, 7.10.3.1, 8.10.3.1, 9.10.3.1, 10.10.3.1, 11.10.3.1, 12.10.3.1, 13.10.3.1, 14.10.3.1, 15.10.3.1, 16.10.3.1, 17.10.3.1, 18.10.3.1, 19.10.3.1, 20.10.3.1, 21.10.3.1, 22.10.3.1, 23.10.3.1, 24.10.3.1, 25.10.3.1, 26.10.3.1, 27.10.3.1, 28.10.3.1, 29.10.3.1, 30.10.3.1, 31.10.3.1, 32.10.3.1, 33.10.3.1, 34.10.3.1, 35.10.3.1, 36.10.3.1, 37.10.3.1, 38.10.3.1, 39.10.3.1, 40.10.3.1, 1.11.3.1, 2.11.3.1, 32.11.3.1, 4.11.3.1, 5.11.3.1, 6.11.3.1, 7.11.3.1, 8.11.3.1, 9.11.3.1, 10.11.3.1, 11.11.3.1, 12.11.3.1, 13.11.3.1, 14.11.3.1, 15.11.3.1, 16.11.3.1, 17.11.3.1, 18.11.3.1, 19.11.3.1, 20.11.3.1, 21.11.3.1, 22.11.3.1, 23.11.3.1, 24.11.3.1, 25.11.3.1, 26.11.3.1, 27.11.3.1, 28.11.3.1, 29.11.31, 30.11.3.1, 31.11.3.1, 32.11.3.1, 33.11.13.1, 34.11.3.1, 35.11.3.1, 36.11.3.1, 37.11.3.1, 38.11.3.1, 39.11.3.1, 40.11.3.1, 1.12.3.1, 2.12.3.1, 3.12.3.1, 4.12.3.1, 5.12.3.1, 6.12.3.1, 7.12.3.1, 8.12.3.1, 9.12.3.1, 10.12.3.1, 11.12.3.1, 12.12.3.1, 13.12.3.1, 14.12.3.1, 15.12.3.1, 16.12.3.1, 17.12.3.1, 18.12.3.1, 19.12.3.1, 20.12.3.1, 21.12.3.1, 22.12.3.1, 23.12.3.1, 24.12.3.1, 25.12.3.1, 26.12.3.1, 27.12.3.1, 28.12.3.1, 29.12.3.1, 30.12.3.1, 31.12 3.1, 32.12.3.1, 33.12.3.1, 34.12.3.1, 35.12.3.1, 36.12.3.1, 37.12.3.1, 38.12.3.1, 39.12.3.1, 40.12.3.1, 1.13.3.1, 2.13.3.1, 3.13.3.1, 4.13.3.1, 5.13.3.1, 6.13.3.1, 7.13.3.1, 8.13.3.1, 9.13.3.1, 10.13.3.1, 11.13.3.1, 12.13.3.1, 13.13.3.1, 14.13.3.1, 15.13.3.1, 16.13.3.1, 17.13.3.1, 18.13.3.1, 19.13.3.1, 20.13.3.1, 21.13.3.1, 22.13.3.1, 23.13.3.1, 24.13.3.1, 25.13.3.1, 26.13.3.1, 27.13.3.1, 28.13.3.1, 29.13.3.1, 30.13.3.1, 31.13.3.1, 32.13.3.1, 33.13.3.1, 34.13.3.1, 35.13.3.1, 36.13.3.1, 37.13.3.1, 38.13.3.1, 39.13.3.1, 40.13.3.1, 1.14.3.1, 2.14.3.1, 3.14.3.1, 4.14.3.1, 5.14.3.1, 6.14.3.1, 7.14.3.1, 8.14.3.1, 9.14.3.1, 10.14.3.1, 11.14.3.1, 12.14.3.1, 13.14.3.1, 14.14.3.1, 15.14.3.1, 16.14.3.1, 17.14.3.1, 18.14.3.1, 19.14.3.1, 20.14.3.1, 21.14.3.1, 22.14.3.1, 23.14.3.1, 24.14.3.1, 25.14.3.1, 26.14.3.1, 27.14.3.1, 28.14.3.1, 29.14.3.1, 30.14.3.1, 31.14.3.1, 32.14.3.1, 33.14.3.1, 34.14.3.1, 35.14.3.1, 36.14.3.1, 37.14.3.1, 38.14.3.1, 39.14.3.1, 40.14.3.1, 1.15.3.1, 2.15.3.1, 3.15.3.1, 4.15.3.1, 5.15.3.1, 6.15.3.1, 7.15.3.1, 8.15.3.1, 9.15.3.1, 10.15.3.1, 11.15.3.1, 12.15.3.1, 13.15.3.1, 14.15.3.1, 15.15.3.1, 16.15.3.1, 17.15.3.1, 18.15.3.1, 19.15.3.1, 20.15.3.1, 21.15.3.1, 22.15.3.1, 23.15.3.1, 24.15.3.1, 25.15.3.1, 26.15.3.1, 27.15.3.1, 28.15.3.1, 29.15.3.1, 30.15.3.1, 31.15.3.1, 32.15.3.1, 33.15.3.1, 34.15.3.1, 35.15.3.1, 36.15.3.1, 37.15.3.1, 38.15.3.1, 39.15.3.1, 40.15.3.1, 1.16.3.1, 2.16.3.1, 3.16.3.1, 4.16.3.1, 5.16.3.1, 6.16.3.1, 7.16.3.1, 8.16.3.1, 9.16.3.1, 10.16.3.1, 11.16.3.1, 12.16.3.1, 13.16.3.1, 14.16.3.1, 15.16.3.1, 16.16.3.1, 17.16.3.1, 18.16.3.1, 19.16.3.1, 20.16.3.1, 21.16.3.1, 22.16.3.1, 23.16.3.1, 24.16.3.1, 25.16.3.1, 26.16.3.1, 27.16.3.1, 28.16.3.1, 29.16.3.1, 30.16.3.1, 31.16.3.1, 32.16.3.1, 33.16.3.1, 34.16.3.1, 35.16.3.1, 36.16.3.1, 37.16.3.1, 38.16.3.1, 39.16.3.1, 40.16.3.1, 1.17.3.1, 2.17.3.1, 3.17.3.1, 4.17.3.1, 5.17.3.1, 6.17.3.1, 7.17.3.1, 8.17.3.1, 9.17.3.1, 10.17.3.1, 11.17.3.1, 12.17.3.1, 13.17.3.1, 14.17.3.1, 15.17.3.1, 16.17.3.1, 17.17.3.1, 18.17.3.1, 19.17.3.1, 20.17.3.1, 21.17.3.1, 22.17.3.1, 23.17.3.1, 24.17.3.1, 25.17.3.1, 26.17.3.1, 27.17.3.1, 28.17.3.1, 29.17.3.1, 30.17.3.1, 31.17.3.1, 32.17.3.1, 33.17.3.1, 34.17.3.1, 35.17.3.1, 36.17.3.1, 37.17.3.1, 38.17.3.1, 39.17.3.1, 40.17.3.1, 1.18.3.1, 2.18.3.1, 3.18.3.1, 4.18.3.1, 5.18.3.1, 6.18.3.1, 7.18.3.1, 8.18.3.1, 9.18.3.1, 10.18.3.1, 11.18.3.1, 12.18.3.1, 13.18.3.1, 14.18.3.1, 15.18.3.1, 16.18.3.1, 17.18.3.1, 18.18.3.1, 19.18.3.1, 20.18.3.1, 21.18.3.1, 22.18.3.1, 23.18.3.1, 24.18.3.1, 25.18.3.1, 26.18.3.1, 27.18.3.1, 28.18.3.1, 29.18.3.1, 30.18.3.1, 31.18.3.1, 32.18.3.1, 33.18.3.1, 34.18.3.1, 35.18.3.1, 36.18.3.1, 37.18.3.1, 38.18.3.1, 39.18.3.1, 40.18.3.1, 1.19.3.1, 2.19.3.1, 3.19.3.1, 4.19.3.1, 5.19.3.1, 6.19.3.1, 7.19.3.1, 8.19.3.1, 9.19.3.1, 10.19.3.1, 11.19.3.1, 12.19.3.1, 13.19.3.1, 14.19.3.1, 15.19.3.1, 16.19.3.1, 17.19.3.1, 18.19.3.1, 19.19.3.1, 20.19.3.1, 21.19.3.1, 22.19.3.1, 23.19.3.1, 24.19.3.1, 25.19.3.1, 26.19.3.1, 27.19.3.1, 28.19.3.1, 29.19.3.1, 30.19.3.1, 31.19.3.1, 32.19.3.1, 33.19.3.1, 34.19.3.1, 35.19.3.1, 36.19.3.1, 37.19.3.1, 38.19.3.1, 39.19.3.1, 40.19.3.1, 1.20.3.1, 2.20.3.1, 3.20.3.1, 4.20.3.1, 5.20.3.1, 6.20.3.1, 7.20.3.1, 8.20.3.1, 9.20.3.1, 10.20.3.1, 11.20.3.1, 12.20.3.1, 13.20.3.1, 14.20.3.1, 15.20.3.1, 16.20.3.1, 17.20.3.1, 18.20.3.1, 19.20.3.1, 20.20.3.1, 21.20.3.1, 22.20.3.1, 23.20.3.1, 24.20.3.1, 25.20.3.1, 26.20.3.1, 27.20.3.1, 28.20.3.1, 29.20.3.1, 30.20.3.1, 31.20.3.1, 32.20.3.1, 33.20.3.1, 34.20.3.1, 35.20.3.1, 36.20.3.1, 37.20.3.1, 38.20.3.1, 39.20.3.1, 40.20.3.1, 1.21.3.1, 2.21.3.1, 3.21.3.1, 4.21.3.1, 5.21.3.1, 6.21.3.1, 7.21.3.1, 8.21.3.1, 9.21.3.1, 10.21.3.1, 11.21.3.1, 12.21.3.1, 13.21.3.1, 14.21.3.1, 15.21.3.1, 16.21.3.1, 17.21.3.1, 18.21.3.1, 19.21.3.1, 20.21.3.1, 21.21.3.1, 22.21.3.1, 23.21.3.1, 24.21.3.1, 25.21.3.1, 26.21.3.1, 27.21.3.1, 28.21.3.1, 29.21.3.1, 30.21.3.1, 31.21.3.1, 32.21.3.1, 33.21.3.1, 34.21.3.1, 35.21.3.1, 36.21.3.1, 37.21.3.1, 38.21.3.1, 39.21.3.1, 40.21.3.1, 1.22.3.1, 2.22.3.1, 3.22.3.1, 4.22.3.1, 5.22.3.1, 6.22.3.1, 7.22.3.1, 8.22.3.1, 9.22.3.1, 10.22.3.1, 11.22.3.1, 12.22.3.1, 13.22.3.1, 14.22.3.1, 15.22.3.1, 16.22.3.1, 17.22.3.1, 18.22.3.1, 19.22.3.1, 20.22.3.1, 21.22.3.1, 22.22.3.1, 23.22.3.1, 24.22.3.1, 25.22.3.1, 26.22.3.1, 27.22.3.1, 28.22.3.1, 29.22.3.1, 30.22.3.1, 31.22.3.1, 32.22.3.1, 33.22.3.1, 34.22.3.1, 35.22.3.1, 36.22.3.1, 37.22.3.1, 38.22.3.1, 39.22.3.1, 40.22.3.1, 1.23.3.1, 2.23.3.1, 3.23.3.1, 4.23.3.1, 5.23.3.1, 6.23.3.1, 7.23.3.1, 8.23.3.1, 9.23.3.1, 10.23.3.1, 11.23.3.1, 12.23.3.1, 13.23.3.1, 14.23.3.1, 15.23.3.1, 16.23.3.1, 17.23.3.1, 18.23.3.1, 19.23.3.1, 20.23.3.1, 21.23.3.1, 22.23.3.1, 23.23.3.1, 24.23.3.1, 25.23.3.1, 26.23.3.1, 27.23.3.1, 28.23.3.1, 29.23.3.1, 30.23.3.1, 31.23.3.1, 32.23.3.1, 33.23.3.1, 34.23.3.1, 35.23.3.1, 36.23.3.1, 37.23.3.1, 38.23.3.1, 39.23.3.1, 40.23.3.1, 1.24.3.1, 2.24.3.1, 3.24.3.1, 4.24.3.1, 5.24.3.1, 6.24.3.1, 7.24.3.1, 8.24.3.1, 9.24.3.1, 10.24.3.1, 11.24.3.1, 12.24.3.1, 13.24.3.1, 14.24.3.1, 15.24.3.1, 16.24.3.1, 17.24.3.1, 18.24.3.1, 19.24.3.1, 20.24.3.1, 21.24.3.1, 22.24.3.1, 23.24.3.1, 24.24.3.1, 25.24.3.1, 26.24.3.1, 27.24.3.1, 28.24.3.1, 29.24.3.1, 30.24.3.1, 31.24.3.1, 32.24.3.1, 33.24.3.1, 34.24.3.1, 35.24.3.1, 36.24.3.1, 37.24.3.1, 38.24.3.1, 39.24.3.1, 40.24.3.1, 1.25.3.1, 2.25.3.1, 3.25.3.1, 4.25.3.1, 5.25.3.1, 6.25.3.1, 7.25.3.1, 8.25.3.1, 9.25.3.1, 10.25.3.1, 11.25.3.1, 12.25.3.1, 13.25.3.1, 14.25.3.1, 15.25.3.1, 16.25.3.1, 17.25.3.1, 18.25.3.1, 19.25.3.1, 20.25.3.1, 21.25.3.1, 22.25.3.1, 23.25.3.1, 24.25.3.1, 25.25.3.1, 26.25.3.1, 27.25.3.1, 28.25.3.1, 29.25.3.1, 30.25.3.1, 31.25.3.1, 32.25.3.1, 33.25.3.1, 34.25.3.1, 35.25.3.1, 36.25.3.1, 37.25.3.1, 38.25.3.1, 39.25.3.1, 40.25.3.1, 1.26.3.1, 2.26.3.1, 3.26.3.1, 4.26.3.1, 5.26.3.1, 6.26.3.1, 7.26.3.1, 8.26.3.1, 9.26.3.1, 10.26.3.1, 11.26.3.1, 12.26.3.1, 13.26.3.1, 14.26.3.1, 15.26.3.1, 16.26.3.1, 17.26.3.1, 18.26.3.1, 19.26.3.1, 20.26.3.1, 21.26.3.1, 22.26.3.1, 23.26.3.1, 24.26.3.1, 25.26.3.1, 26.26.3.1, 27.26.3.1, 28.26.3.1, 29.26.3.1, 30.26.3.1, 31.26.3.1, 32.26.3.1, 33.26.3.1, 34.26.3.1, 35.26.3.1, 36.26.3.1, 37.26.3.1, 38.26.3.1, 39.26.3.1, 40.26.3.1, 1.27.3.1, 2.27.3.1, 3.27.3.1, 4.27.3.1, 5.27.3.1, 6.27.3.1, 7.27.3.1, 8.27.3.1, 9.27.3.1, 10.27.3.1, 11.27.3.1, 12.27.3.1, 13.27.3.1, 14.27.3.1, 15.27.3.1, 16.27.3.1, 17.27.3.1, 18.27.3.1, 19.27.3.1, 20.27.3.1, 21.27.3.1, 22.27.3.1, 23.27.3.1, 24.27.3.1, 25.27.3.1, 26.27.3.1, 27.27.3.1, 28.27.3.1, 29.27.3.1, 30.27.3.1, 31.27.3.1, 32.27.3.1, 33.27.3.1, 34.27.3.1, 35.27.3.1, 36.27.3.1, 37.27.3.1, 38.27.3.1, 39.27.3.1, 40.27.3.1, 1.28.3.1, 2.28.3.1, 3.28.3.1, 4.28.3.1, 5.28.3.1, 6.28.3.1, 7.28.3.1, 8.28.3.1, 9.28.3.1, 10.28.3.1, 11.28.3.1, 12.28.3.1, 13.28.3.1, 14.28.3.1, 15.28.3.1, 16.28.3.1, 17.28.3.1, 18.28.3.1, 19.28.3.1, 20.28.3.1, 21.28.3.1, 22.28.3.1, 23.28.3.1, 24.28.3.1, 25.28.3.1, 26.28.3.1, 27.28.3.1, 28.28.3.1, 29.28.3.1, 30.28.3.1, 31.28.3.1, 32.28.3.1, 33.28.3.1, 34.28.3.1, 35.28.3.1, 36.28.3.1, 37.28.3.1, 38.28.3.1, 39.28.3.1, 40.28.3.1, 1.29.3.1, 2.29.3.1, 3.29.3.1, 4.29.3.1, 5.29.3.1, 6.29.3.1, 7.29.3.1, 8.29.3.1, 9.29.3.1, 10.29.3.1, 11.29.3.1, 12.29.3.1, 13.29.3.1, 14.29.3.1, 15.29.3.1, 16.29.3.1, 17.29.3.1, 18.29.3.1, 19.29.3.1, 20.29.3.1, 21.29.3.1, 22.29.3.1, 23.29.3.1, 24.29.3.1, 25.29.3.1, 26.29.3.1, 27.29.3.1, 28.29.3.1, 29.29.3.1, 30.29.3.1, 31.29.3.1, 32.29.3.1, 33.29.3.1, 34.29.3.1, 35.29.3.11, 36.29.3.1, 37.29.3.1, 38.29.3.1, 39.29.3.1, 40.29.3.1, 1.1.3.2, 2.1.3.2, 3.1.3.2, 4.1.3.2, 5.1.3.2, 6.1.3.2, 7.1.3.2, 8.1.3.2, 9.1.3.2, 10.1.3.2, 11.1.3.2, 12.1.3.2, 13.1.3.2, 14.1.3.2, 15.1.3.2, 16.1.3.2, 17.1.3.2, 18.1.3.2, 19.1.3.2, 20.1.3.2, 21.1.3.2, 22.1.3.2, 23.1.3.2, 24.1.3.2, 25.1.3.2, 26.1.3.2, 27.1.3.2, 28.1.3.2, 29.1.3.2, 30.1.3.2, 31.1.3.2, 32.1.3.2, 33.1.3.2, 34.1.3.2, 35.1.3.2, 36.1.3.2, 37.1.3.2, 38.1.3.2, 39.1.3.2, 40.1.3.2, 1.2.3.2, 2.2.3.2, 3.2.3.2, 4.2.3.2, 5.2.3.2, 6.2.3.2, 7.2.3.2, 8.2.3.2, 9.2.3.2, 10.2.3.2, 11.2.3.2, 12.2.3.2, 13.2.3.2, 14.2.3.2, 15.2.3.2, 16.2.3.2, 17.2.3.2, 18.2.3.2, 19.2.3.2, 20.2.3.2, 21.2.3.2, 22.2.3.2, 23.2.3.2, 24.2.3.2, 25.2.3.2, 26.2.3.2, 27.2.3.2, 28.2.3.2, 29.2.3.2, 30.2.3.2, 31.2.3.2, 32.2.3.2, 33.2.3.2, 34.2.3.2, 35.2.3.2, 36.2.3.2, 37.2.3.2, 38.2.3.2, 39.2.3.2, 40.2.3.2, 1.3.3.2, 2.3.3.2, 3.3.3.2, 4.3.3.2, 5.3.3.2, 6.3.3.2, 7.3.3.2, 8.3.3.2, 9.3.3.2, 10.3.3.2, 11.3.3.2, 12.3.3.2, 13.3.3.2, 14.3.3.2, 15.3.3.2, 16.3.3.2, 17.3.3.2, 18.3.3.2, 19.3.3.2, 20.3.3.2, 21.3.3.2, 22.3.3.2, 23.3.3.2, 24.3.3.2, 25.3.3.2, 26.3.3.2, 27.3.3.2, 28.3.3.2, 29.3.3.2, 30.3.3.2, 31.3.3.2, 32.3.3.2, 33.3.3.2, 34.3.3.2, 35.3.3.2, 36.3.3.2, 37.3.3.2, 38.3.3.2, 39.3.3.2, 40.3.3.2, 1.4.3.2, 2.4.3.2, 3.4.3.2, 4.4.3.2, 5.4.3.2, 6.4.3.2, 7.4.3.2, 8.4.3.2, 9.4.3.2, 10.4.3.2, 11.4.3.2, 12.4.3.2, 13.4.3.2, 14.4.3.2, 15.4.3.2, 16.4.3.2, 17.4.3.2, 18.4.3.2, 19.4.3.2, 20.4.3.2, 21.4.3.2, 22.4.3.2, 23.4.3.2, 24.4.3.2, 25.4.3.2, 26.4.3.2, 27.4.3.2, 28.4.3.2, 29.4.3.2, 30.4.3.2, 31.4.3.2, 32.4.3.2, 33.4.3.2, 34.4.3.2, 35.4.3.2, 36.4.3.2, 37.4.3.2, 38.4.3.2, 39.4.3.2, 40.4.3.2, 1.5.3.2, 2.5.3.2, 3.5.3.2, 4.5.3.2, 5.5.3.2, 6.5.3.2, 7.5.3.2, 8.5.3.2, 9.5.3.2, 10.5.3.2, 11.5.3.2, 12.5.3.2, 13.5.3.2, 14.5.3.2, 15.5.3.2, 16.5.3.2, 17.5.3.2, 18.5.3.2, 19.5.3.2, 20.5.3.2, 21.5.3.2, 22.5.3.2, 23.5.3.2, 24.5.3.2, 25.5.3.2, 26.5.3.2, 27.5.3.2, 28.5.3.2, 29.5.3.2, 30.5.3.2, 31.5.3.2, 32.5.3.2, 33.5.3.2, 34.5.3.2, 35.5.3.2, 36.5.3.2, 37.5.3.2, 38.5.3.2, 39.5.3.2, 40.5.3.2, 1.6.3.2, 2.6.3.2, 3.6.3.2, 4.6.3.2, 5.6.3.2, 6.6.3.2, 7.6.3.2, 8.6.3.2, 9.6.3.2, 10.6.3.2, 11.6.3.2, 12.6.3.2, 13.6.3.2, 14.6.3.2, 15.6.3.2, 16.6.3.2, 17.6.3.2, 18.6.3.2, 19.6.3.2, 20.6.3.2, 21.6.3.2, 22.6.3.2, 23.6.3.2, 24.6.3.2, 25.6.3.2, 26.6.3.2, 27.6.3.2, 28.6.3.2, 29.6.3.2, 30.6.3.2, 31.6.3.2, 32.6.3.2, 33.6.3.2, 34.6.3.2, 35.6.3.2, 36.6.3.2, 37.6.3.2, 38.6.3.2, 39.6.3.2, 40.6.3.2, 1.7.3.2, 2.7.3.2, 3.7.3.2, 4.7.3.2, 5.7.3.2, 6.7.3.2, 7.7.3.2, 8.7.3.2, 9.7.3.2, 10.7.3.2, 11.7.3.2, 12.7.3.2, 13.7.3.2, 14.7.3.2, 15.7.3.2, 16.7.3.2, 17.7.3.2, 18.7.3.2, 19.7.3.2, 20.7.3.2, 21.7.3.2, 22.7.3.2, 23.7.3.2, 24.7.3.2, 25.7.3.2, 26.7.3.2, 27.7.3.2, 28.7.3.2, 29.7.3.2, 30.7.3.2, 31.7.3.2, 32.7.3.2, 33.7.3.2, 34.7.3.2, 35.7.3.2, 36.7.3.2, 37.7.3.2, 38.7.3.2, 39.7.3.2, 40.7.3.2, 1.8.3.2, 2.8.3.2, 3.8.3.2, 4.8.3.2, 5.8.3.2, 6.8.3.2, 7.8.3.2, 8.8.3.2, 9.8.3.2, 10.8.3.2, 11.8.3.2, 12.8.3.2, 13.8.3.2, 14.8.3.2, 15.8.3.2, 16.8.3.2, 17.8.3.2, 18.8.3.2, 19.8.3.2, 20.8.3.2, 21.8.3.2, 22.8.3.2, 23.8.3.2, 24.8.3.2, 25.8.3.2, 26.8.3.2, 27.8.3.2, 28.8.3.2, 29.8.3.2, 30.8.3.2, 31.8.3.2, 32.8.3.2, 33.8.3.2, 34.8.3.2, 35.8.3.2, 36.8.3.2, 37.8.3.2, 38.8.3.2, 39.8.3.2, 40.8.3.2, 1.9.3.2, 2.9.3.2, 3.9.3.2, 4.9.3.2, 5.9.3.2, 6.9.3.2, 7.9.3.2, 8.9.3.2, 9.9.3.2, 10.9.3.2, 11.9.3.2, 12.9.3.2, 13.9.3.2, 14.9.3.2, 15.9.3.2, 16.9.3.2, 17.9.3.2, 18.9.3.2, 19.9.3.2, 20.9.3.2, 21.9.3.2, 22.9.3.2, 23.9.3.2, 24.9.3.2, 25.9.3.2, 26.9.3.2, 27.9.3.2, 28.9.3.2, 29.9.3.2, 30.9.3.2, 31.9.3.2, 32.9.3.2, 33.9.3.2, 34.9.3.2, 35.9.3.2, 36.9.3.2, 37.9.3.2, 38.9.3.2, 39.9.3.2, 40.9.3.2, 1.10.3.2, 2.10.3.2, 3.10.3.2, 4.10.3.2, 5.10.3.2, 6.10.3.2, 7.10.3.2, 8.10.3.2, 9.10.3.2, 10.10.3.2, 11.10.3.2, 12.10.3.2, 13.10.3.2, 14.10.3.2, 15.10.3.2, 16.10.3.2, 17.10.3.2, 18.10.3.2, 19.10.3.2, 20.10.3.2, 21.10.3.2, 22.10.3.2, 23.10.3.2, 24.10.3.2, 25.10.3.2, 26.10.3.2, 27.10.3.2, 28.10.3.2, 29.10.3.2, 30.10.3.2, 31.10.3.2, 32.10.3.2, 33.10.3.2, 34.10.3.2, 35.10.3.2, 36.10.3.2, 37.10.3.2, 38.10.3.2, 39.10.3.2, 40.10.3.2, 1.11.3.2, 2.11.3.2, 3.11.3.2, 4.11.3.2, 5.11.3.2, 6.11.3.2, 7.11.3.2, 8.11.3.2, 9.11.3.2, 10.11.3.2, 11.11.3.2, 12.11.3.2, 13.11.3.2, 14.11.3.2, 15.11.3.2, 16.11.3.2, 17.11.3.2, 18.11.3.2, 19.11.3.2, 20.11.3.2, 21.11.3.2, 22.11.3.2, 23.11.3.2, 24.11.3.2, 25.11.3.2, 26.11.3.2, 27.11.3.2, 28.11.3.2, 29.11.3.2, 30.11.3.2, 31.11.3.2, 32.11.3.2, 33.11.3.2, 34.11.3.2, 35.11.3.2, 36.11.3.2, 37.11.3.2, 38.11.3.2, 39.11.3.2, 40.11.3.2, 1.12.3.2, 2.12.3.2, 3.12.3.2, 4.12.3.2, 5.12.3.2, 6.12.3.2, 7.12.3.2, 8.12.3.2, 9.12.3.2, 10.12.3.2, 11.12.3.2, 12.12.3.2, 13.12.3.2, 14.12.3.2, 15.12.3.2, 16.12.3.2, 17.12.3.2, 18.12.3.2, 19.12.3.2, 20.12.3.2, 21.12.3.2, 22.12.3.2, 23.12.3.2, 24.12.3.2, 25.12.3.2, 26.12.3.2, 27.12.3.2, 28.12.3.2, 29.12.3.2, 30.12.3.2, 31.12.3.2, 32.12.3.2, 33.12.3.2, 34.12.3.2, 35.12.3.2, 36.12.3.2, 37.12.3.2, 38.12.3.2, 39.12.3.2, 40.12.3.2, 1.13.3.2, 2.13.3.2, 3.13.3.2, 4.13.3.2, 5.13.3.2, 6.13.3.2, 7.13.3.2, 8.13.3.2, 9.13.3.2, 10.13.3.2, 11.13.3.2, 12.13.3.2, 13.13.3.2, 14.13.3.2, 15.13.3.2, 16.13.3.2, 17.13.3.2, 18.13.3.2, 19.13.3.2, 20.13.3.2, 21.13.3.2, 22.13.3.2, 23.13.3.2, 24.13.3.2, 25.13.3.2, 26.13.3.2, 27.13.3.2, 28.13.3.2, 29.13.3.2, 30.13.3.2, 31.13.3.2, 32.13.3.2, 33.13.3.2, 34.13.3.2, 35.13.3.2, 36.13.3.2, 37.13.3.2, 38.13.3.2, 39.13.3.2, 40.13.3.2, 1.14.3.2, 2.14.3.2, 3.14.3.2, 4.14.3.2, 5.14.3.2, 6.14.3.2, 7.14.3.2, 8.14.3.2, 9.14.3.2, 10.14.3.2, 11.14.3.2, 12.14.3.2, 13.14.3.2, 14.14.3.2, 15.14.3.2, 16.14.3.2, 17.14.3.2, 18.14.3.2, 19.14.3.2, 20.14.3.2, 21.14.3.2, 22.14.3.2, 23.14.3.2, 24.14.3.2, 25.14.3.2, 26.14.3.2, 27.14.3.2, 28.14.3.2, 29.14.3.2, 30.14.3.2, 31.14.3.2, 32.14.3.2, 33.14.3.2, 34.14.3.2, 35.14.3.2, 36.14.3.2, 37.14.3.2, 38.14.3.2, 39.14.3.2, 40.14.3.2, 1.15.3.2, 2.15.3.2, 3.15.3.2, 4.15.3.2, 5.15.3.2, 6.15.3.2, 7.15.3.2, 8.15.3.2, 9.15.3.2, 10.15.3.2, 11.15.3.2, 12.15.3.2, 13.15.3.2, 14.15.3.2, 15.15.3.2, 16.15.3.2, 17.15.3.2, 18.15.3.2, 19.15.3.2, 20.15.3.2, 21.15.3.2, 22.15.3.2, 23.15.3.2, 24.15.3.2, 25.15.3.2, 26.15.3.2, 27.15.3.2, 28.15.3.2, 29.15.3.2, 30.15.3.2, 31.15.3.2, 32.15.3.2, 33.15.3.2, 34.15.3.2, 35.15.3.2, 36.15.3.2, 37.15.3.2, 38.15.3.2, 39.15.3.2, 40.15.3.2, 1.16.3.2, 2.16.3.2, 3.16.3.2, 4.16.3.2, 5.16.3.2, 6.16.3.2, 7.16.3.2, 8.16.3.2, 9.16.3.2, 10.16.3.2, 11.16.3.2, 12.16.3.2, 13.16.3.2, 14.16.3.2, 15.16.3.2, 16.16.3.2, 17.16.3.2, 18.16.3.2, 19.16.3.2, 20.16.3.2, 21.16.3.2, 22.16.3.2, 23.16.3.2, 24.16.3.2, 25.16.3.2, 26.16.3.2, 27.16.3.2, 28.16.3.2, 29.16.3.2, 30.16.3.2, 31.16.3.2, 32.16.3.2, 33.16.3.2, 34.16.3.2, 35.16.3.2, 36.16.3.2, 37.16.3.2, 38.16.3.2, 39.16.3.2, 40.16.3.2, 1.17.3.2, 2.17.3.2, 3.17.3.2, 4.17.3.2, 5.17.3.2, 6.17.3.2, 7.17.3.2, 8.17.3.2, 9.17.3.2, 10.17.3.2, 11.17.3.2, 12.17.3.2, 13.17.3.2, 14.17.3.2, 15.17.3.2, 16.17.3.2, 17.17.3.2, 18.17.3.2, 19.17.3.2, 20.17.3.2, 21.17.3.2, 22.17.3.2, 23.17.3.2, 24.17.3.2, 25.17.3.2, 26.17.3.2, 27.17.3.2, 28.17.3.2, 29.17.3.2, 30.17.3.2, 31.17.3.2, 32.17.3.2, 33.17.3.2, 34.17.3.2, 35.17.3.2, 36.17.3.2, 37.17.3.2, 38.17.3.2, 39.17.3.2, 40.17.3.2, 1.18.3.2, 2.18.3.2, 3.18.3.2, 4.18.3.2, 5.18.3.2, 6.18.3.2, 7.18.3.2, 8.18.3.2, 9.18.3.2, 10.18.3.2, 11.18.3.2, 12.18.3.2, 13.18.3.2, 14.18.3.2, 15.18.3.2, 16.18.3.2, 17.18.3.2, 18.18.3.2, 19.18.3.2, 20.18.3.2, 21.18.3.2, 22.18.3.2, 23.18.3.2, 24.18.3.2, 25.18.3.2, 26.18.3.2, 27.18.3.2, 28.18.3.2, 29.18.3.2, 30.18.3.2, 31.18.3.2, 32.18.3.2, 33.18.3.2, 34.18.3.2, 35.18.3.2, 36.18.3.2, 37.18.3.2, 38.18.3.2, 39.18.3.2, 40.18.3.2, 1.19.3.2, 2.19.3.2, 3.19.3.2, 4.19.3.2, 5.19.3.2, 6.19.3.2, 7.19.3.2, 8.19.3.2, 9.19.3.2, 10.19.3.2, 11.19.3.2, 12.19.3.2, 13.19.3.2, 14.19.3.2, 15.19.3.2, 16.19.3.2, 17.19.3.2, 18.19.3.2, 19.19.3.2, 20.19.3.2, 21.19.3.2, 22.19.3.2, 23.19.3.2, 24.19.3.2, 25.19.3.2, 26.19.3.2, 27.19.3.2, 28.19.3.2, 29.19.3.2, 30.19.3.2, 31.19.3.2, 32.19.3.2, 33.19.3.2, 34.19.3.2, 35.19.3.2, 36.19.3.2, 37.19.3.2, 38.19.3.2, 39.19.3.2, 40.19.3.2, 1.20.3.2, 2.20.3.2, 3.20.3.2, 4.20.3.2, 5.20.3.2, 6.20.3.2, 7.20.3.2, 8.20.3.2, 9.20.3.2, 10.20.3.2, 11.20.3.2, 12.20.3.2, 13.20.3.2, 14.20.3.2, 15.20.3.2, 16.20.3.2, 17.20.3.2, 18.20.3.2, 19.20.3.2, 20.20.3.2, 21.20.3.2, 22.20.3.2, 23.20.3.2, 24.20.3.2, 25.20.3.2, 26.20.3.2, 27.20.3.2, 28.20.3.2, 29.20.3.2, 30.20.3.2, 31.20.3.2, 32.20.3.2, 33.20.3.2, 34.20.3.2, 35.20.3.2, 36.20.3.2, 37.20.3.2, 38.20.3.2, 39.20.3.2, 40.20.3.2, 1.21.3.2, 2.21.3.2, 3.21.3.2, 4.21.3.2, 5.21.3.2, 6.21.3.2, 7.21.3.2, 8.21.3.2, 9.21.3.2, 10.21.3.2, 11.21.3.2, 12.21.3.2, 13.21.3.2, 14.21.3.2, 15.21.3.2, 16.21.3.2, 17.21.3.2, 18.21.3.2, 19.21.3.2, 20.21.3.2, 21.21.3.2, 22.21.3.2, 23.21.3.2, 24.21.3.2, 25.21.3.2, 26.21.3.2, 27.21.3.2, 28.21.3.2, 29.21.3.2, 30.21.3.2, 31.21.3.2, 32.21.3.2, 33.21.3.2, 34.21.3.2, 35.21.3.2, 36.21.3.2, 37.21.3.2, 38.21.3.2, 39.21.3.2, 40.21.3.2, 1.22.3.2, 2.22.3.2, 3.22.3.2, 4.22.3.2, 5.22.3.2, 6.22.3.2, 7.22.3.2, 8.22.3.2, 9.22.3.2, 10.22.3.2, 11.22.3.2, 12.22.3.2, 13.22.3.2, 14.22.3.2, 15.22.3.2, 16.22.3.2, 17.22.3.2, 18.22.3.2, 19.22.3.2, 20.22.3.2, 21.22.3.2, 22.22.3.2, 23.22.3.2, 24.22.3.2, 25.22.3.2, 26.22.3.2, 27.22.3.2, 28.22.3.2, 29.22.3.2, 30.22.3.2, 31.22.3.2, 32.22.3.2, 33.22.3.2, 34.22.3.2, 35.22.3.2, 36.22.3.2, 37.22.3.2, 38.22.3.2, 39.22.3.2, 40.22.3.2, 1.23.3.2, 2.23.3.2, 3.23.3.2, 4.23.3.2, 5.23.3.2, 6.23.3.2, 7.23.3.2, 8.23.3.2, 9.23.3.2, 10.23.3.2, 11.23.3.2, 12.23.3.2, 13.23.3.2, 14.23.3.2, 15.23.3.2, 16.23.3.2, 17.23.3.2, 18.23.3.2, 19.23.3.2, 20.23.3.2, 21.23.3.2, 22.23.3.2, 23.23.3.2, 24.23.3.2, 25.23.3.2, 26.23.3.2, 27.23.3.2, 28.23.3.2, 29.23.3.2, 30.23.3.2, 31.23.3.2, 32.23.3.2, 33.23.3.2, 34.23.3.2, 35.23.3.2, 36.23.3.2, 37.23.3.2, 38.23.3.2, 39.23.3.2, 40.23.3.2, 1.24.3.2, 2.24.3.2, 3.24.3.2, 4.24.3.2, 5.24.3.2, 6.24.3.2, 7.24.3.2, 8.24.3.2, 9.24.3.2, 10.24.3.2, 11.24.3.2, 12.24.3.2, 13.24.3.2, 14.24.3.2, 15.24.3.2, 16.24.3.2, 17.24.3.2, 18.24.3.2, 19.24.3.2, 20.24.3.2, 21.24.3.2, 22.24.3.2, 23.24.3.2, 24.24.3.2, 25.24.3.2, 26.24.3.2, 27.24.3.2, 28.24.3.2, 29.24.3.2, 30.24.3.2, 31.24.3.2, 32.24.3.2, 33.24.3.2, 34.24.3.2, 35.24.3.2, 36.24.3.2, 37.24.3.2, 38.24.3.2, 39.24.3.2, 40.24.3.2, 1.25.3.2, 2.25.3.2, 3.25.3.2, 43.25.3.2, 6.25.3.2, 7.25.3.2, 8.25.3.2, 9.25.3.2, 10.25.3.2, 11.25.3.2, 12.25.3.2, 13.25.3.2, 14.25.3.2, 15.25.3.2, 16.25.3.2, 17.25.3.2, 18.25.3.2, 19.25.3.2, 20.25.3.2, 21.25.3.2, 22.25.3.2, 23.25.3.2, 24.25.3.2, 25.25.3.2, 26.25.3.2, 27.25.3.2, 28.25.3.2, 29.25.3.2, 30.25.3.2, 31.25.3.2, 32.25.3.2, 33.25.3.2, 34.25.3.2, 35.25.3.2, 36.25.3.2, 37.25.3.2, 38.25.3.2, 39.25.3.2, 40.25.3.2, 1.26.3.2, 2.26.3.2, 3.26.3.2, 43.26.3.2, 6.26.3.2, 7.26.3.2, 8.26.3.2, 9.26.3.2, 10.26.3.2, 11.26.3.2, 12.26.3.2, 13.26.3.2, 14.26.3.2, 15.26.3.2, 16.26.3.2, 17.26.3.2, 18.26.3.2, 19.26.3.2, 20.26.3.2, 21.26.3.2, 22.26.3.2, 23.26.3.2, 24.26.3.2, 25.26.3.2, 26.26.3.2, 27.26.3.2, 28.26.3.2, 29.26.3.2, 30.26.3.2, 31.26.3.2, 32.26.3.2, 33.26.3.2, 34.26.3.2, 35.26.3.2, 36.26.3.2, 37.26.3.2, 38.26.3.2, 39.26.3.2, 40.26.3.2, 1.27.3.2, 2.27.3.2, 3.27.3.2, 4.27.3.2, 5.27.3.2, 6.27.3.2, 7.27.3.2, 8.27.3.2, 9.27.3.2, 10.27.3.2, 11.27.3.2, 12.27.3.2, 13.27.3.2, 14.27.3.2, 15.27.3.2, 16.27.3.2, 17.27.3.2, 18.27.3.2, 19.27.3.2, 20.27.3.2, 21.27.3.2, 22.27.3.2, 23.27.3.2, 24.27.3.2, 25.27.3.2, 26.27.3.2, 27.27.3.2, 28.27.3.2, 29.27.3.2, 30.27.3.2, 31.27.3.2, 32.27.3.2, 33.27.3.2, 34.27.3.2, 35.27.3.2, 36.27.3.2, 37.27.3.2, 38.27.3.2, 39.27.3.2, 40.27.3.2, 1.28.3.2, 2.28.3.2, 3.28.3.2, 4.28.3.2, 5.28.3.2, 6.28.3.2, 7.28.3.2, 8.28.3.2, 9.28.3.2, 10.28.3.2, 11.28.3.2, 12.28.3.2, 13.28.3.2, 14.28.3.2, 15.28.3.2, 16.28.3.2, 17.28.3.2, 18.28.3.2, 19.28.3.2, 20.28.3.2, 21.28.3.2, 22.28.3.2, 23.28.3.2, 24.28.3.2, 25.28.3.2, 26.28.3.2, 27.28.3.2, 28.28.3.2, 29.28.3.2, 30.28.3.2, 31.28.3.2, 32.28.3.2, 33.28.3.2, 34.28.3.2, 35.28.3.2, 36.28.3.2, 37.28.3.2, 38.28.3.2, 39.28.3.2, 40.28.3.2, 1.29.3.2, 2.29.3.2, 3.29.3.2, 4.29.3.2, 5.29.3.2, 6.29.3.2, 7.29.3.2, 8.29.3.2, 9.29.3.2, 10.29.3.2, 11.29.3.2, 12.29.3.2, 13.29.3.2, 14.29.3.2, 15.29.3.2, 16.29.3.2, 17.29.3.2, 18.29.3.2, 19.29.3.2, 20.29.3.2, 21.29.3.2, 22.29.3.2, 23.29.3.2, 24.29.3.2, 25.29.3.2, 26.29.3.2, 27.29.3.2, 28.29.3.2, 29.29.3.2, 30.29.3.2, 31.29.3.2, 32.29.3.2, 33.29.3.2, 34.29.3.2, 35.29.3.2, 36.29.3.2, 37.29.3.2, 38.29.3.2, 39.29.3.2, 40.29.3.2, 1.1.3.4, 2.1.3.4, 3.1.3.4, 4.1.3.4, 5.1.3.4, 6.1.3.4, 7.1.3.4, 8.1.3.4, 9.1.3.4, 10.1.3.4, 11.1.3.4, 12.1.3.4, 13.1.3.4, 14.1.3.4, 15.1.3.4, 16.1.3.4, 17.1.3.4, 18.1.3.4, 19.1.3.4, 20.1.3.4, 21.1.3.4, 22.1.3.4, 23.1.3.4, 24.1.3.4, 25.1.3.4, 26.1.3.4, 27.1.3.4, 28.1.3.4, 29.1.3.4, 30.1.3.4, 31.1.3.4, 32.1.3.4, 33.1.3.4, 34.1.3.4, 35.1.3.4, 36.1.3.4, 37.1.3.4, 38.1.3.4, 39.1.3.4, 40.1.3.4, 1.2.3.4, 2.2.3.4, 3.2.3.4, 4.2.3.4, 5.2.3.4, 6.2.3.4, 7.2.3.4, 8.2.3.4, 9.2.3.4, 10.2.3.4, 11.2.3.4, 12.2.3.4, 13.2.3.4, 14.2.3.4, 15.2.3.4, 16.2.3.4, 17.2.3.4, 18.2.3.4, 19.2.3.4, 20.2.3.4, 21.2.3.4, 22.2.3.4, 23.2.3.4, 24.2.3.4, 25.2.3.4, 26.2.3.4, 27.2.3.4, 28.2.3.4, 29.2.3.4, 30.2.3.4, 31.2.3.4, 32.2.3.4, 33.2.3.4, 34.2.3.4, 35.2.3.4, 36.2.3.4, 37.2.3.4, 38.2.3.4, 39.2.3.4, 40.2.3.4, 1.3.3.4, 2.3.3.4, 3.3.3.4, 4.3.3.4, 5.3.3.4, 6.3.3.4, 7.3.3.4, 8.3.3.4, 9.3.3.4, 10.3.3.4, 11.3.3.4, 12.3.3.4, 13.3.3.4, 14.3.3.4, 15.3.3.4, 16.3.3.4, 17.3.3.4, 18.3.3.4, 19.3.3.4, 20.3.3.4, 21.3.3.4, 22.3.3.4, 23.3.3.4, 24.3.3.4, 25.3.3.4, 26.3.3.4, 27.3.3.4, 28.3.3.4, 29.3.3.4, 30.3.3.4, 31.3.3.4, 32.3.3.4, 33.3.3.4, 34.3.3.4, 35.3.3.4, 36.3.3.4, 37.3.3.4, 38.3.3.4, 39.3.3.4, 40.3.3.4, 1.4.3.4, 2.4.3.4, 3.4.3.4, 4.4.3.4, 5.4.3.4, 6.4.3.4, 7.4.3.4, 8.4.3.4, 9.4.3.4, 10.4.3.4, 11.4.3.4, 12.4.3.4, 13.4.3.4, 14.4.3.4, 15.4.3.4, 16.4.3.4, 17.4.3.4, 18.4.3.4, 19.4.3.4, 20.4.3.4, 21.4.3.4, 22.4.3.4, 23.4.3.4, 24.4.3.4, 25.4.3.4, 26.4.3.4, 27.4.3.4, 28.4.3.4, 29.4.3.4, 30.4.3.4, 31.4.3.4, 32.4.3.4, 33.4.3.4, 34.4.3.4, 35.4.3.4, 36.4.3.4, 37.4.3.4, 38.4.3.4, 39.4.3.4, 40.4.3.4, 1.5.3.4, 2.5.3.4, 3.5.3.4, 4.5.3.4, 5.5.3.4, 6.5.3.4, 7.5.3.4, 8.5.3.4, 9.5.3.4, 10.5.3.4, 11.5.3.4, 12.5.3.4, 13.5.3.4, 14.5.3.4, 15.5.3.4, 16.5.3.4, 17.5.3.4, 18.5.3.4, 19.5.3.4, 20.5.3.4, 21.5.3.4, 22.5.3.4, 23.5.3.4, 24.5.3.4, 25.5.3.4, 26.5.3.4, 27.5.3.4, 28.5.3.4, 29.5.3.4, 30.5.3.4, 31.5.3.4, 32.5.3.4, 33.5.3.4, 34.5.3.4, 35.5.3.4, 36.5.3.4, 37.5.3.4, 38.5.3.4, 39.5.3.4, 40.5.3.4, 1.6.3.4, 2.6.3.4, 3.6.3.4, 4.6.3.4, 5.6.3.4, 6.6.3.4, 7.6.3.4, 8.6.3.4, 9.6.3.4, 10.6.3.4, 11.6.3.4, 12.6.3.4, 13.6.3.4, 14.6.3.4, 15.6.3.4, 16.6.3.4, 17.6.3.4, 18.6.3.4, 19.6.3.4, 20.6.3.4, 21.6.3.4, 22.6.3.4, 23.6.3.4, 24.6.3.4, 25.6.3.4, 26.6.3.4, 27.6.3.4, 28.6.3.4, 29.6.3.4, 30.6.3.4, 31.6.3.4, 32.6.3.4, 33.6.3.4, 34.6.3.4, 35.6.3.4, 36.6.3.4, 37.6.3.4, 38.6.3.4, 39.6.3.4, 40.6.3.4, 1.7.3.4, 2.7.3.4, 3.7.3.4, 4.7.3.4, 5.7.3.4, 6.7.3.4, 7.7.3.4, 8.7.3.4, 9.7.3.4, 10.7.3.4, 11.7.3.4, 12.7.3.4, 13.7.3.4, 14.7.3.4, 15.7.3.4, 16.7.3.4, 17.7.3.4, 18.7.3.4, 19.7.3.4, 20.7.3.4, 21.7.3.4, 22.7.3.4, 23.7.3.4, 24.7.3.4, 25.7.3.4, 26.7.3.4, 27.7.3.4, 28.7.3.4, 29.7.3.4, 30.7.3.4, 31.7.3.4, 32.7.3.4, 33.7.3.4, 34.7.3.4, 35.7.3.4, 36.7.3.4, 37.7.3.4, 38.7.3.4, 39.7.3.4, 40.7.3.4, 1.8.3.4, 2.8.3.4, 3.8.3.4, 4.8.3.4, 5.8.3.4, 6.8.3.4, 7.8.3.4, 8.8.3.4, 9.8.3.4, 10.8.3.4, 11.8.3.4, 12.8.3.4, 13.8.3.4, 14.8.3.4, 15.8.3.4, 16.8.3.4, 17.8.3.4, 18.8.3.4, 19.8.3.4, 20.8.3.4, 21.8.3.4, 22.8.3.4, 23.8.3.4, 24.8.3.4, 25.8.3.4, 26.8.3.4, 27.8.3.4, 28.8.3.4, 29.8.3.4, 30.8.3.4, 31.8.3.4, 32.8.3.4, 33.8.3.4, 34.8.3.4, 35.8.3.4, 36.8.3.4, 37.8.3.4, 38.8.3.4, 39.8.3.4, 40.8.3.4, 1.9.3.4, 2.9.3.4, 3.9.3.4, 4.9.3.4, 5.9.3.4, 6.9.3.4, 7.9.3.4, 8.9.3.4, 9.9.3.4, 10.9.3.4, 11.9.3.4, 12.9.3.4, 13.9.3.4, 14.9.3.4, 15.9.3.4, 16.9.3.4, 17.9.3.4, 18.9.3.4, 19.9.3.4, 20.9.3.4, 21.9.3.4, 22.9.3.4, 23.9.3.4, 24.9.3.4, 25.9.3.4, 26.9.3.4, 27.9.3.4, 28.9.3.4, 29.9.3.4, 30.9.3.4, 31.9.3.4, 32.9.3.4, 33.9.3.4, 34.9.3.4, 35.9.3.4, 36.9.3.4, 37.9.3.4, 38.9.3.4, 39.9.3.4, 40.9.3.4, 1.10.3.4, 2.10.3.4, 3.10.3.4, 4.10.3.4, 5.10.3.4, 6.10.3.4, 7.10.3.4, 8.10.3.4, 9.10.3.4, 10.10.3.4, 11.10.3.4, 12.10.3.4, 13.10.3.4, 14.10.3.4, 15.10.3.4, 16.10.3.4, 17.10.3.4, 18.10.3.4, 19.10.3.4, 20.10.3.4, 21.10.3.4, 22.10.3.4, 23.10.3.4, 24.10.3.4, 25.10.3.4, 26.10.3.4, 27.10.3.4, 28.10.3.4, 29.10.3.4, 30.10.3.4, 31.10.3.4, 32.10.3.4, 33.10.3.4, 34.10.3.4, 35.10.3.4, 36.10.3.4, 37.10.3.4, 38.10.3.4, 39.10.3.4, 40.10.3.4, 1.11.3.4, 2.11.3.4, 3.11.3.4, 4.11.3.4, 5.11.3.4, 6.11.3.4, 7.11.3.4, 8.11.3.4, 9.11.3.4, 10.11.3.4, 11.11.3.4, 12.11.3.4, 13.11.3.4, 14.11.3.4, 15.11.3.4, 16.11.3.4, 17.11.3.4, 18.11.3.4, 19.11.3.4, 20.11.3.4, 21.11.3.4, 22.11.3.4, 23.11.3.4, 24.11.3.4, 25.11.3.4, 26.11.3.4, 27.11.3.4, 28.11.3.4, 29.11.3.4, 30.11.3.4, 31.11.3.4, 32.11.3.4, 33.11.3.4, 34.11.3.4, 35.11.3.4, 36.11.3.4, 37.11.3.4, 38.11.3.4, 39.11.3.4, 40.11.3.4, 1.12.3.4, 2.12.3.4, 3.12.3.4, 4.12.3.4, 5.12.3.4, 6.12.3.4, 7.12.3.4, 8.12.3.4, 9.12.3.4, 10.12.3.4, 11.12.3.4, 12.12.3.4, 13.12.3.4, 14.12.3.4, 15.12.3.4, 16.12.3.4, 17.12.3.4, 18.12.3.4, 19.12.3.4, 20.12.3.4, 21.12.3.4, 22.12.3.4, 23.12.3.4, 24.12.3.4, 25.12.3.4, 26.12.3.4, 27.12.3.4, 28.12.3.4, 29.12.3.4, 30.12.3.4, 31.12.3.4, 32.12.3.4, 33.12.3.4, 34.12.3.4, 35.12.3.4, 36.12.3.4, 37.12.3.4, 38.12.3.4, 39.12.3.4, 40.12.3.4, 1.13.3.4, 2.13.3.4, 3.13.3.4, 4.13.3.4, 5.13.3.4, 6.13.3.4, 7.13.3.4, 8.13.3.4, 9.13.3.4, 10.13.3.4, 11.13.3.4, 12.13.3.4, 13.13.3.4, 14.13.3.4, 15.13.3.4, 16.13.3.4, 17.13.3.4, 18.13.3.4, 19.13.3.4, 20.13.3.4, 21.13.3.4, 22.13.3.4, 23.13.3.4, 24.13.3.4, 25.13.3.4, 26.13.3.4, 27.13.3.4, 28.13.3.4, 29.13.3.4, 30.13.3.4, 31.13.3.4, 32.13.3.4, 33.13.3.4, 34.13.3.4, 35.13.3.4, 36.13.3.4, 37.13.3.4, 38.13.3.4, 39.13.3.4, 40.13.3.4, 1.14.3.4, 2.14.3.4, 3.14.3.4, 4.14.3.4, 5.14.3.4, 6.14.3.4, 7.14.3.4, 8.14.3.4, 9.14.3.4, 10.14.3.4, 11.14.3.4, 12.14.3.4, 13.14.3.4, 14.14.3.4, 15.14.3.4, 16.14.3.4, 17.14.3.4, 18.14.3.4, 19.14.3.4, 20.14.3.4, 21.14.3.4, 22.14.3.4, 23.14.3.4, 24.14.3.4, 25.14.3.4, 26.14.3.4, 27.14.3.4, 28.14.3.4, 29.14.3.4, 30.14.3.4, 31.14.3.4, 32.14.3.4, 33.14.3.4, 34.14.3.4, 35.14.3.4, 36.14.3.4, 37.14.3.4, 38.14.3.4, 39.14.3.4, 40.14.3.4, 1.15.3.4, 2.15.3.4, 3.15.3.4, 4.15.3.4, 5.15.3.4, 6.15.3.4, 7.15.3.4, 8.15.3.4, 9.15.3.4, 10.15.3.4, 11.15.3.4, 12.15.3.4, 13.15.3.4, 14.15.3.4, 15.15.3.4, 16.15.3.4, 17.15.3.4, 18.15.3.4, 19.15.3.4, 20.15.3.4, 21.15.3.4, 22.15.3.4, 23.15.3.4, 24.15.3.4, 25.15.3.4, 26.15.3.4, 27.15.3.4, 28.15.3.4, 29.15.3.4, 30.15.3.4, 31.15.3.4, 32.15.3.4, 33.15.3.4, 34.15.3.4, 35.15.3.4, 36.15.3.4, 37.15.3.4, 38.15.3.4, 39.15.3.4, 40.15.3.4, 1.16.3.4, 2.16.3.4, 3.16.3.4, 4.16.3.4, 5.16.3.4, 6.16.3.4, 7.16.3.4, 8.16.3.4, 9.16.3.4, 10.16.3.4, 11.16.3.4, 12.16.3.4, 13.16.3.4, 14.16.3.4, 15.16.3.4, 16.16.3.4, 17.16.3.4, 18.16.3.4, 19.16.3.4, 20.16.3.4, 21.16.3.4, 22.16.3.4, 23.16.3.4, 24.16.3.4, 25.16.3.4, 26.16.3.4, 27.16.3.4, 28.16.3.4, 29.16.3.4, 30.16.3.4, 31.16.3.4, 32.16.3.4, 33.16.3.4, 34.16.3.4, 35.16.3.4, 36.16.3.4, 37.16.3.4, 38.16.3.4, 39.16.3.4, 40.16.3.4, 1.17.3.4, 2.17.3.4, 3.17.3.4, 4.17.3.4, 5.17.3.4, 6.17.3.4, 7.17.3.4, 8.17.3.4, 9.17.3.4, 10.17.3.4, 11.17.3.4, 12.17.3.4, 13.17.3.4, 14.17.3.4, 15.17.3.4, 16.17.3.4, 17.17.3.4, 18.17.3.4, 19.17.3.4, 20.17.3.4, 21.17.3.4, 22.17.3.4, 23.17.3.4, 24.17.3.4, 25.17.3.4, 26.17.3.4, 27.17.3.4, 28.17.3.4, 29.17.3.4, 30.17.3.4, 31.17.3.4, 32.17.3.4, 33.17.3.4, 34.17.3.4, 35.17.3.4, 36.17.3.4, 37.17.3.4, 38.17.3.4, 39.17.3.4, 40.17.3.4, 1.18.3.4, 2.18.3.4, 3.18.3.4, 4.18.3.4, 5.18.3.4, 6.18.3.4, 7.18.3.4, 8.18.3.4, 9.18.3.4, 10.18.3.4, 11.18.3.4, 12.18.3.4, 13.18.3.4, 14.18.3.4, 15.18.3.4, 16.18.3.4, 17.18.3.4, 18.18.3.4, 19.18.3.4, 20.18.3.4, 21.18.3.4, 22.18.3.4, 23.18.3.4, 24.18.3.4, 25.18.3.4, 26.18.3.4, 27.18.3.4, 28.18.3.4, 29.18.3.4, 30.18.3.4, 31.18.3.4, 32.18.3.4, 33.18.3.4, 34.18.3.4, 35.18.3.4, 36.18.3.4, 37.18.3.4, 38.18.3.4, 39.18.3.4, 40.18.3.4, 1.19.3.4, 2.19.3.4, 3.19.3.4, 4.19.3.4, 5.19.3.4, 6.19.3.4, 7.19.3.4, 8.19.3.4, 9.19.3.4, 10.19.3.4, 11.19.3.4, 12.19.3.4, 13.19.3.4, 14.19.3.4, 15.19.3.4, 16.19.3.4, 17.19.3.4, 18.19.3.4, 19.19.3.4, 20.19.3.4, 21.19.3.4, 22.19.3.4, 23.19.3.4, 24.19.3.4, 25.19.3.4, 26.19.3.4, 27.19.3.4, 28.19.3.4, 29.19.3.4, 30.19.3.4, 31.19.3.4, 32.19.3.4, 33.19.3.4, 34.19.3.4, 35.19.3.4, 36.19.3.4, 37.19.3.4, 38.19.3.4, 39.19.3.4, 40.19.3.4, 1.20.3.4, 2.20.3.4, 3.20.3.4, 4.20.3.4, 5.20.3.4, 6.20.3.4, 7.20.3.4, 8.20.3.4, 9.20.3.4, 10.20.3.4, 11.20.3.4, 12.20.3.4, 13.20.3.4, 14.20.3.4, 15.20.3.4, 16.20.3.4, 17.20.3.4, 18.20.3.4, 19.20.3.4, 20.20.3.4, 21.20.3.4, 22.20.3.4, 23.20.3.4, 24.20.3.4, 25.20.3.4, 26.20.3.4, 27.20.3.4, 28.20.3.4, 29.20.3.4, 30.20.3.4, 31.20.3.4, 32.20.3.4, 33.20.3.4, 34.20.3.4, 35.20.3.4, 36.20.3.4, 37.20.3.4, 38.20.3.4, 39.20.3.4, 40.20.3.4, 1.21.3.4, 2.21.3.4, 3.21.3.4, 4.21.3.4, 5.21.3.4, 6.21.3.4, 7.21.3.4, 8.21.3.4, 9.21.3.4, 10.21.3.4, 11.21.3.4, 12.21.3.4, 13.21.3.4, 14.21.3.4, 15.21.3.4, 16.21.3.4, 17.21.3.4, 18.21.3.4, 19.21.3.4, 20.21.3.4, 21.21.3.4, 22.21.3.4, 23.21.3.4, 24.21.3.4, 25.21.3.4, 26.21.3.4, 27.21.3.4, 28.21.3.4, 29.21.3.4, 30.21.3.4, 31.21.3.4, 32.21.3.4, 33.21.3.4, 34.21.3.4, 35.21.3.4, 36.21.3.4, 37.21.3.4, 38.21.3.4, 39.21.3.4, 40.21.3.4, 1.22.3.4, 2.22.3.4, 3.22.3.4, 4.22.3.4, 5.22.3.4, 6.22.3.4, 7.22.3.4, 8.22.3.4, 9.22.3.4, 10.22.3.4, 11.22.3.4, 12.22.3.4, 13.22.3.4, 14.22.3.4, 15.22.3.4, 16.22.3.4, 17.22.3.4, 18.22.3.4, 19.22.3.4, 20.22.3.4, 21.22.3.4, 22.22.3.4, 23.22.3.4, 24.22.3.4, 25.22.3.4, 26.22.3.4, 27.22.3.4, 28.22.3.4, 29.22.3.4, 30.22.3.4, 31.22.3.4, 32.22.3.4, 33.22.3.4, 34.22.3.4, 35.22.3.4, 36.22.3.4, 37.22.3.4, 38.22.3.4, 39.22.3.4, 40.22.3.4, 1.23.3.4, 2.23.3.4, 3.23.3.4, 4.23.3.4, 5.23.3.4, 6.23.3.4, 7.23.3.4, 8.23.3.4, 9.23.3.4, 10.23.3.4, 11.23.3.4, 12.23.3.4, 13.23.3.4, 14.23.3.4, 15.23.3.4, 16.23.3.4, 17.23.3.4, 18.23.3.4, 19.23.3.4, 20.23.3.4, 21.23.3.4, 22.23.3.4, 23.23.3.4, 24.23.3.4, 25.23.3.4, 26.23.3.4, 27.23.3.4, 28.23.3.4, 29.23.3.4, 30.23.3.4, 31.23.3.4, 32.23.3.4, 33.23.3.4, 34.23.3.4, 35.23.3.4, 36.23.3.4, 37.23.3.4, 38.23.3.4, 39.23.3.4, 40.23.3.4, 1.24.3.4, 2.24.3.4, 3.24.3.4, 4.24.3.4, 5.24.3.4, 16.24.3.4, 7.24.3.4, 8.24.3.4, 9.24.3.4, 10.24.3.4, 11.24.3.4, 12.24.3.4, 13.24.3.4, 14.24.3.4, 15.24.3.4, 16.24.3.4, 17.24.3.4, 18.24.3.4, 19.24.3.4, 20.24.3.4, 21.24.3.4, 22.24.3.4, 23.24.3.4, 24.24.3.4, 25.24.3.4, 26.24.3.4, 27.24.3.4, 28.24.3.4, 29.24.3.4, 30.24.3.4, 31.24.3.4, 32.24.3.4, 33.24.3.4, 34.24.3.4, 35.24.3.4, 36.24.3.4, 37.24.3.4, 38.24.3.4, 39.24.3.4, 40.24.3.4, 1.25.3.4, 2.25.3.4, 3.25.3.4, 4.25.3.4, 5.25.3.4, 6.25.3.4, 7.25.3.4, 8.25.3.4, 9.25.3.4, 10.25.3.4, 11.25.3.4, 12.25.3.4, 13.25.3.4, 14.25.3.4, 15.25.3.4, 16.25.3.4, 17.25.3.4, 18.25.3.4, 19.25.3.4, 20.25.3.4, 21.25.3.4, 22.25.3.4, 23.25.3.4, 24.25.3.4, 25.25.3.4, 26.25.3.4, 27.25.3.4, 28.25.3.4, 29.25.3.4, 30.25.3.4, 31.25.3.4, 32.25.3.4, 33.25.3.4, 34.25.3.4, 35.25.3.4, 36.25.3.4, 37.25.3.4, 38.25.3.4, 39.25.3.4, 40.25.3.4, 1.26.3.4, 2.26.3.4, 3.26.3.4, 4.26.3.4, 5.26.3.4, 6.26.3.4, 7.26.3.4, 8.26.3.4, 9.26.3.4, 10.26.3.4, 11.26.3.4, 12.26.3.4, 13.26.3.4, 14.26.3.4, 15.26.3.4, 16.26.3.4, 17.26.3.4, 18.26.3.4, 19.26.3.4, 20.26.3.4, 21.26.3.4, 22.26.3.4, 23.26.3.4, 24.26.3.4, 25.26.3.4, 26.26.3.4, 27.26.3.4, 28.26.3.4, 29.26.3.4, 30.26.3.4, 31.26.3.4, 32.26.3.4, 33.26.3.4, 34.26.3.4, 35.26.3.4, 36.26.3.4, 37.26.3.4, 38.26.3.4, 39.26.3.4, 40.26.3.4, 1.27.3.4, 2.27.3.4, 3.27.3.4, 35.27.3.4, 6.27.3.4, 7.27.3.4, 8.27.3.4, 9.27.3.4, 10.27.3.4, 11.27.3.4, 12.27.3.4, 13.27.3.4, 14.27.3.4, 15.27.3.4, 16.27.3.4, 17.27.3.4, 18.27.3.4, 19.27.3.4, 20.27.3.4, 21.27.3.4, 22.27.3.4, 23.27.3.4, 24.27.3.4, 25.27.3.4, 26.27.3.4, 27.27.3.4, 28.27.3.4, 29.27.3.4, 30.27.3.4, 31.27.3.4, 32.27.3.4, 33.27.3.4, 34.27.3.4, 35.27.3.4, 36.27.3.4, 37.27.3.4, 38.27.3.4, 39.27.3.4, 40.27.3.4, 1.28.3.4, 2.28.3.4, 3.28.3.4, 4.28.3.4, 5.28.3.4, 6.28.3.4, 7.28.3.4, 8.28.3.4, 9.28.3.4, 10.28.3.4, 11.28.3.4, 12.28.3.4, 13.28.3.4, 14.28.3.4, 15.28.3.4, 16.28.3.4, 17.28.3.4, 18.28.3.4, 19.28.3.4, 20.28.3.4, 21.28.3.4, 22.28.3.4, 23.28.3.4, 24.28.3.4, 25.28.3.4, 26.28.3.4, 27.28.3.4, 28.28.3.4, 29.28.3.4, 30.28.3.4, 31.28.3.4, 32.28.3.4, 33.28.3.4, 34.28.3.4, 35.28.3.4, 36.28.3.4, 37.28.3.4, 38.28.3.4, 39.28.3.4, 40.28.3.4, 1.29.3.4, 2.29.3.4, 3.29.3.4, 4.29.3.4, 5.29.3.4, 6.29.3.4, 7.29.3.4, 8.29.3.4, 9.29.3.4, 10.29.3.4, 11.29.3.4, 12.29.3.4, 13.29.3.4, 14.29.3.4, 15.29.3.4, 16.29.3.4, 17.29.3.4, 18.29.3.4, 19.29.3.4, 20.29.3.4, 21.29.3.4, 22.29.3.4, 23.29.3.4, 24.29.3.4, 25.29.3.4, 26.29.3.4, 27.29.3.4, 28.29.3.4, 29.29.3.4, 30.29.3.4, 31.29.3.4, 32.29.3.4, 33.29.3.4, 34.29.3.4, 35.29.3.4, 36.29.3.4, 37.29.3.4, 38.29.3.4, 39.29.3.4, 40.29.3.4, 1.1.3.5, 2.1.3.5, 3.1.3.5, 4.1.3.5, 5.1.3.5, 6.1.3.5, 7.1.3.5, 8.1.3.5, 9.1.3.5, 10.1.3.5, 11.1.3.5, 12.1.3.5, 13.1.3.5, 14.1.3.5, 15.1.3.5, 16.1.3.5, 17.1.3.5, 18.1.3.5, 19.1.3.5, 20.1.3.5, 21.1.3.5, 22.1.3.5, 23.1.3.5, 24.1.3.5, 25.1.3.5, 26.1.3.5, 27.1.3.5, 28.1.3.5, 29.1.3.5, 30.1.3.5, 31.1.3.5, 32.1.3.5, 33.1.3.5, 34.1.3.5, 35.1.3.5, 36.1.3.5, 37.1.3.5, 38.1.3.5, 39.1.3.5, 40.1.3.5, 1.2.3.5, 2.2.3.5, 3.2.3.5, 4.2.3.5, 5.2.3.5, 6.2.3.5, 7.2.3.5, 8.2.3.5, 9.2.3.5, 10.2.3.5, 11.2.3.5, 12.2.3.5, 13.2.3.5, 14.2.3.5, 15.2.3.5, 16.2.3.5, 17.2.3.5, 18.2.3.5, 19.2.3.5, 20.2.3.5, 21.2.3.5, 22.2.3.5, 23.2.3.5, 24.2.3.5, 25.2.3.5, 26.2.3.5, 27.2.3.5, 28.2.3.5, 29.2.3.5, 30.2.3.5, 31.2.3.5, 32.2.3.5, 33.2.3.5, 34.2.3.5, 35.2.3.5, 36.2.3.5, 37.2.3.5, 38.2.3.5, 39.2.3.5, 40.2.3.5, 1.3.3.5, 2.3.3.5, 3.3.3.5, 4.3.3.5, 5.3.3.5, 6.3.3.5, 7.3.3.5, 8.3.3.5, 9.3.3.5, 10.3.3.5, 11.3.3.5, 12.3.3.5, 13.3.3.5, 14.3.3.5, 15.3.3.5, 16.3.3.5, 17.3.3.5, 18.3.3.5, 19.3.3.5, 20.3.3.5, 21.3.3.5, 22.3.3.5, 23.3.3.5, 24.3.3.5, 25.3.3.5, 26.3.3.5, 27.3.3.5, 28.3.3.5, 29.3.3.5, 30.3.3.5, 31.3.3.5, 32.3.3.5, 33.3.3.5, 34.3.3.5, 35.3.3.5, 36.3.3.5, 37.3.3.5, 38.3.35, 39.3.3.5, 40.3.3.5, 1.4.3.5, 2.4.3.5, 3.4.3.5, 4.4.3.5, 5.4.3.5, 6.4.3.5, 7.4.3.5, 8.4.3.5, 9.4.3.5, 10.4.3.5, 11.4.3.5, 12.4.3.5, 13.4.3.5, 14.4.3.5, 15.4.3.5, 16.4.3.5, 17.4.3.5, 18.4.3.5, 19.4.3.5, 20.4.3.5, 21.4.3.5, 22.4.3.5, 23.4.3.5, 24.4.3.5, 25.4.3.5, 26.4.3.5, 27.4.3.5, 28.4.3.5, 29.4.3.5, 30.4.3.5, 31.4.3.5, 32.4.3.5, 33.4.3.5, 34.4.3.5, 35.4.3.5, 36.4.3.5, 37.4.3.5, 38.4.3.5, 39.4.3.5, 40.4.3.5, 1.5.3.5, 2.5.3.5, 3.5.3.5, 4.5.3.5, 5.5.3.5, 6.5.3.5, 7.5.3.5, 8.5.3.5, 9.5.3.5, 10.5.3.5, 11.5.3.5, 12.5.3.5, 13.5.3.5, 14.5.3.5, 15.5.3.5, 16.5.3.5, 17.5.3.5, 18.5.3.5, 19.5.3.5, 20.5.3.5, 21.5.3.5, 22.5.3.5, 23.5.3.5, 24.5.3.5, 25.5.3.5, 26.5.3.5, 27.5.3.5, 28.5.3.5, 29.5.3.5, 30.5.3.5, 31.5.3.5, 32.5.3.5, 33.5.3.5, 34.5.3.5, 35.5.3.5, 36.5.3.5, 37.5.3.5, 38.5.3.5, 39.5.3.5, 40.5.3.5, 1.6.3.5, 2.6.3.5, 3.6.3.5, 4.6.3.5, 5.6.3.5, 6.6.3.5, 7.6.3.5, 8.6.3.5, 9.6.3.5, 10.6.3.5, 11.6.3.5, 12.6.3.5, 13.6.3.5, 14.6.3.5, 15.6.3.5, 16.6.3.5, 17.6.3.5, 18.6.3.5, 19.6.3.5, 20.6.3.5, 21.6.3.5, 22.6.3.5, 23.6.3.5, 24.6.3.5, 25.6.3.5, 26.6.3.5, 27.6.3.5, 28.6.3.5, 29.6.3.5, 30.6.3.5, 31.6.3.5, 32.6.3.5, 33.6.3.5, 34.6.3.5, 35.6.3.5, 36.6.3.5, 37.6.3.5, 38.6.3.5, 39.6.3.5, 40.6.3.5, 1.7.3.5, 2.7.3.5, 3.7.3.5, 4.7.3.5, 5.7.3.5, 6.7.3.5, 7.7.3.5, 8.7.3.5, 9.7.3.5, 10.7.3.5, 11.7.3.5, 12.7.3.5, 13.7.3.5, 14.7.3.5, 15.7.3.5, 16.7.3.5, 17.7.3.5, 18.7.3.5, 19.7.3.5, 20.7.3.5, 21.7.3.5, 22.7.3.5, 23.7.3.5, 24.7.3.5, 25.7.3.5, 26.7.3.5, 27.7.3.5, 28.7.3.5, 29.7.3.5, 30.7.3.5, 31.7.3.5, 32.7.3.5, 33.7.3.5, 34.7.3.5, 35.7.3.5, 36.7.3.5, 37.7.3.5, 38.7.3.5, 39.7.3.5, 40.7.3.5, 1.8.3.5, 2.8.3.5, 3.8.3.5, 4.8.3.5, 5.8.3.5, 6.8.3.5, 7.8.3.5, 8.8.3.5, 9.8.3.5, 10.8.3.5, 11.8.3.5, 12.8.3.5, 13.8.3.5, 14.8.3.5, 15.8.3.5, 16.8.3.5, 17.8.3.5, 18.8.3.5, 19.8.3.5, 20.8.3.5, 21.8.3.5, 22.8.3.5, 23.8.3.5, 24.8.3.5, 25.8.3.5, 26.8.3.5, 27.8.3.5, 28.8.3.5, 29.8.3.5, 30.8.3.5, 31.8.3.5, 32.8.3.5, 33.8.3.5, 34.8.3.5, 35.8.3.5, 36.8.3.5, 37.8.3.5, 38.8.3.5, 39.8.3.5, 40.8.3.5, 1.9.3.5, 2.9.3.5, 3.9.3.5, 4.9.3.5, 5.9.3.5, 6.9.3.5, 7.9.3.5, 8.9.3.5, 9.9.3.5, 10.9.3.5, 11.9.3.5, 12.9.3.5, 13.9.3.5, 14.9.3.5, 15.9.3.5, 16.9.3.5, 17.9.3.5, 18.9.3.5, 19.9.3.5, 20.9.3.5, 21.9.3.5, 22.9.3.5, 23.9.3.5, 24.9.3.5, 25.9.3.5, 26.9.3.5, 27.9.3.5, 28.9.3.5, 29.9.3.5, 30.9.3.5, 31.9.3.5, 32.9.3.5, 33.9.3.5, 34.9.3.5, 35.9.3.5, 36.9.3.5, 37.9.3.5, 38.9.3.5, 39.9.3.5, 40.9.3.5, 1.10.3.5, 2.10.3.5, 3.10.3.5, 4.10.3.5, 5.10.3.5, 6.10.3.5, 7.10.3.5, 8.10.3.5, 9.10.3.5, 10.10.3.5, 11.10.3.5, 12.10.3.5, 13.10.3.5, 14.10.3.5, 15.10.3.5, 16.10.3.5, 17.10.3.5, 18.10.3.5, 19.10.3.5, 20.10.3.5, 21.10.3.5, 22.10.3.5, 23.10.3.5, 24.10.3.5, 25.10.3.5, 26.10.3.5, 27.10.3.5, 28.10.3.5, 29.10.3.5, 30.10.3.5, 31.10.3.5, 32.10.3.5, 33.10.3.5, 34.10.3.5, 35.10.3.5, 36.10.3.5, 37.10.3.5, 38.10.3.5, 39.10.3.5, 40.10.3.5, 1.11.3.5, 2.11.3.5, 3.11.3.5, 4.11.3.5, 5.11.3.5, 6.11.3.5, 7.11.3.5, 8.11.3.5, 9.11.3.5, 10.11.3.5, 11.11.3.5, 12.11.3.5, 13.11.3.5, 14.11.3.5, 15.11.3.5, 16.11.3.5, 17.11.3.5, 18.11.3.5, 19.11.3.5, 20.11.3.5, 21.11.3.5, 22.11.3.5, 23.11.3.5, 24.11.3.5, 25.11.3.5, 26.11.3.5, 27.11.3.5, 28.11.3.5, 29.11.3.5, 30.11.3.5, 31.11.3.5, 32.11.3.5, 33.11.3.5, 34.11.3.5, 35.11.3.5, 36.11.3.5, 37.11.3.5, 38.11.3.5, 39.11.3.5, 40.11.3.5, 1.12.3.5, 2.12.3.5, 3.12.3.5, 4.12.3.5, 5.12.3.5, 6.12.3.5, 7.12.3.5, 8.12.3.5, 9.12.3.5, 10.12.3.5, 11.12.3.5, 12.12.3.5, 13.12.3.5, 14.12.3.5, 15.12.3.5, 16.12.3.5, 17.12.3.5, 18.12.3.5, 19.12.3.5, 20.12.3.5, 21.12.3.5, 22.12.3.5, 23.12.3.5, 24.12.3.5, 25.12.3.5, 26.12.3.5, 27.12.3.5, 28.12.3.5, 29.12.3.5, 30.12.3.5, 31.12.3.5, 32.12.3.5, 33.12.3.5, 34.12.3.5, 35.12.3.5, 36.12.3.5, 37.12.3.5, 38.12.3.5, 39.12.3.5, 40.12.3.5, 1.13.3.5, 2.13.3.5, 3.13.3.5, 4.13.3.5, 5.13.3.5, 6.13.3.5, 7.13.3.5, 8.13.3.5, 9.13.3.5, 10.13.3.5, 11.13.3.5, 12.13.3.5, 13.13.3.5, 14.13.3.5, 15.13.3.5, 16.13.3.5, 17.13.3.5, 18.13.3.5, 19.13.3.5, 20.13.3.5, 21.13.3.5, 22.13.3.5, 23.13.3.5, 24.13.3.5, 25.13.3.5, 26.13.3.5, 27.13.3.5, 28.13.3.5, 29.13.3.5, 30.13.3.5, 31.13.3.5, 32.13.3.5, 33.13.3.5, 34.13.3.5, 35.13.3.5, 36.13.3.5, 37.13.3.5, 38.13.3.5, 39.13.3.5, 40.13.3.5, 1.14.3.5, 2.14.3.5, 3.14.3.5, 4.14.3.5, 5.14.3.5, 6.14.3.5, 7.14.3.5, 8.14.3.5, 9.14.3.5, 10.14.3.5, 11.14.3.5, 12.14.3.5, 13.14.3.5, 14.14.3.5, 15.14.3.5, 16.14.3.5, 17.14.3.5, 18.14.3.5, 19.14.3.5, 20.14.3.5, 21.14.3.5, 22.14.3.5, 23.14.3.5, 24.14.3.5, 25.14.3.5, 26.14.3.5, 27.14.3.5, 28.14.3.5, 29.14.3.5, 30.14.3.5, 31.14.3.5, 32.14.3.5, 33.14.3.5, 34.14.3.5, 35.14.3.5, 36.14.3.5, 37.14.3.5, 38.14.3.5, 39.14.3.5, 40.14.3.5, 1.15.3.5, 2.15.3.5, 3.15.3.5, 4.15.3.5, 5.15.3.5, 6.15.3.5, 7.15.3.5, 8.15.3.5, 9.15.3.5, 10.15.3.5, 11.15.3.5, 12.15.3.5, 13.15.3.5, 14.15.3.5, 15.15.3.5, 16.15.3.5, 17.15.3.5, 18.15.3.5, 19.15.3.5, 20.15.3.5, 21.15.3.5, 22.15.3.5, 23.15.3.5, 24.15.3.5, 25.15.3.5, 26.15.3.5, 27.15.3.5, 28.15.3.5, 29.15.3.5, 30.15.3.5, 31.15.3.5, 32.15.3.5, 33.15.3.5, 34.15.3.5, 35.15.3.5, 36.15.3.5, 37.15.3.5, 38.15.3.5, 39.15.3.5, 40.15.3.5, 1.16.3.5, 2.16.3.5, 3.16.3.5, 4.16.3.5, 5.16.3.5, 6.16.3.5, 7.16.3.5, 8.16.3.5, 9.16.3.5, 10.16.3.5, 11.16.3.5, 12.16.3.5, 13.16.3.5, 14.16.3.5, 15.16.3.5, 16.16.3.5, 17.16.3.5, 18.16.3.5, 19.16.3.5, 20.16.3.5, 21.16.3.5, 22.16.3.5, 23.16.3.5, 24.16.3.5, 25.16.3.5, 26.16.3.5, 27.16.3.5, 28.16.3.5, 29.16.3.5, 30.16.3.5, 31.16.3.5, 32.16.3.5, 33.16.3.5, 34.16.3.5, 35.16.3.5, 36.16.3.5, 37.16.3.5, 38.16.3.5, 39.16.3.5, 40.16.3.5, 1.17.3.5, 2.17.3.5, 3.17.3.5, 4.17.3.5, 5.17.3.5, 6.17.3.5, 7.17.3.5, 8.17.3.5, 9.17.3.5, 10.17.3.5, 11.17.3.5, 12.17.3.5, 13.17.3.5, 14.17.3.5, 15.17.3.5, 16.17.3.5, 17.17.3.5, 18.17.3.5, 19.17.3.5, 20.17.3.5, 21.17.3.5, 22.17.3.5, 23.17.3.5, 24.17.3.5, 25.17.3.5, 26.17.3.5, 27.17.3.5, 28.17.3.5, 29.17.3.5, 30.17.3.5, 31.17.3.5, 32.17.3.5, 33.17.3.5, 34.17.3.5, 35.17.3.5, 36.17.3.5, 37.17.3.5, 38.17.3.5, 39.17.3.5, 40.17.3.5, 1.18.3.5, 2.18.3.5, 3.18.3.5, 4.18.3.5, 5.18.3.5, 6.18.3.5, 7.18.3.5, 8.18.3.5, 9.18.3.5, 10.18.3.5, 11.18.3.5, 12.18.3.5, 13.18.3.5, 14.18.3.5, 15.18.3.5, 16.18.3.5, 17.18.3.5, 18.18.3.5, 19.18.3.5, 20.18.3.5, 21.18.3.5, 22.18.3.5, 23.18.3.5, 24.18.3.5, 25.18.3.5, 26.18.3.5, 27.18.3.5, 28.18.3.5, 29.18.3.5, 30.18.3.5, 31.18.3.5, 32.18.3.5, 33.18.3.5, 34.18.3.5, 35.18.3.5, 36.18.3.5, 37.18.3.5, 38.18.3.5, 39.18.3.5, 40.18.3.5, 1.19.3.5, 2.19.3.5, 3.19.3.5, 4.19.3.5, 5.19.3.5, 6.19.3.5, 7.19.3.5, 8.193.5, 9.19.3.5, 10.19.3.5, 11.19.3.5, 12.19.3.5, 13.19.3.5, 14.19.3.5, 15.19.3.5, 16.19.3.5, 17.19.3.5, 18.19.3.5, 19.19.3.5, 20.19.3.5, 21.19.3.5, 22.19.3.5, 23.19.3.5, 24.19.3.5, 25.19.3.5, 26.19.3.5, 27.19.3.5, 28.19.3.5, 29.19.3.5, 30.19.3.5, 31.19.3.5, 32.19.3.5, 33.19.3.5, 34.19.3.5, 35.19.3.5, 36.19.3.5, 37.19.3.5, 38.19.3.5, 39.19.3.5, 40.19.3.5, 1.20.3.5, 2.20.3.5, 3.20.3.5, 4.20.3.5, 5.20.3.5, 6.20.3.5, 7.20.3.5, 8.20.3.5, 9.20.3.5, 10.20.3.5, 11.20.3.5, 12.20.3.5, 13.20.3.5, 14.20.3.5, 15.20.3.5, 16.20.3.5, 17.20.3.5, 18.20.3.5, 19.20.3.5, 20.20.3.5, 21.20.3.5, 22.20.3.5, 23.20.3.5, 24.20.3.5, 25.20.3.5, 26.20.3.5, 27.20.3.5, 28.20.3.5, 29.20.3.5, 30.20.3.5, 31.20.3.5, 32.20.3.5, 33.20.3.5, 34.20.3.5, 35.20.3.5, 36.20.3.5, 37.20.3.5, 38.20.3.5, 39.20.3.5, 40.20.3.5, 1.21.3.5, 2.21.3.5, 3.21.3.5, 4.21.3.5, 5.21.3.5, 6.21.3.5, 7.21.3.5, 8.21.3.5, 9.21.3.5, 10.21.3.5, 11.21.3.5, 12.21.3.5, 13.21.3.5, 14.21.3.5, 15.21.3.5, 16.21.3.5, 17.21.3.5, 18.21.3.5, 19.21.3.5, 20.21.3.5, 21.21.3.5, 22.21.3.5, 23.21.3.5, 24.21.3.5, 25.21.3.5, 26.21.3.5, 27.21.3.5, 28.21.3.5, 29.21.3.5, 30.21.3.5, 31.21.3.5, 32.21.3.5, 33.21.3.5, 34.21.3.5, 35.21.3.5, 36.21.3.5, 37.21.3.5, 38.21.3.5, 39.21.3.5, 40.21.3.5, 1.22.3.5, 2.22.3.5, 3.22.3.5, 4.22.3.5, 5.22.3.5, 6.22.3.5, 7.22.3.5, 8.22.3.5, 9.22.3.5, 10.22.3.5, 11.22.3.5, 12.22.3.5, 13.22.3.5, 14.22.3.5, 15.22.3.5, 16.22.3.5, 17.22.3.5, 18.22.3.5, 19.22.3.5, 20.22.3.5, 21.22.3.5, 2.22.3.5, 23.22.3.5, 24.22.3.5, 25.22.3.5, 26.22.3.5, 27.22.3.5, 28.22.3.5, 29.22.3.5, 30.22.3.5, 31.22.3.5, 32.22.3.5, 33.22.3.5, 34.22.3.5, 35.22.3.5, 36.22.3.5, 37.22.3.5, 38.22.3.5, 39.22.3.5, 40.22.35, 1.23.3.5, 2.23.3.5, 3.23.3.5, 4.23.3.5, 5.23.3.5, 6.23.3.5, 7.23.3.5, 8.23.3.5, 9.23.3.5, 10.23.3.5, 11.23.3.5, 12.23.3.5, 13.23.3.5, 14.23.3.5, 15.23.3.5, 16.23.3.5, 17.23.3.5, 18.23.3.5, 19.23.3.5, 20.23.3.5, 21.23.3.5, 22.23.3.5, 23.23.3.5, 24.23.3.5, 25.23.3.5, 26.23.3.5, 27.23.3.5, 28.23.3.5, 29.23.3.5, 30.23.3.5, 31.23.3.5, 32.23.3.5, 33.23.3.5, 34.23.3.5, 35.23.3.5, 36.23.3.5, 37.23.3.5, 38.23.3.5, 39.23.3.5, 40.23.3.5, 1.24.3.5, 2.24.3.5, 3.24.3.5, 4.24.3.5, 5.24.3.5, 6.24.3.5, 7.24.3.5, 8.24.3.5, 9.24.3.5, 10.24.3.5, 11.24.3.5, 12.24.3.5, 13.24.3.5, 14.24.3.5, 15.24.3.5, 16.24.3.5, 17.24.3.5, 18.24.3.5, 19.24.3.5, 20.24.3.5, 21.24.3.5, 22.24.3.5, 23.24.3.5, 24.24.3.5, 25.24.3.5, 26.24.3.5, 27.24.3.5, 28.24.3.5, 29.24.3.5, 30.24.3.5, 31.24.3.5, 32.24.3.5, 33.24.3.5, 34.24.3.5, 35.24.3.5, 36.24.3.5, 37.24.3.5, 38.24.3.5, 39.24.3.5, 40.24.3.5, 1.25.3.5, 2.25.3.5, 3.25.3.5, 4.25.3.5, 5.25.3.5, 6.25.3.5, 7.25.3.5, 8.25.3.5, 9.25.3.5, 10.25.3.5, 11.25.3.5, 12.25.3.5, 13.25.3.5, 14.25.3.5, 15.25.3.5, 16.25.3.5, 17.25.3.5, 18.25.3.5, 19.25.3.5, 20.25.3.5, 21.25.3.5, 22.25.3.5, 23.25.3.5, 24.25.3.5, 25.25.3.5, 26.25.3.5, 27.25.3.5, 28.25.3.5, 29.25.3.5, 30.25.3.5, 31.25.3.5, 32.25.3.5, 33.25.3.5, 34.25.3.5, 35.25.3.5, 36.25.3.5, 37.25.3.5, 38.25.3.5, 39.25.3.5, 40.25.3.5, 1.26.3.5, 2.26.3.5, 3.26.3.5, 4.26.3.5, 5.26.3.5, 6.26.3.5, 7.26.3.5, 8.26.3.5, 9.26.3.5, 10.26.3.5, 11.26.3.5, 12.26.3.5, 13.26.3.5, 14.26.3.5, 15.26.3.5, 16.26.3.5, 17.26.3.5, 18.26.3.5, 19.26.3.5, 20.26.3.5, 21.26.3.5, 22.26.3.5, 23.26.3.5, 24.26.3.5, 25.26.3.5, 26.26.3.5, 27.26.3.5, 28.26.3.5, 29.26.3.5, 30.26.3.5, 31.26.3.5, 32.26.3.5, 33.26.3.5, 34.26.3.5, 35.26.3.5, 36.26.3.5, 37.26.3.5, 38.26.3.5, 39.26.3.5, 40.26.3.5, 1.27.3.5, 2.27.3.5, 3.27.3.5, 4.27.3.5, 5.27.3.5, 6.27.3.5, 7.27.3.5, 8.27.3.5, 9.27.3.5, 10.27.3.5, 11.27.3.5, 12.27.3.5, 13.27.3.5, 14.27.3.5, 15.27.3.5, 16.27.3.5, 17.27.3.5, 18.27.3.5, 19.27.3.5, 20.27.3.5, 21.27.3.5, 22.27.3.5, 23.27.3.5, 24.27.3.5, 25.27.3.5, 26.27.3.5, 27.27.3.5, 28.27.3.5, 29.27.3.5, 30.27.3.5, 31.27.3.5, 32.27.3.5, 33.27.3.5, 34.27.3.5, 35.27.3.5, 36.27.3.5, 37.27.3.5, 38.27.3.5, 39.27.3.5, 40.27.3.5, 1.28.3.5, 2.28.3.5, 3.28.3.5, 4.28.3.5, 5.28.3.5, 6.28.3.5, 7.28.3.5, 8.28.3.5, 9.28.3.5, 10.28.3.5, 11.28.3.5, 12.28.3.5, 13.28.3.5, 14.28.3.5, 15.28.3.5, 16.28.3.5, 17.28.3.5, 18.28.3.5, 19.28.3.5, 20.28.3.5, 21.28.3.5, 22.28.3.5, 23.28.3.5, 24.28.3.5, 25.28.3.5, 26.28.3.5, 27.28.3.5, 28.28.3.5, 29.28.3.5, 30.28.3.5, 31.28.3.5, 32.28.3.5, 33.28.3.5, 34.28.3.5, 35.28.3.5, 36.28.3.5, 37.28.3.5, 38.28.3.5, 39.28.3.5, 40.28.3.5, 1.29.3.5, 2.29.3.5, 3.29.3.5, 4.29.3.5, 5.29.3.5, 6.29.3.5, 7.29.3.5, 8.29.3.5, 9.29.3.5, 10.29.3.5, 11.29.3.5, 12.29.3.5, 13.29.3.5, 14.29.3.5, 15.29.3.5, 16.29.3.5, 17.29.3.5, 18.29.3.5, 19.29.3.5, 20.29.3.5, 21.29.3.5, 22.29.3.5, 23.29.3.5, 24.29.3.5, 25.29.3.5, 26.29.3.5, 27.29.3.5, 28.29.3.5, 29.29.3.5, 30.29.3.5, 31.29.3.5, 32.29.3.5, 33.29.3.5, 34.29.3.5, 35.29.3.5, 36.29.3.5, 37.29.3.5, 38.29.3.5, 39.29.3.5 and 40.29.3.5.

Table 2 lists a group of cyclic nucleotide analogs of structure I wherein Z forms a heterocyclic ring containing the phosphorus atom of the phosphonate group and two oxygen atoms as shown. Hydrolysis of the $L^1$ group linked to the phosphorus atom and subsequent ring hydrolysis results in formation of an HPMP nucleoside such as HPMPC (1-(2-phosphonomethoxy-3-hydroxypropyl)-cytosine).

TABLE 2

$L^{1*}$

1. —NH—$CH_2$—C(O)—$OR^4$
2. —NH—CH($CH_3$)—C(O)—$OR^4$
3. —NH—CH($CH_3$)$_2$—C(O)—$OR^4$
4. —NH—CH(CH($CH_3$)$_2$)—C(O)—$OR^4$
5. —NH—CH($CH_3$)($CH_3$)$_2$—C(O)—$OR^4$
6. —N—$CH_2$—$CH_2$—$CH_2$—CH—C(O)—$OR^4$
7. —NH—CH($CH_2$—$C_6H_5$)—C(O)—$OR^4$
8. —NH—CH($CH_2$—$C_8NH_6$)—C(O)—$OR^4$
9. —NH—CH($CH_2$—$CH_2$—S—$CH_3$)—C(O)—$OR^4$
10. —NH—CH($CH_2OH$)—C(O)—$OR^4$
11. —NH—CH(CH(OH)($CH_3$))—C(O)—$OR^4$
12. —NH—CH(—$CH_2SH$)—C(O)—$OR^4$
13. —NH—CH(CH2—$C_6H_5OH$)—C(O)—$OR^4$
14. —NH—CH($CH_2$—C(O)—$NH_2$)—C(O)—$OR^4$
15. —NH—CH($CH_2$—$CH_2$—C(O)—$NH_2$)—C(O)—$OR^4$
16. —NH—CH($CH_2C(O)OR^4$)—C(O)—$OR^4$
17. —NH—CH($CH_2CH_2C(O)OR^4$)—C(O)—$OR^4$
18. —NH—CH($CH_2CH_2CH_2CH_2NH_2$)—C(O)—$OR^4$
19. —NH—CH($CH_2CH_2CH_2NHC(NH)(NH_2)$)—C(O)—$OR^4$
20. —NH—CH($CH_2C_3N_2H_3$)—C(O)—$OR^4$
21. —NH—CH($CH_2CH_2CH_2NH_2$)—$CH_2$—C(O)—$OR^4$
22. —NH—CH($CH_2CH_2CH_2NH_2$)—$CH_2$—C(O)—$OR^4$
23. —NH—CH($CH_2CH_2NHC(NH)(NH_2)$)—$CH_2$—C(O)—$OR^4$
24. —NH—CH(C(O)$OR^4$)—$CH_2$—C(O)—$OR^4$
25. —NH—CH($CH_2C(O)OR^4$)—$CH_2$—C(O)—$OR^4$
26. —NH—CH($CH_2CH_2C(O)OR^4$)—$CH_2$—C(O)—$OR^4$

Z-B**

B 1. adenin-9-yl
2. guanin-9-yl
3. cytosin-1-yl
4. 2,6-diaminopurin-9-yl
5. 2-aminopurin-9-yl
6. 6-azacytosin-1-yl
7. 1-deazaadenin-9-yl
8. 3-deazaadenin-9-yl
9. 8-azaadenin-9-yl
10. 7-deaza-8-azaadenin-9-yl

*See Table 1 footnote.
**See Table 1 footnote.
See Table 1 footnote.

Compounds listed in Table 2 are designated herein by numbers assigned to $L^1$, Z and B according to the following convention, L.Z.B. Thus, compounds 1.1.3 and 1.2.3 represent, when R4 is H, glycinyl cyclic HPMPC and alanyl cyclic HPMPC. Exemplary compounds include 1.1.1, 1.1.2, 1.1.3, 1.1.4, 1.1.5, 1.1.6, 1.1.7, 1.1.8, 1.1.9, 1.1.10, 2.1.1, 2.1.2, 2.1.3, 2.1.4, 2.1.5, 2.1.6, 2.1.7, 2.1.8, 2.1.9, 2.1.10, 3.1.1, 3.1.2, 3.1.3, 3.1.4, 3.1.5, 3.1.6, 3.1.7, 3.1.8, 3.1.9, 3.1.10, 4.1.1, 4.1.2, 4.1.3, 4.1.4, 4.1.5, 4.1.6, 4.1.7, 4.1.8, 4.1.9, 4.1.10, 5.1.1, 5.1.2, 5.1.3, 5.1.4, 5.1.5, 5.1.6, 5.1.7, 5.1.8, 5.1.9, 5.1.10, 6.1.1, 6.1.2, 6.1.3, 6.1.4, 6.1.5, 6.1.6, 6.1.7, 6.1.8, 6.1.9, 6.1.10, 7.1.1, 7.1.2, 7.1.3, 7.1.4, 7.1.5, 7.1.6, 7.1.7, 7.1.8, 7.1.9, 7.1.10, 8.1.1, 8.1.2, 8.1.3, 8.1.4, 8.1.5, 8.1.6, 8.1.7, 8.1.8, 8.1.9, 8.1.10, 9.1.1, 9.1.2, 9.1.3, 9.1.4, 9.1.5, 9.1.6, 9.1.7, 9.1.8, 9.1.9, 9.1.10, 10.1.1, 10.1.2, 10.1.3, 10.1.4, 10.1.5, 10.1.6, 10.1.7, 10.1.8, 10.1.9, 10.1.10, 11.1.1, 11.1.2, 11.1.3, 11.1.4, 11.1.5, 11.1.6, 11.1.7, 11.1.8, 11.1.9, 11.1.10, 12.1.1, 12.1.2, 12.1.3, 12.1.4, 12.1.5, 12.1.6, 12.1.7, 12.1.8, 12.1.9, 12.1.10, 13.1.1, 13.1.2, 13.1.3, 13.1.4, 13.1.5, 13.1.6, 13.1.7, 13.1.8, 13.1.9, 13.1.10, 14.1.1, 14.1.2, 14.1.3, 14.1.4, 14.1.5, 14.1.6, 14.1.7, 14.1.8, 14.1.9, 14.1.10, 15.1.1, 15.1.2, 15.1.3, 15.1.4, 15.1.5, 15.1.6, 15.1.7, 15.1.8, 15.1.9, 15.1.10, 16.1.1, 16.1.2, 16.1.3, 16.1.4, 16.1.5, 16.1.6, 16.1.7, 16.1.8, 16.1.9, 16.1.10, 17.1.1, 17.1.2, 17.1.3, 17.1.4, 17.1.5, 17.1.6, 17.1.7, 17.1.8, 17.1.9, 17.1.10, 18.1.1, 18.1.2, 18.1.3, 18.1.4, 18.1.5, 18.1.6, 18.1.7, 18.1.8, 18.1.9, 18.1.10, 19.1.1, 19.1.2, 19.1.3, 19.1.4, 19.1.5, 19.1.6, 19.1.7, 19.1.8, 19.1.9, 19.1.10, 20.1.1, 20.1.2, 20.1.3, 20.1.4, 20.1.5, 20.1.6, 20.1.7, 20.1.8, 20.1.9, 20.1.10, 21.1.1, 21.1.2, 21.1.3, 21.1.4, 21.1.5, 21.1.6, 21.1.7, 21.1.8, 21.1.9, 21.1.10, 22.1.1, 22.1.2, 22.1.3, 22.1.4, 22.1.5, 22.1.6, 22.1.7, 22.1.8, 22.1.9, 22.1.10, 23.1.1, 23.1.2, 23.1.3, 23.1.4, 23.1.5, 23.1.6, 23.1.7, 23.1.8, 23.1.9, 23.1.10, 24.1.1, 24.1.2, 24.1.3, 24.1.4, 24.1.5, 24.1.6, 24.1.7, 24.1.8, 24.1.9, 24.1.10, 25.1.1, 25.1.2, 25.1.3, 25.1.4, 25.1.5, 25.1.6, 25.1.7, 25.1.8, 25.1.9, 25.1.10, 26.1.1, 26.1.2, 26.1.3, 26.1.4, 26.1.5, 26.1.6, 26.1.7, 26.1.8, 26.1.9, 26.1.10, 27.1.1, 27.1.2, 27.1.3, 27.1.4, 27.1.5, 27.1.6, 27.1.7, 27.1.8, 27.1.9, 27.1.10, 28.1.1, 28.1.2, 28.1.3, 28.1.4, 28.1.5, 28.1.6, 28.1.7, 28.1.8, 28.1.9, 28.1.10, 1.2.1, 1.2.2, 1.2.3, 1.2.4, 1.2.5, 1.2.6, 1.2.7, 1.2.8, 1.2.9, 1.2.10, 2.2.1, 2.2.2, 2.2.3, 2.2.4, 2.2.5, 2.2.6, 2.2.7, 2.2.8, 2.2.9, 2.2.10, 3.2.1, 3.2.2, 3.2.3, 3.2.4, 3.2.5, 3.2.6, 3.2.7, 3.2.8, 3.2.9, 3.2.10, 4.2.1, 4.2.2, 4.2.3, 4.2.4, 4.2.5, 4.2.6, 4.2.7, 4.2.8, 4.2.9, 4.2.10, 5.2.1, 5.2.2, 5.2.3, 5.2.4, 5.2.5, 5.2.6, 5.2.7, 5.2.8, 5.2.9, 5.2.10, 6.2.1, 6.2.2, 6.2.3, 6.2.4, 6.2.5, 6.2.6, 6.2.7, 6.2.8, 6.2.9, 6.2.10, 7.2.1, 7.2.2, 7.2.3, 7.2.4, 7.2.5, 7.2.6, 7.2.7, 7.2.8, 7.2.9, 7.2.10, 8.2.1, 8.2.2, 8.2.3, 8.2.4, 8.2.5, 8.2.6, 8.2.7, 8.2.8, 8.2.9, 8.2.10, 9.2.1, 9.2.2, 9.2.3, 9.2.4, 9.2.5, 9.2.6, 9.2.7, 9.2.8, 9.2.9, 9.2.10, 10.2.1, 10.2.2, 10.2.3, 10.2.4, 10.2.5, 10.2.6, 10.2.7, 10.2.8, 10.2.9, 10.2.10, 11.2.1, 11.2.2, 11.2.3, 11.2.4, 11.2.5, 11.2.6, 11.2.7, 11.2.8, 11.2.9, 11.2.10, 12.2.1, 12.2.2, 12.2.3, 12.2.4, 12.2.5, 12.2.6, 12.2.7, 12.2.8, 12.2.9, 12.2.10, 13.2.1, 13.2.2, 13.2.3, 13.2.4, 13.2.5, 13.2.6, 13.2.7, 13.2.8, 13.2.9, 13.2.10, 14.2.1, 14.2.2, 14.2.3, 14.2.4, 14.2.5, 14.2.6, 14.2.7, 14.2.8, 14.2.9, 14.2.10, 15.2.1, 15.2.2, 15.2.3, 15.2.4, 15.2.5, 15.2.6, 15.2.7, 15.2.8, 15.2.9, 15.2.10, 16.2.1, 16.2.2, 16.2.3, 16.2.4, 16.2.5, 16.2.6, 16.2.7, 16.2.8, 16.2.9, 16.2.10, 17.2.1, 17.2.2, 17.2.3, 17.2.4, 17.2.5, 17.2.6, 17.2.7, 17.2.8, 17.2.9, 17.2.10, 18.2.1, 18.2.2, 18.2.3, 18.2.4, 18.2.5, 18.2.6, 18.2.7, 18.2.8, 18.2.9, 18.2.10, 19.2.1, 19.2.2, 19.2.3, 19.2.4, 19.2.5, 19.2.6, 19.2.7, 19.2.8, 19.2.9, 19.2.10, 20.2.1, 20.2.2, 20.2.3, 20.2.4, 20.2.5, 20.2.6, 20.2.7, 20.2.8, 20.2.9, 20.2.10, 21.2.1, 21.2.2, 21.2.3, 21.2.4, 21.2.5, 21.2.6, 21.2.7, 21.2.8, 21.2.9, 21.2.10, 22.2.1, 22.2.2, 22.2.3, 22.2.4, 22.2.5, 22.2.6, 22.2.7, 22.2.8, 22.2.9, 22.2.10, 23.2.1, 23.2.2, 23.2.3, 23.2.4, 23.2.5, 23.2.6, 23.2.7, 23.2.8, 23.2.9, 23.2.10, 24.2.1, 24.2.2, 24.2.3, 24.2.4, 24.2.5, 24.2.6, 24.2.7, 24.2.8, 24.2.9, 24.2.10, 25.2.1, 25.2.2, 25.2.3, 25.2.4, 25.2.5, 25.2.6, 25.2.7, 25.2.8, 25.2.9, 25.2.10, 26.2.1, 26.2.2, 26.2.3, 26.2.4, 26.2.5, 26.2.6, 26.2.7, 26.2.8, 26.2.9 and 26.2.10.

Table 3 lists a group of cyclic nucleotide analog amidates of structure I wherein $L^1$ forms a heterocydic ring containing the phosphorus atom of the phosphonate group. Hydrolysis of the heterocyclic ring linked through the phosphorus atom results in formation of a phosphonate nudeotide analog such as HPMPC, PMEA, PMEG or PMPDAP depending on the Z group that is present.

TABLE 3

$L^1$

1. —NH—CH$_2$—C(O)—O—CH$_2$—O—
2. —NH—CH(CH$_3$)—C(O)—O—CH$_2$O—
3. —NH—CH(CH$_3$)$_2$—C(O)—O—CH$_2$—O—
4. —NH—CH(CH(CH$_3$)$_2$)—C(O)—O—CH$_2$—O—
5. —NH—CH(CH$_3$)(CH$_3$)$_2$—C(O)—O—CH$_2$—O—
6. —NH—CH$_2$—CH$_2$—CH$_2$—CH—C(O)—O—CH$_2$—O—
7. —NH—CH(CH$_2$—C$_6$H$_5$)—C(O)—O—CH$_2$—O—
8. —NH—CH(CH$_2$C$_8$NH$_6$)—C(O)—O—CH$_2$—O—
9. —NH—CH(CH$_2$—S—CH$_3$)—C(O)—O—
10. —NH—CH(CH$_2$OH)—C(O)—O—CH$_2$—O—
11. —NH—CH(CH(OH)(CH$_3$))—C(O)—O—CH$_2$—O—
12. —NH—CH(—CH$_2$SH)—C(O)—O—CH$_2$—O—
13. —NH—CH(CH$_2$—C$_6$H$_5$OH)—(O)—O—CH$_2$—O—
14. —NH—CH(CH$_2$—C(O)—NH$_2$)—C(O)—O—CH$_2$—O—
15. —NH—CH(CH$_2$—CH$_2$—C(O)—NH$_2$)—C(O)—O—CH$_2$—O—
16. —NH—CH(CH$_2$C(O)—OR$^4$)—C(O)—O—CH$_2$—O—
17. —NH—CH(CH$_2$CH$_2$C(O)—OR$^4$)—C(O)—O—CH$_2$—O—
18. —NH—CH(CH$_2$CH$_2$CH$_2$CH$_2$NH$_2$)—C(O)—O—CH$_2$—O—
19. —NH—CH(CH$_2$CH$_2$CH$_2$NHC(NH)(NH$_2$))—C(O)—O—CH$_2$—O—
20. —NH—CH(CH$_2$C$_3$N$_2$H$_3$)—C(O)—O—CH$_2$—O—
21. —NH—CH(CH$_2$CH$_2$CH$_2$NH$_2$)—CH$_2$—C(O)—O—CH$_2$—O—
22. —NH—CH(CH$_2$CH$_2$CH$_2$CH$_2$NH$_2$)—CH$_2$—C(O)—O—CH$_2$—O—
23. —NH—CH(CH$_2$CH$_2$NHC(NH)(NH$_2$))—CH$_2$—C(O)—O—CH$_2$—O—
24. —NH—CH(C(O)—OR$^4$)—CH$_2$—C(O)—O—CH$_2$—O—
25. —NH—CH(CH$_2$C(O)—OR$^4$)—CH$_2$—C(O)—O—
26. —NH—CH(CH$_2$CH$_2$C(O)OR$^4$)—CH$_2$—C(O)—O—CH$_2$—O—
27. —NH—CH2—C(O)—O—CH(C(O)OR$^4$)—N—
28. —NH—CH(CH$_3$)—C(O)—O—CH(C(O)OR$^4$)—N—

**Z—B\*\***

1. —CH$_2$—O—CH$_2$—CH$_2$—B
2. —CH$_2$—O—C$^\#$H(CH$_2$—OR$^4$)—CH$_2$—B
3. —CH$_2$—O—C$^\#$HCH(CH$_3$)—CH$_2$—B
4. —CH$_2$—O—C$^\#$H(CH$_2$F)—CH$_2$—B
5. —CH$_2$—O—C$^\#$H(CH=CH$_2$)—CH$_2$—B
6. —CH$_2$—O—C$^\#$H(CH$_2$N$_3$)—CH$_2$—B

B

1. adenin-9-yl
2. guanin-9-yl
3. cytosin-1-yl
4. 2,6-diaminopurin-9-yl
5. 2-aminopurin-9-yl
6. 6-azacytosin-1-yl
7. 1-deazaadenin-9-yl
8. 3-deazaadenin-9-yl
9. 8-deazaadenin-9-yl
10. 7-deaza-8-azaadenin-9-yl \*- See Table 1 footnote; the terminal nitrogen and oxygen or nitrogen atoms are both linked to the phosphorus atom of the phosphonate group.
\*\*- See Table 1 footnote.
$^\#$- See Table 1 footnote.

Compounds listed in Table 3 are designated herein by numbers assigned to $L^1$, Z and B according to the following convention, $L^1$.Z.B. Thus, compounds 1.1.1 and 2.3.4 represent compounds designated cyclic glycinylPMEA and cyclic alanylPMPDAP. Exemplary compounds include 1.1.1, 1.1.2, 1.1.3, 1.1.4, 1.1.5, 1.1.6, 1.1.7, 1.1.8, 1.1.9, 1.1.10, 2.1.1, 2.1.2, 2.1.3, 2.1.4, 2.1.5, 2.1.6, 2.1.7, 2.1.8, 2.1.9, 2.1.10, 3.1.1, 3.1.2, 3.1.3, 3.1.4, 3.1.5, 3.1.6, 3.1.7, 3.1.8, 3.1.9, 3.1.10, 4.1.1, 4.1.2, 4.1.3, 4.1.4, 4.1.5, 4.1.6, 4.1.7, 4.1.8, 4.1.9, 4.1.10, 5.1.1, 5.1.2, 5.1.3, 5.1.4, 5.1.5, 5.1.6, 5.1.7, 5.1.8, 5.1.9, 5.1.10, 6.1.1, 6.1.2, 6.1.3, 6.1.4, 6.1.5, 6.1.6, 6.1.7, 6.1.8, 6.1.9, 6.1.10, 7.1.1, 7.1.2, 7.1.3, 7.1.4, 7.1.5, 7.1.6, 7.1.7, 7.1.8, 7.1.9, 7.1.10, 8.1.1, 8.1.2, 8.1.3, 8.1.4, 8.1.5, 8.1.6, 8.1.7, 8.1.8, 8.1.9, 8.1.10, 9.1.1, 9.1.2, 9.1.3, 9.1.4, 9.1.5, 9.1.6, 9.1.7, 9.1.8, 9.1.9, 9.1.10, 10.1.1, 10.1.2, 10.1.3, 10.1.4, 10.1.5, 10.1.6, 10.1.7, 10.1.8, 10.1.9, 10.1.10, 11.1.1, 11.1.2, 11.1.3, 11.1.4, 11.1.5, 11.1.6, 11.1.7, 11.1.8, 11.1.9, 11.1.10, 12.1.1, 12.1.2, 12.1.3, 12.1.4, 12.1.5, 12.1.6, 12.1.7, 12.1.8, 12.1.9, 12.1.10, 13.1.1, 13.1.2, 13.1.3, 13.1.4, 13.1.5, 13.1.6, 13.1.7, 13.1.8, 13.1.9, 13.1.10, 14.1.1, 14.1.2, 14.1.3, 14.1.4, 14.1.5, 14.1.6, 14.1.7, 14.1.8, 14.1.9, 14.1.10, 15.1.1, 15.1.2, 15.1.3, 15.1.4, 15.1.5, 15.1.6, 15.1.7, 15.1.8, 15.1.9, 15.1.10, 16.1.1, 16.1.2, 16.1.3, 16.1.4, 16.1.5, 16.1.6, 16.1.7, 16.1.8, 16.1.9, 16.1.10, 17.1.1, 17.1.2, 17.1.3, 17.1.4, 17.1.5, 17.1.6, 17.1.7, 17.1.8, 17.1.9, 17.1.10, 18.1.1, 18.1.2, 18.1.3, 18.1.4, 18.1.5, 18.1.6, 18.1.7, 18.1.8, 18.1.9, 18.1.10, 19.1.1, 19.1.2, 19.1.3, 19.1.4, 19.1.5, 19.1.6, 19.1.7, 19.1.8, 19.1.9, 19.1.10, 20.1.1, 20.1.2, 20.1.3, 20.1.4, 20.1.5, 20.1.6, 20.1.7, 20.1.8, 20.1.9, 20.1.10, 21.1.1, 21.1.2, 21.1.3, 21.1.4, 21.1.5, 21.1.6, 21.1.7, 21.1.8, 21.1.9, 21.1.10, 22.1.1, 22.1.2, 22.1.3, 22.1.4, 22.1.5, 22.1.6, 22.1.7, 22.1.8, 22.1.9, 22.1.10, 23.1.1, 23.1.2, 23.1.3, 23.1.4, 23.1.5, 23.1.6, 23.1.7, 23.1.8, 23.1.9, 23.1.10, 24.1.1, 24.1.2, 24.1.3, 24.1.4, 24.1.5, 24.1.6, 24.1.7, 24.1.8, 24.1.9, 24.1.10, 25.1.1, 25.1.2, 25.1.3, 25.1.4, 25.1.5, 25.1.6, 25.1.7, 25.1.8, 25.1.9, 25.1.10, 26.1.1, 26.1.2, 26.1.3, 26.1.4, 26.1.5, 26.1.6, 26.1.7, 26.1.8, 26.1.9, 26.1.10, 27.1.1, 27.1.2, 27.1.3, 27.1.4, 27.1.5, 27.1.6, 27.1.7, 27.1.8, 27.1.9, 27.1.10, 28.1.1, 28.1.2, 28.1.3, 28.1.4, 28.1.5, 28.1.6, 28.1.7, 28.1.8, 28.1.9, 28.1.10, 1.2.1, 1.2.2, 1.2.3, 1.2.4, 1.2.5, 1.2.6, 1.2.7, 1.2.8, 1.2.9, 1.2.10, 2.2.1, 2.2.2, 2.2.3, 2.2.4, 2.2.5, 2.2.6, 2.2.7, 2.2.8, 2.2.9, 2.2.10, 3.2.1, 3.2.2, 3.2.3, 3.2.4, 3.2.5, 3.2.6, 3.2.7, 3.2.8, 3.2.9, 3.2.10, 4.2.1, 4.2.2, 4.2.3, 4.2.4, 4.2.5, 4.2.6, 4.2.7, 4.2.8, 4.2.9, 4.2.10, 5.2.1, 5.2.2, 5.2.3, 5.2.4, 5.2.5, 5.2.6, 5.2.7, 5.2.8, 5.2.9, 5.2.10, 6.2.1, 6.2.2, 6.2.3, 6.2.4, 6.2.5, 6.2.6, 6.2.7, 6.2.8, 6.2.9, 6.2.10, 7.2.1, 7.2.2, 7.2.3, 7.2.4, 7.2.5, 7.2.6, 7.2.7, 7.2.8, 7.2.9, 7.2.10, 8.2.1, 8.2.2, 8.2.3, 8.2.4, 8.2.5, 8.2.6, 8.2.7, 8.2.8, 8.2.9, 8.2.10, 9.2.1, 9.2.2, 9.2.3, 9.2.4, 9.2.5, 9.2.6, 9.2.7, 9.2.8, 9.2.9, 9.2.10, 10.2.1, 10.2.2, 10.2.3, 10.2.4, 10.2.5, 10.2.6, 10.2.7, 10.2.8, 10.2.9, 10.2.10, 11.2.1, 11.2.2, 11.2.3, 11.2.4, 11.2.5, 11.2.6, 11.2.7, 11.2.8, 11.2.9, 11.2.10, 12.2.1, 12.2.2, 12.2.3, 12.2.4, 12.2.5, 12.2.6, 12.2.7, 12.2.8, 12.2.9, 12.2.10, 13.2.1, 13.2.2, 13.2.3, 13.2.4, 13.2.5, 13.2.6, 13.2.7, 13.2.8, 13.2.9, 13.2.10, 14.2.1, 14.2.2, 14.2.3, 14.2.4, 14.2.5, 14.2.6, 14.2.7, 14.2.8, 14.2.9, 14.2.10, 15.2.1, 15.2.2, 15.2.3, 15.2.4, 15.2.5, 15.2.6, 15.2.7, 15.2.8, 15.2.9, 15.2.10, 16.2.1, 16.2.2, 16.2.3, 16.2.4, 16.2.5, 16.2.6, 16.2.7, 16.2.8, 16.2.9, 16.2.10, 17.2.1, 17.2.2, 17.2.3, 17.2.4, 17.2.5, 17.2.6, 17.2.7, 17.2.8, 17.2.9, 17.2.10, 18.2.1, 18.2.2, 18.2.3, 18.2.4, 18.2.5, 18.2.6, 18.2.7, 18.2.8, 18.2.9, 18.2.10, 19.2.1, 19.2.2, 19.2.3, 19.2.4, 19.2.5, 19.2.6, 19.2.7, 19.2.8, 19.2.9, 19.2.10, 20.2.1, 20.2.2, 20.2.3, 20.2.4, 20.2.5, 20.2.6, 20.2.7, 20.2.8, 20.2.9, 20.2.10, 21.2.1, 21.2.2, 21.2.3, 21.2.4, 21.2.5, 21.2.6, 21.2.7, 21.2.8, 21.2.9, 21.2.10, 22.2.1, 22.2.2, 22.2.3, 22.2.4, 22.2.5, 22.2.6, 22.2.7, 22.2.8, 22.2.9, 22.2.10, 23.2.1, 23.2.2, 23.2.3, 23.2.4, 23.2.5, 23.2.6, 23.2.7, 23.2.8, 23.2.9, 23.2.10, 24.2.1, 24.2.2, 24.2.3, 24.2.4, 24.2.5, 24.2.6, 24.2.7, 24.2.8, 24.2.9, 24.2.10, 25.2.1, 25.2.2, 25.2.3, 25.2.4, 25.2.5, 25.2.6, 25.2.7, 25.2.8, 25.2.9, 25.2.10, 26.2.1, 26.2.2, 26.2.3, 26.2.4, 26.2.5, 26.2.6, 26.2.7, 26.2.8, 26.2.9, 26.2.10, 27.2.1, 27.2.2, 27.2.3, 27.2.4, 27.2.5, 27.2.6, 27.2.7, 27.2.8, 27.2.9, 27.2.10, 28.2.1, 28.2.2, 28.2.3, 28.2.4, 28.2.5, 28.2.6, 28.2.7, 28.2.8, 28.2.9, 28.2.10, 1.3.1, 1.3.2, 1.3.3, 1.3.4, 1.3.5, 1.3.6, 1.3.7, 1.3.8, 1.3.9, 1.3.10, 2.3.1, 2.3.2, 2.3.3, 2.3.4, 2.3.5, 2.3.6, 2.3.7, 2.3.8, 2.3.9, 2.3.10, 3.3.1, 3.3.2, 3.3.3, 3.3.4, 3.3.5, 3.3.6, 3.3.7, 3.3.8, 3.3.9, 3.3.10, 4.3.1, 4.3.2, 4.3.3, 4.3.4, 4.3.5, 4.3.6, 4.3.7, 4.3.8, 4.3.9, 4.3.10, 5.3.1, 5.3.2, 5.3.3, 5.3.4, 5.3.5, 5.3.6, 5.3.7, 5.3.8, 5.3.9, 5.3.10, 6.3.1, 6.3.2, 6.3.3, 6.3.4, 6.3.5, 6.3.6, 6.3.7, 6.3.8, 6.3.9, 6.3.10, 7.3.1, 7.3.2, 7.3.3, 7.3.4, 7.3.5, 7.3.6, 7.3.7, 7.3.8, 7.3.9, 7.3.10, 8.3.1, 8.3.2, 8.3.3, 8.3.4, 8.3.5, 8.3.6, 8.3.7, 8.3.8, 8.3.9, 8.3.10, 9.3.1, 9.3.2, 9.3.3, 9.3.4, 9.3.5, 9.3.6, 9.3.7, 9.3.8, 9.3.9, 9.3.10, 10.3.1, 10.3.2, 10.3.3, 10.3.4, 10.3.5, 10.3.6, 10.3.7, 10.3.8, 10.3.9, 10.3.10, 11.3.1, 11.3.2, 11.3.3, 11.3.4, 11.3.5, 11.3.6, 11.3.7, 11.3.8, 11.3.9, 11.3.10, 12.3.1, 12.3.2, 12.3.3, 12.3.4, 12.3.5, 12.3.6, 12.3.7, 12.3.8, 12.3.9, 12.3.10, 13.3.1, 13.3.2, 13.3.3, 13.3.4, 13.3.5, 13.3.6, 13.3.7, 13.3.8, 13.3.9, 13.3.10, 14.3.1, 14.3.2, 14.3.3, 14.3.4, 14.3.5, 14.3.6, 14.3.7, 14.3.8, 14.3.9, 14.3.10, 15.3.1, 15.3.2, 15.3.3, 15.3.4, 15.3.5, 15.3.6, 15.3.7, 15.3.8, 15.3.9, 15.3.10, 16.3.1, 16.3.2, 16.3.3, 16.3.4, 16.3.5, 16.3.6, 16.3.7, 16.3.8, 16.3.9, 16.3.10, 17.3.1, 17.3.2, 17.3.3, 17.3.4, 17.3.5, 17.3.6, 17.3.7, 17.3.8, 17.3.9, 17.3.10, 18.3.1, 18.3.2, 18.3.3, 18.3.4, 18.3.5, 18.3.6, 18.3.7, 18.3.8, 18.3.9, 18.3.10, 19.3.1, 19.3.2, 19.3.3, 19.3.4, 19.3.5, 19.3.6, 19.3.7, 19.3.8, 19.3.9, 19.3.10, 20.3.1, 20.3.2, 20.3.3, 20.3.4, 20.3.5, 20.3.6, 20.3.7, 20.3.8, 20.3.9, 20.3.10, 21.3.1, 21.3.2, 21.3.3, 21.3.4, 21.3.5, 21.3.6, 21.3.7, 21.3.8, 21.3.9, 21.3.10, 22.3.1, 22.3.2, 22.3.3, 22.3.4, 22.3.5, 22.3.6, 22.3.7, 22.3.8, 22.3.9, 22.3.10, 23.3.1, 23.3.2, 23.3.3, 23.3.4, 23.3.5, 23.3.6, 23.3.7, 23.3.8, 23.3.9, 23.3.10, 24.3.1, 24.3.2, 24.3.3, 24.3.4, 24.3.5, 24.3.6, 24.3.7, 24.3.8, 24.3.9, 24.3.10, 25.3.1, 25.3.2, 25.3.3, 25.3.4, 25.3.5, 25.3.6, 25.3.7, 25.3.8, 25.3.9, 25.3.10, 26.3.1, 26.3.2, 26.3.3, 26.3.4, 26.3.5, 26.3.6, 26.3.7, 26.3.8, 26.3.9, 26.3.10, 27.3.1, 27.3.2, 27.3.3, 27.3.4, 27.3.5, 27.3.6, 27.3.7, 27.3.8, 27.3.9, 27.3.10, 28.3.1, 28.3.2, 28.3.3, 28.3.4, 28.3.5, 28.3.6, 28.3.7, 28.3.8, 28.3.9 and 28.3.10.

Table 4 lists a group of cyclic nucleotide analogs of structure I wherein a heterocyclic ring comprising $L^1$ and the phosphorus atom of the phosphonate group along with part of the Z-B substructure $-O-CH_2-C^\#H(CH_2-)-CH_2-B$. The unbonded O atom in the Z substructure is linked to $L^1$ through the a carboxyl group of the amino acid while the $CH_2$ moiety on the right side is linked to the P atom and the $CH_2$ moiety linked to the chiral carbon is linked to B (i.e., $-L^1-O-CH_2-CH(CH_2-B)-O-CH_2-P(O)(L^2)-$ with $-P(O)(L^2)-$ and $-L^1-$ linked together). Hydrolysis of the compound results in formation of an HPMP nucleoside phosphonate. A related group of compounds comprises a heterocyclic ring linked through a side chain or other carboxyl group instead of through the carboxyl group linked to the a carbon atom. Hydrolysis of these compounds also result in formation of an HPMP nucleoside phosphonate.

TABLE 4

$L^{1*}-Z(B)-P(O)(L^2)-$

1 $-NH-CH_2-C(O)-O-CH_2-C^\#H(CH_2-B)-O-CH_2P(O)(L^2)-$
2 $-NH-CH(CH_3)-C(O)-O-CH_2-C^\#H(CH_2-B)-O-CH_2-P(O)(L^2)-$
3 $-NH-CH(CH_3)_2-C(O)-O-CH_2-C^\#H(CH_2-B)-O-CH_2-P(O)(L^2)-$
4 $-NH-CH(CH(CH_3)_2)-C(O)-O-CH_2-C^\#H(CH_2-B)-O-CH_2-P(O)(L^2)-$
5 $-NH-CH(CH_3)(CH_3)_2)-C(O)-O-CH_2-C^\#H(CH_2-B)-O-CH_2-P(O)(L^2)-$
6 $-NH-CH_2-CH_2-CH_2-CH-C(O)-O-CH_2-C^\#H(CH_2-B)-O-CH_2-P(O)(L^2)-$
7 $-NH-CH(CH_2-C_6H_5)-C(O)-O-CH_2-C^\#H(CH_2-B)-O-CH_2-P(O)(L^2)-$
8 $-NH-CH(CH_2-C_8NH_6)-C(O)-O-CH_2-C^\#H(CH_2-B)-O-CH_2-P(O)(L^2)-$
9 $-NH-CH(CH_2CH-S-CH_3)-C(O)-O-CH_2-C^\#H(CH_2-B)-O-CH_2-P(O)(L^2)-$
10 $-NH-CH(CH_2OH)-C(O)-O-CH_2O-CH_2-C^\#H(CH_2-B)-O-CH_2-P(O)(L^2)-$
11 $-NH-CH(CH(OH)(CH_3))-C(O)-O-CH_2-C^\#H(CH_2-B)-O-CH_2-P(O)(L^2)-$
12 $-NH-CH(-CH_2SH)-C(O)-O-CH_2-C^\#H(CH_2-B)-O-CH_2-P(O)(L^2)-$
13 $-NH-CH(CH2-C_6H_5OH)-C(O)-O-CH_2-C^\#H(CH_2-B)-O-CH_2-P(O)(L^2)-$
14 $-NH-CH(CH_2-C(O)-NH_2)-C(O)-O-CH_2-C^\#H(CH_2-B)-O-CH_2-P(O)(L^2)-$
15 $-NH-CH(CH_2-CH_2-C(O)-NH_2)-C(O)-O-CH_2-C^\#H(CH_2-B)-O-CH_2-P(O)(L^2)-$
16 $-NH-CH(CH_2CH_2C(O)-OR^4)-C(O)-O-CH_2-C^\#H(CH_2-B)-O-CH_2-P(O)(L^2)-$
17 $-NH-CH(CH_2CH_2C(O)OR^4)-C(O)-O-CH_2-C^\#H(CH_2-B)-O-CH_2-P(O)(L^2)-$
18 $-NH-CH(CH_2CH_2CH_2CH_2NH_2)-C(O)-O-CH_2-C^\#H(CH_2-B)-O-CH_2-P(O)(L^2)-$
19 $-NH-CH(CH_2CH_2CH_2NHC(NH)(NH_2))-C(O)-O-CH_2-C^\#H(CH_2-B)-O-CH_2-P(O)(L^2)-$
20 $-NH-CH(CH_2C_3N_2H_3)-C(O)-O-CH_2-C^\#H(CH_2-B)-O-CH_2-P(O)(L^2)-$
21 $-NH-CH(CH_3)-CH_2-C(O)-O-CH_2-C^\#H(CH_2-B)-O-CH_2-P(O)(L^2)-$
22 $-NH-CH(CH_2CH_2CH_2NH_2)-CH_2-C(O)-O-CH_2-C^\#H(CH_2-B)-O-CH_2-P(O)(L^2)-$ $L^2$

1 $-NH-CH_2-C(O)-OR^4$
2 $-NH-CH(CH_3)-C(O)-OR^4$
3 $-O-CH_2-O-C(O)-C(CH_3)_3$
4 $-O-CH_2C_6H_5$
5 $-O-C_6H_5$
6 $-O-CH(CH_3)_2$
7 $-NH-CH(CH_2C_6H_4)-C(O)-OR^4$

TABLE 4-continued

8 —OH

B 1. adenin-9-yl
2. guanin-9-yl
3. cytosin-1-yl
4. 2,6-diaminopurin-9-yl
5. 2-aminopurin-9-yl
6. 6-azacytosin-1-yl
7. 1-deazaadenin-9-yl
8. 3-deazaadenin-9-yl
9. 8-azaadenin-9-yl
10. 7-deaza-8-azaadenin-9-yl

*- See Table 1 footnote; the terminal nitrogen and phosphorus atoms are linked to each other.

Compounds listed in Table 4 are designated herein by numbers assigned to $L^1$, $L^2$, and B according to the following convention, $L^1.L^2.B$. All Z correspond to the esterified HPMP substructure moiety. Thus, compounds 1.1.3 and 2.4.3 represent compounds designated "glycyl cyclic glycinyl HPMPC" and "benzyl cyclic alanyl HPMPC" esters. Exemplary compounds include 1.1.1, 1.1.2, 1.1.3, 1.1.4, 1.1.5, 1.1.6, 1.1.7, 1.1.8, 1.1.9, 1.1.10, 2.1.1, 2.1.2, 2.1.3, 2.1.4, 2.1.5, 2.1.6, 2.1.7, 2.1.8, 2.1.9, 2.1.10, 3.1.1, 3.1.2, 3.1.3, 3.1.4, 3.1.5, 3.1.6, 3.1.7, 3.1.8, 3.1.9, 3.1.10, 4.1.1, 4.1.2, 4.1.3, 4.1.4, 4.1.5, 4.1.6, 4.1.7, 4.1.8, 4.1.9, 4.1.10, 5.1.1, 5.1.2, 5.1.3, 5.1.4, 5.1.5, 5.1.6, 5.1.7, 5.1.8, 5.1.9, 5.1.10, 6.1.1, 6.1.2, 6.1.3, 6.1.4, 6.1.5, 6.1.6, 6.1.7, 6.1.8, 6.1.9, 6.1.10, 7.1.1, 7.1.2, 7.1.3, 7.1.4, 7.1.5, 7.1.6, 7.1.7, 7.1.8, 7.1.9, 7.1.10, 8.1.1, 8.1.2, 8.1.3, 8.1.4, 8.1.5, 8.1.6, 8.1.7, 8.1.8, 8.1.9, 8.1.10, 9.1.1, 9.1.2, 9.1.3, 9.1.4, 9.1.5, 9.1.6, 9.1.7, 9.1.8, 9.1.9, 9.1.10, 10.1.1, 10.1.2, 10.1.3, 10.1.4, 10.1.5, 10.1.6, 10.1.7, 10.1.8, 10.1.9, 10.1.10, 11.1.1, 11.1.2, 11.1.3, 11.1.4, 11.1.5, 11.1.6, 11.1.7, 11.1.8, 11.1.9, 11.1.10, 12.1.1, 12.1.2, 12.1.3, 12.1.4, 12.1.5, 12.1.6, 12.1.7, 12.1.8, 12.1.9, 12.1.10, 13.1.1, 13.1.2, 13.1.3, 13.1.4, 13.1.5, 13.1.6, 13.1.7, 13.1.8, 13.1.9, 13.1.10, 14.1.1, 14.1.2, 14.1.3, 14.1.4, 14.1.5, 14.1.6, 14.1.7, 14.1.8, 14.1.9, 14.1.10, 15.1.1, 15.1.2, 15.1.3, 15.1.4, 15.1.5, 15.1.6, 15.1.7, 15.1.8, 15.1.9, 15.1.10, 16.1.1, 16.1.2, 16.1.3, 16.1.4, 16.1.5, 16.1.6, 16.1.7, 16.1.8, 16.1.9, 16.1.10, 17.1.1, 17.1.2, 17.1.3, 17.1.4, 17.1.5, 17.1.6, 17.1.7, 17.1.8, 17.1.9, 17.1.10, 18.1.1, 18.1.2, 18.1.3, 18.1.4, 18.1.5, 18.1.6, 18.1.7, 18.1.8, 18.1.9, 18.1.10, 19.1.1, 19.1.2, 19.1.3, 19.1.4, 19.1.5, 19.1.6, 19.1.7, 19.1.8, 19.1.9, 19.1.10, 20.1.1, 20.1.2, 20.1.3, 20.1.4, 20.1.5, 20.1.6, 20.1.7, 20.1.8, 20.1.9, 20.1.10, 21.1.1, 21.1.2, 21.1.3, 21.1.4, 21.1.5, 21.1.6, 21.1.7, 21.1.8, 21.1.9, 21.1.10, 22.1.1, 22.1.2, 22.1.3, 22.1.4, 22.1.5, 22.1.6, 22.1.7, 22.1.8, 22.1.9, 22.1.10, 1.2.1, 1.2.2, 1.2.3, 1.2.4, 1.2.5, 1.2.6, 1.2.7, 1.2.8, 1.2.9, 1.2.10, 2.2.1, 2.2.2, 2.2.3, 2.2.4, 2.2.5, 2.2.6, 2.2.7, 2.2.8, 2.2.9, 2.2.10, 3.2.1, 3.2.2, 3.2.3, 3.2.4, 3.2.5, 3.2.6, 3.2.7, 3.2.8, 3.2.9, 3.2.10, 4.2.1, 4.2.2, 4.2.3, 4.2.4, 4.2.5, 4.2.6, 4.2.7, 4.2.8, 4.2.9, 4.2.10, 5.2.1, 5.2.2, 5.2.3, 5.2.4, 5.2.5, 5.2.6, 5.2.7, 5.2.8, 5.2.9, 5.2.10, 6.2.1, 6.2.2, 6.2.3, 6.2.4, 6.2.5, 6.2.6, 6.2.7, 6.2.8, 6.2.9, 6.2.10, 7.2.1, 7.2.2, 7.2.3, 7.2.4, 7.2.5, 7.2.6, 7.2.7, 7.2.8, 7.2.9, 7.2.10, 8.2.1, 8.2.2, 8.2.3, 8.2.4, 8.2.5, 8.2.6, 8.2.7, 8.2.8, 8.2.9, 8.2.10, 9.2.1, 9.2.2, 9.2.3, 9.2.4, 9.2.5, 9.2.6, 9.2.7, 9.2.8, 9.2.9, 9.2.10, 10.2.1, 10.2.2, 10.2.3, 10.2.4, 10.2.5, 10.2.6, 10.2.7, 10.2.8, 10.2.9, 10.2.10, 11.2.1, 11.2.2, 11.2.3, 11.2.4, 11.2.5, 11.2.6, 11.2.7, 11.2.8, 11.2.9, 11.2.10, 12.2.1, 12.2.2, 12.2.3, 12.2.4, 12.2.5, 12.2.6, 12.2.7, 12.2.8, 12.2.9, 12.2.10, 13.2.1, 13.2.2, 13.2.3, 13.2.4, 13.2.5, 13.2.6, 13.2.7, 13.2.8, 13.2.9, 13.2.10, 14.2.1, 14.2.2, 14.2.3, 14.2.4, 14.2.5, 14.2.6, 14.2.7, 14.2.8, 14.2.9, 14.2.10, 15.2.1, 15.2.2, 15.2.3, 15.2.4, 15.2.5, 15.2.6, 15.2.7, 15.2.8, 15.2.9, 15.2.10, 16.2.1, 16.2.2, 16.2.3, 16.2.4, 16.2.5, 16.2.6, 16.2.7, 16.2.8, 16.2.9, 16.2.10, 17.2.1, 17.2.2, 17.2.3, 17.2.4, 17.2.5, 17.2.6, 17.2.7, 17.2.8, 17.2.9, 17.2.10, 18.2.1, 18.2.2, 18.2.3, 18.2.4, 18.2.5, 18.2.6, 18.2.7, 18.2.8, 18.2.9, 18.2.10, 19.2.1, 19.2.2, 19.2.3, 19.2.4, 19.2.5, 19.2.6, 19.2.7, 19.2.8, 19.2.9, 19.2.10, 20.2.1, 20.2.2, 20.2.3, 20.2.4, 20.2.5, 20.2.6, 20.2.7, 20.2.8, 20.2.9, 20.2.10, 21.2.1, 21.2.2, 21.2.3, 21.2.4, 21.2.5, 21.2.6, 21.2.7, 21.2.8, 21.2.9, 21.2.10, 22.2.1, 22.2.2, 22.2.3, 22.2.4, 22.2.5, 22.2.6, 22.2.7, 22.2.8, 22.2.9, 22.2.10, 1.3.1, 1.3.2, 1.3.3, 1.3.4, 1.3.5, 1.3.6, 1.3.7, 1.3.8, 1.3.9, 1.3.10, 2.3.1, 2.3.2, 2.3.3, 2.3.4, 2.3.5, 2.3.6, 2.3.7, 2.3.8, 2.3.9, 2.3.10, 3.3.1, 3.3.2, 3.3.3, 3.3.4, 3.3.5, 3.3.6, 3.3.7, 3.3.8, 3.3.9, 3.3.10, 4.3.1, 4.3.2, 4.3.3, 4.3.4, 4.3.5, 4.3.6, 4.3.7, 4.3.8, 4.3.9, 4.3.10, 5.3.1, 5.3.2, 5.3.3, 5.3.4, 5.3.5, 5.3.6, 5.3.7, 5.3.8, 5.3.9, 5.3.10, 6.3.1, 6.3.2, 6.3.3, 6.3.4, 6.3.5, 6.3.6, 6.3.7, 6.3.8, 6.3.9, 6.3.10, 7.3.1, 7.3.2, 7.3.3, 7.3.4, 7.3.5, 7.3.6, 7.3.7, 7.3.8, 7.3.9, 7.3.10, 8.3.1, 8.3.2, 8.3.3, 8.3.4, 8.3.5, 8.3.6, 8.3.7, 8.3.8, 8.3.9, 8.3.10, 9.3.1, 9.3.2, 9.3.3, 9.3.4, 9.3.5, 9.3.6, 9.3.7, 9.3.8, 9.3.9, 9.3.10, 10.3.1, 10.3.2, 10.3.3, 10.3.4, 10.3.5, 10.3.6, 10.3.7, 10.3.8, 10.3.9, 10.3.10, 11.3.1, 11.3.2, 11.3.3, 11.3.4, 11.3.5, 11.3.6, 11.3.7, 11.3.8, 11.3.9, 11.3.10, 12.3.1, 12.3.2, 12.3.3, 12.3.4, 12.3.5, 12.3.6, 12.3.7, 12.3.8, 12.3.9, 12.3.10, 13.3.1, 13.3.2, 13.3.3, 13.3.4, 13.3.5, 13.3.6, 13.3.7, 13.3.8, 13.3.9, 13.3.10, 14.3.1, 14.3.2, 14.3.3, 14.3.4, 14.3.5, 14.3.6, 14.3.7, 14.3.8, 14.3.9, 14.3.10, 15.3.1, 15.3.2, 15.3.3, 15.3.4, 15.3.5, 15.3.6, 15.3.7, 15.3.8, 15.3.9, 15.3.10, 16.3.1, 16.3.2, 16.3.3, 16.3.4, 16.3.5, 16.3.6, 16.3.7, 16.3.8, 16.3.9, 16.3.10, 17.3.1, 17.3.2, 17.3.3, 17.3.4, 17.3.5, 17.3.6, 17.3.7, 17.3.8, 17.3.9, 17.3.10, 18.3.1, 18.3.2, 18.3.3, 18.3.4, 18.3.5, 18.3.6, 18.3.7, 18.3.8, 18.3.9, 18.3.10, 19.3.1, 19.3.2, 19.3.3, 19.3.4, 19.3.5, 19.3.6, 19.3.7, 19.3.8, 19.3.9, 19.3.10, 20.3.1, 20.3.2, 20.3.3, 20.3.4, 20.3.5, 20.3.6, 20.3.7, 20.3.8, 20.3.9, 20.3.10, 21.3.1, 21.3.2, 21.3.3, 21.3.4, 21.3.5, 21.3.6, 21.3.7, 21.3.8, 21.3.9, 21.3.10, 22.3.1, 22.3.2, 22.3.3, 22.3.4, 22.3.5, 22.3.6, 22.3.7, 22.3.8, 22.3.9, 22.3.10, 1.4.1, 1.4.2, 1.4.3, 1.4.4, 1.4.5, 1.4.6, 1.4.7, 1.4.8, 1.4.9, 1.4.10, 2.4.1, 2.4.2, 2.4.3, 2.4.4, 2.4.5, 2.4.6, 2.4.7, 2.4.8, 2.4.9, 2.4.10, 3.4.1, 3.4.2, 3.4.3, 3.4.4, 3.4.5, 3.4.6, 3.4.7, 3.4.8, 3.4.9, 3.4.10, 4.4.1, 4.4.2, 4.4.3, 4.4.4, 4.4.5, 4.4.6, 4.4.7, 4.4.8, 4.4.9, 4.4.10, 5.4.1, 5.4.2, 5.4.3, 5.4.4, 5.4.5, 5.4.6, 5.4.7, 5.4.8, 5.4.9, 5.4.10, 6.4.1, 6.4.2, 6.4.3, 6.4.4, 6.4.5, 6.4.6, 6.4.7, 6.4.8, 6.4.9, 6.4.10, 7.4.1, 7.4.2, 7.4.3, 7.4.4, 7.4.5, 7.4.6, 7.4.7, 7.4.8, 7.4.9, 7.4.10, 8.4.1, 8.4.2, 8.4.3, 8.4.4, 8.4.5, 8.4.6, 8.4.7, 8.4.8, 8.4.9, 8.4.10, 9.4.1, 9.4.2, 9.4.3, 9.4.4, 9.4.5, 9.4.6, 9.4.7, 9.4.8, 9.4.9, 9.4.10, 10.4.1, 10.4.2, 10.4.3, 10.4.4, 10.4.5, 10.4.6, 10.4.7, 10.4.8, 10.4.9, 10.4.10, 11.4.1, 11.4.2, 11.4.3, 11.4.4, 11.4.5, 11.4.6, 11.4.7, 11.4.8, 11.4.9, 11.4.10, 12.4.1, 12.4.2, 12.4.3, 12.4.4, 12.4.5, 12.4.6, 12.4.7, 12.4.8, 12.4.9, 12.4.10, 13.4.1, 13.4.2, 13.4.3, 13.4.4, 13.4.5, 13.4.6, 13.4.7, 13.4.8, 13.4.9, 13.4.10, 14.4.1, 14.4.2, 14.4.3, 14.4.4, 14.4.5, 14.4.6, 14.4.7, 14.4.8, 14.4.9, 14.4.10, 15.4.1, 15.4.2, 15.4.3, 15.4.4, 15.4.5, 15.4.6, 15.4.7, 15.4.8, 15.4.9, 15.4.10, 16.4.1, 16.4.2, 16.4.3, 16.4.4, 16.4.5, 16.4.6, 16.4.7, 16.4.8, 16.4.9, 16.4.10, 17.4.1, 17.4.2, 17.4.3, 17.4.4, 17.4.5, 17.4.6, 17.4.7, 17.4.8, 17.4.9, 17.4.10, 18.4.1, 18.4.2, 18.4.3, 18.4.4, 18.4.5, 18.4.6, 18.4.7, 18.4.8, 18.4.9, 18.4.10, 19.4.1, 19.4.2, 19.4.3, 19.4.4, 19.4.5, 19.4.6, 19.4.7, 19.4.8, 19.4.9, 19.4.10, 20.4.1, 20.4.2, 20.4.3, 20.4.4, 20.4.5, 20.4.6, 20.4.7, 20.4.8, 20.4.9, 20.4.10, 21.4.1, 21.4.2, 21.4.3, 21.4.4, 21.4.5, 21.4.6, 21.4.7, 21.4.8, 21.4.9, 21.4.10, 22.4.1, 22.4.2, 22.4.3, 22.4.4, 22.4.5, 22.4.6, 22.4.7, 22.4.8, 22.4.9, 22.4.10, 1.5.1, 1.5.2, 1.5.3, 1.5.4, 1.5.5, 1.5.6, 1.5.7, 1.5.8, 1.5.9, 1.5.10, 2.5.1, 2.5.2, 2.5.3, 2.5.4, 2.5.5, 2.5.6, 2.5.7, 2.5.8, 2.5.9, 2.5.10, 3.5.1, 3.5.2, 3.5.3, 3.5.4, 3.5.5, 3.5.6, 3.5.7, 3.5.8, 3.5.9, 3.5.10, 4.5.1, 4.5.2, 4.5.3, 4.5.4, 4.5.5, 4.5.6, 4.5.7, 4.5.8, 4.5.9, 4.5.10, 5.5.1, 5.5.2, 5.5.3, 5.5.4, 5.5.5, 5.5.6, 5.5.7, 5.5.8, 5.5.9, 5.5.10, 6.5.1, 6.5.2, 6.5.3, 6.5.4, 6.5.5, 6.5.6, 6.5.7, 6.5.8, 6.5.9, 6.5.10, 7.5.1, 7.5.2, 7.5.3, 7.5.4, 7.5.5, 7.5.6, 7.5.7, 7.5.8, 7.5.9, 7.5.10, 8.5.1, 8.5.2, 8.5.3, 8.5.4, 8.5.5, 8.5.6, 8.5.7, 8.5.8, 8.5.9, 8.5.10, 9.5.1, 9.5.2, 9.5.3, 9.5.4, 9.5.5, 9.5.6, 9.5.7, 9.5.8, 9.5.9, 9.5.10, 10.5.1, 10.5.2, 10.5.3, 10.5.4, 10.5.5, 10.5.6, 10.5.7, 10.5.8, 10.5.9, 10.5.10, 11.5.1, 11.5.2, 11.5.3, 11.5.4, 11.5.5, 11.5.6, 11.5.7, 11.5.8, 11.5.9, 11.5.10, 12.5.1, 12.5.2, 12.5.3, 12.5.4, 12.5.5, 12.5.6, 12.5.7, 12.5.8, 12.5.9, 12.5.10, 13.5.1, 13.5.2, 13.5.3, 13.5.4, 13.5.5, 13.5.6, 13.5.7, 13.5.8, 13.5.9, 13.5.10, 14.5.1, 14.5.2, 14.5.3, 14.5.4, 14.5.5, 14.5.6, 14.5.7, 14.5.8, 14.5.9, 14.5.10, 15.5.1, 15.5.2, 15.5.3, 15.5.4, 15.5.5, 15.5.6, 15.5.7, 15.5.8, 15.5.9, 15.5.10, 16.5.1, 16.5.2, 16.5.3, 16.5.4, 16.5.5, 16.5.6, 16.5.7, 16.5.8, 16.5.9, 16.5.10, 17.5.1, 17.5.2, 17.5.3, 17.5.4, 17.5.5, 17.5.6, 17.5.7, 17.5.8, 17.5.9, 17.5.10, 18.5.1, 18.5.2, 18.5.3, 18.5.4, 18.5.5, 18.5.6, 18.5.7, 18.5.8, 18.5.9, 18.5.10, 19.5.1, 19.5.2, 19.5.3, 19.5.4, 19.5.5, 19.5.6, 19.5.7, 19.5.8, 19.5.9, 19.5.10, 20.5.1, 20.5.2, 20.5.3, 20.5.4, 20.5.5, 20.5.6, 20.5.7, 20.5.8, 20.5.9, 20.5.10, 21.5.1, 21.5.2, 21.5.3, 21.5.4, 21.5.5, 21.5.6, 21.5.7, 21.5.8, 21.5.9, 21.5.10, 22.5.1, 22.5.2, 22.5.3, 22.5.4, 22.5.5, 22.5.6, 22.5.7, 22.5.8, 22.5.9, 22.5.10, 1.6.1, 1.6.2, 1.6.3, 1.6.4, 1.6.5, 1.6.6, 1.6.7, 1.6.8, 1.6.9, 1.6.10, 2.6.1, 2.6.2, 2.6.3, 2.6.4, 2.6.5, 2.6.6, 2.6.7, 2.6.8, 2.6.9, 2.6.10, 3.6.1, 3.6.2, 3.6.3, 3.6.4, 3.6.5, 3.6.6, 3.6.7, 3.6.8, 3.6.9, 3.6.10, 4.6.1, 4.6.2, 4.6.3, 4.6.4, 4.6.5, 4.6.6, 4.6.7, 4.6.8, 4.6.9, 4.6.10, 5.6.1, 5.6.2, 5.6.3, 5.6.4, 5.6.5, 5.6.6, 5.6.7, 5.6.8, 5.6.9, 5.6.10, 6.6.1, 6.6.2, 6.6.3, 6.6.4, 6.6.5, 6.6.6, 6.6.7, 6.6.8, 6.6.9, 6.6.10, 7.6.1, 7.6.2, 7.6.3, 7.6.4, 7.6.5, 7.6.6, 7.6.7, 7.6.8, 7.6.9, 7.6.10, 8.6.1, 8.6.2, 8.6.3, 8.6.4, 8.6.5, 8.6.6, 8.6.7, 8.6.8, 8.6.9, 8.6.10, 9.6.1, 9.6.2, 9.6.3, 9.6.4, 9.6.5, 9.6.6, 9.6.7, 9.6.8, 9.6.9, 9.6.10, 10.6.1, 10.6.2, 10.6.3, 10.6.4, 10.6.5, 10.6.6, 10.6.7, 10.6.8, 10.6.9, 10.6.10, 11.6.1, 11.6.2, 11.6.3, 11.6.4, 11.6.5, 11.6.6, 11.6.7, 11.6.8, 11.6.9, 11.6.10, 12.6.1, 12.6.2, 12.6.3, 12.6.4, 12.6.5, 12.6.6, 12.6.7, 12.6.8, 12.6.9, 12.6.10, 13.6.1, 13.6.2, 13.6.3, 13.6.4, 13.6.5, 13.6.6, 13.6.7, 13.6.8, 13.6.9, 13.6.10, 14.6.1, 14.6.2, 14.6.3, 14.6.4, 14.6.5, 14.6.6, 14.6.7, 14.6.8, 14.6.9, 14.6.10, 15.6.1, 15.6.2, 15.6.3, 15.6.4, 15.6.5, 15.6.6, 15.6.7, 15.6.8, 15.6.9, 15.6.10, 16.6.1, 16.6.2, 16.6.3, 16.6.4, 16.6.5, 16.6.6, 16.6.7, 16.6.8, 16.6.9, 16.6.10, 17.6.1, 17.6.2, 17.6.3, 17.6.4, 17.6.5, 17.6.6, 17.6.7, 17.6.8, 17.6.9, 17.6.10, 18.6.1, 18.6.2, 18.6.3, 18.6.4, 18.6.5, 18.6.6, 18.6.7, 18.6.8, 18.6.9, 18.6.10, 19.6.1, 19.6.2, 19.6.3, 19.6.4, 19.6.5, 19.6.6, 19.6.7, 19.6.8, 19.6.9, 19.6.10, 20.6.1, 20.6.2, 20.6.3, 20.6.4, 20.6.5, 20.6.6, 20.6.7, 20.6.8, 20.6.9, 20.6.10, 21.6.1, 21.6.2, 21.6.3, 21.6.4, 21.6.5, 21.6.6, 21.6.7, 21.6.8, 21.6.9, 21.6.10, 22.6.1, 22.6.2, 22.6.3, 22.6.4, 22.6.5, 22.6.6, 22.6.7, 22.6.8, 22.6.9, 22.6.10, 1.7.1, 1.7.2, 1.7.3, 1.7.4, 1.7.5, 1.7.6, 1.7.7, 1.7.8, 1.7.9, 1.7.10, 2.7.1, 2.7.2, 2.7.3, 2.7.4, 2.7.5, 2.7.6, 2.7.7, 2.7.8, 2.7.9, 2.7.10, 3.7.1, 3.7.2, 3.7.3, 3.7.4, 3.7.5, 3.7.6, 3.7.7, 3.7.8, 3.7.9, 3.7.10, 4.7.1, 4.7.2, 4.7.3, 4.7.4, 4.7.5, 4.7.6, 4.7.7, 4.7.8, 4.7.9, 4.7.10, 5.7.1, 5.7.2, 5.7.3, 5.7.4, 5.7.5, 5.7.6, 5.7.7, 5.7.8, 5.7.9, 5.7.10, 6.7.1, 6.7.2, 6.7.3, 6.7.4, 6.7.5, 6.7.6, 6.7.7, 6.7.8, 6.7.9, 6.7.10, 7.7.1, 7.7.2, 7.7.3, 7.7.4, 7.7.5, 7.7.6, 7.7.7, 7.7.8, 7.7.9, 7.7.10, 8.7.1, 8.7.2, 8.7.3, 8.7.4, 8.7.5, 8.7.6, 8.7.7, 8.7.8, 8.7.9, 8.7.10, 9.7.1, 9.7.2, 9.7.3, 9.7.4, 9.7.5, 9.7.6, 9.7.7, 9.7.8, 9.7.9, 9.7.10, 10.7.1, 10.7.2, 10.7.3, 10.7.4, 10.7.5, 10.7.6, 10.7.7, 10.7.8, 10.7.9, 10.7.10, 11.7.1, 11.7.2, 11.7.3, 11.7.4, 11.7.5, 11.7.6, 11.7.7, 11.7.8, 11.7.9, 11.7.10, 12.7.1, 12.7.2, 12.7.3, 12.7.4, 12.7.5, 12.7.6, 12.7.7, 12.7.8, 12.7.9, 12.7.10, 13.7.1, 13.7.2, 13.7.3, 13.7.4, 13.7.5, 13.7.6, 13.7.7, 13.7.8, 13.7.9, 13.7.10, 14.7.1, 14.7.2, 14.7.3, 14.7.4, 14.7.5, 14.7.6, 14.7.7, 14.7.8, 14.7.9, 14.7.10, 15.7.1, 15.7.2, 15.7.3, 15.7.4, 15.7.5, 15.7.6, 15.7.7, 15.7.8, 15.7.9, 15.7.10, 16.7.1, 16.7.2, 16.7.3, 16.7.4, 16.7.5, 16.7.6, 16.7.7, 16.7.8, 16.7.9, 16.7.10, 17.7.1, 17.7.2, 17.7.3, 17.7.4, 17.7.5, 17.7.6, 17.7.7, 17.7.8, 17.7.9, 17.7.10, 18.7.1, 18.7.2, 18.7.3, 18.7.4, 18.7.5, 18.7.6, 18.7.7, 18.7.8, 18.7.9, 18.7.10, 19.7.1, 19.7.2, 19.7.3, 19.7.4, 19.7.5, 19.7.6, 19.7.7, 19.7.8, 19.7.9, 19.7.10, 20.7.1, 20.7.2, 20.7.3, 20.7.4, 20.7.5, 20.7.6, 20.7.7, 20.7.8, 20.7.9, 20.7.10, 21.7.1, 21.7.2, 21.7.3, 21.7.4, 21.7.5, 21.7.6, 21.7.7, 21.7.8, 21.7.9, 21.7.10, 22.7.1, 22.7.2, 22.7.3, 22.7.4, 22.7.5, 22.7.6, 22.7.7, 22.7.8, 22.7.9, 22.7.10, 1.8.1, 1.8.2, 1.8.3, 1.8.4, 1.8.5, 1.8.6, 1.8.7, 1.8.8, 1.8.9, 1.8.10, 2.8.1, 2.8.2, 2.8.3, 2.8.4, 2.8.5, 2.8.6, 2.8.7, 2.8.8, 2.8.9, 2.8.10, 3.8.1, 3.8.2, 3.8.3, 3.8.4, 3.8.5, 3.8.6, 3.8.7, 3.8.8, 3.8.9, 3.8.10, 4.8.1, 4.8.2, 4.8.3, 4.8.4, 4.8.5, 4.8.6, 4.8.7, 4.8.8, 4.8.9, 4.8.10, 5.8.1, 5.8.2, 5.8.3, 5.8.4, 5.8.5, 5.8.6, 5.8.7, 5.8.8, 5.8.9, 5.8.10, 6.8.1, 6.8.2, 6.8.3, 6.8.4, 6.8.5, 6.8.6, 6.8.7, 6.8.8, 6.8.9, 6.8.10, 7.8.1, 7.8.2, 7.8.3, 7.8.4, 7.8.5, 7.8.6, 7.8.7, 7.8.8, 7.8.9, 7.8.10, 8.8.1, 8.8.2, 8.8.3, 8.8.4, 8.8.5, 8.8.6, 8.8.7, 8.8.8, 8.8.9, 8.8.10, 9.8.1, 9.8.2, 9.8.3, 9.8.4, 9.8.5, 9.8.6, 9.8.7, 9.8.8, 9.8.9, 9.8.10, 10.8.1, 10.8.2, 10.8.3, 10.8.4, 10.8.5, 10.8.6, 10.8.7, 10.8.8, 10.8.9, 10.8.10, 11.8.1, 11.8.2, 11.8.3, 11.8.4, 11.8.5, 11.8.6, 11.8.7, 11.8.8, 11.8.9, 11.8.10, 12.8.1, 12.8.2, 12.8.3, 12.8.4, 12.8.5, 12.8.6, 12.8.7, 12.8.8, 12.8.9, 12.8.10, 13.8.1, 13.8.2, 13.8.3, 13.8.4, 13.8.5, 13.8.6, 13.8.7, 13.8.8, 13.8.9, 13.8.10, 14.8.1, 14.8.2, 14.8.3, 14.8.4, 14.8.5, 14.8.6, 14.8.7, 14.8.8, 14.8.9, 14.8.10, 15.8.1, 15.8.2, 15.8.3, 15.8.4, 15.8.5, 15.8.6, 15.8.7, 15.8.8, 15.8.9, 15.8.10, 16.8.1, 16.8.2, 16.8.3, 16.8.4, 16.8.5, 16.8.6, 16.8.7, 16.8.8, 16.8.9, 16.8.10, 17.8.1, 17.8.2, 17.8.3, 17.8.4, 17.8.5, 17.8.6, 17.8.7, 17.8.8, 17.8.9, 17.8.10, 18.8.1, 18.8.2, 18.8.3, 18.8.4, 18.8.5, 18.8.6, 18.8.7, 18.8.8, 18.8.9, 18.8.10, 19.8.1, 19.8.2, 19.8.3, 19.8.4, 19.8.5, 19.8.6, 19.8.7, 19.8.8, 19.8.9, 19.8.10, 20.8.1, 20.8.2, 20.8.3, 20.8.4, 20.8.5, 20.8.6, 20.8.7, 20.8.8, 20.8.9, 20.8.10, 21.8.1, 21.8.2, 21.8.3, 21.8.4, 21.8.5, 21.8.6, 21.8.7, 21.8.8, 21.8.9, 21.8.10, 22.8.1, 22.8.2, 22.8.3, 22.8.4, 22.8.5, 22.8.6, 22.8.7, 22.8.8, 22.8.9 and 22.8.10.

Identification of Active Precursors.

It is desirable to select the amino acid residue or sequence of the invention compounds having one or more peptide bonds, such as formula VII compounds, based on the substrate specificity of esterases and/or carboxypeptidases expected to be found within cells where precursor hydrolysis is desired. To the extent that the specificity of these enzymes is unknown, one will screen a plurality of nucleotide analogs or esters until the desired substrate specificity is found. This will be apparent from assay either of the generation of free phosphonate or of antimicrobial activity. One selects compounds that are (i) not hydrolyzed or hydrolyzed comparatively slowly in the upper gut, (ii) gut and cell permeable and (iii) hydrolyzed in the cell cytoplasm and/or systemic circulation. Screens with cells from particular tissues are used to identify precursors that are released in organs susceptible to a target viral or microbial infection, e.g. in the case of liver, precursor drugs capable of hydrolysis in the liver. Other infections, e.g. CMV or HIV, are treated with a precursor that is hydrolyzed at substantially the same rate and to substantially the same degree in all tissues, with no one tissue preferentially hydrolyzing the precursor nucleosides.

The assays used can be those known in the art including intestinal lumen stability, cell permeation, liver homogenate stability and plasma stability assays. These assays are used to determine the bioavailability characteristics of particular active precursors according to routinely used methods.

Therapeutic Indications.

The hydrolysis products of the invention compounds have activity against viruses, malignant cells and/or parasitic protozoans. For example, 9-(3-hydroxy-2-phosphonylmethoxypropyl (HPMP) and (2-phosphonylmethoxy)ethyl (PME) analogs of purine (adenine (A), guanine (G), 2,6-diaminopurine (DAP), 2-monoaminopurine (MAP), hypoxanthine (Hx) and pyrimidine (cytosine (C), uracil (U), thymine (T) were evaluated for antiviral properties. (S)-HPMPA, (S)-cyclic HPMPA, (S)-HPMPC, (S)-HPMPG, (S)-HPMPDAP, PMEDAP, PMEG and PMEA were active against herpes simplex virus, type 1 and 2 (HSV-1 and -2). (S)-HPMPA and (S)-cyclic HPMPA were active against varicella zoster virus (VZV). (S)-HPMPC was active against human cytomegalovirus (HCMV). (S)-HPMPA and (S)-cyclic HPMPA were shown to be active against adenovirus and vaccinia virus. PMEA, PMEDAP, and PMEMAP are active against human immunodeficiency virus (HIV).

Acyclic nucleotide analogs having a common PME side chain covalently linked to a purine or pyrimidine heterocyclic base were prepared and tested for in vivo antiviral activity against retroviruses and herpes viruses. The adenine analog, PMEA, was active in vitro against HIV and Rauscher murine leukemia virus (R-MuLV), and was more potent in vivo than 3'-azido-3'-deoxythymidine (AZT) in the treatment of R-MuLV in mice. PMEA also had a significant antiviral effect in vivo against murine cytomegalovirus (MCMV), and in vitro activity against HCMV. The guanine analog, PMEG, was active in vitro against herpes viruses. In vivo, PMEG was >50-fold more potent than acyclovir against HSV 1 infection in mice.

(S)-HPMPA has potent and selective activity against a broad spectrum of DNA viruses, including HSV-1 and 2, VZV, thymidine kinase-defident (TK⁻) mutants of herpes simplex virus, HCMV, phocid herpesvirus type 1 (seal herpesvirus, SeHV), simian herpesvirus type 1 (SHV-1), or pseudorabies virus or Aujeszky's disease virus), bovid herpesvirus type 1 (infectious bovine rhinotracheitis virus, BHV-1), equid herpesvirus type 1 (equine abortion virus, EHV-1), African swine fever (ASF) virus, vaccinia virus; and human adenoviruses, and retroviruses such as murine sarcoma virus (MSV). It is also reported that, in mice and rabbits in vivo, the compound is effective against both local and systemic infections with herpes simplex virus type 1, including herpetic keratitis caused by a TK⁻ mutant which is resistant to the classical antiherpes drugs (DeClercq, E., et al, *Antiviral Res* (1987) 8:261–272; DeClercq, E., et al, *Nature* (1986) 323:464–467; Gil-Fernandez, C., et al, *Antiviral Res* (1987) 7:151–160; Baba, M., et al, *Antimicrob Agents Chemother* (1987) 31:337–339).

Phosphonylmethoxyalkylpurine analogs have also been evaluated for their antitumor activity in murine tumor models. HPMPA, PMEA, and PMEG were found to be active against intraperitoneal P388 leukemia. PMEG was also found to be active against B16 melanoma.

As indicated above, the compounds of the invention are useful for treatment of microbial infections, for treatment of tumors or for other indications described below. Microbial infections include infection by viruses, parasites, yeasts and fungi. Exemplary viral infections that may be treated include infections mediated by DNA or RNA viruses including herpesviruses (CMV, HSV 1, HSV 2, EBV, varicella zoster virus, bovid herpesvirus type 1, equid herpesvirus type 1), papillomaviruses (HPV types 1–55), flaviviruses (including African swine fever virus and Japanese encephalitis virus), togaviruses (including Venezuelan equine encephalomyelitis virus), influenza viruses (types A–C), retroviruses (HIV 1, HIV 2, HTLV I, HTLV II, SIV, HBV, FeLV, FIV, MoMSV), adenoviruses (types 1–8), poxviruses (vaccinia virus), enteroviruses (polio virus type 1–3, hepatitis A virus), gastroenteritis viruses (Norwalk viruses, rotaviruses), hantaviruses (Hantaan virus), papovaviruses, rhinoviruses, parainfluenza virus types 1–4, rabies virus, and the like.

Some of the phosphonate compounds (such as PMEA) have a broad spectrum of antimicrobial activity and are thus unusual antiviral or antiparasitic agents. The activity of individual nucleotide analogs and nucleotide analog amidates is determined by routine assay of antiviral (or other antimicrobial) activity using enzyme inhibition assays, tissue culture assays, animal model assays and/or other acceptable assays.

Nucleotide analogs (phosphonates such as HPMPC, PMEA, etc) are believed to exert their antimicrobial activity, at least in part, by a two step enzyme-mediated conversion to a diphosphate, followed by incorporation of the diphosphorylated nucleotide analog into nucleic acids. The incorporation of the diphosphates into nucleic acid is mediated by viral or other microbial DNA or RNA polymerases (bacterial, retroviral, etc). Thus, nucleotide analogs (when diphosphorylated) are useful as chain terminators for dideoxynucleotide-type DNA sequencing protocols, provided that the nucleotide analog lacks a free hydroxyl group suitable for polymerase mediated chain elongation. These compounds will not have a hydroxyl group at $R^{27}$ in compounds of formulas IV and VI or are acyclic. Nucleotide analogs of formula XV, $(HO)_2P(O)$—O—$P(O)(OH)$—O—$(HO)P(O)$-Z-B, can be prepared (Otvos, et al, *Nucl Acids Res* (1987) 15:1763–1777) and provided in a kit with other reagents (such as klenow polymerase or T4 polymerase, dNTPs, etc) needed for DNA sequencing. The invention nudeotide analogs and nucleotide analog amidates can also be (1) applied to tissue culture systems to eliminate or reduce viral spread or growth during the production of biopharmaceuticals or other products (such as proteins or vaccines), (2) used to eliminate or reduce viral spread or growth in clinical samples (such as blood), and (3) used to stop growth of tissue culture or bacterial cells (using toxic amounts of compound) without interfering with protein production.

Infections mediated by protozoan parasites can be treated using the compounds of the invention. Such infections can also be treated using the corresponding nucleotide analogs of the invention nucleotide analog amidates. The term protozoa is intended to include those members of the subphyla Sarcomastigophora and Sporozoa of the phylum Protozoa. More particularly, the term protozoa as used herein is intended to include those genera of parasitic protozoa which are important to man because they either cause disease in man or in his domestic animals. These genera are for the most part found classified in the superclass Mastighphora of the subphylum Sarcomastigophora and the class Telosporea of the subphylum Sporozoa in the classification according to Baker (1969). Illustrative genera of these parasitic protozoa include Histomonas, Pneumocystis, Trypanosoma, Giardia, Trichomonas, Eimeria, Isopora, Leishmania, Entamoeba, Toxoplasma and Plasmodium. Parasitic protozoans include *Plasmodium falciparum, Plasmodium berghei, Plasmodium malariae, Plasmodium vivax, Leishmania braziliensis, Leishmania donovani, Trypanosoma cruzi, Trypanosoma brucei, Trypanosoma rhodesiense, Pneumocystis carinii, Entamoeba histolytica, Trichomonas vaginalis* and the like (de Vries, E., et al, *Mol Biochem Parasitol* (1991) 47:43–50). Nucleoside analog amidates of the invention and/or their corresponding nucleotide analogs can also be used to treat yeast or fungal infections caused by *Candida glabrata, Candida tropicalis, Candida albicans*, and other Candida species Cryptococcus species including *Cryptococcus neoformans*, Blastomyces species including *Blastomyces dermatidis*, Torulopsis species including *Torulopsis glabrata*, Coccidioides species including *Coccidioides immitis*, Aspergillus species and the like.

Pharmaceutical Formulations.

Compounds of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone it is preferably to present them as pharmaceutical formulations. The formulations, both for veterinary and for human use, of the present invention comprise at least one active ingredient, as above defined, together with one or more acceptable carriers therefor and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the present invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents such as pentamidine for treatment of pneumocystis pneumonia.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

The present invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods. Controlled release formulations may be employed for the treatment or prophylaxis of various microbial infections particularly human bacterial, human parasitic protozoan or human viral infections caused by microbial species including Plasmodium, Pneumocystis, herpesviruses (CMV, HSV 1, HSV 2, VZV, and the like), retroviruses, adenoviruses and the like. The controlled release formulations can be used to treat HIV infections and related conditions such as tuberculosis, malaria, pneumocystis pneumonia, CMV retinitis, AIDS, AIDS-related complex (ARC) and progressive generalized lymphadeopathy (PGL), and AIDS-related neurological conditions such as multiple sclerosis, and tropical spastic paraparesis. Other human retroviral infections that may be treated with the controlled release formulations according to the invention include Human T-cell Lymphotropic virus (HTLV)-I and IV and HIV-2 infections.

The invention accordingly provides pharmaceutical formulations for use in the treatment or prophylaxis of the above-mentioned human or vetrinary conditions and microbial infections.

Therapeutic Administration.

For each of the above-indicated utilities and indications the amount required of an active ingredient (as above defined) will depend upon a number of factors including the severity of the condition to be treated and the identity of the recipient and will ultimately be at the discretion of the attendant physician or veterinarian. In general however, for each of these utilities and indications, a suitable, effective dose will be in the range 0.1 to 250 mg per kilogram bodyweight of recipient per dose (including active ingredient(s) in a range between 0.1 mg and 250 mg/Kg/dose in increments of 0.5 mg/Kg/dose such as 2.5 mg/Kg/dose, 3.0 mg/Kg/dose, 3.5 mg/Kg/dose, etc), preferably in the range 0.5 to 50 mg per kilogram body weight per dose and most preferably in the range 1 to 15 mg per kilogram body weight per dose; an optimum dose is about 3.0 mg per kilogram body weight per dose. (Unless otherwise indicated all weights of active ingredient are calculated as the parent compound of formula I: for salts thereof the figures would be increased proportionately). The desired dose is preferably presented as one dose or two sub-doses administered at appropriate intervals throughout a period of one to seven days. It is preferred to administer a dose once every 2, 3, 4, 5 or 6 days. The doses may be administered in unit dosage forms. The desired dose is may be presented as one, two, or three sub-doses administered at appropriate intervals throughout the one to seven day period. These sub-doses may be administered in unit dosage form, for example, containing 10 to 1000 mg, and or 100 to 500 mg of active ingredient per unit dosage form. The formulations should be desirably administered to achieve peak plasma concentrations of the active compound of from about 1 to about 100 $\mu$M, preferably about 2 to 50 $\mu$M, most preferably about 3 to about 30 $\mu$M. Compounds such as those of structures XXXI, XXXII and XXXIII (defined below) will generally (1) have a higher oral bioavailability than the corresponding uncyclized nucleotide analog (e.g., cHPMPC compared to HPMPC) and/or (2) will exibit reduced toxicity when compared with the same dose of the corresponding uncyclized nucleotide analog, and/or (3) will have greater efficacy when compared with the same dose of the corresponding uncyclized nucleotide analog.

The compounds of the invention may be employed in combination with other therapeutic agents for the treatment or prophylaxis of the infections or conditions indicated above. Examples of such further therapeutic agents include agents that are effective for the treatment or prophylaxis of viral, parasitic or bacterial infections or associated conditions or for treatment of tumors or related conditions include 3'-azido-3'-deoxythymidine (zidovudine, AZT), 2'-deoxy-3'-thiacytidine (3TC), 2',3'-dideoxy-2',3'-didehydroadenosine (D4A), 2',3'-dideoxy-2',3'-didehydrothymidine (D4T), carbovir (carbocyclic 2',3'-dideoxy-2',3'-didehydroguanosine), 3'-azido-2',3'-dideoxyuridine, 5-fluorothymidine, (E)-5-(2-bromovinyl)-2'-deoxyuridine (BVDU), 2-chlorodeoxyadenosine, 2-deoxycoformycin, 5-fluorouracil, 5-fluorouridine, 5-fluoro-2'-deoxyuridine, 5-trifluoromethyl-2'-deoxyuridine, 6-azauridine, 5-fluoroorotic acid, methotrexate, triacetyluridine, 1-(2'-deoxy-2'-fluoro-1-β-arabinosyl)-5-iodocytidine (FIAC), tetrahydro-imidazo(4,5,1-jk)-(1,4)-benzodiazepin-2(1H)-thione (TIBO), 2'-nor-cyclicGMP, 6-methoxypurine arabinoside (ara-M), 6-methoxypurine arabinoside 2'-O-valerate, cytosine arabinoside (ara-C), 2',3'-dideoxynucleosides such as 2',3'-dideoxycytidine (ddC), 2',3'-dideoxyadenosine (ddA) and 2',3'-dideoxyinosine (ddI), acyclic nucleosides such as acyclovir, penciclovir, famciclovir, ganciclovir, HPMPC, PMEA, PMEG, PMPA, PMPDAP, FPMPA, HPMPA, HPMPDAP, (2R,5R)-9-[tetrahydro-5-(phosphonomethoxy)-2-furanyl]adenine, (2R,5R)-1-[tetrahydro-5-(phosphonomethoxy)-2-furanyl]thymine, other antivirals including ribavirin (adenine arabinoside), 2-thio-6-azauridine, tubercidin, aurintricarboxylic acid, 3-deazaneoplanocin, neoplanocin, rimantidine, adamantine, and foscarnet (trisodium phosphonoformate), antibacterial agents including bactericidal fluoroquinolones (ciprofloxacin, pefloxacin and the like), aminoglycoside bactericidal antibiotics (streptomycin, gentamicin, amicacin and the like) β-lactamase inhibitors (cephalosporins, penicillins and the like), other antibacterials including tetracycline, isoniazid, rifampin, cefoperazone, claithromycin and azithromycin, antiparasite or antifungal agents including pentamidine (1,5-bis(4'-aminophenoxy)pentane), 9-deazainosine, sulfamethoxazole, sulfadiazine, quinapyramine, quinine, fluconazole, ketoconazole, itraconazole, Amphotericin B, 5-fluorocytosine, clotrimazole, hexadecylphosphocholine and nystatin, renal excretion inhibitors such as probenicid, nucleoside transport inhibitors such as dipyridamole, dilazep and nitrobenzyithioinosine, immunomodulators such as FK506, cyclosporin A, thymosin α-1, cytokines including TNF and TGF-β, interferons including IFN-α, IFN-β and IFN-γ, interleukins including interleukin I, II, III, IV, V, VI, VII, VIII, X, XI, XIII macrophage/granulocyte colony stimulating factors including GM-CSF, G-CSF, M-CSF, cytokine antagonists including anti-TNF antibodies, anti-interleukin antibodies, soluble interleukin receptors, protein kinase C inhibitors and the like.

Immunogens and Antibodies.

The compounds of this invention, or the biologically active substances produced from these compounds by hydrolysis in vivo, are used as immunogens to prepare antibodies capable of binding specifically to the compounds or their hydrolysis products. The immunogenic compositions therefore are useful as intermediates in the preparation of antibodies for use in diagnostic or quality control assays for the compounds or their hydrolysis products. The antibodies are useful for measuring the presence, absence or amounts of the compounds by any convenient homogenous or heterogenous procedure such as fluorescence polarization immunoassay, fluorescence immunoassay (using fluorescent labels such as fluorescein and the like), radioimmunoassay, enzyme immunoassay (using enzyme indicators such as alkaline phosphatase, horseradish peroxidase, glucose oxidase, urease and the like) and nephelometric inhibition assay by described methods (WO 92/22639, incorporated herein by reference). Such assays usually require a tracer (such as a fluorescent or radiolabeled labeled invention compound), an antibody and the sample to be analyzed containing the compound.

The hydrolysis products of interest are the phosphonates resulting from the hydrolysis of the amidate or ester bond(s) of the precursor compounds of this invention, for example HPMPC, 6-aza-HPMPC, cyclic HPMPC, PMEA, PMEG, PMPDAP, PMPA, D4TMPI, D4AMPI, cyclic HPMPA, FPMPA, PMEDAP, PMEMAP, 7-deaza-8-aza-FPMPA, 7-deaza-8-aza-HPMPA, cyclic 7-deaza-8-aza-HPMPA, 7-deaza-8-aza-PMPA, 8-aza-FPMPA, 8-aza-HPMPA, cyclic 8-aza-HPMPA, 8-aza-PMPA, PMPG, PMPMAP, 1-deaza-HPMPA, cyclic 1-deaza-HPMPA, 1-deaza-PMPA, 1-deaza-PMPG, 1-deaza-PMPMAP, 1-deaza-PMPDAP, 3-deaza-HPMPA, cyclic 3-deaza-HPMPA or 3-deaza-PMPA. Thus, the antibodies of this invention will be capable of binding to the precursors without binding to the hydrolysis products, will be capable of binding to the hydrolysis products without binding to the precursors, or will be capable of binding specifically to both. The antibodies will not cross-react with naturally-occurring nucleotides or nucleosides.

The immunogens of this invention contain the precursor or hydrolytic products in association with an immunogenic substance such as a protein or peptide. Immunogenic substances include adjuvants such as Freund's adjuvant, immunogenic proteins such as viral, bacterial, yeast, plant and animal polypeptides, in particular keyhole limpet hemocyanin, serum albumin, bovine thyroglobulin or soybean trypsin inhibitor, and immunogenic polysaccharides. Typically, the precursor or a compound having the structure of a precursor hydrolytic product is covalently conjugated to an immunogenic polypeptide or polysaccharide by the use of a polyfunctional (ordinarily bifunctional) cross-linking agent. Methods for the manufacture hapten immunogens are conventional per se, and any of the methods used heretofore for conjugating haptens to immunogenic polypeptides or the like are suitably employed here as well, taking into account the functional groups on the precursors or hydrolytic products which are available for cross-linking.

Typically the polypeptide is conjugated to a site on the heterocyclic base functionality of the compound or hydrolysis product rather than to a site on the alkyl or substituted-alkyl phosphonate moiety. In general, the site will be an amino group located on the purine or pyrimidine moiety of the nucleoside phosphonate, at the 5 position of pyrimidines (such as cytosine or uracil), at the 1 position of purines (such as adenosine or guanine) or, for compounds having a cyclic structure corresponding to a sugar or sugar analog and having a free hydroxyl group, through the hydroxyl group (usually at the 3' or 2' positions). Alternatively, the precursor compound is cross-linked through the phosphonate, typically by amidation or esterification of the phosphonate by the polypeptide itself or by a cross-linking functionality covalently bonded to the polypeptide. Thus, the groups $L^1$ or $L^2$ in structures $(L^1)(L^2)$-P(O)-Z-B can be immunogenic proteins (having more than 50 amino acid residues, usually less than 1000 residues) or peptides (about 5 to 50 amino acid residues).

The conjugates are prepared in conventional fashion. For example, N-hydroxysuccinimide, succinic anhydride or alkN═C═Nalk are useful in preparing the conjugates of this invention. The conjugates contain a precursor, its hydrolysis product, or both. Ordinarily, the conjugates will comprise the hydrolysis product, i.e., the biologically active drug. The conjugates are separated from starting materials and byproducts using chromatography or the like, and then are sterile filtered and vialed for storage.

Animals are typically immunized against the immunogenic conjugates or derivatives by combining 1 mg or 1 µg of conjugate (for rabbits or mice, respectively) with 3 volumes of Freund's complete adjuvant and injecting the solution intradermally at multiple sites. One month later the animals are boosted with ⅕ to ⅒ the original amount of conjugate in Freund's complete adjuvant (or other suitable adjuvant) by subcutaneous injection at multiple sites. 7 to 14 days later animals are bled and the serum is assayed for the desired antibody titer. Animals are boosted until the titer plateaus. Preferably, the animal is boosted with the conjugate in which the precursor or product is linked to a different protein, through a different cross-linking agent or both. Optionally, aggregating agents such as alum are used to enhance the immune response.

After immunization, monoclonal antibodies are prepared by recovering immune lymphoid cells (typically spleen cells or lymphocytes from lymph node tissue) from immunized animals and immortalizing the cells in conventional fashion, e.g., by fusion with myeloma cells or by Epstein-Barr virus transformation and screening for clones expressing the desired antibody. The hybridoma technique described originally be Kohler and Milstein, *Eur. J. Immunol.* (1976) 6:511 has been widely applied to produce hybrid cell lines that secrete high levels of monoclonal antibodies against many specific antigens.

It is possible to fuse cells of one species with another. However, it is preferably that the source of the immunized antibody producing cells and the myeloma be from the same species.

The hybrid cell lines are maintained in culture in vitro. The cell lines of this invention are selected or maintained in a hypoxanthine-aminopterin thymidine (HAT) medium. However, the established hybridoma cell line can be maintained on a variety of nutritionally adequate media. The secreted antibody is recovered from culture by conventional methods such as precipitation, ion exchange chromatography, affinity chromatography, or the like. The antibodies described herein are also recovered from hybridoma cell cultures by conventional methods for purification of IgG or IgM as the case may be that heretofore have been used to purify immunoglobulins from pooled plasma, e.g., ethanol or polyethylene glycol precipitation procedures. The purified antibodies are sterile filtered, and optionally are conjugated to a detectable marker such as an enzyme or spin label for use in diagnostic assays of test samples.

The antibodies of this invention are obtained from any animal species, but ordinarily are murine or rat. Once a monoclonal antibody having the desired specificity and affinity is obtained, other conventional modifications of the antibodies are within the scope of this invention. For example, the complementarity determining regions of an animal antibody, together with as much of the framework domain as is needed, are substituted into an antibody of another animal species or class to produce a cross-class or cross-species chimeric antibody. Fragments or other amino acid sequence variants of monoclonal antibodies also are encompassed within the meaning of antibody as that term is used herein, for example, Fab, Fab' or (Fab')2 fragments, single chain antibodies, bi or polyspecific antibodies, and the like.

The antibodies of this invention are from any suitable class or isotype, e.g. IgG, IgM, IgA, IgD or IgE. They may or may not participate in complement binding or ADCC.

Typically, hybridomas which are capable of binding to the immunogen are screened for the ability to bind to the hapten itself in typical test samples (plasma, serum and the like) with the requisite degree of affinity. The desired affinity will depend upon the use intended for the antibody, but should be adequate to function in a conventional competitive-type ELISA or radioimmunoassays, or in conventional EMIT immunoassays.

The antibodies of this invention are used in such assays together with a labeled from of the precursor or its hydrolytic product. Alternatively, the antibody is labeled. Suitable labels are well-known and include radioisotopes, enzymes, stable free radicals, fluorophors, chemiluminescent moieties and other detectable groups heretofore employed to prepare covalent conjugates for use in assays. Methods for linking the labels to ligand amino groups, or amino acid side chains or termini of polypeptides, are known and are suitable for use herein. Other suitable linking methods will be apparent to the ordinary artisan.

The antibodies and labeled ligands herein optionally are assembled into kits for use in therapeutic drug monitoring or evaluation, or for process quality control, and used in the conventional manner.

Diagnostic Applications.

Novel compounds described herein are useful as intermediates in the preparation of detectable labels for oligonucleotide probes. The compounds are hydrolyzed to the diacid, diphosphorylated and then incorporated into an oligonucleotide by conventional enzymatic or chemical means. The incorporated heterocyclic base from the invention will generally be capable of participating in heterocyclic base pairing and thus will not interfere substantially with the binding of the oligonucleotide to its complementary sequence (E. DeClerq (1993) 3:85–96); should it interfere with oligonucleotide binding to its complementary sequence, the nucleotide analog is incorporated as the final 3' terminal residue, an innocuous position and a conventional site for oligonucleotide labeling. The nucleotide analog compound in the oligonucleotide is detected by any means, such as NMR, immune, fluorescence or radiolabel detection.

Bis Amidate Synthesis.

Synthesis of bis-phosphoroamidate nucleotide analogs of Formula Id,

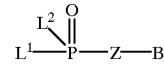

where $L^1$ and $L^2$ are the same and are an amino acid, dipeptide, tripeptide or oligopeptide (4, 5 or 6 amino acid residues) are prepared by conversion of a nucleotide analog (such as PMEA, HPMPC, HPMPA, PMEG, FPMPA, PMPDAP, 9-[2,3-dideoxy-2,3-didehydro-4-phosphonomethoxy-β-D-erythrofuranosyl]adenine (D4AMPI; reg no. 132178-53-1), 1-[2,3-dideoxy-2,3-didehydro-4-phosphonomethoxy-β-D-erythrofuranosyl] thymine (D4TMPI; reg no. 132178-49-5) and the like) directly to the corresponding bis-phosphoroamidate compound. $L^1$ is a protein, an amino acid, dipeptide, tripeptide or oligopeptide (4 to 6 amino acid residues) which is esterified at free α-carboxyl group(s) by $R^4$. Suitable $R^4$ groups include methyl, ethyl, propyl, isopropyl, butyl, t-butyl, phenyl, benzyl, N-ethylmorpholino, pivaloyloxymethyl and the like. The amino acids can comprise an aliphatic or aromatic side group (such as ala, phe, pro, leu, ile, met, trp and the like) or a dipeptide comprising amino acids having aliphatic or aromatic side groups (such as gly-gly, ala-ala, gly-ala, ala-gly, phe-gly, gly-phe, ala-phe, phe-ala, leu-ala, ala-leu and the like), or is a tripeptide comprising amino acids having aliphatic or aromatic side groups or is an oligopeptide comprising amino acids having aliphatic or aromatic side groups.

The procedure is suitable for all of the nucleotide analogs described herein. The synthesis is accomplished by suspension of the nucleotide analog and approximately 2 equivalents of the $L^1$ species in a solvent such as dry pyridine or DMF (dimethylformamide) optionally containing a non-nucleophilic organic base such as triethylamine (about 3 to 10 equivalents). The dehydration step is accomplished by modification of a described reaction (Mukaiyama, T. et al, *J Am Chem Soc* (1972) 94:8528–8532) by adding a 1:1 mixture of triphenylphosphine (reg. no. 603-35-0; Aldrich) and 2,2'-dipyridyl disulfide (2 to 4 equivalents; reg. no. 2127-03-9; Aldrich) in pyridine to the nucleotide analog/amino acid mixture and (a) stirring at room temperature for about 4 to 16 hours or (b) heating to 60° C. to 100° C. (including any temperature in one degree C. increments between 60° and 100° C. such as 70°, 80° or 90° C.) for about 4 to 16 hours. The resulting reaction mixture is then concentrated and the final bis-amidate product is recovered and purified by conventional methods.

An alternative reaction suitable for synthesizing most amidate compounds is converting a nucleotide analog phosphonate to the corresponding chloridate by reaction with thionyl chloride in solvent (DMF) as described in EP 481 214. An amino acid, dipeptide or other molecule bearing a free amine is then reacted with the chloridate to yield the corresponding bis-amidate.

Synthesis of compounds of Formula Id having amino acids that contain amino, guanidino or carboxyl groups (such as lys, arg, his, asn, gln, lys-lys, arg-arg, lys-arg and the like) is accomplished by the same method, but using protected amine or carboxyl groups. After synthesis of the protected bis-amidate compound, the protecting groups are removed by conventional methods. Suitable protecting groups are well known and include acid labile groups such as p-tosyl, BOC (t-butoxycarbonyl) and FMOC (fluorene methoxycarbonyl) for protecting amine groups. Groups such as t-butyl, methyl, ethyl, benzyl and the like can be used to protect carboxyl groups. These groups can be removed under acid, base or hydrogenolysis conditions or can be removed with an esterase according to conventional methods.

Synthesis of compounds of Formula Id having amino acids such as tyr, cys, ser and thr is accomplished by optionally protecting hydroxyl or thiol groups using protecting groups know in the art. For example, the hydroxyl group of ser, thr or tyr can be protected using benzyl, ethyl and the like and the thiol group of cys can be protected using trityl, p-methylbenzyl and the like. The choice of a protecting group will depend on the stability of the bis-amidate toward conditions used to remove a particular protecting group. Appropriate protecting groups can be selected or determined by the skilled artisan using routine methods.

Dipeptide or tripeptide species can be selected on the basis of known transport properties and/or susceptibility to peptidases that can affect transport to intestinal mucosal or other cell types. Dipeptides and tripeptides lacking an α-amino group are transport substrates for the peptide transporter found in brush border membrane of intestinal mucosal cells (Bai, J. P. F., *Pharm Res* (1992) 2:969–978).

Transport competent peptides can thus be used to enhance bioavailability of bis amidate compounds. Di- or tripeptides having one or more amino acids in the D configuration are also compatible with peptide transport and can be utilized in bis amidate compounds. Amino acids in the D configuration can be used to reduce the susceptibility of a di- or tripeptide to hydrolysis by proteases common to the brush border such as aminopeptidase N (EC 3.4.11.2). In addition, di- or tripeptides with amino acid residues can be selected on the basis of their relative resistance to hydrolysis by proteases found in the lumen of the intestine. For example, tripeptides or oligopeptides lacking asp and/or glu are poor substrates for aminopeptidase A (EC 3.4.11.7) and di- or tripeptides lacking amino acid residues on the N-terminal side of hydrophobic amino acids (leu, tyr, phe, val, trp) are poor substrates for endopeptidase 24.11 (EC 3.4.24.11) while peptides lacking a pro residue at the penultimate position at a free carboxyl terminus are poor substrates for carboxypeptidase P (EC 3.4.17). Similar considerations can also be applied to the selection of peptides that are either relatively resistant or relatively susceptible to hydrolysis by cytosolic, renal, hepatic, serum or other peptidases.

Synthesis of N-alkylamine amidates (where —$NHR^{40}$ is linked to the phosphorus atom and $R^{40}$ is $C_{1-20}$ alkyl, including $C_{4-16}$ alkyl) is accomplished essentially as described (Saito *Chem. Pharm. Bull.* (1991) 39:3207). Thus, compounds such as, for example, of structure $(R^{40}HN)(L^1)P(O)$-Z-$B^2$ or

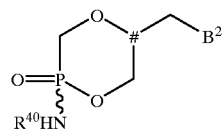

wherein $B^2$ is B or $B^1$, are synthesized in this manner.

Amidate-ester Synthesis.

Synthesis of mixed amidate-ester nucleotide analog amidates of Formula Id where $L^1$ is an amino acid ester and $L^2$ is a group of the formula OR, SR or $OR^{31}$ is accomplished by conversion of a nucleotide analog (such as PMEA, HPMPC, HPMPA, PMEG, FPMPA, PMPDAP, D4AMPI, D4TMPI and the like) di- or bis-ester to a corresponding mixed ester-phosphoroamidate compound. A bis ester is converted to a mono ester by treatment with a base such as ammonia to remove one ester group. The resulting mono ester is then converted to a mixed amidate-ester as described for synthesis of bis amidate compounds.

Bis ester synthesis.

Bis esters of the formula $(RO)_2P(O)$-Z-B are generally synthesized as described in EP 481 214 or as described in Mukaiyama, T. et al, *J Am Chem Soc* (1972) 94:8528–8532. Dialkyl phosphonate esters are synthesized via conversion of a dichlorophosphonate (chloridate) such as $(Cl)_2P(O)$-Z-B (Quast, H. et al, *Synthesis* (1974) 7:489–490; Quast, H. et al, *Synthesis* (1974) 7:490; Moedritzer, K. et al, *Synth Reac Inorg Met—Org Chem* (1974) 5:417–27; Moedritzer, K., *Chem Abs* 82:86340; Stowell, M. H. B., et al *Tet Lett* (1990) 31:3261–3262) to a corresponding dialkylester (or dialkylamide) by reaction with alcohols (or amines). Monoalkylesters (or mono alkylamides) are obtained by hydrolysis of the disubstituted phosphonate in base (NaOH, KOH and the like). Disubstituted diacyloxyalkyl phosphonates are obtained by reaction of the unsubstituted phosphonate with a substituted chloromethyl ester (R—C(O)—O—CH(R)—Cl). A corresponding monosubstituted acyloxyalkyl phosphonate is obtained by hydrolysis in acid or base.

For synthesis of Z substructures having a free hydroxyl group, such as (RO)$_2$P(O)—CH$_2$—O—CH(CH$_2$OH)—CH$_2$—, the hydroxyl is, in some cases, protected by a protecting group such as benzyl, acetyl, trityl, dimethoxytrityl and the like.

Bis esters having aryl, substituted aryl, alkyl-aryl or substituted alkyl-aryl (such as phenyl, alkoxyphenyl, benzyl, alkoxybenzyl) are also synthesized as described by reaction of (OH)$_2$P(O)-B-Z with thionyl chloride and a catalytic amount of DMF in a solvent such as acetonitrile. The resulting dichloridate, P(O)(Cl)$_2$-Z-B is then reacted with about 4, 5 or 6 equivalents of the sodium or potassium alkoxide or a sodium or potassium aryloxide obtained from reaction with sodium hydride or potassium hydride and the alcohol (such as phenol, benzyl alcohol and the like) in a solvent such as THF or acetonitrile at a reduced temperature (below about −70° C., preferably about −76° C. to −78° C.).

cHPMPC and the cyclic analogues of other cHPMPs are prepared by a number of methods from the free hydroxy phosphonic acid. These methods include treatment with DCC in DMF, reaction with Vilsmeier's reagent (ClCH=N(CH$_3$)$_2$Cl), or methods of phosphate activation known per se. In one embodiment of this invention for the preparation of a cHPMP from the corresponding phosphonate nucleotide analog, the phosphonate is (a) treated with ClCH=N(CH$_3$)$_2$Cl to yield the phosphonylchloridate and (b) optionally the phosphonylchoridate is reacted with a nucleophile (preferably at low temperature, e.g. lower than about −20° C.) such as an alcohol or amine to produce one of the intermediates described above. In a further step the product of steps (a) or (b) are subject to hydrolysis or protonolysis (typically acid protonolysis) respectively to yield the cHSNA (treatment of the product of step (a)) or its intermediate (treatment of the product of step (b)). Vilsmeier's reagent is advantageously produced in situ by combining SOCl$_2$, PCl$_5$, POCl$_3$, COCl$_2$ or the like with DMF. Advantageously, the product of step (a) is not purified or separated from the reaction mixture before being reacted with the nucleophile, a distinct economic advantage for this synthetic route. The compounds of structure (Ia) and (Va) are readily made from their uncyclized counterparts by the same methods, e.g. treatment with DCC in DMF.

Substituted and unsubstituted alkyl, aryl, heteroaryl, arylalkyl, heteroarylalkyl and other L$^1$ esters and amidates of cHPMPs typically are made by reacting the appropriate HPMP compound with SOCl$_2$/DMF to yield the activated phosphonylchloride (see Scheme 1), followed by treatment with the corresponding nucleophile (e.g. alkoxide, phenolate, amine, etc.) to yield the protected intermediate formamidine which is subsequently hydrolyzed to the target compound. Alternatively, esters can also be prepared as depicted in Scheme 2. The N-,O-protected intermediate phosphonate diester is obtained from the three building blocks by known methods. The N- and O-protecting groups are subsequently removed followed by treatment of the phosphonate diester 3 with NaH leading to cyclization yielding target compound 4. A third method for the synthesis of cHSNA esters entails alkylation of the cHSNA using common alkylating agents D$^1$L (where L is a leaving group) such as alkyl halides, tosylates, diazoalkanes and the like (see Scheme 3). This method is particularly useful for preparing acyloxyalkyl esters by treatment of the cHSNA with the corresponding acyloxyalkylhalide. In an exemplary method for the preparation of acyloxyalkyl esters of cHPMPs, as shown in more detail in Example 12, DCC and R$^{45}$C(O)OCH$_2$Cl are reacted with the cyclic compound; but in contradistinction with prior methods the stoichiometric proportion of DCC: R$^{45}$C(O)OCH$_2$Cl, cyclic HPMP is 1–2:1–2:1. Use of such low proportions of reactants lessens side reactions with any exocyclic amino group of B and thereby greatly improves yields. R$^{45}$ is H or is C$_3$–C$_{12}$ alkyl which is unsubstituted or substituted by substituents independently selected from the group consisting of OH, O, N and halogen, C$_3$–C$_6$ aryl which is unsubstituted or substituted by substituents independently selected from the group consisting of OH, O, N and halogen or C$_3$–C$_9$ aryl-alkyl which is unsubstituted or substituted by substituents independently selected from the group consisting of OH, O, N and halogen.

Each of the following schemes exemplify HPMPC as the nucleotide analog. However, any B is employed in place of cytosine, provided that any exocydic oxo or amino groups are protected as required. Also, step 3 of scheme 1 will be omitted when B contains no exocyclic amine.

Scheme 1

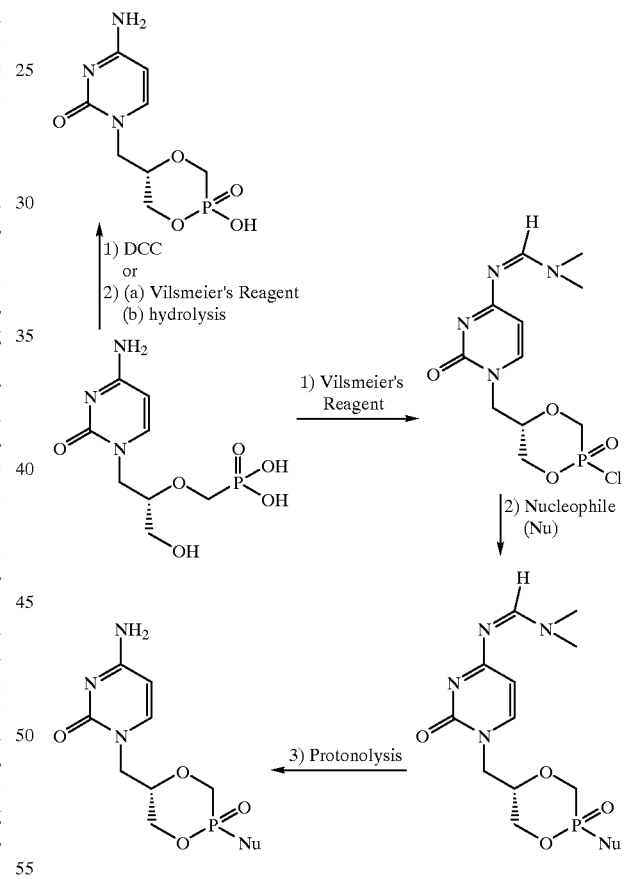

Scheme 2

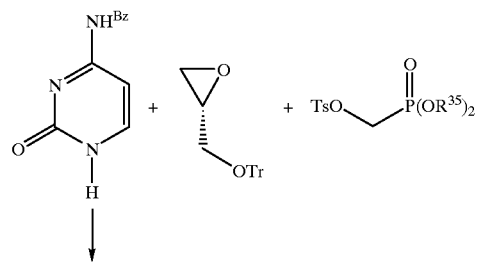

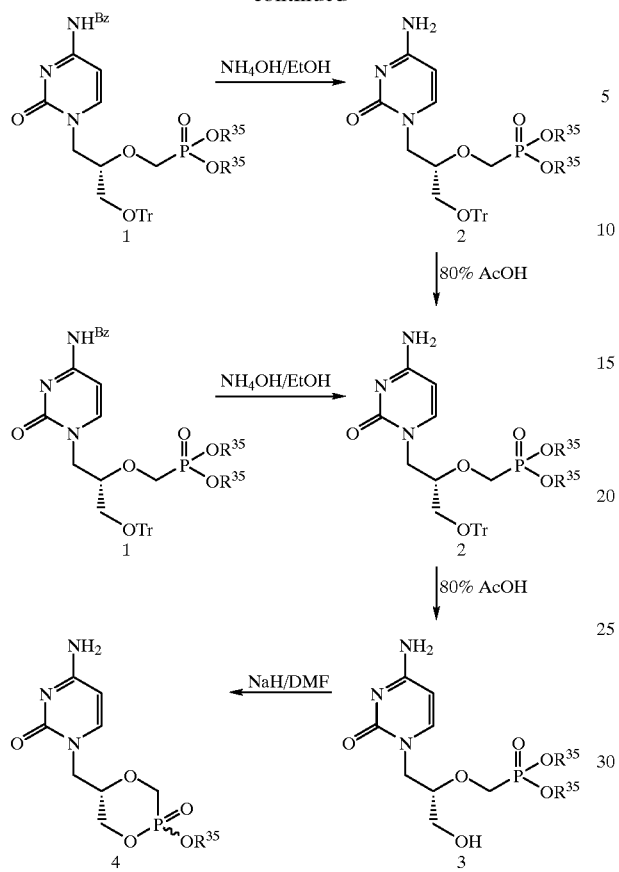

Scheme 3

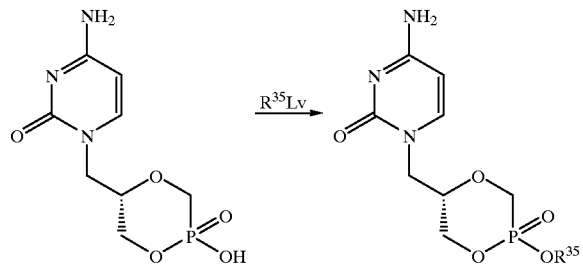

A third method for the synthesis of cyclic HPMP esters entails alkylation of the cyclic HPMP ester as shown in Scheme 3 using common alkylating agents $R^{35}Lv$ (where Lv is a leaving group) such as alkyl halides, tosylates, diazoalkanes and the like. This method is particularly useful for preparing acyloxyalkyl esters by treatment of the cyclic HPMP (cHPMP) with the corresponding acyloxyalkylhalide.

Compounds where Z is of structure V and $R^{25}$ and $R^{29}$ is oxygen are synthesized by addition-elimination reaction using a compound of structure

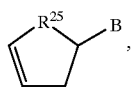, previously described for B=adenine (EP 398 231) with iodine (about 2 equivants) in organic solvent (such as acetonitrile or methylene chloride) at about 15–24° C. and a compound having the structure $(R^{35}O)_2P(O)$—$CH_2$—OH, wherein $R^{35}$ is R or $R^{31}$ (defined below), to yield the 3-iodophosphonate diester of structure 51,

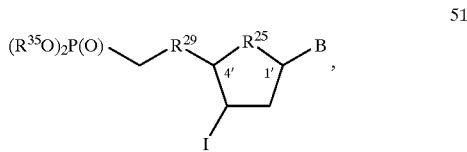

which is then eliminated to yield the corresponding structure V compound by reaction with about 5 equivalents of a base such as sodium methoxide or DBU in anhydrous organic solvent such as methanol or tetrahydrofuran at room temperature for about 2–12 hours. The following schemes show synthesis of intermediates having fluorine or iodine at the 3' position that are converted to structure V compounds by elimination with a base. N-Fluorodibenzenesulfonamide is available commercially (Aldrich). Structure V compounds where B and the phosphonate ester substituent at the 4' position are either both up or down (i.e., substituents at the 1' and 4' positions are cis with respect to each other) are obtained by using the corresponding structure 50 reactant as follows

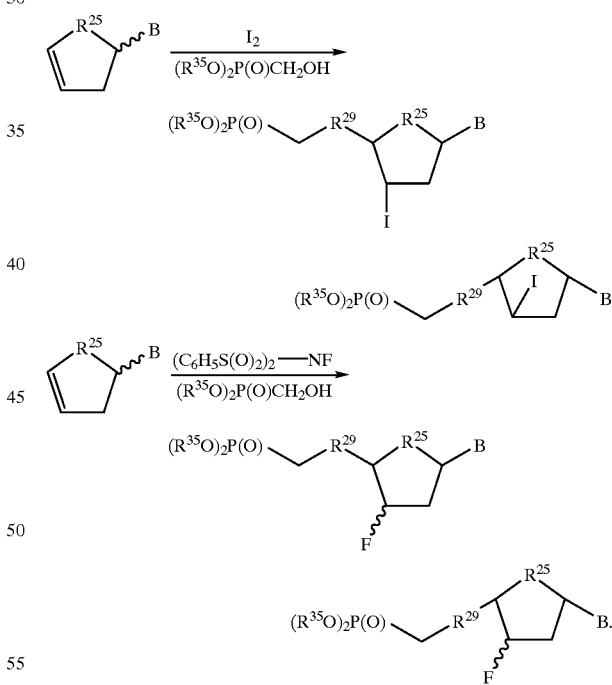

When the reaction with iodine is conducted at high temperature (about 50–80° C., usually about 60–70° C.), a scalemic intermediate results as follows

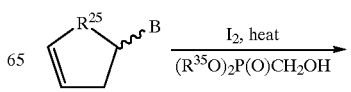

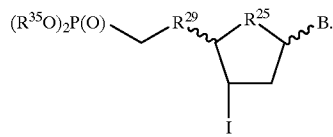

The intermediate is then converted to the corresponding structure V compound and the various cis and trans isomers can be separated using standard methods such as HPLC, RPLC or crystallization.

Exemplary esters are of the formula, $(R^{31}O)_2P(O)$-Z-B, $(RO)(R^{31}O)P(O)$-Z-B or $(RO)_2P(O)$-Z-B, wherein $R^{31}$ is independently 2,3-dihydro-6-hydroxyindene, sesamol, catechol monoester, —$CH_2$—$C(O)$—$N(R^7)_2$ wherein each $R^7$ is the same or different, —$CH_2$—$S(O)(R^7)$, —$CH_2$—$S(O)_2$ $(R^7)$, —$CH_2$—$CH(OC(O)CH_2R^7)$—$CH_2(OC(O)CH_2R^7)$, cholesteryl, a 5 or 6 carbon monosaccharide, disaccharide or oligosaccharide (3 to 9 monosaccharide residues), enolpyruvate (HOOC—C(=$CH_2$)O), glycerol, α-D-β-diglycerides (wherein the fatty acids composing glyceride lipids generally are naturally occurring saturated or unsaturated $C_{6-26}$, $C_{6-18}$ or $C_{6-10}$ fatty acids such as linoleic, lauric, myristic, palmitic, stearic, oleic, palmitoleic, linolenic and the like fatty acids), trimethoxybenzyl, triethoxybenzyl, 2-alkyl pyridinyl ($C_{1-4}$ alkyl),

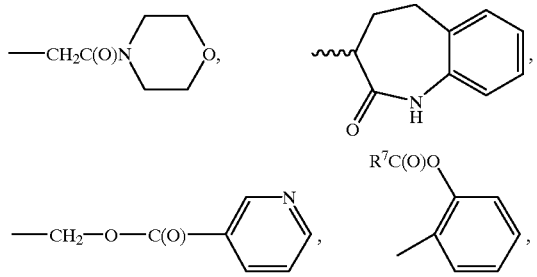

$C_3$-$C_6$ aryl (including phenyl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 2-, 3- and 4-pyridinyl and 2-, 4- and 5-pyrimidinyl) substituted by 3, 4 or 5 halogen atoms or 1 or 2 atoms or groups selected from halogen, $C_1$-$C_{12}$ alkoxy (including methoxy, ethoxy, 2,3-, 2,4-, 2,5-, 2,6-, 3,4- and 3,5-dimethoxy and 2,3-, 2,4-, 2,5-, 2,6-, 3,4- and 3,5-diethoxy substituted phenyl), cyano, nitro, OH, $C_1$-$C_{12}$ haloalkyl (1 to 6 halogen atoms), $C_1$-$C_{12}$ alkyl (including methyl and ethyl), $C_2$-$C_{12}$ alkenyl or $C_2$-$C_{12}$ alkynyl; or $R^{31}$ is $C_1$-$C_4$ alkylene-$C_3$-$C_6$ aryl (including benzyl, —$CH_2$-pyrrolyl, —$CH_2$-thienyl, —$CH_2$-imidazolyl, —$CH_2$-oxazolyl, —$CH_2$-isoxazolyl, —$CH_2$-thiazolyl, —$CH_2$-isothiazolyl, —$CH_2$-pyrazolyl, —$CH_2$-pyridinyl and —$CH_2$-pyrimidinyl) substituted in the aryl moiety by 3 to 5 halogen atoms or 1 to 2 atoms or groups selected from halogen, $C_1$-$C_{12}$ alkoxy (including methoxy and ethoxy), cyano, nitro, OH, $C_1$-$C_{12}$ haloalkyl (1 to 6 halogen atoms; including —$CH_2$—$CCl_3$), $C_1$-$C_{12}$ alkyl (including methyl and ethyl), $C_2$-$C_{12}$ alkenyl or $C_2$-$C_{12}$ alkynyl. Methods for linking cholesteryl, saccharide and other moieties to reactive groups have been described (Hadfield *Adv. Pharmacol. Chemother.* (1984) 20:21; Gouyette *Tet. Lett.* (1989) 30:6019; Ksander *J. Med. Chem.* (1994) 37:1823).

The compounds are used as intermediates in the synthesis of mixed amidate-ester nucleotide analog amidates, or in some cases, as drugs per se. Additional exemplary ester compounds have the formulas $(R^{31}O)_2P(O)$-$Z^1$-B or (RO) $(R^{31}O)P(O)$-$Z^1$-B, where $Z^1$ is defined to mean the substructure in the following representative structures; $(R^{31}O)_2$-P (O)—$CH_2$—O—$CH_2$—$CH_2$-B, $(R^{31}O)_2$-P(O)—$CH^{\#}H$ ($CH_2OH$)—$CH_2$—B, $(R^{31}O)_2$-P(O)—$CH_2$—O—$C\#H$ ($CH_3$)—$CH_2$—B, $(R^{31}O)_2$-P(O)—$CH_2$—O—$C\#H$ ($CH_2F$)—$CH_2$—B, $(R^{31}O)_2$-P(O)—$CH_2$—O—$C\#H$ (CH=$CH_2$)—$CH_2$—B, $(R^{31}O)_2$-P(O)—$CH_2$—O—$C\#H$ ($CH_2N_3$)—$CH_2$—B,

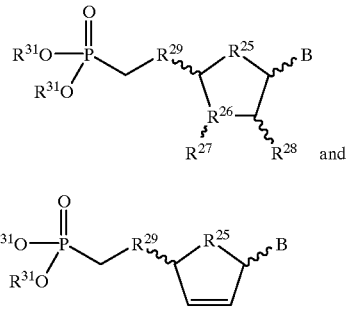

XXIX where $C^{\#}$, $R^{25}$–$R^{29}$, $R^{31}$ and B have the meanings previously defined with the proviso that PMEA bis(4-nitrobenzyl ester) and PMEA bis(4-trifluoromethyl ester) are excluded and for structure XXIX, $R^{29}$ and $R^{25}$ are both O. Additional ester and nucleotide compounds are of the formula

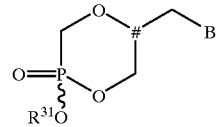

XXXI where substituents linked to the carbon atom designated # are in the R, S or RS configuration and $R^{31}$ and B are as previously defined. Nucleotides and esters of the formulas

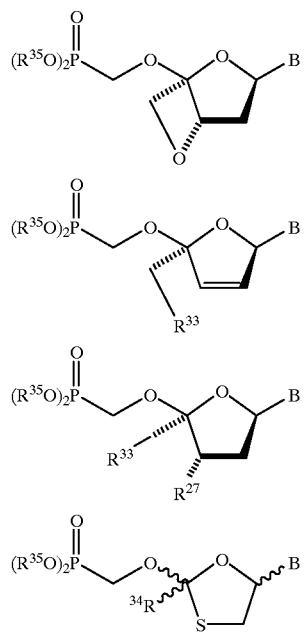

-continued

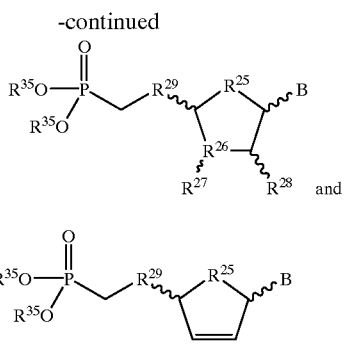

XXX wherein #, B, $R^{25}$, $R^{26}$ $R^{27}$, $R^{28}$, $R^{29}$, $R^{31}$, $R^{33}$ and $R^{34}$ are as defined, $R^{35}$ is defined as R or $R^{31}$ and for structure XXX, when $R^{29}$ is $CH_2$ or O and $R^{25}$ is $CH_2$ or O, $R^{35}$ is not H or $C_1$–$C_6$ alkyl, are new. Compounds having $R^{35}$ include species where both $R^{35}$ are both H and their salts including pharmaceutically acceptable salts.

Exemplary $R^{31}$ include 2-, 3- and 4-alkoxyphenyl ($C_1$–$C_{12}$ alkyl including 2-, 3- and 4-methoxyphenyl and 2-, 3- and 4-ethoxyphenyl), 2-, 3- and 4-carboethoxyphenyl, 2- and 3-carboethoxy-4-hydroxyphenyl, 2- and 3-ethoxy-4-hydroxyphenyl, 2- and 3-ethoxy-5-hydroxyphenyl, 2- and 3-ethoxy-6-hydroxyphenyl, 2-, 3- and 4-O-acetylphenyl, 2-, 3- and 4-dimethylaminophenyl, 2-, 3- and 4-methylmercaptophenyl, 2-, 3- and 4-halophenyl (including 2-, 3- and 4-fluorophenyl and 2-, 3- and 4-chlorophenyl), 2,3-, 2,4-, 2,5-, 2,6-, 3,4- and 3,5-dimethylphenyl, 2,3-, 2,4-, 2,5-, 2,6-, 3,4- and 3,5-biscarboxyethylphenyl, 2,3-, 2,4-, 2,5-, 2,6-, 3,4- and 3,5-dimethoxyphenyl, 2,3-, 2,4-, 2,5-, 2,6-, 3,4- and 3,5-dihalophenyl (including 2,4-difluorophenyl and 3,5-difluorophenyl), 2-, 3- and 4-haloalkylphenyl (1 to 5 halogen atoms, $C_1$–$C_{12}$ alkyl including 4-trifluoromethylphenyl), 2-, 3- and 4-cyanophenyl, and 2-, 3- and 4-nitrophenyl, 2-, 3- and 4-haloalkylbenzyl (1 to 5 halogen atoms, $C_1$–$C_{12}$ alkyl including 4-trifluoromethylbenzyl), α-D-galactose, α-D-glucose, α-D-fructose. The bis esters of formula $(OR^{31})$ $(OR^{31})P(O)$-Z-B and $(OR)(OR^{31})P(O)$-Z-B are novel and are useful as intermediates in the synthesis of the mixed amidate-ester nucleotide analog amidates of the invention. These compounds can also be used directly as antimicrobial agents per se. Table 5 lists a group of exemplary bis esters of compounds having the structure $(OR^{35})_2P(O)$-Z-B which includes novel compounds of struture $(OR^{31})_2P(O)$-Z-B.

TABLE 5

| $OR^{35}$* | —P(O)—Z—B** |
|---|---|
| 1 —O—$C_6H_4F$ | 1 —P(O)—$CH_2$—O—$CH_2$—$CH_2$—B |
| 2 —O—$C_6H_3F_2$ | 2 —P(O)—$CH_2$—O—$C^{\#}H(CH_2$—$OR^4)$—$CH_2$—B |
| 3 —O—$C_6H_4$—$OCH_3$ | 3 —P(O)—$CH_2$—O—$C^{\#}H(CH_3)$—$CH_2$—B |
| 4 —O—$C_6H_3$—$(OCH_3)_2$ | 4 —P(O)—$CH_2$—O—$C^{\#}H(CH_2F)$—$CH_2$—B |
| 5 —O—$C_6H_4OC_2H_5$ | 5 —P(O)—$CH_2$—O—$C^{\#}H(CH$=$CH_2)$—$CH_2$—B |
| 6 —O—$C_6H_3$—$(OC_2H_5)_2$ | 6 —P(O)—$CH_2$—O—$C^{\#}H(CH_2N_3)$—$CH_2$—B |
| 7 —O—$CH_2$—$C_6H_4F$ | 7 ** |
| 8 —O—$C_6H_4$—$(C(O)$—O—$C_2H_5)_2$ | 8 ** |
| 9 —O—$C_6H_4$—$C(O)$—O—$C_2H_5$ | |
| 10 —O—$C_6H_3$—$(O$—$C(O)$—$CH_3)_2$ | |
| 11 —O—$C_6H_3$—$C(O)$—O—$C_3H_7$ | |
| 12 —O—$CH_2$—$C_6H_4$—O—CO—$CH_3$ | |
| 13 —O—$C_5H_4N$ | |
| 14 —O—$C_6H_3$—$(OC_2H_5)(OH)$ | |
| 15 —O—$C_6H_5$ | |
| 16 —O—$CH_2$—$C(O)$—$C(CH_3)_3$ | |
| B | |
| 1 adenin-9-yl | |
| 2 guanin-9-yl | |
| 3 cytosin-1-yl | |
| 4 2, 6-diaminopurin-9-yl | |
| 5 2-aminopurin-9-yl | |
| 6 thymidin-1-yl | |
| 7 5-fluorocytosin-1-yl | |

*Monosubstituted phenyl and benzyl compounds (i.e., $R^{35}$ numbers 1, 3, 5, etc) include 2-, 3- and 4-substituted compounds and disubstituted phenyl compounds (i.e., $R^{35}$ numbers 2, 4, 6, etc) include 2,3-, 2,4-, 2,5-, 2,6-, 3,4- and 3,5-substituted compounds.
**The structure = P(O)— indicates that two bonds are occupied by $OR^{35}$; Z structure 7 is of formula IV where $R^{25}$ and $R^{29}$ are O, $R^{26}$ is S, $R^{27}$ is absent and $R^{28}$ is H and includes the (+) and (−) enantiomers; structure 8 is of formula V where $R^{25}$ and $R^{29}$ are O.

Compounds listed in Table 5 are designated herein by numbers assigned to $(OR^{35})_2$ (where each $R^{35}$ is the same), Z and B according to the following convention, $R^{35}$.Z.B. Exemplary compounds include 1.1.1, 2.1.1, 3.1.1, 4.1.1, 5.1.1, 6.1.1, 7.1.1, 8.1.1, 9.1.1, 10.1.1, 11.1.1, 12.1.1, 13.1.1, 14.1.1, 15.1.1, 16.1.1, 1.2.1, 2.2.1, 3.2.1, 4.2.1, 5.2.1, 6.2.1, 7.2.1, 8.2.1, 9.2.1, 10.2.1, 11.2.1, 12.2.1, 13.2.1, 14.2.1, 15.2.1, 16.2.1, 1.3.1, 2.3.1, 3.3.1, 4.3.1, 5.3.1, 6.3.1, 7.3.1, 8.3.1, 9.3.1, 10.3.1, 11.3.1, 12.3.1, 13.3.1, 14.3.1, 15.3.1, 16.3.1, 1.4.1, 2.4.1, 3.4.1, 4.4.1, 5.4.1, 6.4.1, 7.4.1, 8.4.1, 9.4.1, 10.4.1, 11.4.1, 12.4.1, 13.4.1, 14.4.1, 15.4.1, 16.4.1, 1.5.1, 2.5.1, 3.5.1, 4.5.1, 5.5.1, 6.5.1, 7.5.1, 8.5.1, 9.5.1, 10.5.1, 11.5.1, 12.5.1, 13.5.1, 14.5.1, 15.5.1, 16.5.1, 1.6.1, 2.6.1, 3.6.1, 4.6.1, 5.6.1, 6.6.1, 7.6.1, 8.6.1, 9.6.1, 10.6.1, 11.6.1, 12.6.1, 13.6.1, 14.6.1, 15.6.1, 16.6.1, 1.7.1, 2.7.1, 3.7.1, 4.7.1, 5.7.1, 6.7.1, 7.7.1, 8.7.1, 9.7.1, 10.7.1, 11.7.1, 12.7.1, 13.7.1, 14.7.1, 15.7.1, 16.7.1, 1.8.1, 2.8.1, 3.8.1, 4.8.1, 5.8.1, 6.8.1, 7.8.1, 8.8.1, 9.8.1, 10.8.1, 11.8.1, 12.8.1, 13.8.1, 14.8.1, 15.8.1, 16.8.1, 1.1.2, 2.1.2, 3.1.2, 4.1.2, 5.1.2, 6.1.2, 7.1.2, 8.1.2, 9.1.2, 10.1.2, 11.1.2, 12.1.2, 13.1.2, 14.1.2, 15.1.2, 16.1.2, 1.2.2, 2.2.2, 3.2.2, 4.2.2, 5.2.2, 6.2.2, 7.2.2, 8.2.2, 9.2.2, 10.2.2, 11.2.2, 12.2.2, 13.2.2, 14.2.2, 15.2.2, 16.2.2, 1.3.2, 2.3.2, 3.3.2, 4.3.2, 5.3.2, 6.3.2, 7.3.2, 8.3.2, 9.3.2, 10.3.2, 11.3.2, 12.3.2, 13.3.2, 14.3.2, 15.3.2, 16.3.2, 1.4.2, 2.4.2, 3.4.2, 4.4.2, 5.4.2, 6.4.2, 7.4.2, 8.4.2, 9.4.2, 10.4.2, 11.4.2, 12.4.2, 13.4.2, 14.4.2, 15.4.2, 16.4.2, 1.5.2, 2.5.2, 3.5.2, 4.5.2, 5.5.2, 6.5.2, 7.5.2, 8.5.2, 9.5.2, 10.5.2, 11.5.2, 12.5.2, 13.5.2, 14.5.2, 15.5.2, 16.5.2, 1.6.2, 2.6.2, 3.6.2, 4.6.2, 5.6.2, 6.6.2, 7.6.2, 8.6.2, 9.6.2, 10.6.2, 11.6.2, 12.6.2, 13.6.2, 14.6.2, 15.6.2, 16.6.2, 1.7.2, 2.7.2, 3.7.2, 4.7.2, 5.7.2, 6.7.2, 7.7.2, 8.7.2, 9.7.2, 10.7.2, 11.7.2, 12.7.2, 13.7.2, 14.7.2, 15.7.2, 16.7.2, 1.8.2, 2.8.2, 3.8.2, 4.8.2, 5.8.2, 6.8.2, 7.8.2, 8.8.2, 9.8.2, 10.8.2, 11.8.2, 12.8.2, 13.8.2, 14.8.2, 15.8.2, 16.8.2, 1.1.3, 2.1.3, 3.1.3, 4.1.3, 5.1.3, 6.1.3, 7.1.3, 8.1.3, 9.1.3, 10.1.3, 11.1.3, 12.1.3, 13.1.3, 14.1.3, 15.1.3, 16.1.3, 1.2.3, 2.2.3, 3.2.3, 4.2.3, 5.2.3, 6.2.3, 7.2.3, 8.2.3, 9.2.3, 10.2.3, 11.2.3, 12.2.3, 13.2.3, 14.2.3, 15.2.3, 16.2.3, 1.3.3, 2.3.3, 3.3.3, 4.3.3, 5.3.3, 6.3.3, 7.3.3, 8.3.3, 9.3.3, 10.3.3, 11.3.3, 12.3.3, 13.3.3, 14.3.3, 15.3.3, 16.3.3, 1.4.3, 2.4.3, 3.4.3, 4.4.3, 5.4.3, 6.4.3, 7.4.3, 8.4.3, 9.4.3, 10.4.3, 11.4.3, 12.4.3, 13.4.3, 14.4.3, 15.4.3, 16.4.3, 1.5.3, 2.5.3, 3.5.3, 4.5.3, 5.5.3, 6.5.3, 7.5.3, 8.5.3, 9.5.3, 10.5.3, 11.5.3, 12.5.3, 13.5.3, 14.5.3, 15.5.3, 16.5.3, 1.6.3, 2.6.3, 3.6.3, 4.6.3, 5.6.3, 6.6.3, 7.6.3, 8.6.3, 9.6.3, 10.6.3, 11.6.3, 12.6.3, 13.6.3, 14.6.3, 15.6.3, 16.6.3, 1.7.3, 2.7.3, 3.7.3, 4.7.3, 5.7.3, 6.7.3, 7.7.3, 8.7.3, 9.7.3, 10.7.3, 11.7.3, 12.7.3, 13.7.3, 14.7.3, 15.7.3, 16.7.3, 1.8.3, 2.8.3, 3.8.3, 4.8.3, 5.8.3, 6.8.3, 7.8.3, 8.8.3, 9.8.3, 10.8.3, 11.8.3, 12.8.3, 13.8.3, 14.8.3, 15.8.3, 16.8.3, 1.1.4, 2.1.4, 3.1.4, 4.1.4, 5.1.4, 6.1.4, 7.1.4, 8.1.4, 9.1.4, 10.1.4, 11.1.4, 12.1.4, 13.1.4, 14.1.4, 15.1.4, 16.1.4, 1.2.4, 2.2.4, 3.2.4, 4.2.4, 5.2.4, 6.2.4, 7.2.4, 8.2.4, 9.2.4, 10.2.4, 11.2.4, 12.2.4, 13.2.4, 14.2.4, 15.2.4, 16.2.4, 1.3.4, 2.3.4, 3.3.4, 4.3.4, 5.3.4, 6.3.4, 7.3.4, 8.3.4, 9.3.4, 10.3.4, 11.3.4, 12.3.4, 13.3.4, 14.3.4, 15.3.4, 16.3.4, 1.4.4, 2.4.4, 3.4.4, 4.4.4, 5.4.4, 6.4.4, 7.4.4, 8.4.4, 9.4.4, 10.4.4, 11.4.4, 12.4.4, 13.4.4, 14.4.4, 15.4.4, 16.4.4, 1.5.4, 2.5.4, 3.5.4, 4.5.4, 5.5.4, 6.5.4, 7.5.4, 8.5.4, 9.5.4, 10.5.4, 11.5.4, 12.5.4, 13.5.4, 14.5.4, 15.5.4, 16.5.4, 1.6.4, 2.6.4, 3.6.4, 4.6.4, 5.6.4, 6.6.4, 7.6.4, 8.6.4, 9.6.4, 10.6.4, 11.6.4, 12.6.4, 13.6.4, 14.6.4, 15.6.4, 16.6.4, 1.7.4, 2.7.4, 3.7.4, 4.7.4, 5.7.4, 6.7.4, 7.7.4, 8.7.4, 9.7.4, 10.7.4, 11.7.4, 12.7.4, 13.7.4, 14.7.4, 15.7.4, 16.7.4, 1.8.4, 2.8.4, 3.8.4, 4.8.4, 5.8.4, 6.8.4, 7.8.4, 8.8.4, 9.8.4, 10.8.4, 11.8.4, 12.8.4, 13.8.4, 14.8.4, 15.8.4, 16.8.4, 1.1.5, 2.1.5, 3.1.5, 4.1.5, 5.1.5, 6.1.5, 7.1.5, 8.1.5, 9.1.5, 10.1.5, 11.1.5, 12.1.5, 13.1.5, 14.1.5, 15.1.5, 16.1.5, 1.2.5, 2.2.5, 3.2.5, 4.2.5, 5.2.5, 6.2.5, 7.2.5, 8.2.5, 9.2.5, 10.2.5, 11.2.5, 12.2.5, 13.2.5, 14.2.5, 15.2.5, 16.2.5, 1.3.5, 2.3.5, 3.3.5, 4.3.5, 5.3.5, 6.3.5, 7.3.5, 8.3.5, 9.3.5, 10.3.5, 11.3.5, 12.3.5, 13.3.5, 14.3.5, 15.3.5, 16.3.5, 1.4.5, 2.4.5, 3.4.5, 4.4.5, 5.4.5, 6.4.5, 7.4.5, 8.4.5, 9.4.5, 10.4.5, 11.4.5, 12.4.5, 13.4.5, 14.4.5, 15.4.5, 16.4.5, 1.5.5, 2.5.5, 3.5.5, 4.5.5, 5.5.5, 6.5.5, 7.5.5, 8.5.5, 9.5.5, 10.5.5, 11.5.5, 12.5.5, 13.5.5, 14.5.5, 15.5.5, 16.5.5, 1.6.5, 2.6.5, 3.6.5, 4.6.5, 5.6.5, 6.6.5, 7.6.5, 8.6.5, 9.6.5, 10.6.5, 11.6.5, 12.6.5, 13.6.5, 14.6.5, 15.6.5, 16.6.5, 1.7.5, 2.7.5, 3.7.5, 4.7.5, 5.7.5, 6.7.5, 7.7.5, 8.7.5, 9.7.5, 10.7.5, 11.7.5, 12.7.5, 13.7.5, 14.7.5, 15.7.5, 16.7.5, 1.8.5, 2.8.5, 3.8.5, 4.8.5, 5.8.5, 6.8.5, 7.8.5, 8.8.5, 9.8.5, 10.8.5, 11.8.5, 12.8.5, 13.8.5, 14.8.5, 15.8.5, 16.8.5, 1.1.6, 2.1.6, 3.1.6, 4.1.6, 5.1.6, 6.1.6, 7.1.6, 8.1.6, 9.1.6, 10.1.6, 11.1.6, 12.1.6, 13.1.6, 14.1.6, 15.1.6, 16.1.6, 1.2.6, 2.2.6, 3.2.6, 4.2.6, 5.2.6, 6.2.6, 7.2.6, 8.2.6, 9.2.6, 10.2.6, 11.2.6, 12.2.6, 13.2.6, 14.2.6, 15.2.6, 16.2.6, 1.3.6, 2.3.6, 3.3.6, 4.3.6, 5.3.6, 6.3.6, 7.3.6, 8.3.6, 9.3.6, 10.3.6, 11.3.6, 12.3.6, 13.3.6, 14.3.6, 15.3.6, 16.3.6, 1.4.6, 2.4.6, 3.4.6, 4.4.6, 5.4.6, 6.4.6, 7.4.6, 8.4.6, 9.4.6, 10.4.6, 11.4.6, 12.4.6, 13.4.6, 14.4.6, 15.4.6, 16.4.6, 1.5.6, 2.5.6, 3.5.6, 4.5.6, 5.5.6, 6.5.6, 7.5.6, 8.5.6, 9.5.6, 10.5.6, 11.5.6, 12.5.6, 13.5.6, 14.5.6, 15.5.6, 16.5.6, 1.6.6, 2.6.6, 3.6.6, 4.6.6, 5.6.6, 6.6.6, 7.6.6, 8.6.6, 9.6.6, 10.6.6, 11.6.6, 12.6.6, 13.6.6, 14.6.6, 15.6.6, 16.6.6, 1.7.6, 2.7.6, 3.7.6, 4.7.6, 5.7.6, 6.7.6, 7.7.6, 8.7.6, 9.7.6, 10.7.6, 11.7.6, 12.7.6, 13.7.6, 14.7.6, 15.7.6, 16.7.6, 1.8.6, 2.8.6, 3.8.6, 4.8.6, 5.8.6, 6.8.6, 7.8.6, 8.8.6, 9.8.6, 10.8.6, 11.8.6, 12.8.6, 13.8.6, 14.8.6, 15.8.6, 16.8.6, 1.1.7, 2.1.7, 3.1.7, 4.1.7, 5.1.7, 6.1.7, 7.1.7, 8.1.7, 9.1.7, 10.1.7, 11.1.7, 12.1.7, 13.1.7, 14.1.7, 15.1.7, 16.1.7, 1.2.7, 2.2.7, 3.2.7, 4.2.7, 5.2.7, 6.2.7, 7.2.7, 8.2.7, 9.2.7, 10.2.7, 11.2.7, 12.2.7, 13.2.7, 14.2.7, 15.2.7, 16.2.7, 1.3.7, 2.3.7, 3.3.7, 4.3.7, 5.3.7, 6.3.7, 7.3.7, 8.3.7, 9.3.7, 10.3.7, 11.3.7, 12.3.7, 13.3.7, 14.3.7, 15.3.7, 16.3.7, 1.4.7, 2.4.7, 3.4.7, 4.4.7, 5.4.7, 6.4.7, 7.4.7, 8.4.7, 9.4.7, 10.4.7, 11.4.7, 12.4.7, 13.4.7, 14.4.7, 15.4.7, 16.4.7, 1.5.7, 2.5.7, 3.5.7, 4.5.7, 5.5.7, 6.5.7, 7.5.7, 8.5.7, 9.5.7, 10.5.7, 11.5.7, 12.5.7, 13.5.7, 14.5.7, 15.5.7, 16.5.7, 1.6.7, 2.6.7, 3.6.7, 4.6.7, 5.6.7, 6.6.7, 7.6.7, 8.6.7, 9.6.7, 10.6.7, 11.6.7, 12.6.7, 13.6.7, 14.6.7, 15.6.7, 16.6.7, 1.7.7, 2.7.7, 3.7.7, 4.7.7, 5.7.7, 6.7.7, 7.7.7, 8.7.7, 9.7.7, 10.7.7, 11.7.7, 12.7.7, 13.7.7, 14.7.7, 15.7.7, 16.7.7, 1.8.7, 2.8.7, 3.8.7, 4.8.7, 5.8.7, 6.8.7, 7.8.7, 8.8.7, 9.8.7, 10.8.7, 11.8.7, 12.8.7, 13.8.7, 14.8.7, 15.8.7 and 16.8.7.

Exemplary bis esters include bis(pivaloyloxymethyl) PMEA (i.e. bis(pivaloyloxymethyl)-9-(2-phosphonylmethoxyethyl)adenine), bis(pivaloyloxymethyl) HPMPC, bis(pivaloyloxymethyl)D4AMPI, bis (pivaloyloxymethyl)D4TMPI, bis(N-ethylmorpholino) PMEA, bis(N-ethylmorpholino)HPMPC, bis(N-ethyimorpholino)PMPDAP, bis(N-ethylmorpholino) HPMPA, bis(N-ethylmorpholino)PMEG, bis(N-ethylmorpholino)D4AMPI, bis(N-ethylmorpholino) D4TMPI, bis(phenyl)PMEA, bis(phenyl)HPMPC, bis (phenyl)HPMPA, bis(phenyl)D4AMPI, bis(phenyl) D4TMPI, bis(t-butyl)PMEA, bis(t-butyl)D4AMPI, bis(t-butyl)D4TMPI, bis(t-butyl)HPMPC, bis(2-ethoxyphenyl) PMEA, bis(2-ethoxyphenyl)HPMPC, bis(4-fluorophenyl) PMEA, bis(4-fluorophenyl)HPMPC, bis(3,5-dimethoxyphenyl)PMEA, bis(3,5-dimethoxyphenyl) HPMPC and the like. $L^1$ is an amino acid which is, in general, esterified at free α-carboxyl group(s) by $R^4$, or is a dipeptide, tripeptide or oligopeptide which is optionally esterified at the free α-carboxyl group by $R^4$. $L^2$ is an ester or thioester group. Suitable $L^2$ esters (and the corresponding thioesters) include methyl ester, ethyl ester, propyl ester, isopropyl ester, butyl ester, t-butyl ester, phenyl ester, benzyl ester, N-ethylmorpholino ester (—O—$CH_2$—$CH_2$—N [$(CH_2)_2(CH_2)_2$]O), pivaloyloxymethyl ester (—O—$CH_2$—O—(O)—$C(CH_3)_3$) and the like. The suitability of the presence or absence of any particular $L^2$ or $R^4$ group is determined by stability and/or bioavailability assays (e.g., stability assay in aqueous conditions such as low pH/intestinal lumen conditions or assay in the presence of cellular extracts containing esterases or by bioavailability assay using animal models) known in the art. These assays are routinely performed by the skilled artisan.

The bis ester is then converted to a monoester by chemical hydrolysis in base or acid according to the bis ester used. For example, treatment with NaOH (0.5 to 2 N) or $NH_4OH$ in a solvent such as THF (tetrahydrofuran), dioxane or an alcohol for 1 to 24 hours at 22° to 90° is suitable for most esters. The choice of solvent will depend on the characteristics of the bis ester used. The stability of the ester groups of phosphonate bis esters and phosphonate bis thioesters toward hydrolysis is unequal and provides a means for obtaining the monoester. Selection of hydrolysis conditions is determined by routine testing. Alkaline hydrolysis yields the phosphonate monoester and a corresponding alcohol or phenol. $L^1$ is then linked to the monoester or monothioester using reagents and conditions (i.e., a 1:1 mixture of triphenylphosphine ($PPh_3$) and 2,2'-dipyridyl disulfide in a suitable solvent such as pyridine or DMF) essentially as described for synthesis of bis amidates.

Nucleoside bis esters of formulas VI, VII and VIII compounds are shown in FIGS. 4–7. 3',4'-Unsaturated nucleosides that are used as a starting material was previously described (Zemlicka, et al *J Am Chem Soc* (1970) 92:4744–4745). 4'-Modified nucleosides have also been described (Yang, et al *Tet Lett* (1992) 33: 41–44; Yang, et al *Tet Lett* (1992) 33: 37–40; Prisbe, et al *Nucleosides and Nucleotides as Antitumor and Antiviral Agents* (1993) Plemun Press, New York, Chu, C. K. et al eds., p. 101–113). The phosphonate ester is condensed with the unsaturated nucleoside using an oxidizing agent such as MCPBA (m-chloroperoxybenzoic acid), IBr or N-iodosuccinimide (NIS). The choice of a particular oxidizing agent will be guided by considerations such as the type of heterocyclic base or sugar substituent that is present. For example, IBr may not be generally compatible with a substituent such as azide (at $R^{27}$ or $R^{33}$) or 1-propynyl (at B). In these cases, NIS or MCPBA is used. A further example is reduction of the 2',3'-double bond using $H_2$/Pd/C, which is generally not compatible with an alkynyl group that can be present at B. In this case, the alkynyl group would be added to an appropriate heterocyclic base (a purine such as 7-deaza-7-iodoadenine or 7-deaza-7-iodoguanine, etc or a pyrimidine such as 5-iodocytosine, 5-iodouracil, uracil, etc) that is later converted to the alkynyl derivative (7-deaza-7-(1-propynyl) adenine, 5-(1-propynyl)uracil, etc) using an alkyne such as propyne and palladium (08/050,698; PCT/US92/10115; Hobbs et al, *J Org Chem* (1989) 54:3420–3422). For FIGS. 3–7, $R^{33}$ is H, OH, TBSO, halogen, cyano, $CH_2N_3$, $C_1$–$C_4$ alkyl, $C_1$–$C_4$ alkoxy (including $OCH_3$), $CH_2OH$ or azido; $R^{34}$ is H, OH halogen (fluorine is preferred), azide, O-alkyl ($C_1$–$C_6$ including O-methyl and O-ethyl), S-alkyl ($C_1$–$C_6$ including S-methyl and S-ethyl) and O-alkenyl (including O-allyl); R is as defined above, except that for the structure $(RO)_2P(O)$—$CH_2$—OH, R is not hydrogen, and R includes $C_1$–$C_{20}$ alkoxyacyl groups including methoxyacyl (pivaloyloxymethyl, adamantoyl oxymethyl and the like) and ethoxyacyl (pivaloyloxyethyl and the like) moieties; TBSO is t-butyldimethylsilyl ether. The phosphonates and monoesters shown in FIGS. 4–7 are converted to bis amidates or mixed amidate ester compounds using reagents and conditions (e.g., a 1:1 mixture of triphenylphosphine ($PPh_3$) and 2,2'-dipyridyl disulfide in a suitable solvent such as pyridine or DMF) essentially as described above.

Mixed Bis Amidate Synthesis.

Synthesis of compounds of formula Id where $L^1$ and $L^2$ are both amino acids or where $L^1$ is an amino acid and $L^2$ is an amine ($NH_2$, $NHR^6$, $N(R^6)_2$) but are not both the same is accomplished by direct conversion as described above for bis amidates followed by separation of the final products. Another method to synthesize mixed bis amidates is amidation of an appropriate phosphonate monoester to give a compound of formula Id, followed by removal of the ester group under conditions that do not remove the first amide. Synthesis of phosphonate monoester compounds has been described (EP 481 214). This compound is then converted to a mixed bis amide by condensation with a second amino acid to yield the final product as described (i.e., using a 1:1 mixture of triphenylphosphine and 2,2'-dipyridyl disulfide).

Mono Amidate Synthesis.

Synthesis of compounds of formula Ib where $L^1$ is an amino acid and $X^1$ is O (oxygen) is accomplished essentially as described for bis amidate synthesis using a cyclic nucleotide analog such as cHPMPC (cyclic HPMPC), cHFMPA, cHPMPDAP, cHPMPG and the like. Cydic HPMP series compounds (cHPMPC, etc) are prepared by direct dehydration of the corresponding HPMP nucleotide analog using DCC (dicyclohexylcarbodiimide) or using 4-morpholino-N, N'-dicyclohexylcarboxamide as described (Ho et al *Mol Pharmacol* (1992) 41:197–202). The cyclic phosphonate is condensed with an optionally protected amino acid ester in the presence of a 1:1 mixture of triphenylphosphine and 2,2'-dipyridyl disulfide in a suitable solvent such as pyridine or DMF.

Synthesis of formula Ib compounds where $X^1$ is S is accomplished as shown in FIG. 1. Conversion of the six-membered heterocycle to an amidate is accomplished in essentially the same manner as described (i.e., using triphenylphosphine and 2,2'-dipyridyl disulfide).

Figure 3:
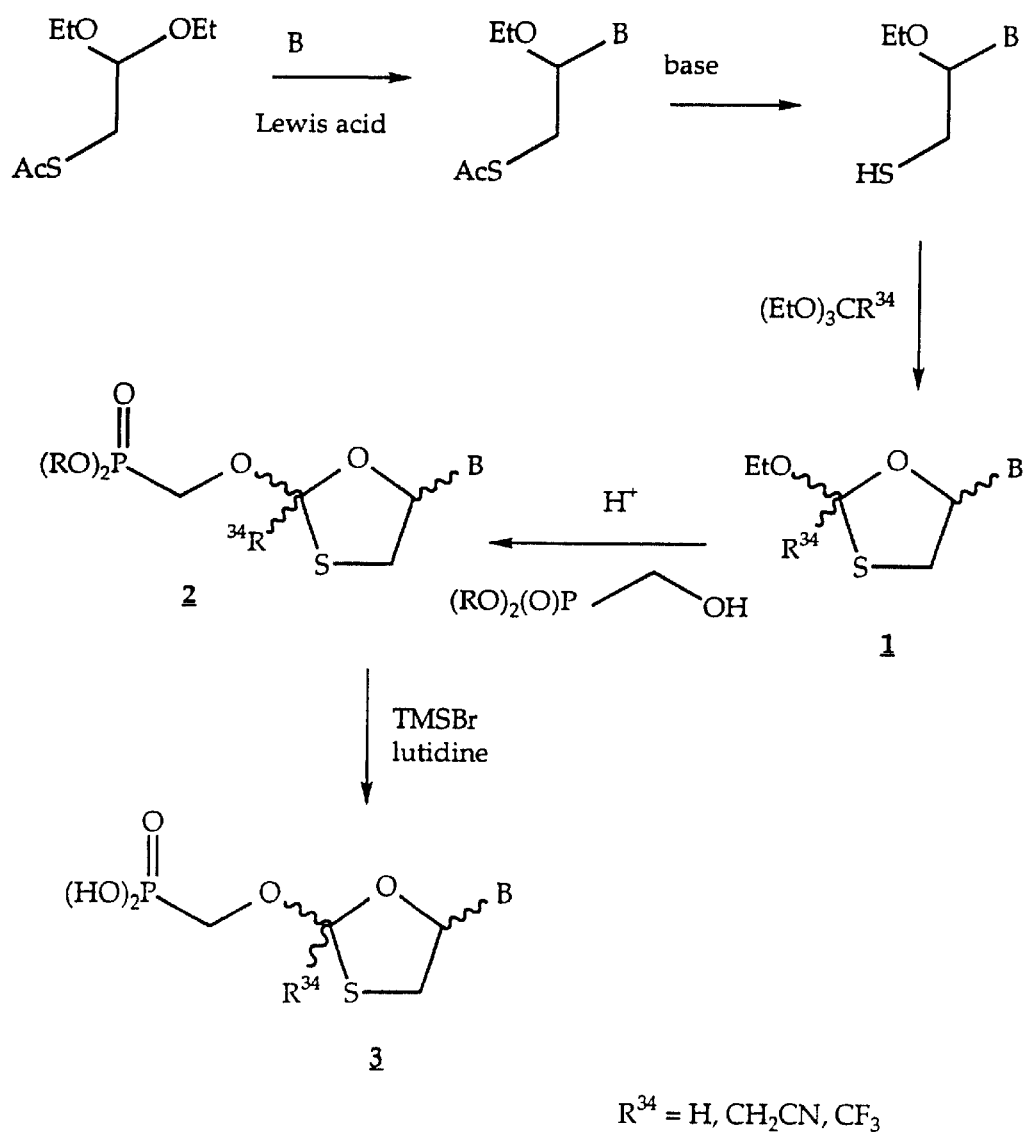
FIG. 3. Synthesis of formula IV compounds.
Figure 4:
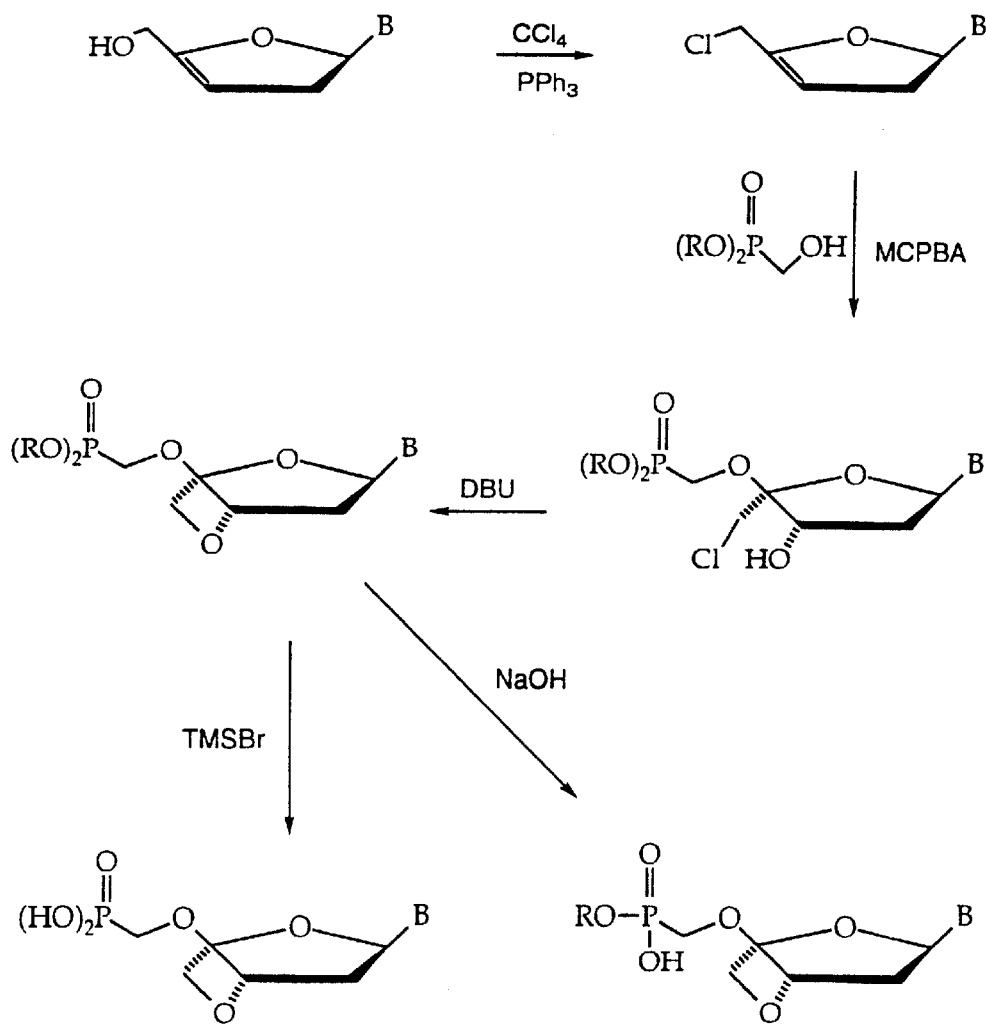
FIG. 4. Synthesis of formula VII compounds.
Figure 5:
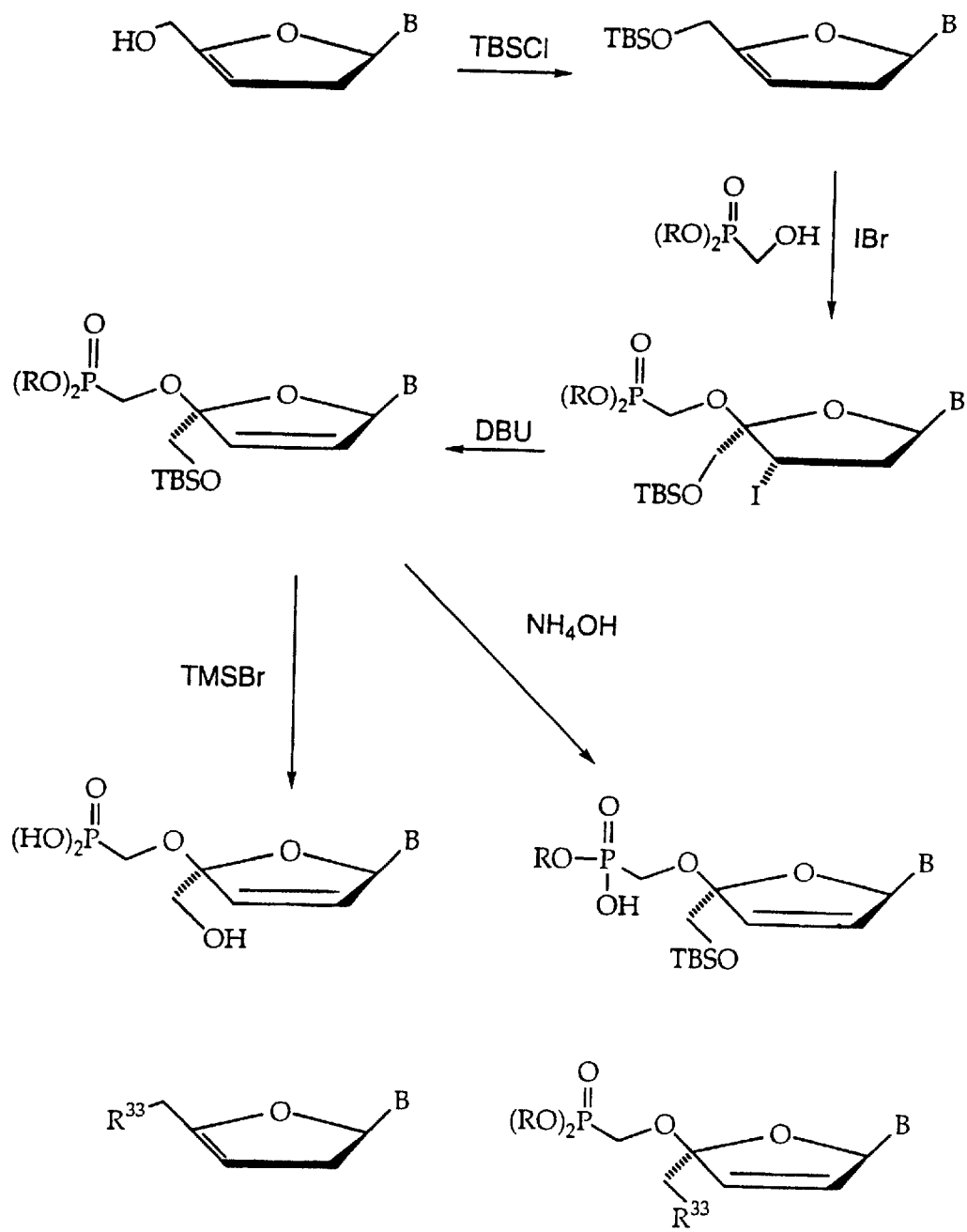
FIG. 5. Synthesis of formula VIII compounds.
Figure 6:
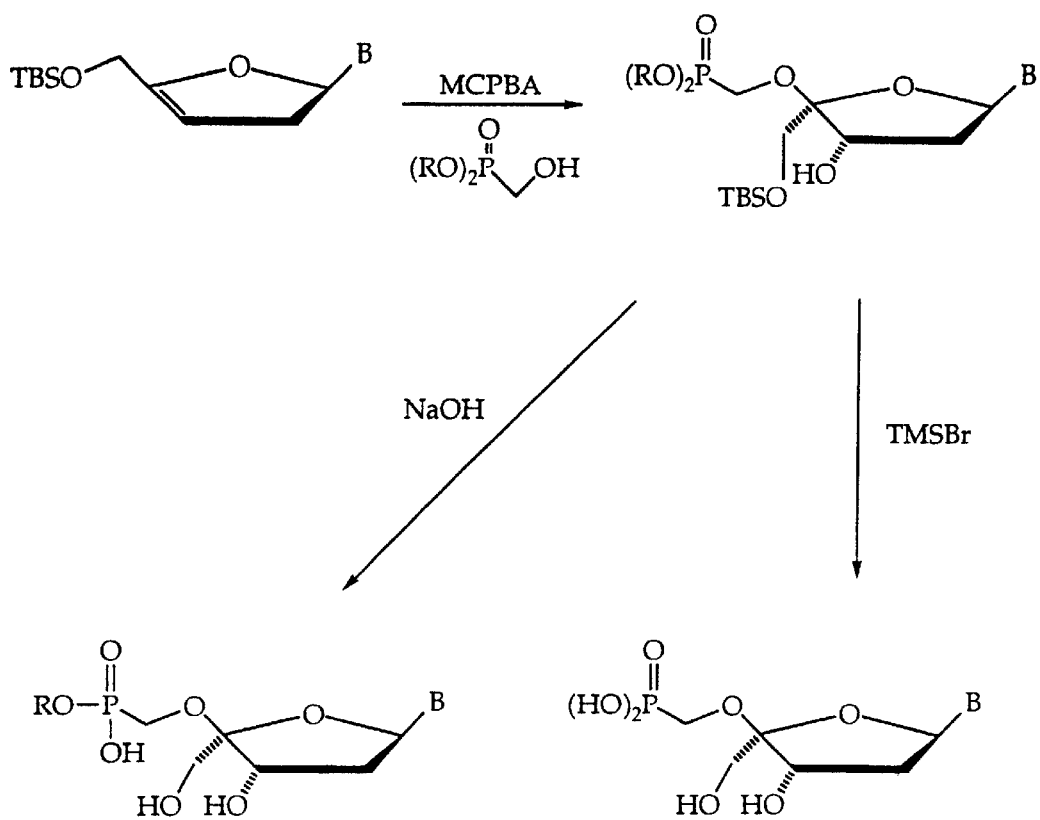
FIG. 6. Synthesis of formula VI compounds.
Figure 7:
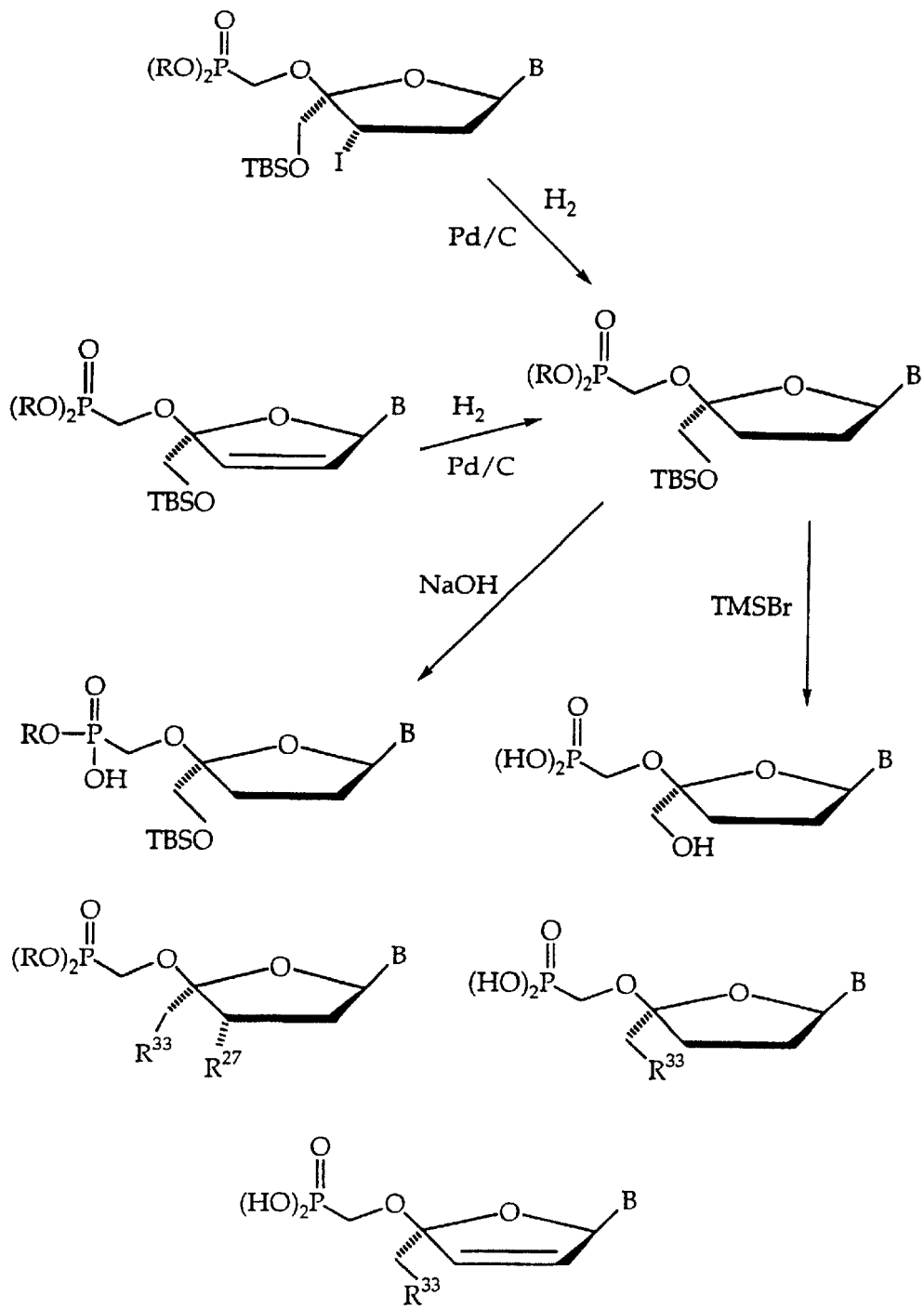
FIG. 7. Synthesis of formula VI compounds.

Synthesis of formula IV compounds where $R^{26}$ is S and $R^{25}$ and $R^{29}$ are O is accomplished as shown in FIG. 3. The starting material is synthesized by reaction of thiolacetic acid (Aldrich Cat. No. T3,080-5), bromoacetaldehyde diethyl acetal (Aldrich Cat. No. 12,398-6) and potassium tert-butoxide (Aldrich Cat. No. 15,667-1) in DMF. Synthesis of 1 where $R^{34}$ is H is accomplished using neat $(EtO)_3CH$. Synthesis of 1 where $R^{34}$ is $CH_2CN$ or $CF_3$ is accomplished using $(EtO)_3CH_2CN$ or $(EtO)_3CF_3$ in methylene chloride with a catalytic acid (such as p-toluenesulfonic acid). Conversion of the thiaorthoester 1 to the phosphonate 2 is accomplished using an acid such as tosic acid or perchloric acid in catalytic amounts. The resulting bis ester is then converted to a bis amidate in essentially the same manner as described (i.e., using triphenylphosphine and 2,2'-dipyridyl disulfide). Mixed ester-amidate compounds are obtained by removing a single ester from the bis ester using base (NaOH, $NH_4OH$, etc) as described. The phosphonate 3 is obtained by treatment with a base such as TMSBr or TMSI in a solvent (such as methylene chloride, DMF or acetonitrile) in the presence of lutidine (where R is alkyl, aryl or substituted aryl, acyloxyalkyl such as isopropyl, phenyl, 2-ethoxyphenyl) or by treatment with Pd/C/$H_2$ (where R is alkaryl or substituted alkaryl such as benzyl and the like). $R^{34}$ in FIG. 3 is H, $CF_3$ or $CH_2CN$.

Protected Heterocyclic Base Compounds.

The present invention includes nucleotide analogs that comprise a protected heterocyclic base. These compounds are useful as synthetic intermediates and/or, as therapeutic agents per se. Protected heterocyclic base compounds structures, their isomers, tautomers and the salts of such compounds having the formula $(R^{35}O)_2P(O)$-Z-$B^1$, $(L^{1A}O)(L^{2A}O)P(O)$-Z-$B^1$, $(HO)_2P(O)$-Z-$B^1$

XXXII

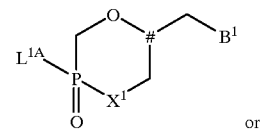

or

-continued

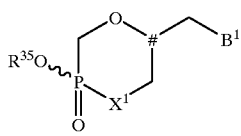

XXXIII where $L^{1A}$ is $L^1$, R or $NHR^{40}$, wherein $R^{40}$ is $C_1$–$C_{20}$ alkyl; $L^{2A}$ is $L^2$, $R^{35}$ or $NHR^{40}$; $B^1$ is a protected heterocycle base having the formula Xa, XIa, XIb, XIIa or XIIIa previously defined.

Suitable exemplary Z include compounds of formulas IV, V, VI, VII, VIII, —$CH_2$—O—$CH_2$—$CH_2$—, —$CH_2$—O—C#H($CH_3$)—$CH_2$— and —$CH_2$—O—C#H($CH_2OH$)—$CH_2$— having a heterocyclic base with an exocyclic amine can be converted to nucleotide analog amidates or esters comprising a protected heterocyclic base either by reacting the nucleotide analog amidate or ester with $R^{36}$C(O)Cl or $(CH_3O)_2CHR^{38}$. Protected heterocyclic bases include species having protecting groups at exocyclic amine groups such as the $N^4$-amine of cytosine, the $N^6$-amine of adenine and the $N^2$-amine of guanine. The phosphonate moiety of compounds containing $B^1$ may be present as an ester, an amidate or as the free acid.

Bases having $NHR^{40}$ at an exocyclic amine are synthesized to obtain a protected pyrimidine or purine essentially as described (Gilliam *Anal. Biochem.* (1986) 157:199; Gallo-Rodriguez *J. Med. Chem.* (1994) 37:636; Maillard *J. Pharm. Sci.* (1994) 83:46).

The exemplary reaction schemes used to synthesize protected heterocyclic base compounds shown below utilize cHPMPC as an example. Analogous reactions will generate compounds comprising other Z moieties such as —$CH_2$—O—$CH_2$—$CH_2$— or —$CH_2$—O—CH($CH_3$)—$CH_2$— linked to $B^1$. Phosphonate alkyl and aryl esters of compounds comprising $B^1$ are prepared, using HPMPC and cHPMPC as an example, according to the following procedures

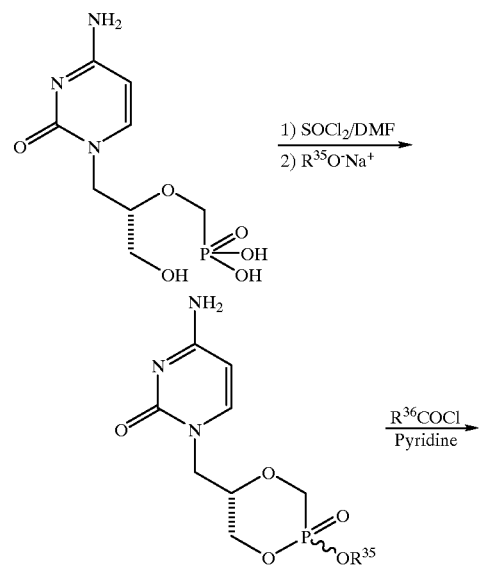

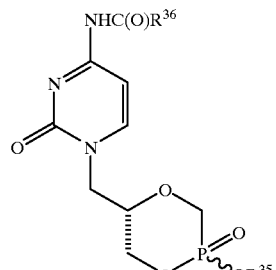

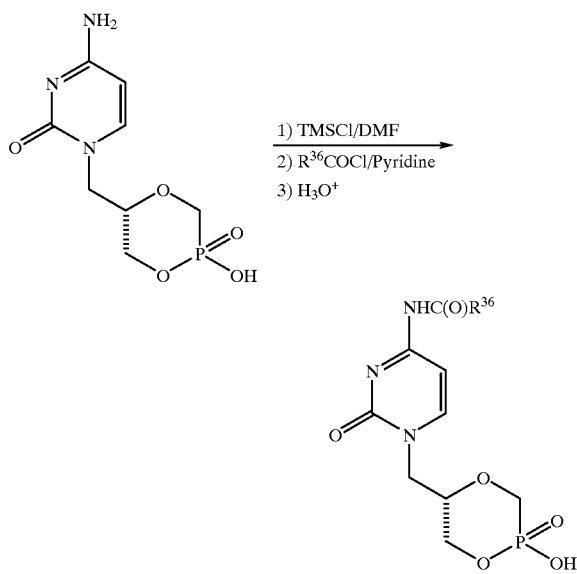

wherein $R^{36}$ is as defined above. Either procedure is readily adapted to synthesizing compounds containing protected heterocyclic bases other than cytosine, e.g., adenine, guanine, 2,6-diaminopurine or 2-aminopurine. Exemplary $R^{35}$ and/or $R^{36}$, which can be the same or different, include phenyl, substituted phenyl, —$C_{10}H_{15}$ (where $C_{10}H_{15}$ is adamantoyl), —$CH_2$—$C_6H_5$, —$C_6H_5$, —$C(CH_3)_3$, —CH($CH_3$)$_2$, —$CH_2CH_3$, methyl, ethyl, butyl, t-butyl, heptanyl, nonanyl, undecanyl, lauryl, steryl, undecenyl and the like. The amide linkage is conveniently formed by reaction of the acyl chloride with the exocyclic amine linked to the base. When $R^1$ is linked to the free phosphonate the resulting ester will comprise a single isomer or a scalemic mixture at the phosphorus atom. Low temperature reaction conditions (lower than about −20°, e.g., about −20° to about −40° C. or about −40° to about −80° C.) tend to favor single isomer products, while reaction at higher temperatures (above about −20°, e.g. −20° to 40° C.) generally results in a scalemic mix. When a scalemic mixture is obtained, the isomers can be conveniently separated by, for example, HPLC, although the mixture can be used, for example, as a synthetic intermediate or as an active antimicrobial agent, without resolution. Synthesis of the phenyl ester of cHPMPC at −78° C. by reaction of the chloridate and phenoxide yielded a scalemic mixture consisting of about ≧90% of the product as one isomer (isomer #1) at the phosphorus atom while the remaining∼≦10% was present as the other isomer (isomer #2). The scalemic mixture was converted to isomer #2 (≧90%) by incubation at room temperature for about 10 minutes (about 10 to 30 minutes is generally suitable) with a catalytic amount of sodium phenoxide in DMF. This method can be used to convert one isomer of cHPMP-B or cHPMP-$B^1$ (such as cHPMPC or cHPMPA) aryloxy or alkoxy ester to the other isomer with catalytic amounts of the corresponding aryloxide ion or alkoxide ion.

The cHPMPC pivaloyloxymethyl ester synthesis yields a scalemic mixture at the phosphorus atom. The mixture was separated by HPLC into the two isomers which were then exposed to an rat intestinal homogenate or to a rat intestinal wash. One of the isomers was converted to cHPMPC after incubation in the homogenate while the other isomer was converted to HPMPC pivaloyloxymethyl monoester. Both isomers were converted to HPMPC pivaloyloxymethyl monoester after incubation in the intestinal wash. These results suggested that (1) in at least some cases, enzyme activity can have a differential effect on the metabolic fate of a cHPMPC ester depending on which phosphorus isomer is present and (2) chemical activity (i.e., the acidity of the intestinal wash) can affect the metabolic fate of a given compound in a manner that differs from enzyme activity.

A method to obtain heterocyclic bases comprising the $C(O)R^{36}$ protecting group is accomplished as follows using the acyl chloride ($R^{36}C(O)Cl$) using HPMPC and cHPMPC as an example

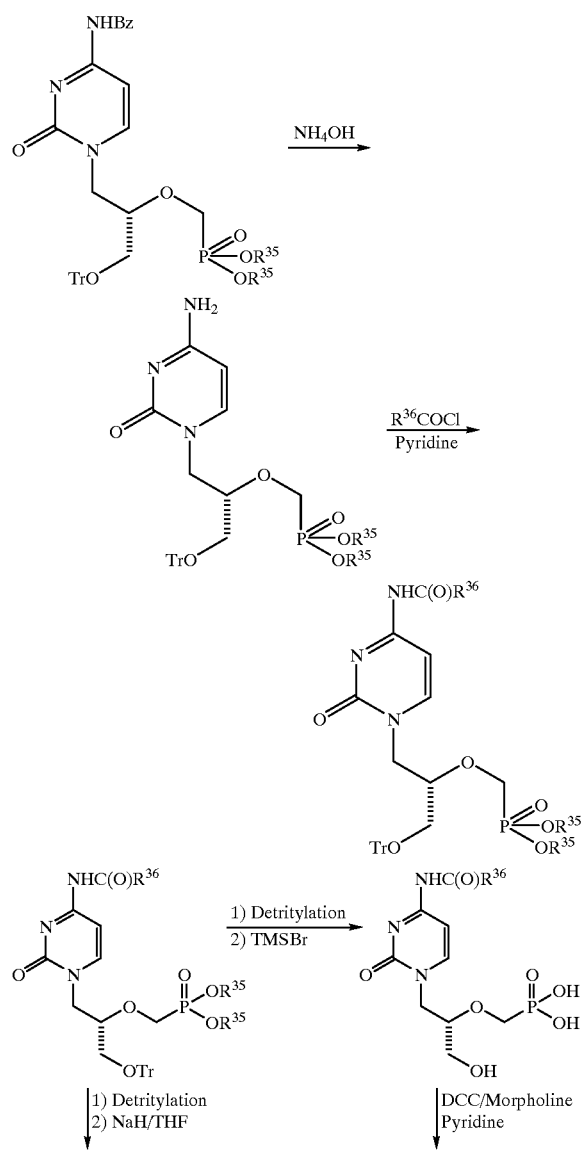

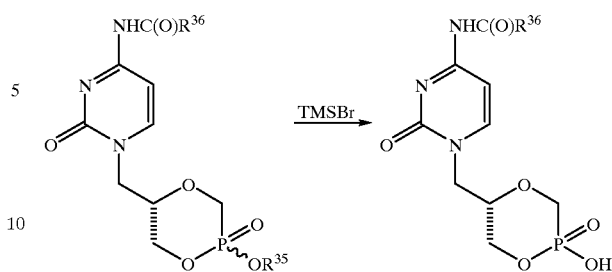

wherein Tr is the hydroxyl protecting group trityl. The detritylation step is accomplished by acid treatment, such as 80% acetic acid at about 10° to 60° C. for 1–2 hours. The $R^{35}$ moiety is removed using a Lewis acid such as TMSBr to yield the free phosphonate.

Phosphonate compounds comprising $B^1$ and a $C_2$–$C_{20}$ 1-acyloxy-1-alkyl or a $C_4$–$C_{20}$ 1-acyloxy-1-alkyl-1-aryl ester group are prepared as follows

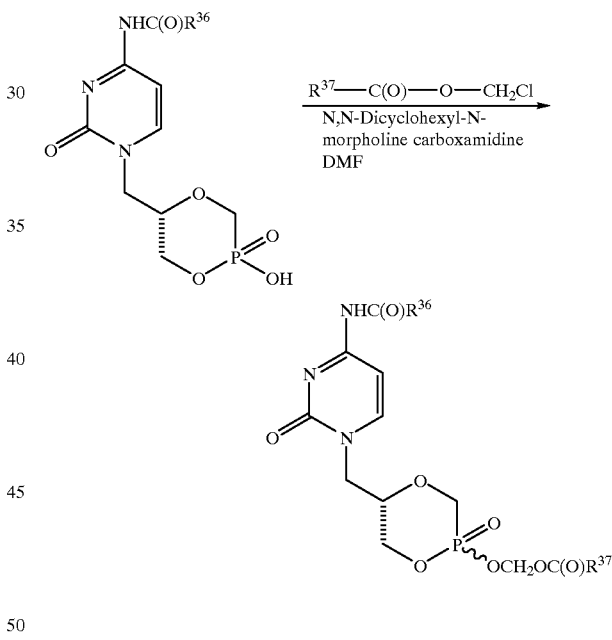

wherein $R^{37}$ is $C_1$–$C_{20}$ alkyl which is unsubstituted or substituted by substituents independently selected from the group consisting of $C_1$–$C_6$ alkyl, $C_1$–$C_6$ alkoxy, $C_1$–$C_6$ haloalkyl (1 to 3 halogen atoms), cyano, nitro, OH, O, NH and halogen (including ethyl, propyl, isopropyl, t-butyl, isobutyl and adamantoyl), or $C_3$–$C_{10}$ aryl which is unsubstituted or substituted by substituents independently selected from the group consisting of $C_1$–$C_6$ alkyl, $C_1$–$C_6$ alkoxy, $C_1$–$C_6$ haloalkyl (1 to 3 halogen atoms), cyano, nitro, OH, O, N and halogen (including phenyl, and 3- or 4-pyridyl).

The amine protecting group $=CR^{41}N(R^{38})_2$ is incorporated into an exocyclic amine to yield protected heterocyclic base compounds as follows

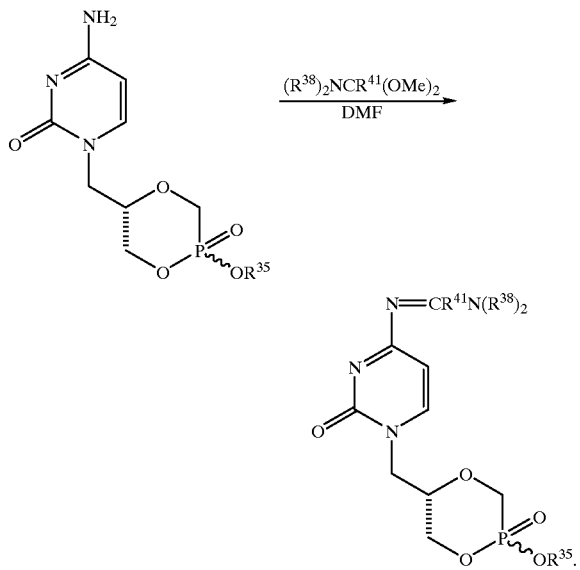

Exemplary R³⁸ alkyl groups include methyl, ethyl, propyl, isopropyl, cyclopropyl, butyl, isobutyl and cyclobutyl. In general, both R³⁸ alkyl groups will be the same. The reaction can be carried out in dry DMF at room temperature (about 20–30° C.) as previously described (Kerr et al J. Pharm. Sci. (1994) 83:582; Kerr et al J. Med. Chem. (1992) 35:1996), or DMF can be substituted with $CH_3CN$ and 4 Å molecular sieves. Exemplary compounds include species where R is hydrogen, alkyl (including ethyl, propyl, isopropyl), aryl (including phenyl) or acyloxymethyl. Protected heterocyclic bases where $R^{41}$ is hydrogen are stable under neutral anhydrous conditions and are generally labile under acidic aqueous conditions. When $R^{41}$ is methyl, the protecting group is more stable to aqueous acidic or basic conditions.

Compounds containing a protected heterocyclic base and 1 or 2 amino acids, dipeptides or oligopeptides attached to the phosphorus atom via an amidate linkage are obtained as described for synthesis of bis-amidate or amidate-ester compounds.

Table 5A lists $R^{35}$ ester and $L^1$ amidate moieties that can be incorporated into the phosphorus atom of both cyclic Z moieties (such as cHPMPC comprising a protected heterocyclic base or cHPMPC) or linear Z moieties (such as HPMPC comprising a protected heterocyclic base or PMEA comprising a protected heterocyclic base or PMEA). Esters of structures 1–5, 8–10 and 16, 17, 19–22 are synthesized by reacting a nucleotide analog (such as cHPMPC) the corresponding halide (chloride or acyl chloride and the like) and N,N-dicylohexyl-N-morpholine carboxamidine (or another base such as DBU, triethylamine, $CsCO_3$, N,N-dimethylaniline and the like) in DMF (or other solvent such as acetonitrile or N-methylpyrrolidone). Esters of structures 5–7, 11, 12, 21, and 23–26 are synthesized by reaction of the alcohol or alkoxide salt (or the corresponding amines in the case of compounds such as 13, 14 and 15) with a nucleotide analog monochlorophosphonate or dichlorophosphonate (such as cHPMPC monochlorophosphonate or PMEA dichlorophosphonate) or another activated phosphonate.

TABLE 5A

| | |
|---|---|
| 1. | —CH₂—C(O)—N(R⁷)₂* |
| 2. | —CH₂—S(O)(R⁷) |
| 3. | —CH₂—S(O)₂(R⁷) |
| 4. | —CH₂—O—C(O)—CH₂—C₆H₅ |
| 5. | 3-cholesteryl |
| 6. | 3-pyridyl |
| 7. | N-ethylmorpholino |
| 8. | —CH₂—O—C(O)—C₆H₅ |
| 9. | —CH₂—O—C(O)—CH₂CH₃ |
| 10. | —CH₂—O—C(O)—C(CH₃)₃ |
| 11. | —CH₂CCl₃ |
| 12. | —C₆H₅ |
| 13. | —NH—CH₂—C(O)O—CH₂CH₃ |
| 14. | —N(CH₃)—CH₂—C(O)O—CH₂CH₃ |
| 15. | —NHR⁴⁰ |
| 16. | —CH₂—O—C(O)—C₁₀H₁₅ |
| 17. | —CH₂—O—C(O)—CH(CH₃)₂ |
| 18. | —CH₂—C#H(OC(O)CH₂R⁷)—CH₂—(OC(O)CH₂R⁷)* |
| 19. | —CH₂C(O)N⟨morpholino⟩ |
| 20. | [benzazepinone structure] |
| 21. | [sugar structure with HO, OH, HO] |
| 22. | —CH₂—O—C(O)—[3-pyridyl] |
| 23. | —CH₂CH₂—[2-pyridyl] |
| 24. | CH₃C(O)O—[2-methylphenyl] |
| 25. | CH₃CH₂C(O)O—[2-methylphenyl] |
| 26. | —CH₂—[3,4,5-trimethoxyphenyl] |

*Each R⁷ is the same or different (includes methyl, ethyl, propyl, isopropyl and t-butyl).

All citations are hereby expressly incorporated by reference. The following examples are illustrative and do not limit the scope of this invention.

EXAMPLE 1
Synthesis of Phosphonate Amidate Compounds.

The compounds of structural formula Id shown are in Table 6 (bis(glycyl benzyl ester)PMEA (compound Ex 4), bis(alanyl benzyl ester)PMEA (Ex 1), bis(phenylalanyl benzyl ester)PMEA (Ex 5), etc. Compounds Ex 1–Ex 12 were synthesized by the following procedure. PMEA (Z-B=—CH$_2$—O—CH$_2$—CH$_2$—B, where B is adenin-9-yl) (0.3 g; 1.1 mmol) and amino acid ester·HCl (2.2 mmol; Sigma) were suspended in dry pyridine (6 mL) containing triethylamine (0.3 mL; 22.2 mmol), followed by addition to a mixture of freshly prepared triphenylphosphine (3.3 mmol) and 2,2'-dipyridyl disulfide (3.3 mmol) in pyridine (3 mL). The mixture was stirred at room temperature overnight, concentrated and partitioned between methylene chloride and water. The organic solution was dried over MgSO$_4$, concentrated and purified by flash column chromatography on silica gel.

Ex 14 was synthesized using freshly prepared triphenylphosphine (6.0 mmol) and 2,2'-dipyridyl disulfide (6.0 mmol) in pyridine (20 mL) at room temperature to which PMEA (2.0 mmol) was added. The suspension was stirred for 10 min. and ethyl sarcosine HCl (N-methylglycine HCl ethyl ester; 1.2 g, 8.0 mmol) was added. The suspension was warmed to 90° C. and stirred for 24 hours. Crude product was concentrated by rotary evaporation and purified by silica flash chromatography (mobile phase 1% methanol gradient to 20% methanol/80% methylene chloride).

Compound Ex 13 was synthesized in a similar manner using PMEA and phenylalanine N-ethylmorpholino ester.

TABLE 6

| Compound | L$^1$ |
| --- | --- |
| Ex 1 | —NH—CH(CH$_3$)—C(O)OCH$_2$C$_6$H$_5$ |
| Ex 2 | —NH—CH(CH$_2$C$_6$H$_5$)—C(O)OCH$_2$C$_6$H$_5$ |
| Ex 3 | —NH—CH(CH$_2$CH(CH$_3$)$_2$)—C(O)OCH$_2$C$_6$H$_5$ |
| Ex 4 | —NH—CH$_2$—C(O)OCH$_2$C$_6$H$_5$ |
| Ex 5 | —NH—CH(CH$_3$)—C(O)OC$_2$H$_5$ |
| Ex 6 | —NH—CH(CH$_2$CH(CH$_3$)$_2$)—C(O)OC$_2$H$_5$ |
| Ex 7 | —NH—CH$_2$—C(O)OC$_2$H$_5$ |
| Ex 8 | —NH—CH(CH$_2$C$_6$H$_5$)—C(O)OC(CH$_3$)$_3$ |
| Ex 9 | —NH—CH(CH$_2$CH(CH$_3$)$_2$)—C(O)OC(CH$_3$)$_3$ |
| Ex 10 | —NH—CH(CH$_3$)—C(O)OC(CH$_3$)$_3$ |
| Ex 11 | —NH—CH$_2$—C(O)OC(CH$_3$)$_3$ |
| Ex 12 | —NH—CH(CH$_2$C$_6$H$_5$)—C(O)OC$_2$H$_5$ |
| Ex 13 | —NH—CH(CH$_2$C$_6$H$_5$)C(O)O—(CH$_2$)$_2$—N[(CH$_2$)$_2$(CH$_2$)$_2$]O |
| Ex 14 | —N(CH$_3$)—CH$_2$—C(O)OC$_2$H$_5$ |

EXAMPLE 2
Antiviral Activity.

Compounds were individually tested for activity against HSV-1 and/or HSV-2. HSV-2 (strain 414-92) was tested using MA 104 cells in the following assay protocol. 96-Well plates were seeded with 1×10$^4$ MA 104 cells per well using 200 μL minimal essential medium (MEM) containing 10% calf serum per well, and incubated overnight at 37° C. The compounds were dissolved in MEM Earle's Salts without serum. The medium was removed by aspiration and 100 μL MEM Earle's Salts without serum was added to the wells. Serial 3-fold dilutions of the compounds were prepared by serial transfer of 50 μL of medium from wells containing compound to wells lacking compound. The plates were incubated 15 minutes at 37° C. followed by addition of 100 PFU/well of virus in MEM Earle's Salts with 2% fetal bovine serum. The plates were then incubated at 37° C. for three days until approximately 90% of the cells in virus infected control wells containing no compound were killed. Following incubation, medium was aspirated and the wells were washed with sterile PBS. 100 μL 0.5% crystal violet in 20% methanol was then added to the wells for 5 minutes, aspirated and the wells were washed two or three times with distilled water. 200 μL of 0.01 N HCl was added to the wells and the absorbance of each well at 595 nm was determined. The results, shown in Table 6, were expressed as the IC$_{50}$, the concentration (μM) that inhibits cell killing mediated by HSV-2 by 50%. IC$_{50}$ values varied from 2 μM to >100 μM compared to an IC$_{50}$ for PMEA of 21 μM. Thus, some of the compounds were more active against HSV-1 than PMEA. The toxicity of the compounds were expressed as the CC$_{50}$, the concentration that kills 50% of uninfected cells.

The compounds were also tested for activity against the KOS strain of HSV-1 in VERO cells. The results, shown in Table 7, were expressed as the EC$_{50}$, the concentration (EM) that inhibits cell killing mediated by HSV-2 by 50%. EC$_{50}$ values varied from 2 μM to >200 μM compared to an EC$_{50}$ for PMEA of 138 μM. Thus, some of the compounds were more active against HSV-2 than PMEA.

TABLE 7

| | HSV-1 | HSV-2 | |
| --- | --- | --- | --- |
| compound | EC$_{50}$ | IC$_{50}$ | CC$_{50}$ |
| Ex 7 | >200 | >100 | >100 |
| Ex 5 | nt* | >100 | >100 |
| Ex 6 | 20 | 33 | >100 |
| Ex 12 | nt | 20 | 80 |
| Ex 11 | >200 | >100 | >100 |
| Ex 10 | >200 | >100 | >100 |
| Ex 9 | 63 | 63 | >100 |
| Ex 8 | 3 | 9 | 20 |
| Ex 4 | nt | 60 | >100 |
| Ex 1 | nt | 20 | >100 |
| Ex 3 | nt | 2 | 30 |
| Ex 2 | nt | 4 | 20 |

*nt - not tested

EXAMPLE 3
PMEA, Monophenyl Ester, Mono N-ethylmorpholinophenylalanyl Phosphoroamidate.

Bis(phenyl)PMEA is selectively hydrolyzed to the monophenyl ester of PMEA using NaOH in THF. The reaction mixture is neutralized with acid (1 N HCl), and the monophenyl PMEA is isolated by filtration. The anhydrous monophenyl PMEA and 2 equivalents of a freshly prepared 1:1 mixture of triphenylphosphine and 2,2'-dipyridyl disulfide in pyridine is condensed with 1 equivalent of phenylalanine N-ethyl-morpholino ester in triethylamine and pyridine to afford the title compound. The title compound is recovered by evaporation of the solvents under reduced pressure and purified by silica gel chromatography.

EXAMPLE 4
Antiviral Activity of PMEA Esters.

PMEA and PMEA esters were tested for inhibition of cytopathic effects by HSV II in MA 104 cells as described except that CPE was determined after incubation with virus by addition of 100 μL XTT, 1 mg/mL in deficient DME containing 25 μM PMF followed by measuring absorbance. The esters tested were bis(POM)PMEA, bis(phenyl)PMEA, monophenylPMEA, bis(3-dimethylaminophenyl)PMEA, bis(3-methoxyphenyl)PMEA, bis(2-carboethoxyphenyl)

PMEA, bis(adamantoyl oxymethyl)PMEA, bis(4-fluorophenyl)PMEA and bis(2-ethoxyphenyl)PMEA. All of the compounds tested were active, which indicated that the ester groups were removed, thereby allowing free PMEA to inhibit virus replication and/or cytopathic effects. The $IC_{50}$ and $CC_{50}$ of PMEA in the assay was 19.3 μM and 2000 μM respectively and the $IC_{50}$ and $CC_{50}$ of bis(POM)PMEA in the assay was 0.5 μM and >10 μM respectively. $IC_{50}$ values for the mono and bis esters ranged from 1.1 μM to 67.5 μM and the $CC_{50}$ values ranged from 70 μM to 500 μM.

EXAMPLE 5

Oral Bioavailability of Nucleotide Analog Amidates and PMEA Esters.

Nucleotide analog amidates and nucleotide analogs are tested for their bioavailabililty when administered to cynomologous (or rhesus) monkeys by oral, subcutaneous or intramuscular routes. Bioavailability is determined by measuring PMEA levels in plasma or urine at different times after administering the drug using radiolabeled ($^3$H, $^{14}$C, etc) compound or, for compounds having adenine, essentially as described (Naesens, et al, *Clin Chem* (1992) 38:480–485; Russell, et al, *J Chromatogr* (*Netherlands*) (1991) 572:321–326). Radiolabeled compounds are obtained commercially (Moravek Biochemicals, Brea, Calif.) or by standard procedures, such as catalytic hydrogen exchange for $^3$H labeling. Compounds such as bis(2-ethoxyphenyl)PMEA, bis(2-carboethoxyphenyl)PMEA, bis(O-benzylphenylalanyl)PMEA, bis(3,5-dimethoxyphenyl)PMEA, bis(4-fluorophenyl)PMEA, bis(adamantoyl oxymethyl)PMEA, bis(phenyl)PMEA, bis(3-methoxyphenyl)PMEA are tested for oral bioavailability by administering about 10–30 mg/Kg (usually 15 to 25 mg/Kg) containing about 20–50 μCi/Kg (usually about 40 μCi/Kg) of radiolabeled compound, followed by withdrawing blood samples at several times after administration (exemplary time points are 0.1, 0.25, 0.5, 1.0, 1.5, 2.0, 2.5, 3.0, 4, 6, 12, 18, 24, 36, 48, 72, 96 hours after administration), obtaining plasma and determining the amount of radiolabeled compound present per volume (about 0.1–1.0 mL) of serum. Oral bioavailability of the tested compounds is 2–80% (or any value between 2% and 80% in 1% increments), preferably 10–80% and more preferably 15 to 80%. The oral bioavailability of bis(POM)PMEA by this type of assay is typically about 25% in monkeys and PMEA is about 2–4% (Balzarini et al, *Animal Models in AIDS* (1990) p. 131–138, Schellekens, H. et al (ed), Elsevier Science Publications, Amsterdam) while nudeotide analog amidates and nudeotide analogs (including mono- and diesters) can have oral bio-availabilities of about 5%, 10%, 15%, 30%, 40%, 50%, 60% or 80%.

Total radioactivity in plasma is determined by mixing about 200 μL of plasma with a scintillation counting cocktail (such as 10 mL of Scinti-Safe plus LSC cocktail) and counting in a scintillation counter (usually for about 5–30 minutes). Detailed analysis of the radiochemical composition is accomplished using about 350 μL of plasma, denaturing proteins in the serum (using about 700 μL 0.1% trifluoroacetic acid in acetonitrile for example), drying the resulting sample under reduced pressure, suspending the sample in an appropriate buffer (for example using about 100 μL of 2% acetonitrile in 25 mM potassium phosphate buffer with 10 mM tetrabutyl ammonium hydrogen phosphate (TBAHP), pH 6.0 for HPLC analysis), centrifuging the sample and analyzing the supernatant for individual radiolabeled species by reverse phase HPLC on commercially available columns (The Separation Group, Hesperia, Calif.; Vydac C18, 5 μm, 250×4.6 mm column with an injection volume of about 50 μL and a flow rate of about 1.0 mL/min. at about 35° C. using buffer for 2 minutes followed by a linear gradient to about 65% acetonitrile in 25 mM potassium phosphate buffer with 10 mM TBAHP, pH 6.0 over 13 about minutes). Radiolabel detection is accomplished using means such as commercially available radioactive flow detection systems or scintillation counting systems (Packard, Meridian, Conn.).

Fluorescence detection of PMEA in plasma is accomplished by measuring fluorescence emission (420 nm, with excitation at about 236 nm) with a detector (model F2000, Spectra Physics, San Jose, Calif.) from the HPLC gradient essentially as described above (2 to 65% acetonitrile). Samples for analysis are prepared from plasma (200 μL) by protein precipitation with TFA (400 μL 0.1% in acetonitrile), drying and conversion of adenine to N6-ethenoadenine in 200 μL of reaction buffer (0.34% chloroacetaldehyde, 100 mM sodium acetate, pH 4.5) for 40 minutes at 95° C. followed by HPLC analysis using 50 μL.

EXAMPLE 6

Bis(adamantoyl oxymethyl)PMEA Ester.

DBU (1,8-diazabicyclo[5.4.0]undec-7-ene; 1.53 g, 10 mmol) was added to a suspension of PMEA (1.365 g, 5 mmol) in DMF (25 mL). Adamantoyl oxymethyl chloride (5.72 g, 25 mmol) in DMF (25 mL) was added to the reaction mixture which was then stirred for four days at room temperature and the volatiles were removed under vacuum. The crude product obtained after removal of the solvent was loaded onto a silica gel column and washed with 3% $MeOH/CH_2Cl_2$ to remove nonpolar impurities. 1 g (30%) of bis(adamantoyl oxymethyl)PMEA ester was eluted in 8% $MeOH/CH_2Cl_2$. Adamantoyl oxymethyl chloride was obtained by conversion of 1-adamantanecarbonyl chloride (Aldrich No. 11,772-2) with $(CH_2O)_n/ZnCl_2$ and has been described (Bodor, et al *J Med Chem* (1980) 23:474–480).

EXAMPLE 7

Bis(phenyl)PMEA and bis(2-ethoxyphenyl)PMEA Esters.

PMEA (2.0 g, 7.3 mmol), acetonitrile (20 mL), thionyl chloride (20 mL) and N,N-dimethylformamide (2 drops) were added to a 250 mL single neck round bottom flask equipped with a magnetic stirrer, water cooled condenser and $N_2$ atmosphere. The flask was immersed in a 85° C. oil bath and the resulting suspension was stirred for two hours. The resulting solution was then concentrated to dryness and acetonitrile (50 mL) was added to redissolve the crude chloridate.

To a separate 250 mL single neck round bottom flask equipped with a mechanical stirrer, and $N_2$ atmosphere, phenol (3.25 g, 35 mmol), tetrahydrofuran (80 mL) and sodium hydride (1.4 g, 34 mmol, 60% (w/w) dispersion in mineral oil) was charged. After stirring for 30 minutes, the solution was cooled to −78° C. with a dry ice-acetone bath. The acetonitrile from the previous step was then added drop-wise at a rate that the internal temperature did not rise above −76° C. After the addition was complete, the resulting suspension was poured into saturated aqueous $NaHCO_3$ (100 mL) and extracted with methylene chloride (3×150 mL). The combined organic extracts were washed with $H_2O$ (100 mL), brine (100 mL) and dried with anhydrous $Na_2SO_4$. Concentration by rotary evaporation afforded a yellow solid. Purification by recrystallization (ethyl acetate/hexanes) afforded pure bis(phenyl)PMEA (1.64 g, 53%). Bis(2-ethoxyphenyl)PMEA was made similarly using 2-ethoxyphenol in place of phenol in 36% yield.

EXAMPLE 8

(R)-9-(2-Di-2 ethoxyphenylphosphonylmethoxypropyl) Adenine.

To a solution of 2-ethoxyphenol (45 mmol, 6.22 g) in pyridine (75 mL) was added (R)-9-(2-phosphonylmethoxypropyl) adenine (PMPA, 15 mmol, 4.3 g), creating a white suspension. A separate solution of 2,2'-dipyridyl disulfide (45 mmol, 9.91 g) and triphenyl phosphine (45 mmol, 11.81 g) in pyridine (75 mL) was added at 22° C. in a single portion to the white suspension. Then, triethylamine (30 mmol, 4.18 mL) was added in a single portion to the entire mixture, which was stirred at 75° C. for 21 h (TLC:10% MeOH/EtoAc). The dark amber slurry was then coevaporated with toluene (100 mL). It was then dissolved in dichloromethane (200 mL) and extracted twice with water (200 mL). The organic phase was dried ($NaSO_4$), filtered and concentrated (in vacuo) to a brown syrup (25.4 g). The syrup was purified by flash chromatography: 1–5% MeOH/EtoAc to elute impurities, then 6–12% MeOH/EtoAc (title compound elutes at 10–11%). The desired fractions were concentrated to afford 1.04 g of a brown solid. The solid was then recrystalized (EtoAc) to give the title compound (780 mg, 12% yield) as a tan solid. HNMR ($CDCl_3$) δ 1.25 (d, J=7.5 Hz, 3H, $CH_3$), δ 1.46 (m, 6H ($OCH_2CH_3$)$_2$), 4H ($OCH_2CH_3$)$_2$), 33.9 (m, 2H, O—$CH_2$P), δ 4.04 (m, 1H, H-2'), δ 4.09–4.39 (m, 2H, H-1'), 7.24 (m, 8H, ($C_6H_4$)$_2$), 7.92 (S, 1H, ($C_8$-H), 8.19 (S, 1H, $C_2$-H).

EXAMPLE 9 cHPMPU.

CHPMPU was synthesized by adding thionyl chloride (60 mL, 0.812 mmol, 2.02 eq) dropwise to a suspension of disodium HPMPU (131 mg, 0.404 mmol) in N,N-dimethylformamide (1.25 mL) at ambient temperature. The resulting light-yellow solution was stirred for 20 min at ambient temperature and then concentrated to dryness (in vacuo, 45° C.). $H_2O$ (2 mL) was added and the resulting solution was concentrated to dryness. Methanol (4 mL) was added and the resulting solution was concentrated to dryness to afford the crude product as a light-yellow solid. Purification by silica flash chromatography (mobile phase: 30% methanol: 70% $CH_2Cl_2$ gradient to 50% methanol:50% $CH_2Cl_2$) afforded pure cHPMPU in 69% yield as a white amorphous solid. $^1$H NMR (300 MHz, $D_2O$) d 7.62 d (1H, J=7.1 Hz, CH═CH), 5.82 d (1H, J=7.8 Hz, CH═CH), 4.30–3.71 m (7H, $CH_2CH(OCH_2P)CH_2OH$), NH and OH not observed in $D_2O$. $^{13}$C NMR (75 MHz, $D_2O$) d, 169.6 s (4-C), 155.1 s (2-C), 150.4 s (6-C), 104.2 s (5-C), 76.71 d (JP,C=3.6 Hz, 2'-$CH_2$), 72.30 d (JP,C=6.2 Hz, 3'-$CH_2$), 67.90 d (JP,C=142.0 Hz, P-$CH_2$), 50.71 s (1'-C). $^{31}$P NMR (121 MHz, $D_2O$) d 9.23 s.

EXAMPLE 10 cHPMPC Ethyl Ester.

To a stirred solution of diethyl HPMPC (1.1 g) in DMF, NaH (115 mg) was added. After 15 min, the reaction mixture was quenched with acetic acid (1 eq). The solvents were removed under reduced pressure. The crude mixture was dissolved in $CH_2Cl_2$ and water. The organic layer was washed with NaCl solution and the crude material obtained was purified on a silica gel column (elution with 5%–10% MeOH in $CH_2Cl_2$) to get cyclic ethyl HPMPC (950 mg) as a diastereomeric mixture (approximately 70%).

EXAMPLE 11 cHPMPC Esters.

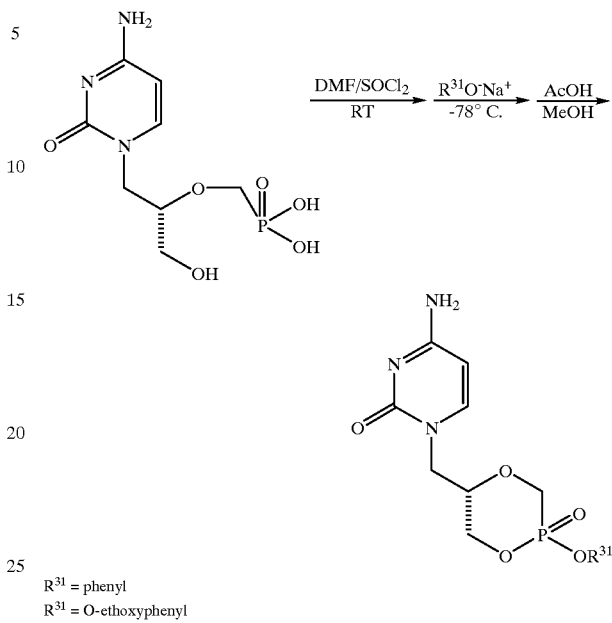

$R^{31}$ = phenyl
$R^{31}$ = O-ethoxyphenyl

To a stirred suspension of HPMPC (2.79 g) in DMF, thionylchloride (2.1 mL) was added dropwise under anhydrous conditions and the mixture was stirred for 1 hr. In another flask, sodium aryloxide (using the appropriate aryl substituent) was made using the corresponding phenol (8.9 g) and NaH (1.8 g) in 1:1 DMF/THF (50 mL). This solution was cooled to −78° C. and the chloridate solution was added dropwise under anhydrous conditions. After 2 hrs, the reaction mixture was quenched with acetic acid (5 eq) and the solvents were evaporated under vacuum. The crude mixture was partitioned between water and $CH_2Cl_2$. The organic layer was concentrated and the residue was purified on a silica gel column (elution with 5%–10% MeOH in $CH_2Cl_2$) to get the cyclic aryl compound as a single diastereomer in approximately 60% yield. This method is suitable for all substituted or unsubstituted $R^{31}$ groups, especially aryl, subject of course to conventional protection of labile groups other than amino for which reaction is undesired (amino is protected by reaction with DMF and deprotected with acetic acid and alkanol treatment). This method offers the advantages of producing substantially stereochemically pure product, superior yield and ease of synthesis.

EXAMPLE 12 cHPMPC Esters.

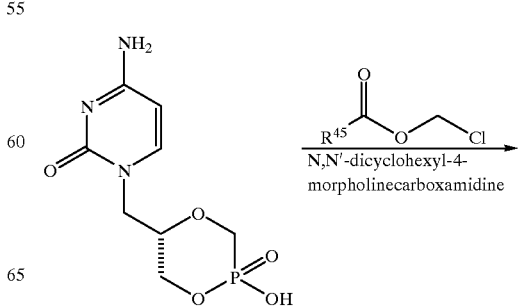

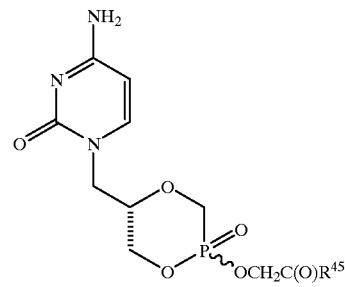

$R^{45}$ = t-Bu
$R^{45}$ = Adamantyl

To a stirred suspension of cyclic HPMPC (1 mmol) was added N,N'-dicyclohexyl-4-morpholinecarboxamidine (2 mmol) followed by the corresponding acyloxymethyl chloride (1.5 mmol). The reaction was stirred for 3 days and the DMF was evaporated under reduced pressure. The crude was purified on a silica gel column (eluted with 5% methanol in methylene chloride) to get the pure cyclic HPMPC derivatives (approximately 30% yield).

The final product was obtained in higher yield by the same reaction using cyclic HPMPC (1 mmol), N,N'-dicyclohexyl-4-morpholinecarboxamidine (1.1 mmol) followed by the corresponding acyloxymethyl chloride (1.2 mmol). $N^4$-benzoyl cHPMPC pivaloyloxymethyl ester was synthesized in a similar manner using $N^4$-benzoyl cHPMPC as the starting material.

EXAMPLE 13
cHPMPC Esters.

cHPMPC esters were synthesized using appropriate reactants essentially as described in Example 11 for ester moieties corresponding to structure numbers 6, 7, 11, 12, 13, 23, 24, 25 and 26 in Table 5A. cHPMPC esters were synthesized using approrpiate reactants essentially as described in Example 12 for ester moieties corresponding to structure numbers 8, 9, 10, 16 and 17 in Table 5A. Melting point data for cHPMPC esters of compound numbers 6, 8, 9, 11, 24, 25 and 26 was as follows: cHPMPC 3-pyridyl ester (#6)—268–273° C. (decomposes); cHPMPC N-ethylmorpholino ester (#7)—241° C.; cHPMPC —$CH_2$—O—C(O)—$C_6H_5$ ester (#8)—198–201° C.; cHPMPC #9 ortho ester—176° C.; cHPMPC #11 ester—100–250° C. (decomposes); cHPMPC phenyl ester (#12)—190° C.; cHPMPC #24 ester—218–225° C. (waxy liquid); cHPMPC #25 ester—171° C.; cHPMPC #26 ester—181° C.

EXAMPLE 14
9-[2,3-dideoxy-2,3-didehydro-4-phosphonomethoxy-β-D-erythrofuranosyl]adenine Esters.

Compounds where Z is of structure V and $R^{25}$ and $R^{29}$ is oxygen were synthesized by addition-elimination reaction using

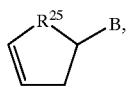

where B was adenine with iodine (2 equivalents) in acetonitrile and a compound having the structure $(R^{35}O)_2P(O)$—$CH_2$—OH (where $R^{35}$ was isopropyl, phenyl or 2-ethoxyphenyl) to yield the 3-iodophosphonate diester,

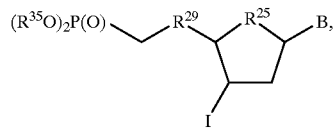

which was then eliminated to yield the corresponding structure V compound by reaction with 5 equivalents of sodium methoxide or DBU in anhydrous organic solvent such as methanol or tetrahydrofuran at room temperature for 12 hours.

Corresponding compounds where $R^{29}$ is sulfur, are synthesized by the same method using $(R^{35}O)_2P(O)$—$CH_2$—SH as a reactant. The compound of structure $(R^{35}O)_2P(O)$—$CH_2$—OH where $R^{35}$ is isopropyl has been described (Kluge Organic Synthesis (1986) 64:80–83).

Compounds of structure $(R^{35}O)_2P(O)$—$CH_2$—OH where $R^{35}$ was phenyl or 2-ethoxyphenyl were obtained by reaction of 1 equivalent of $PCl_3$ with 1 equivalent of t-butanol at 55° C. to obtain $(R^{35}O)_2P(O)H$ (U.S. Pat. No. 3,329,742). $(R^{35}O)_2P(O)H$ was then silylated using 1 equivalent of bis(trimethylsilyl)-trifluoroacetamide and the resulting $(R^{35}O)_2P(OTMS)$ was dried under vacuum. $(R^{35}O)_2P(OTMS)$ was then converted to $(R^{35}O)_2P(O)$—$CH_2$—OH by reaction in paraformaldehyde containing catalytic amounts of titanium isopropoxide (or another lewis acid such as titanium tetrachloride and the like can be used) for 12 hrs (12–16 hours) at 70° C. (65 to 75° C.). The 2-ethoxyphenyl product was isolated by crystallization. The bis-phenyl product was isolated by silica gel chromatography.

bis(2-ethoxyphenyl) D4AMPI ester: $^1$H-NMR (300 MHz, $CDCL_3$) δ 8.38 (s, 1H), 7.97 (s, 1H), 7.21–6.82 (m, 9H), 6.40 (d, 1H, J=5.7 Hz), 6.30 (d, 1H, J=5.8 Hz), 6.16 (s, 1H), 5.61 (s, 2H), 4.48 (dd, 1H, J=14, 8.8 Hz), 4.38 (dd, 1H, J=14, 6.5 Hz), 4.10–3.93 (m, 4H), 1.38 (t, 3H, J=7.1 Hz), 1.35 (t, 3H, J=7.1 Hz); $^{31}$P-NMR (121 MHz, $CDCL_3$) δ 14.6.

bis(phenyl) D4AMPI ester: $^1$H-NMR (300 MHz, $CDCL_3$) δ 8.38 (s, 1H), 7.93 (s, 1H), 7.34–7.10 (m, 10H), 7.03 (s, 1H), 6.42 (d, 1H, J=5.6 Hz), 6.34 (d, 1H, J=5.6 Hz), 5.98 (s, 1H), 5.83 (s, 2H), 4.32 (dd, 1H, J=14, 6.5 Hz), 4.19 (dd, 1H, J=14, 6.5 Hz); $^{31}$P-NMR (121 MHz, $CDCL_3$) δ 13.3.

$(C_6H_4(OC_2H_5)$—O$)_2P(O)$—$CH_2$—OH: $^1$H-NMR (300 MHz, $CDCL_3$) δ 7.36–7.16 (m, 10H), 4.19 (dd, 2H, J=6.7, 5.9 Hz), OH not detected; $^{31}$P-NMR (121 MHz, $CDCL_3$) δ 17.0.

$(C_6H_5$—O$)_2P(O)$—$CH_2$—OH: $^1$H-NMR (300 MHz, $CDCL_3$) δ 7.25–6.89 (m, 8H), 4.24 (d, 2H, J=5.01 Hz), 4.18–4.08 (m, 4H), 1.46 (t, 6H, J=7.0 Hz); $^{31}$P-NMR (121 MHz, $CDCL_3$) δ 19.9.

EXAMPLE 14
Nibenzoyl cHPMPC.

The title compound was synthesized using $N^4$-benzoyl HPMPC diethyl ester tritylated at the hydroxyl group as a starting material. The starting material was detritylated using acetic acid and then converted to $N^4$-benzoyl HPMPC using TMSBr. The resulting compound was converted to $N^4$-benzoyl cHPMPC using DCC and morpholine in pyridine. The title compound was tested for activity against HCMV in tissue culture (NHDF cell line) and was found to be active with an $IC_{50}$ of 22 μM compared with 0.4 μM for HPMPC.

$^1$HNMR (300 MHz, $CDCL_3$) δ 8.02 ($H_6$, 1H, d, 7.2 Hz), 7.97 (aromatic, 2H, d, 7.2 Hz), 7.62 (aromatic, 1H, t, 7.2 Hz), 7.5 (aromatic, 2H, t, 7.2 Hz), 7.26 ($H_5$, 1H, d, 7.2 Hz), 4.28 (1H, t, 14.7 Hz), 4.15 (1H, t, 10.8 Hz), 4.0 (m, 3H), 3.84(1H, m), 2.49 (1H, d, 14.1 Hz); $^{31}$P-NMR (121 MHz, CDCL$_3$) δ 10.07. Melting point 243–246° C.

The claims shall be construed to exclude any subject matter that, at the date of the invention, would not have been patentable under applicable statutory and judicial authority.

What is claimed is:

1. A compound included for antiviral use having the formula Id

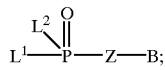

wherein L$^1$ is of the formula III

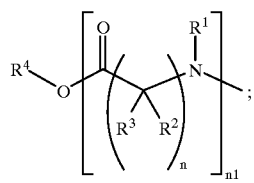

wherein L$^2$ is OR, SR or independently is L$^1$;
wherein n and n1 are 1;

R is N-ethylmorpholino, pivaloyloxymethyl, phenyl, benzyl, isopropyl, t-butyl, ethyl, isopropyl, butyl, adamantoyloxymethyl, 3-methoxyphenyl, 2-carboethoxyphenyl, 4-fluorophenyl, 2,4-difluorophenyl, 3,5-dimethoxyphenyl, 2,4-dichlorophenyl, 2-ethoxyphenyl, 3-dimethylaminophenyl, 4-trifluoromethylbenzyl, 2-ethylsalicyl, —O—CH$_2$—O—C(O)—C$_{10}$H$_{15}$, —C$_6$H$_4$—CH$_2$—N(CH$_3$)$_2$, —CH$_2$—CH$_2$F, —CH$_2$—CH$_2$Cl, —CH$_2$—CF$_3$, —CH$_2$—CCl$_3$, R$^5$, NHR$^6$ or N(R$^6$)$_2$;

wherein,
R$^5$ is CH$_2$C(O)N(R$^6$)$_2$, CH$_2$C(O)OR$^6$, CH$_2$OC(O)R$^6$, CH(R$^6$)OC(O)R$^6$, CH$_2$C(R$^6$)$_2$CH$_2$OH, or CH$_2$OR$^6$, and R$^6$ is C$_1$–C$_{20}$ alkyl which is unsubstituted or substituted by substituents independently selected from the group consisting of OH, O, N and halogen (1 to 5 halogen atoms), C$_6$–C$_{20}$ aryl which is unsubstituted or substituted by substituents independently selected from the group consisting of OH, O, N and halogen (1 to 5 halogen atoms) or C$_7$–C$_{20}$ aryl-alkyl which is unsubstituted or substituted by substituents independently selected from the group consisting of OH, O, N and halogen (1 to 5 halogen atoms);

R$^1$ is H, methyl, ethyl, isopropyl, phenyl or benzyl;
R$^2$ is H;
R$^3$ is H, —CH$_3$, —CH(CH$_3$)$_2$, —CH$_2$—CH(CH$_3$)$_2$, —CHCH$_3$—CH$_2$—CH$_3$, —CH$_2$—CH$_6$H$_5$, —CH$_2$CH$_2$—S—CH$_3$, —CH$_2$OH, —CH(OH)—CH$_3$, —CH$_2$—SH, —CH$_2$—C$_6$H$_4$OH, —CH$_2$—CO—NH$_2$, —CH$_2$—CH$_2$—CO—NH$_2$, —CH$_2$—COOH, —CH$_2$—CH$_2$—COOH, —(CH$_2$)$_4$—NH$_2$, —(CH$_2$)$_3$—NH—C(NH$_2$)—NH$_2$, 1-guanidinoprop-3-yl, benzyl, 4-hydroxybenzyl, imidazol-4-yl, indol-3-yl, methoxyphenyl or ethoxyphenyl;

R$^4$ is methyl, ethyl, propyl, isopropyl, butyl, t-butyl, phenyl, benzyl, 1-pyridyl, 3-pyridyl, 1-pyrimidinyl, pivaloyloxymethyl, N-ethylmorpholino, N-2-propylmorpholino, methoxyethyl, 4-N-methylpiperidyl, 3-N-methylpiperidyl, 1-ethylpiperazinyl 2-, 3-, and 4-N,N-dimethylaminophenyl or 2-, 3-, or 4-N,N-diethylaminophenyl;

Z is —CH$_2$—O—CH$_2$—CH$_2$—, —CH$_2$—O—CH$_2$—CH(CH$_2$OH)—, —CH$_2$—O—CH$_2$—CH(CH$_2$F)—, —CH$_2$—O—CH$_2$—CH(CH$_3$)—, —CH$_2$—O—CH$_2$—CH(CH=CH$_2$)— or —CH$_2$—O—CH$_2$—CH(CH$_2$N$_3$)—, or is of formula IV or V

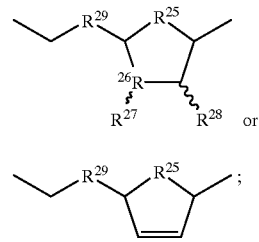

wherein
R$^{25}$ and R$^{29}$ are O;
R$^{26}$ is CH;
R$^{27}$ and R$^{28}$ are H; and
B is adenin-9-yl, 1-deazaadenin-9-yl, 3-deazaadenin-9-yl, 7-deaza-8-azaadenin-9-yl, 8-azaadenin-9-yl, guanin-9-yl, 2,6-diaminopurin-9-yl, 2-aminopurin-9-yl, thymin-1-yl, cytosin-1-yl, 5-fluorocytosin-1-yl, 6-azacytosin-1-yl, 5-methylcytosin-1-yl, 5-bromovinyluracil-1-yl, 5-fluorouracil-1-yl or 5-trifluoromethyluracil-1-yl.

2. A compound having the structure

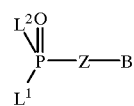

wherein L$^2$ is —OC$_6$H$_5$, L$^1$ is —NH—CH(CH$_3$)—C(O)—OR$^4$, Z is —CH$_2$—O—CH(CH$_3$)—CH$_2$—, B is adenin-9-yl and R$^4$ is H, propyl, isopropyl, t-butyl, phenyl, benzyl, 1-pyridinyl, 1-pyrimidinyl, N-ethylmorpholino, methoxyethyl, 4-hydroxy-N-methylpiperidinyl, 3-hydroxy-N-methylpiperidinyl or 1-ethylpiperazinyl.

* * * * *